US012486234B2

(12) United States Patent
Agarwal et al.

(10) Patent No.: US 12,486,234 B2
(45) Date of Patent: Dec. 2, 2025

(54) PAPD5 INHIBITORS AND METHODS OF USE THEREOF

(71) Applicant: Children's Medical Center Corporation, Boston, MA (US)

(72) Inventors: Suneet Agarwal, Lexington, MA (US); John J. Piwinski, Lebanon, NJ (US); Patricia C. Weber, Yardley, PA (US); Neha Nagpal, Boston, MA (US)

(73) Assignee: Children's Medical Center Corporation, Boston, MA (US)

( * ) Notice: Subject to any disclaimer, the term of this patent is extended or adjusted under 35 U.S.C. 154(b) by 938 days.

(21) Appl. No.: 17/605,763

(22) PCT Filed: Apr. 23, 2020

(86) PCT No.: PCT/US2020/029593

§ 371 (c)(1),
(2) Date: Oct. 22, 2021

(87) PCT Pub. No.: WO2020/219729

PCT Pub. Date: Oct. 29, 2020

(65) Prior Publication Data

US 2022/0274928 A1 Sep. 1, 2022

Related U.S. Application Data

(60) Provisional application No. 62/952,775, filed on Dec. 23, 2019, provisional application No. 62/838,221, filed on Apr. 24, 2019.

(51) Int. Cl.

| | |
|---|---|
| ***C07D 215/42*** | (2006.01) |
| ***C07D 215/44*** | (2006.01) |
| ***C07D 215/54*** | (2006.01) |
| ***C07D 401/04*** | (2006.01) |
| ***C07D 401/06*** | (2006.01) |
| ***C07D 401/12*** | (2006.01) |
| ***C07D 405/04*** | (2006.01) |
| ***C07D 405/12*** | (2006.01) |
| ***C07D 413/04*** | (2006.01) |
| ***C07D 413/06*** | (2006.01) |
| ***C07D 413/12*** | (2006.01) |
| ***C07D 413/14*** | (2006.01) |
| ***C07D 417/12*** | (2006.01) |
| ***C07D 471/04*** | (2006.01) |
| ***C07D 471/14*** | (2006.01) |
| ***C07D 471/16*** | (2006.01) |

(52) U.S. Cl.

CPC ......... *C07D 215/42* (2013.01); *C07D 215/44* (2013.01); *C07D 215/54* (2013.01); *C07D 401/04* (2013.01); *C07D 401/06* (2013.01); *C07D 401/12* (2013.01); *C07D 405/04* (2013.01); *C07D 405/12* (2013.01); *C07D 413/04* (2013.01); *C07D 413/06* (2013.01); *C07D 413/12* (2013.01); *C07D 413/14* (2013.01); *C07D 417/12* (2013.01); *C07D 471/04* (2013.01); *C07D 471/14* (2013.01); *C07D 471/16* (2013.01)

(58) Field of Classification Search

CPC ............................ C07D 215/42; C07D 215/44
USPC .................................................... 514/210.21
See application file for complete search history.

(56) References Cited

U.S. PATENT DOCUMENTS

| | | | | |
|---|---|---|---|---|
| 3,458,519 | A | 7/1969 | Scherrer | |
| 4,343,804 | A | 8/1982 | Munson, Jr. et al. | |
| 4,806,537 | A | 2/1989 | Roberts | |
| 4,806,549 | A | 2/1989 | Ife et al. | |
| 5,143,920 | A | 9/1992 | Ife et al. | |
| 5,215,999 | A * | 6/1993 | Uchida | A61P 1/04 546/160 |
| 5,304,121 | A | 4/1994 | Sahatjian | |
| 5,886,026 | A | 3/1999 | Hunter et al. | |
| 6,099,562 | A | 8/2000 | Ding et al. | |
| 6,503,713 | B1 | 1/2003 | Rana | |
| 6,797,692 | B1 | 9/2004 | Ikonomidou | |
| 6,803,031 | B2 | 10/2004 | Rabinowitz et al. | |
| 9,458,153 | B2 | 10/2016 | Han et al. | |
| 9,949,966 | B2 | 4/2018 | Han et al. | |
| 11,220,689 | B2 | 1/2022 | Agarwal et al. | |
| 12,171,755 | B2 | 12/2024 | Agarwal et al. | |
| 2006/0189643 | A1 | 8/2006 | Chen et al. | |
| 2006/0194805 | A1 | 8/2006 | Bakthavatchalam et al. | |
| 2009/0221624 | A1 | 9/2009 | Olivo et al. | |
| 2009/0226422 | A1 | 9/2009 | Chaudhary et al. | |
| 2009/0270450 | A1 | 10/2009 | Dakin et al. | |
| 2011/0053934 | A1 | 3/2011 | Angell et al. | |

(Continued)

FOREIGN PATENT DOCUMENTS

| | | | |
|---|---|---|---|
| CN | 1890223 | A | 1/2007 |
| CN | 102958930 | A | 3/2013 |

(Continued)

OTHER PUBLICATIONS

Balatsos et al., "Competitive inhibition of human poly (A)-specific ribonuclease (PARN) by synthetic fluoro-pyranosyl nucleosides," Biochemistry, Jul. 7, 2009, 48(26):6044-51.
Balatsos et al., "Inhibition of human poly (A)-specific ribonuclease (PARN) by purine nucleotides: kinetic analysis," Journal of Enzyme Inhibition and Medicinal Chemistry, Apr. 1, 2009, 24(2):516-23.

(Continued)

*Primary Examiner* — Kahsay Habte
(74) *Attorney, Agent, or Firm* — Fish & Richardson P.C.

(57) ABSTRACT

The present application provides compounds that are PAPD5 inhibitors and are useful in treating a variety of conditions such as cancer, telomere diseases, and aging-related and other degenerative disorders.

22 Claims, 20 Drawing Sheets

Specification includes a Sequence Listing.

(56) References Cited

U.S. PATENT DOCUMENTS

| | | | |
|---|---|---|---|
| 2013/0217671 A1 | 8/2013 | Matsuo et al. |
| 2014/0045849 A1 | 2/2014 | McGowan et al. |
| 2016/0122344 A1 | 5/2016 | Han et al. |
| 2021/0177827 A1 | 6/2021 | Agarwal et al. |
| 2021/0330678 A1 | 10/2021 | Agarwal et al. |
| 2025/0026769 A1 | 1/2025 | Agarwal et al. |

FOREIGN PATENT DOCUMENTS

| | | |
|---|---|---|
| CN | 103153063 A | 6/2013 |
| EP | 0480052 | 4/1992 |
| JP | H04211661 | 8/1992 |
| JP | 2007509985 | 4/2007 |
| JP | 2013529658 | 7/2013 |
| JP | 2013532727 | 8/2013 |
| JP | 2014504269 | 2/2014 |
| WO | WO9114677 A1 * | 11/1991 |
| WO | WO 2007/139496 A1 | 12/2007 |
| WO | WO 2008/056148 | 5/2008 |
| WO | WO 2008/119771 A2 | 10/2008 |
| WO | WO 2012/000595 | 1/2012 |
| WO | WO 2012/061557 | 5/2012 |
| WO | WO 2013/103317 A1 | 7/2013 |
| WO | WO 2015/113990 A1 | 8/2015 |
| WO | WO 2015/173164 A1 | 11/2015 |
| WO | WO 2016/107832 | 7/2016 |
| WO | WO 2016/128335 A1 | 8/2016 |
| WO | WO 2016/177655 | 11/2016 |
| WO | WO 2017/017042 A1 | 2/2017 |
| WO | WO 2017/066712 A2 | 4/2017 |
| WO | WO 2017/066796 | 4/2017 |
| WO | WO 2017/198756 A1 | 11/2017 |
| WO | WO 2017/216391 | 12/2017 |
| WO | WO 2018/154466 A1 | 8/2018 |
| WO | WO 2019/084271 | 5/2019 |
| WO | WO 2020/219729 A1 | 10/2020 |
| WO | WO 2023/086220 A2 | 5/2023 |

OTHER PUBLICATIONS

Balatsos et al., "Kinetic and in silico analysis of the slow-binding inhibition of human poly (A)-specific ribonuclease (PARN) by novel nucleoside analogues," Biochimie, Jan. 1, 2012, 94(1):214-21.

Balatsos et al., "Modulation of poly (A)-specific ribonuclease (PARN): current knowledge and perspectives," Current Medicinal Chemistry, Oct. 1, 2012, 19(28):4838-49.

Belloni et al., "IFN-α inhibits HBV transcription and replication in cell culture and in humanized mice by targeting the epigenetic regulation of the nuclear cccDNA minichromosome," The Journal of Clinical Investigation, Feb. 1, 2012, 122(2):529-37.

Blackburn et al., "Human telomere biology: a contributory and interactive factor in aging, disease risks, and protection," Science, Dec. 4, 2015, 350(6265):1193-8.

Boitano et al., "Aryl hydrocarbon receptor antagonists promote the expansion of human hematopoietic stem cells," Science, Sep. 10, 2010, 329(5997):1345-8.

Buster et al., "HBV 99-01 study group. Peginterferon alpha-2b is safe and effective in HBeAg-positive chronic hepatitis B patients with advanced fibrosis," Hepatology, Aug. 2007, 46(2):388-94.

cas.org, "List of compounds commercially available from various catalogs," retrieved from CAS Registry database URL <https://www.cas.org/cas-data/cas-registry>, Mar. 2019, 173 pages.

Chen et al., "Chain termination and inhibition of mammalian poly (A) polymerase by modified ATP analogues," Biochemical Pharmacology, Mar. 1, 2010, 79(5):669-77.

Childs et al., "Cellular senescence in aging and age-related disease: from mechanisms to therapy," Nature Medicine, Dec. 2015, 21(12):1424-35.

Codd et al., "Identification of seven loci affecting mean telomere length and their association with disease," Nature Genetics, Apr. 2013, 45(4):422-7.

ENA Accession No. FR872509, "Homo sapiens mRNA for PAP associated domain containing 5 (PAPD5 gene), Trf4-2 isoform," Sep. 29, 2011, 2 pages.

Fares et al., "Pyrimidoindole derivatives are agonists of human hematopoietic stem cell self-renewal," Science, Sep. 19, 2014, 345(6203):1509-12.

Fisicaroet al., "Antiviral intrahepatic T-cell responses can be restored by blocking programmed death-1 pathway in chronic hepatitis B," Gastroenterology, Feb. 1, 2010, 138(2):682-93.

Fok et al., "Posttranscriptional modulation of TERC by PAPD5 inhibition rescues hematopoietic development in dyskeratosis congenita," Blood, The Journal of the American Society of Hematology, Mar. 21, 2019, 133(12): 1308-12.

Haycock et al., "Leucocyte telomere length and risk of cardiovascular disease: systematic review and meta-analysis," Bmj, Jul. 8, 2014, 349(g4227), 11 pages.

Illum, "Is nose-to-brain transport of drugs in man a reality?," Journal of Pharmacy and Pharmacology, Jan. 2004, 56(1):3-17.

Illum, "Transport of drugs from the nasal cavity to the central nervous system," European Journal of Pharmaceutical Sciences, Jul. 2000, 11(1):1-8.

Janssen et al., "Pegylated interferon alfa-2b alone or in combination with lamivudine for HBeAg-positive chronic hepatitis B: a randomised trial," The Lancet, Jan. 8, 2005, 365(9454):123-9.

Kim et al., "Exosome cofactors connect transcription termination to RNA processing by guiding terminated transcripts to the appropriate exonuclease within the nuclear exosome," Journal of Biological Chemistry, Jun. 17, 2016, 291(25):13229-42.

Kiss et al., "Box H/ACA small ribonucleoproteins," Molecular Cell, Mar. 2010, 37(5):597-606.

Kondo et al., "Hepatitis B surface antigen could contribute to the immunopathogenesis of hepatitis B virus infection," International Scholarly Research Notices, Jan. 2013, vol. 2013, 9 pages.

Kondo et al., "Recovery of functional cytotoxic T lymphocytes during lamivudine therapy by acquiring multi-specificity," Journal of Medical Virology, Nov. 2004, 74(3):425-33.

Körner et al., "Poly (A) tail shortening by a mammalian poly (A)-specific 3'-exoribonuclease," Journal of Biological Chemistry, Apr. 18, 1997, 272(16):10448-56.

Kumar et al., "Hepatitis B virus regulatory HBx protein binds to adaptor protein IPS-1 and inhibits the activation of beta interferon," Journal of Virology, Jan. 15, 2011, 85(2):987-95.

Lambert et al., "Posttranslational N-glycosylation of the hepatitis B virus large envelope protein," Virology Journal, Dec. 2007, 4(1):1-9.

Lardelli et al., "Biallelic mutations in the 3' exonuclease TOE1 cause pontocerebellar hypoplasia and uncover a role in snRNA processing," Nature Genetics, Mar. 2017, 49(3):457-64.

Locarnini, "Molecular virology and the development of resistant mutants: implications for therapy," Seminars in Liver Disease, Feb. 2005, 25(S1):9-19.

Mao et al., "Indoleamine 2, 3-dioxygenase mediates the antiviral effect of gamma interferon against hepatitis B virus in human hepatocyte-derived cells," Journal of Virology, Jan. 15, 2011, 85(2):1048-57.

Mao et al., "Inhibition of hepatitis B virus replication by the host zinc finger antiviral protein," PLoS pathogens, Jul. 11, 2013, 9(7):e1003494, 18 pages.

Marcellinet al., "Peginterferon alfa-2a alone, lamivudine alone, and the two in combination in patients with HBeAg-negative chronic hepatitis B," New England Journal of Medicine, Sep. 16, 2004, 351(12):1206-17.

Mitchell et al., "A telomerase component is defective in the human disease dyskeratosis congenita," Nature, Dec. 1999, 402(6761):551-5.

Mueller et al., "A novel orally available small molecule that inhibits hepatitis B virus expression," Journal of Hepatology, Mar. 1, 2018, 68(3):412-20.

Nagpal et al., "Small-molecule PAPDS inhibitors restore telomerase activity in patient stem cells," Cell Stem Cell, Jun. 4, 2020, 26(6):896-909.

(56) References Cited

OTHER PUBLICATIONS

Nayersina et al., "HLA A2 restricted cytotoxic T lymphocyte responses to multiple hepatitis B surface antigen epitopes during hepatitis B virus infection," The Journal of Immunology, May 15, 1993, 150(10):4659-71.
Op den Brouw et al., "Hepatitis B virus surface antigen impairs myeloid dendritic cell function: a possible immune escape mechanism of hepatitis B virus," Immunology, Feb. 2009, 126(2):280-9.
Quasdorff et al., "Control of hepatitis B virus at the level of transcription," Journal of Viral Hepatitis, Aug. 2010, 17(8):527-36.
Ren et al., "Inhibition of Klenow DNA polymerase and poly (A)-specific ribonuclease by aminoglycosides," Rna, Nov. 2002, 8(11):1393-400.
Schulze et al., "Hepatitis B virus infection initiates with a large surface protein-dependent binding to heparan sulfate proteoglycans," Hepatology, Dec. 2007, 46(6):1759-68.
Shi et al., "Hepatitis B virus suppresses the functional interaction between natural killer cells and plasmacytoid dendritic cells," Journal of Viral Hepatitis, Feb. 2012, 19(2):e26-33.
Son et al., "PARN and TOE1 constitute a 3' end maturation module for nuclear non-coding RNAs," Cell Reports, Apr. 17, 2018, 23(3):888-98.
Thuresson et al., "Inhibition of poly (A) polymerase by aminoglycosides," Biochimie, Oct. 1, 2007, 89(10):1221-7.
Venteicher et al., "A human telomerase holoenzyme protein required for Cajal body localization and telomere synthesis," Science, Jan. 30, 2009, 323(5914):644-8.
Vulliamy et al., "Mutations in the telomerase component NHP2 cause the premature ageing syndrome dyskeratosis congenita," Proceedings of the National Academy of Sciences, Jun. 10, 2008, 105(23):8073-8.
Walne et al., "Genetic heterogeneity in autosomal recessive dyskeratosis congenita with one subtype due to mutations in the telomerase-associated protein NOP10," Human Molecular Genetics, Jul. 1, 2007, 16(13):1619-29.
Wieland et al., "Stealth and cunning: hepatitis B and hepatitis C viruses," Journal of Virology, Aug. 1, 2005, 79(15):9369-80.
Woltman et al., "Hepatitis B virus lacks immune activating capacity, but actively inhibits plasmacytoid dendritic cell function," PloS one, Jan. 5, 2011, 6(1):e15324.
Yan et al., "Molecular determinants of hepatitis B and D virus entry restriction in mouse sodium taurocholate cotransporting polypeptide," Journal of Virology, Jul. 15, 2013, 87(14):7977-91.
Zhan et al., "Telomere length shortening and Alzheimer disease—a Mendelian randomization study," JAMA Neurology, Oct. 1, 2015, 72(10):1202-3.
Zhao et al., "Association between telomere length and type 2 diabetes mellitus: a meta-analysis," PloS one, Nov. 21, 2013, 8(11):e79993, 7 pages.
Zhou et al., "HBsAg mRNA degradation induced by a dihydroquinolizinone compound depends on the HBV post-transcriptional regulatory element," Antiviral Research, Jan. 1, 2018, 149:191-201.
cas.org, "List of compounds commercially available from various catalogs: CAS 1359225-01-6(Mar. 1, 2012), 1359177-86-8(Mar. 1, 2012), 1359087-20-9(Mar. 1, 2012), 1358946-16-3(Mar. 1, 2012), 1351797-82-4(Dec. 23, 2011), 1340821-46-6(Nov. 4, 2011), 1340771-47-2(Nov. 4, 2011), 1340718-13-9(Nov. 4, 2011), 791555-39-0 (Dec. 2, 2004)" retrieved from CAS Registry database URL <https://www.cas.org/cas-data/cas-registry>, dated Dec. 2, 2004 through Mar. 1, 2012, 10 pages.
JP Office Action in Japanese Appln. No. 2021-563059, mailed on Apr. 9, 2024, 9 pages (with English translation).
CAS Registry No. 1340821-46-6, "Benzoic Acid," Nov. 4, 2011, 3 pages.
CN Office Action in Chinese Appln. No. 202080044298.X, mailed on Dec. 23, 2023, 21 pages (with English translation).
EP European Search Report in European Appln. No. 20794201.2, dated Sep. 9, 2022, 7 pages.
CA Office Action in Canadian Appln. No. 3,137,768, mailed on Feb. 15, 2024, 4 pages.
Ahmadian et al., "Single nucleotide polymorphism analysis by pyrosequencing," Anal. Biochem., 2000, 280:103-110.
Bernard et al., "Real-time PCR Technology for Cancer Diagnostics," Clin. Chem., 2002, 48(8):1178-1185.
Bianchi et al., "A Serum Circulating miRNA Diagnostic Test to Identify Asymptomatic High-Risk Individuals With Early Stage Lung Cancer," EMBO Mol. Med., 2011, 3:495-503.
Boyraz et al., "Posttranscriptional manipulation of TERC reverses molecular hallmarks of telomere disease," The Journal of Clinical Investigation, Sep. 1, 2016, 126(9):3377-82.
Carneiro et al., "Bosutinib therapy ameliorates lung inflammation and fibrosis in experimental silicosis," Frontiers in Physiology, Mar. 15, 2017, 8:159.
Castillo-González et al., "Prediction of telomerase inhibitory activity for acridinic derivatives based on chemical structure," European Journal of Medicinal Chemistry, Dec. 1, 2009, 44(12):4826-40.
Czarnik, "Encoding Methods for Combinatorial Chemistry," Curr. Opin. Chem. Bio., 1997, 1:60-66.
Diehl et al., "BEAMing: single-molecule PCR on microparticles in water-in-oil emulsions," Nat. Methods, 2006, 3:551-559.
Ekins and Chu, "Microarrays: Their Origins and Applications," Trends in Biotechnology, 1999, 17:217-218.
EP European Search Report in European Appln. No. 18870786.3, dated Nov. 9, 2020, 18 pages.
EP Extended Search Report in European Appln. No. 18870786.3, dated Feb. 9, 2021, 15 pages.
EP Office Action in European Appln. No. 18870786.3, mailed on Mar. 31, 2023, 4 pages.
GenBank Accession No. CCB84642.1, "PAP associated domain containing 5 [*Homo sapiens*]," dated Sep. 29, 2011, 2 pages.
GenBank Accession No. FR872509.1, "*Homo sapiens* mRNA for PAP associated domain containing 5 (PAPD5 gene), Trf4-2 isoform," dated Sep. 29, 2011, 2 pages.
GenBank Accession No. NM 001040284.3, "*Homo sapiens* terminal nucleotidyltransferase 4B (TENT4B), transcript variant 1, mRNA," dated Sep. 13, 2020, 6 pages.
GenBank Accession No. NM_001040285.3, "*Homo sapiens* terminal nucleotidyltransferase 4B (TENT4B), transcript variant 2, mRNA," dated Sep. 13, 2020, 6 pages.
GenBank Accession No. NM_001134477.3, "*Homo sapiens* poly(A)-specific ribonuclease (PARN), transcript variant 2, mRNA," dated Oct. 19, 2020, 5 pages.
GenBank Accession No. NM_001242992.2, "*Homo sapiens* poly(A)-specific ribonuclease (PARN), transcript variant 3, mRNA," dated Oct. 19, 2020, 5 pages.
GenBank Accession No. NM 002582.4, "*Homo sapiens* poly(A)-specific ribonuclease (PARN), transcript variant 1, mRNA," dated Oct. 13, 2020, 7 pages.
GenBank Accession No. NR 001566.3, "*Homo sapiens* telomerase RNA component (TERC), telomerase RNA," dated Jul. 4, 2020, 3 pages.
Gómez-Pinto et al., "Discovery of ligands for a novel target, the human telomerase RNA, based on flexible-target virtual screening and NMR," Journal of Medicinal Chemistry, Nov. 27, 2008, 51(22):7205-15.
Ife et al., "Reversible inhibitors of the gastric (H+/K+)-ATPase. 3. 3-Substituted-4-(phenylamino) quinolines," Journal of Medicinal Chemistry, Sep. 1992, 35(18):3413-22.
International Preliminary Report on Patentability in International Appln. No. PCT/US2020/029593, mailed on Nov. 4, 2021, 7 pages.
International Preliminary Report on Patentability in International Appln. No. PCT/US2022/048187, mailed on May 10, 2024, 7 pages.
International Search Report and Written Opinion in International Appln. No. PCT/US2022/048187, mailed on Aug. 15, 2023, 10 pages.
Kim et al., "Viral hijacking of the TENT4-ZCCHC14 complex protects viral RNAs via mixed tailing," Nature Structural & Molecular Biology, May 2020, 27:581-588, 17 pages.

(56) References Cited

OTHER PUBLICATIONS

Kulsuptrakul et al., "A genome-wide CRISPR screen identifies UFMylation and TRAMP-like complexes as host factors required for hepatitis A virus infection," Cell Reports, Mar. 2021, 34(11):108859, 19 pages.
Liu et al., "Synthesis and anti-tumor activities of 4-anilinoquinoline derivatives," Molecules, Dec. 2015, 21(1):21.
MacBeath et al., "Printing proteins as microarrays for high-throughput function determination," Science, Sep. 8, 2000, 289(5485):1760-3.
Miranda et al., "Nucleic acids within urinary exosomes/microvesicles are potential biomarkers for renal disease," Kidney International, Jul. 2, 2010, 78(2):191-9.
Nagpal et al., "Therapeutic Targeting of Telomere Diseases Via Novel Small Molecule Modulators of Non-Coding RNA Biogenesis," Blood, Nov. 29, 2018, 132:647, 3 pages.
Nordström et al., "Direct analysis of single-nucleotide polymorphism on double-stranded DNA by pyrosequencing," Biotechnology and Applied Biochemistry, Apr. 2000, 31(2):107-12.
PCT International Preliminary Report on Patentability in PCT Appln. No. PCT/US2018/057514, dated Apr. 28, 2020, 7 pages.
PCT International Search Report and Written Opinion in PCT Appln. No. PCT/US2018/057514, dated Mar. 18, 2019, 11 pages.
PubChem ID 14983001, "Substance Record for SID 14983001," Oct. 25, 2006, 5 pages.
Sells et al., "Production of hepatitis B virus particles in Hep G2 cells transfected with cloned hepatitis B virus DNA," PNAS, Feb. 1987, 84(4):1005-1009.
Taylor et al., "The origin, function, and diagnostic potential of RNA within extracellular vesicles present in human biological fluids," Frontiers in Genetics, Jul. 30, 2013, 4:142, 12 pages.
UniProt Accession No. G4U4J3; H3BQM0, "PAP associated domain containing 5," dated Oct. 7, 2020, 3 pages.
UniProt Accession No. O95453, "Poly(A)-specific ribonuclease PARN," dated Oct. 7, 2020, 14 pages.
UniProt Accession No. Q8NDF8, "Terminal nucleotidyltransferase 4B," dated Aug. 12, 2020, 8 pages.
Yang et al., "Detection of tumor cell-specific mRNA and protein in exosome-like microvesicles from blood and saliva," PloS one, Nov. 14, 2014, 9(11), 10 pages.
Zhang, "The risk of gastric cancer in patients with duodenal and gastric ulcer: research progresses and clinical implications," Journal of Gastrointestinal Cancer, Jan. 2007, 38:38-45.
PCT International Search Report and Written Opinion in International Appln. No. PCT/US2020/029593, dated Sep. 28, 2020, 11 pages.
PubChem ID 53001702, "Methyl 2-{[6-fluoro-3-(piperidin-1-ylcarbonyl)quinolin-4-yl]amino}benzoate," Jun. 21, 2011, 10 pages.

* cited by examiner

PARN Mutant
Patient iPS Cells
1 μM Compound
7 Days

26A

16A

61A

Northern Blot

PAPD5 INHIBITORS AND METHODS OF USE THEREOF

CROSS-REFERENCE TO RELATED APPLICATIONS

This application is a U.S. National Phase application under 35 U.S.C. § 371 of International Patent Application No. PCT/US2020/029593, filed on Apr. 23, 2020, which claims priority to U.S. Provisional Patent Application Ser. No. 62/952,775, filed on Dec. 23, 2019; and U.S. Provisional Patent Application Ser. No. 62/838,221, filed on Apr. 24, 2019, the entire contents of which are hereby incorporated by reference.

FEDERALLY SPONSORED RESEARCH AND DEVELOPMENT

This invention was made with government support under grant number DK107716 awarded by National Institutes of Health (NIH). The government has certain rights in the invention.

SEQUENCE LISTING

This application contains a Sequence Listing that has been submitted electronically as an ASCII text file named Sequence_Listing.Txt. The ASCII text file, created on Sep. 30, 2021, is 6.23 kilobytes in size. The material in the ASCII text file is hereby incorporated by reference in its entirety.

TECHNICAL FIELD

The present disclosure relates to compounds that inhibit PAP Associated Domain Containing 5 (PAPD5), and to methods of using these compounds to treat conditions such as telomere diseases, and aging-related and other degenerative disorders.

BACKGROUND

A telomere is a region of repetitive nucleotide sequences at each end of a chromosome, which protects the end of the chromosome from deterioration or from fusion with neighboring chromosomes. The length of a telomere is a key determinant of cellular self-renewal capacity. The telomerase ribonucleoprotein maintains telomere length in tissue stem cells, and its function is critical for human health and longevity.

Short telomeres, due to genetic or acquired insults, cause a loss of cellular self-renewal and result in life-threatening diseases, for which there are few if any effective medical therapies. In these diseases involving short telomeres, e.g., aplastic anemia, pulmonary fibrosis, hepatic cirrhosis, bone marrow failure, etc., there is an unmet clinical need for new therapies.

SUMMARY

Poly(A) ribonuclease (PARN) mutations can result in the accumulation of 3' oligo-adenylated forms of nascent Telomerase RNA Component (TERC) RNA transcripts, which are targeted for destruction, thus causing telomerase deficiency and telomere diseases. Disruption of the non-canonical poly(A) polymerase PAP Associated Domain Containing 5 (PAPD5; also known as Topoisomerase-related function protein 4-2 (TRF4-2)) may restore TERC levels, telomerase activity, and telomere elongation in PARN-mutant patient cells. This disclosure relates, at least in part, to PAPD5 inhibitors and methods of using such inhibitors.

In one general aspect, the present disclosure provides a compound of Formula (I):

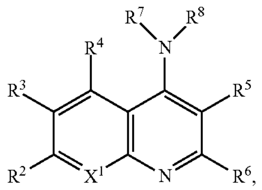

(I)

or a pharmaceutically acceptable salt thereof, wherein $X^1$, $R^2$, $R^3$, $R^4$, $R^5$, $R^6$, $R^7$, and $R^8$ are as described herein.

In another general aspect, the present disclosure provides a compound of Formula (II):

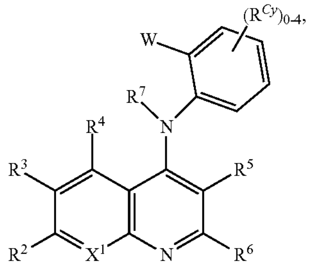

(II)

or a pharmaceutically acceptable salt thereof, wherein $X^1$, $R^2$, $R^3$, $R^4$, $R^5$, $R^6$, $R^7$, and $R^{Cy}$ are as described herein, and W is a carboxylic acid bioisostere, for example, as described herein.

In yet another general aspect, the present disclosure provides a compound of Formula (III):

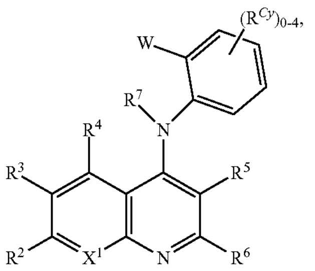

(III)

or a pharmaceutically acceptable salt thereof, wherein $X^1$, $R^2$, $R^3$, $R^4$, $R^6$, $R^7$, W, and $R^{Cy}$ are as described herein, $R^5$ is selected from $C(O)NR^{c1}R^{d1}$, $S(O)_2NR^{c1}R^{d1}$, and $Cy^1$, and $R^{c1}$, $R^{d1}$, and $Cy^1$ are as described herein.

In yet another general aspect, the present disclosure provides a compound of Formula (IV):

(IV)

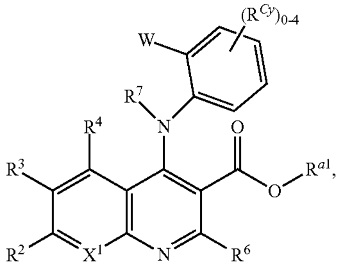

or a pharmaceutically acceptable salt thereof, wherein $X^1$, $R^2$, $R^3$, $R^4$, $R^6$, $R^7$, W, $R^{a1}$, and $R^{Cy}$ are as described herein.

In yet another general aspect, the present disclosure provides a compound of Formula (V):

(V)

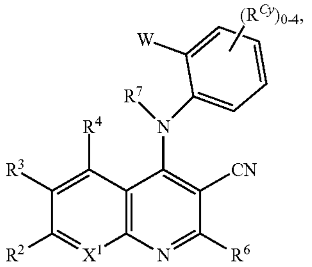

or a pharmaceutically acceptable salt thereof, wherein $X^1$, $R^2$, $R^3$, $R^4$, $R^6$, $R^7$, W, and $R^{Cy}$.

In yet another general aspect, the present disclosure provides a pharmaceutical composition comprising a compound of Formula (I), Formula (II), Formula (III), Formula (IV), or Formula (V) as described herein, or a pharmaceutically acceptable salt thereof, and a pharmaceutically acceptable carrier.

In yet another general aspect, the present disclosure provides a method selected from:

(a) treating a disorder associated with telomere or telomerase dysfunction in a subject;

(b) treating a disorder associated with aging in a subject;

(c) treating a pre-leukemic or pre-cancerous condition in subject;

(d) treating or preventing HBV infection in a subject;

(e) treating or preventing a neurodevelopmental disorder in a subject;

(f) treating an acquired or genetic disease or condition associated with alterations in RNA in a subject;

(g) decreasing PAPD5 activity in a subject;

(h) inhibiting of HBsAg production or secretion in a subject;

(i) inhibiting HBV DNA production in a subject (j) decreasing PAPD5 activity in a cell;

(k) inhibiting of HBsAg production or secretion in a cell;

(l) inhibiting HBV DNA production in a cell;

(m) modulating non-coding RNAs in a cell; and (n) modulating ex vivo expansion of a stem cell, the method comprising contacting the cell with an effective amount of, or administering to a subject in need thereof a therapeutically effective amount of, a compound of Formula (I), Formula (II), Formula (III), Formula (IV), or Formula (V), or a pharmaceutically acceptable salt thereof, or a pharmaceutical composition comprising same.

In yet another general aspect, the present disclosure provides a method of expanding a cell, the method comprising culturing the cell in the presence of an effective amount of a compound as described herein (e.g., the compound of Formulae (I), (II), (III), (IV), or (V)), or a pharmaceutically acceptable salt thereof.

Unless otherwise defined, all technical and scientific terms used herein have the same meaning as commonly understood by one of ordinary skill in the art to which the present application belongs. Methods and materials are described herein for use in the present application; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the present application will be apparent from the following detailed description and figures, and from the claims.

DETAILED DESCRIPTION

Figure 1:
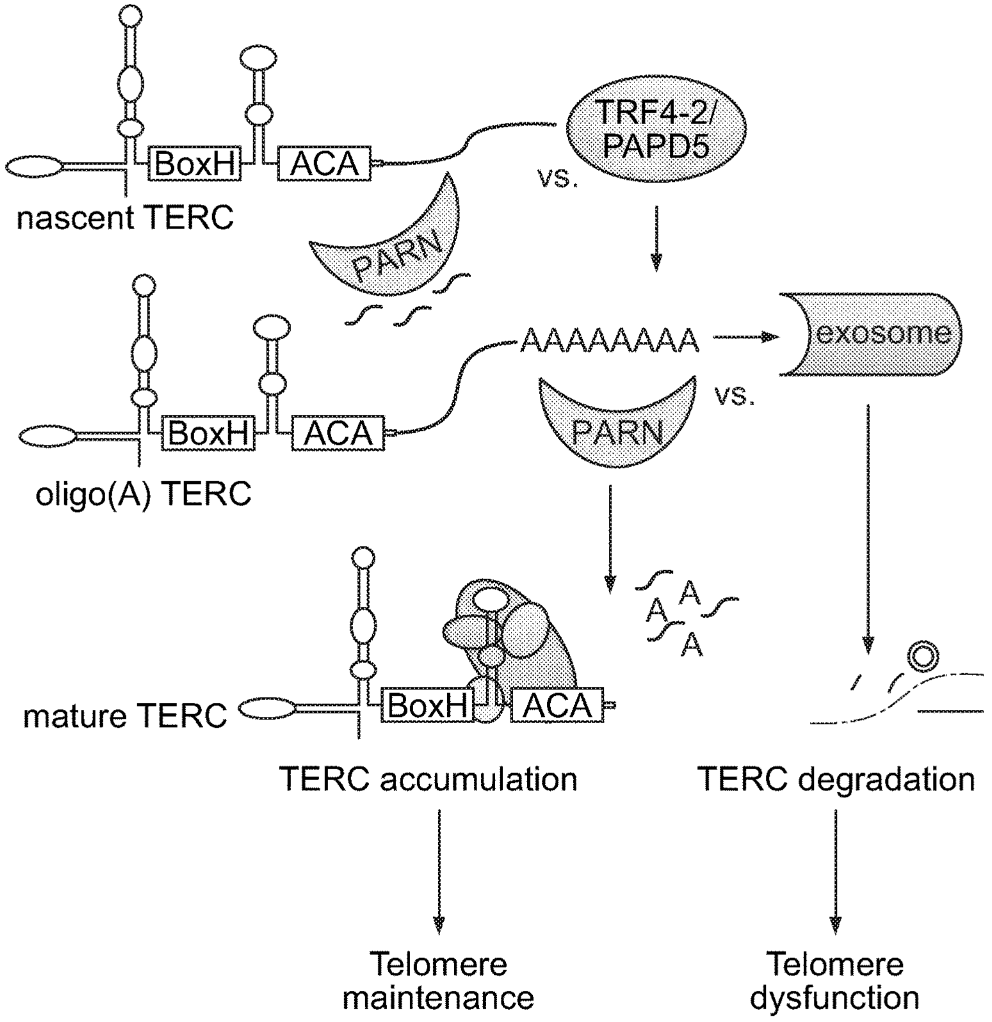
FIG. 1 is a schematic diagram showing an exemplary model for TERC 3' end maturation by PARN.

A telomere is a region of repetitive nucleotide sequences at each end of a chromosome. For vertebrates, the sequence of nucleotides in telomeres is TTAGGG. In humans, this sequence of TTAGGG is repeated approximately hundreds to thousands of times. Telomerase is a ribonucleoprotein that adds the telomere repeat sequence to the 3' end of telomeres. Cells with impaired telomerase function often have limited capacity for self-renewal, i.e., an abnormal state or condition characterized by an inability of cells (e.g., stem cells) to divide sufficiently. This deficiency in cells can, for example, lead to various diseases and disorders.

Telomerase RNA component (TERC) serves at least two functions: (1) it encodes the template sequence used by telomerase reverse transcriptase (TERT) for the addition of hexanucleotide repeats to telomeres, and (2) it is the scaffold that nucleates multiple proteins that target telomerase to the Cajal body, where telomeres are extended.

The disclosure provides compounds and methods to modulate TERC levels, e.g., by using compounds that target TERC, or compounds that modulate the level or activity of PAP Associated Domain Containing 5 (PAPD5) and/or Poly (A) specific ribonuclease (PARN), both of which are involved in the 3'-end maturation of TERC. Various implementations of these compounds and methods are described herein.

Therapeutic Compounds

In some embodiments, the present disclosure provides a compound of Formula (I)

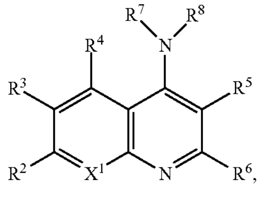

or a pharmaceutically acceptable salt thereof, wherein:

$X^1$ is selected from N and $CR^1$;

$R^1$, $R^2$, $R^3$, $R^4$, $R^5$, and $R^6$ are each independently selected from H, $C_{1-6}$ alkyl, $C_{2-6}$ alkenyl, $C_{2-6}$ alkynyl, $C_{1-4}$ haloalkyl, $Cy^1$, halo, CN, $NO_2$, $OR^{a1}$, $SR^{a1}$, $C(O)R^{b1}$, $C(O)NR^cR^{d1}$, $C(O)OR^{a1}$,$NR^{c1}R^{d1}$, $NR^{c1}C(O)R^{b1}$, $NR^{c1}S(O)_2R^{b1}$, $S(O)R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, 3, 4, or 5 substituents independently selected from $Cy^1$, halo, CN, $NO_2$, $OR^{a1}$, $SR^{a1}$, $C(O)R^{b1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2R^{b1}$, $S(O)_2R^{b1}$, and $S(O)_2NR^{c1}R^{d1}$;

each $Cy^1$ is independently selected from $C_{6-10}$ aryl, 5-10 membered heteroaryl, and 4-7 membered heterocycloalkyl, each of which is optionally substituted with 1, 2, or 3 substituents independently selected from $R^{Cy}$;

$R^7$ is selected from H, $C_{1-3}$ alkyl, $C(O)C_{1-6}$ alkyl, $C(O)OR^{a1}$, $S(O)_2NR^{c1}R^{d1}$, and phenyl, wherein said phenyl is optionally substituted with $R^{Cy}$, halo, CN, $OR^{a1}$, $SR^{a1}$, or $NR^{c1}R^{d1}$;

$R^8$ is selected from a 4-7 membered heterocycloalkyl, $C_{3-10}$ cycloalkyl, and a 5-10 membered heteroaryl, which is substituted with W, and is optionally substituted with 1, 2, or 3 substituents independently selected from $R^{Cy}$;

W is selected from $C(O)OR^{a2}$ and a carboxylic acid bioisostere;

$R^{Cy}$ is selected from halo, CN, $NO_2$, $C_{1-6}$ alkyl, $C_{1-6}$ haloalkyl, $C_{2-6}$ alkenyl, $C_{2-6}$ alkynyl, $OR^{a2}$, $C(O)R^{b2}$, $C(O)NR^{c2}R^{d2}$, $NR^{c2}R^{d2}$, $NR^{c2}C(O)R^{b2}$, $NR^{c2}C(O)OR^{a2}$, $NR^{c2}S(O)_2R^{b2}$, $S(O)_2R^{b2}$, and $S(O)_2NR^{c2}R^{d2}$; wherein said $C_{1-6}$ alkyl, $C_{2-6}$ alkenyl, and $C_{2-6}$ alkynyl are each optionally substituted with 1, 2, or 3 substituents independently selected from halo, CN, $NO_2$, $OR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$; $NR^{c2}C(O)OR^{a2}$, $NR^{c2}S(O)_2R^{b2}$, $S(O)_2R^{b2}$, and $S(O)_2NR^{c2}R^{d2}$;

or $R^5$ and $R^8$, together with the atoms to which they are attached, form a 5-10 membered heteroaryl ring or a 4-7 membered heterocycloalkyl ring, each of which is optionally substituted with 1, 2, 3, 4, or 5 substituents independently selected from $R^{Cy1}$;

or $R^4$ and $R^8$, together with the atoms to which they are attached, form a 5-10 membered heteroaryl ring or a 4-10 membered heterocycloalkyl ring, each of which is optionally substituted with 1, 2, 3, 4, or 5 substituents independently selected from $R^{Cy1}$;

$R^{Cy1}$ is selected from halo, CN, $NO_2$, $C_{1-6}$ alkyl, $C_{1-6}$ haloalkyl, $C_{2-6}$ alkenyl, $C_{2-6}$ alkynyl, $OR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}C(O)OR^{a3}$, $NR^{c3}S(O)_2R^{b3}$, $S(O)_2R^{b3}$, and $S(O)_2NR^{c3}R^{d3}$; wherein said $C_{1-6}$ alkyl, $C_{2-6}$ alkenyl, and $C_{2-6}$ alkynyl are each optionally substituted with 1, 2, or 3 substituents independently selected from halo, CN, $NO_2$, $OR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}C(O)OR^{a3}$, $NR^{c3}S(O)_2R^{b3}$, $S(O)_2R^{b3}$, and $S(O)_2NR^{c3}R^{d3}$;

or any two $R^{Cy1}$ together with the atoms to which they are attached, form a 5-10 membered heteroaryl ring or a 4-7 membered heterocycloalkyl ring, each of which is optionally substituted with 1, 2, 3, 4, or 5 substituents independently selected from $R^{Cy2}$;

or $R^7$ and $R^{Cy1}$, together with the atoms to which they are attached, form a 5-10 membered heteroaryl ring or a 4-7 membered heterocycloalkyl ring, each of which is optionally substituted with 1, 2, 3, 4, or 5 substituents independently selected from $R^{Cy2}$;

$R^{Cy2}$ is selected from halo, CN, $NO_2$, $C_{1-6}$ alkyl, $C_{1-6}$ haloalkyl, $C_{2-6}$ alkenyl, $C_{2-6}$ alkynyl, $OR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}S(O)_2R^{b4}$, $S(O)_2R^{b4}$, and $S(O)_2NR^{c4}R^{d4}$; wherein said $C_{1-6}$ alkyl, $C_{2-6}$ alkenyl, and $C_{2-6}$ alkynyl are each optionally substituted with 1, 2, or 3 substituents independently selected from halo, CN, $NO_2$, $OR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}S(O)_2R^{b4}$, $S(O)_2R^{b4}$, and $S(O)_2NR^{c4}R^{d4}$;

each $R^{a1}$, $R^{b1}$, $R^{c1}$, $R^{d1}$, $R^{a2}$, $R^{b2}$, 1 $R^{c2}$, $R^{d2}$, 1 $R^{a3}$, $R^{b3}$, $R^{c3}$, $R^{d3}$, $R^{a4}$, $R^{b4}$, $R^{c4}$, and $R^{d4}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$;

or any $R^{c2}$ and $R^{d2}$ together with the N atom to which they are attached form a 4-7 membered heterocycloalkyl, which is optionally substituted with 1, 2, or 3 substituents independently selected from $R^g$;

or any $R^{c3}$ and $R^{d3}$ together with the N atom to which they are attached form a 4-7 membered heterocycloalkyl, which is optionally substituted with 1, 2, or 3 substituents independently selected from $R^g$; and or any $R^{c4}$ and $R^{d4}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments:

$X^1$ is selected from N and $CR^1$;

$R^1$, $R^2$, $R^3$, $R^4$, $R^5$, and $R^6$ are each independently selected from H, $C_{1-6}$ alkyl, $C_{2-6}$ alkenyl, $C_{2-6}$ alkynyl, $C_{1-4}$ haloalkyl, $Cy^1$, halo, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2R^{b1}$, $S(O)R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, 3, 4, or 5 substituents independently selected from $Cy^1$, halo, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2R^{b1}$, $S(O)_2R^{b1}$, and $S(O)_2{}^{c1}R^{d1}$;

each $Cy^1$ is independently selected from $C_{6-10}$ aryl, 5-10 membered heteroaryl, and 4-7 membered heterocycloalkyl, each of which is optionally substituted with 1, 2, or 3 substituents independently selected from $R^{Cy}$;

$R^7$ is selected from H, $C_{1-3}$ alkyl, $C(O)C_{1-6}$ alkyl, $C(O)OR^{a1}$, $S(O)_2NR^{c1}R^{d1}$, and phenyl, wherein said phenyl is optionally substituted with halo, CN, $OR^{a1}$, $SR^{a1}$, or $NR^{c1}R^{d1}$;

$R^8$ is selected from a 4-7 membered heterocycloalkyl and a 5-10 membered heteroaryl, which is substituted with W, and is optionally substituted with 1, 2, or 3 substituents independently selected from $R^{Cy}$;

W is selected from $C(O)OR^{a2}$ and a carboxylic acid bioisostere;

$R^{Cy}$ is selected from halo, CN, $NO_2$, $C_{1-6}$ alkyl, $C_{1-6}$ haloalkyl, $C_{2-6}$ alkenyl, $C_{2-6}$ alkynyl, $OR^{a2}$, $C(O)R^{b2}$, $C(O)NR^{c2}R^{d2}$, $NR^{c2}R^{d2}$, $NR^{c2}C(O)R^{b2}$, $NR^{c2}C(O)OR^{a2}$, $NR^{c2}S(O)_2R^{b2}$, $S(O)_2R^{b2}$, and $S(O)_2NR^{c2}R^{d2}$; wherein said $C_{1-6}$ alkyl, $C_{2-6}$ alkenyl, and $C_{2-6}$ alkynyl are each optionally substituted with 1, 2, or 3 substituents independently selected from halo, CN, $NO_2$, $OR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$, $NR^{c2}C(O)OR^{a2}$, $NR^{c2}S(O)_2R^{b2}$, $S(O)_2R^{b2}$, and $S(O)_2NR^{c2}R^{d2}$;

or $R^5$ and $R^8$, together with the atoms to which they are attached, form a 5-10 membered heteroaryl ring or a 4-7 membered heterocycloalkyl ring, each of which is optionally substituted with 1, 2, 3, 4, or 5 substituents independently selected from $R^{Cy1}$;

$R^{Cy1}$ is selected from halo, CN, $NO_2$, $C_{1-6}$ alkyl, $C_{1-6}$ haloalkyl, $C_{2-6}$ alkenyl, $C_{2-6}$ alkynyl, $OR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}C(O)OR^{a3}$, $NR^{c3}S(O)_2R^{b3}$, $S(O)_2R^{b3}$, and $S(O)_2NR^{c3}R^{d3}$; wherein said $C_{1-6}$ alkyl, $C_{2-6}$ alkenyl, and $C_{2-6}$ alkynyl are each optionally substituted with 1, 2, or 3 substituents independently selected from halo, CN, $NO_2$, $OR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}C(O)OR^{a3}$, $NR^{c3}S(O)_2R^{b3}$, $S(O)_2R^{b3}$, and $S(O)_2NR^{c3}R^{d3}$;

or any two $R^{Cy1}$ together with the atoms to which they are attached, form a 5-10 membered heteroaryl ring or a 4-7 membered heterocycloalkyl ring, each of which is optionally substituted with 1, 2, 3, 4, or 5 substituents independently selected from $R^{Cy2}$;

or $R^7$ and $R^{Cy1}$, together with the atoms to which they are attached, form a 5-10 membered heteroaryl ring or a 4-7 membered heterocycloalkyl ring, each of which is optionally substituted with 1, 2, 3, 4, or 5 substituents independently selected from $R^{Cy2}$;

$R^{Cy2}$ is selected from halo, CN, $NO_2$, $C_{1-6}$ alkyl, $C_{1-6}$ haloalkyl, $C_{2-6}$ alkenyl, $C_{2-6}$ alkynyl, $OR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}S(O)_2R^{b4}$, $S(O)_2R^{b4}$, and $S(O)_2NR^{c4}R^{d4}$; wherein said $C_{1-6}$ alkyl, $C_{2-6}$ alkenyl, and $C_{2-6}$ alkynyl are each optionally substituted with 1, 2, or 3 substituents independently selected from halo, CN, $NO_2$, $OR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $R^{c4}C(O)OR^{a4}$, $NR^{c4}S(O)_2R^{b4}$, $S(O)_2R^{b4}$, and $S(O)_2NR^{c4}R^{d4}$;

each $R^{a1}$, $R^{b1}$, 1 $R^{c1}$, $R^{d1}$, $R^{a2}$, $R^{b2}$, $R^{c2}$, $R^{d2}$, $R^{a3}$, $R^{b3}$, $R^{c3}$, $R^{d3}$, $R^{a4}$, $R^{b4}$, $R^{c4}$, and $R^{d4}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$;

or any $R^{c2}$ and $R^{c2}$ together with the N atom to which they are attached form a 4-7 membered heterocycloalkyl, which is optionally substituted with 1, 2, or 3 substituents independently selected from $R^g$;

or any $R^{c3}$ and $R^{d3}$ together with the N atom to which they are attached form a 4-7 membered heterocycloalkyl, which is optionally substituted with 1, 2, or 3 substituents independently selected from $R^g$; and or any $R^{c4}$ and $R^{d4}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments:

$R^1$, $R^2$, $R^3$, $R^4$, $R^5$, and $R^6$ are each independently selected from H, $C_{1-6}$ alkyl, $C_{2-6}$ alkenyl, $C_{2-6}$ alkynyl, $C_{1-4}$ haloalkyl, $Cy^1$, halo, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, 3, 4, or 5 substituents independently selected from $Cy^1$, halo, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2R^{b1}$, $S(O)_2R^{b1}$, and $S(O)_2NR^{c1}R^{d1}$; and $R^7$ is selected from H and $C_{1-3}$ alkyl.

In some embodiments, $X^1$ is N.

In some embodiments, $X^1$ is $CR^1$.

In some embodiments, $R^1$, $R^2$, $R^3$, $R^4$, $R^5$, and $R^6$ are each independently selected from H, $Cy^1$, halo, CN, $OR^{a1}$, $C(O)NR^{c1}R^{d1}$, $C(O)OR^{a1}$, and $S(O)_2NR^{c1}R^{d1}$.

In some embodiments, at least one, at least two, or at least three of $R^1$, $R^2$, $R^3$, $R^4$, $R^5$, and $R^6$ are H. In some embodiments, at least one of $R^1$, $R^2$, $R^3$, $R^4$, $R^5$, and $R^6$ is $Cy^1$. In some embodiments, at least one of $R^1$, $R^2$, $R^3$, $R^4$, $R^5$, and $R^6$ is halo. In some embodiments, at least one of $R^1$, $R^2$, $R^3$, $R^4$, $R^5$, and $R^6$ is CN. In some embodiments, at least one of $R^1$, $R^2$, $R^3$, $R^4$, $R^5$, and $R^6$ is $OR^{a1}$. In some embodiments, at least one of $R^1$, $R^2$, $R^3$, $R^4$, $R^5$, and $R^6$ is $C(O)NR^{c1}R^{d1}$. In some embodiments, at least one of $R^1$, $R^2$, $R^3$, $R^4$, $R^5$, and $R^6$ is $C(O)OR^{a1}$. In some embodiments, at least one of $R^1$, $R^2$, $R^3$, $R^4$, $R^5$, and $R^6$ is $S(O)_2NR^{c1}R^{d1}$.

In some embodiments:

$R^1$, $R^2$, $R^4$, and $R^6$ are each H, and $R^3$ and $R^5$ are each independently selected from $Cy^1$, halo, CN, $OR^{a1}$, $C(O)NR^{c1}R^{d1}$, $C(o)OR^{a1}$, and $S(O)_2NR^{c1}R^{d1}$.

In some embodiments:

$R^1$, $R^4$, and $R^6$ are each H, $R^2$ is selected from H, $Cy^1$, $OR^{a1}$, $C(O)NR^{c1}R^{d1}$, and halo, $R^3$ is selected from $Cy^1$, $OR^{a1}$, $C(O)NR^{c1}R^{d1}$, and halo, and $R^5$ is selected from $Cy^1$, $C(O)OR^{a1}$, $C(O)NR^{c1}R^{d1}$, $S(O)_2NR^{c1}R^{d1}$, and CN.

In some embodiments:

$R^1$, $R^2$, $R^4$, and $R^6$ are each H, $R^3$ is selected from $Cy^1$, $OR^{a1}$, $C(O)NR^{c1}R^{c1}$, and halo, and $R^5$ is selected from $Cy^1$, $C(O)OR^{a1}$, $C(O)NR^{c1}R^{d1}$, $S(O)_2NR^{c1}R^{d1}$, and CN.

In some embodiments, $R^3$ is halo. In some embodiments, $R^3$ is $Cy^1$. In some embodiments, $R^3$ is $OR^{a1}$. In some embodiments, $R^3$ is $C(O)NR^{c1}R^{d1}$. In some embodiments, $R^5$ is $Cy^1$. In some embodiments, $R^5$ is $C(O)OR^{a1}$. In some embodiments, $R^5$ is $C(O)NR^{c1}R^{d1}$. In some embodiments, $R^5$ is $S(O)_2NR^{c1}R^{d1}$. In some embodiments, $R^5$ is CN.

In some embodiments, $R^3$ is $OR^{a1}$ and $R^5$ is $C(O)OR^{a1}$. In some embodiments, $R^3$ is $OR^{a1}$ and $R^5$ is $C(O)NR^{c1}R^{d1}$. In some embodiments, $R^3$ is $C_{1-6}$ haloalkoxy and $R^5$ is $C(O)OR^{a1}$. In some embodiments, $R^3$ is $C_{1-6}$ haloalkoxy and $R^5$ is $C(O)NR^{c1}R^{d1}$.

In some embodiments:

$R^2$ is selected from H and $OR^{a1}$;

$R^3$ is selected from $C_{1-6}$ alkoxy and $C_{1-6}$ haloalkoxy; and $R^5$ is $C(O)OR^{a1}$.

In some embodiments, $Cy^1$ is selected from $C_{6-10}$ aryl and 5-10 membered heteroaryl, each of which is optionally substituted with 1 or 2 substituents independently selected from $R^{Cy}$.

In some embodiments, $Cy^1$ is selected from $C_{6-10}$ aryl, optionally substituted with $R^{Cy}$. In some embodiments, $Cy^1$ is 5-10 membered heteroaryl, optionally substituted with $R^{Cy}$. In some embodiments, $Cy^1$ is selected from indolyl and isoxazolyl, each of which is optionally substituted with $R^{Cy}$.

In some embodiments, $R^{a1}$ is selected from H, $C_{1-6}$ alkyl, $C_{1-4}$ haloalkyl, 5-10 membered heteroaryl, and 4-10 membered heterocycloalkyl.

In some embodiments, $R^{a1}$ is H. In some embodiments, $R^{a1}$ is $C_{1-6}$ alkyl. In some embodiments, $R^{a1}$ is $C_{1-4}$ haloalkyl. In some embodiments, $R^{a1}$ is 5-10 membered heteroaryl (e.g., indolyl, such as indol-5-yl or indol-4-yl). In some embodiments, $R^{a1}$ is 4-10 membered heterocycloalkyl (e.g., piperidinyl).

In some embodiments, $R^{c1}$ and $R^{d1}$ are each independently selected from H and $C_{1-6}$ alkyl. In some embodiments, $R^{c1}$ and $R^{d1}$ are both H. In some embodiments, at least one of $R^{c1}$ and $R^{d1}$ is not H. In some embodiments, $R^{c1}$ is H and $R^{d1}$ is $C_{1-6}$ alkyl. In some embodiments, $R^{c1}$ and $R^{d1}$ are both $C_{1-6}$ alkyl.

In some embodiments, $R^{c1}$ and $R^{d1}$ together with the N atom to which they are attached form a 4-7 membered heterocycloalkyl, which is optionally substituted with $R^g$. In some embodiments, $R^{c1}$ and $R^{d1}$ together with the N atom to which they are attached form piperazinyl or morpholinyl, each of which is optionally substituted with $R^g$.

In some embodiments, $R^7$ is H. In some embodiments, $R^7$ is $C_{1-3}$ alkyl.

In some embodiments, $R^8$ is a 4-7 membered heterocycloalkyl, optionally substituted with $R^{Cy}$. In some embodiments, $R^8$ is a 5-10 membered heteroaryl, optionally substituted with $R^{Cy}$. In some embodiments, $R^8$ is selected from pyridinyl, imidazolyl, thiazolyl, pyrazinyl, pyrimidinyl, oxazolyl, isoxazolyl, isothiazolyl, and pyrazolyl, each of which is optionally substituted with $R^{Cy}$. In some embodiments, $R^8$ is selected from thiophenyl, pyrrolidinyl, and pyrrolyl. In some embodiments, $R^8$ is not thiophenyl, pyrrolidinyl, or pyrrolyl.

In some embodiments:

$R^1$, $R^2$, $R^3$, $R^4$, $R^5$, and $R^6$ are each independently selected from H, $Cy^1$, halo, CN, $OR^{a1}$, $C(O)NR^{c1}R^{d1}$, $C(O)OR^{a1}$, and $S(O)_2NR^{c1}R^{d1}$;

$Cy^1$ is selected from $C_{6-10}$ aryl and 5-10 membered heteroaryl, each of which is optionally substituted with 1 or 2 substituents independently selected from $R^{Cy}$;

$R^{a1}$ is selected from H, $C_{1-6}$ alkyl, $C_{1-4}$ haloalkyl, 5-10 membered heteroaryl, and 4-10 membered heterocycloalkyl;

$R^{c1}$ and $R^{d1}$ are each independently selected from H and $C_{1-6}$ alkyl; or $R^{c1}$ and $R^{d1}$ together with the N atom to which they are attached form a 4-7 membered heterocycloalkyl, which is optionally substituted with $R^g$;

$R^7$ is H; and $R^8$ is a 4-7 membered heterocycloalkyl or 5-10 membered heteroaryl, each of which is optionally substituted with $R^{Cy}$.

In some embodiments:

$R^1$, $R^2$, $R^4$, and $R^6$ are each H;

$R^3$ and $R^5$ are each independently selected from $Cy^1$, halo, CN, $OR^{a1}$, $C(O)NR^{c1}R^{d1}$, $C(O)OR^{a1}$, and $S(O)_2NR^{c1}R^{d1}$;

$Cy^1$ is 5-10 membered heteroaryl, optionally substituted with $R^{Cy}$;

$R^{a1}$ is selected from H, $C_{1-6}$ alkyl, $C_{1-4}$ haloalkyl, 5-10 membered heteroaryl, and 4-10 membered heterocycloalkyl;

$R^{c1}$ and $R^{d1}$ are each independently selected from H and $C_{1-6}$ alkyl; or $R^{c1}$ and $R^{d1}$ together with the N atom to which they are attached form a 4-7 membered heterocycloalkyl, which is optionally substituted with $R^g$;

$R^7$ is H; and $R^8$ is a 5-10 membered heteroaryl, optionally substituted with $R^{Cy}$.

In some embodiments:

$R^1$, $R^2$, $R^4$, and $R^6$ are each H, $R^3$ is $C_{1-6}$ haloalkoxy, $R^5$ is $C(O)OR^{a1}$, $R^{a1}$ is selected from H and $C_{1-6}$ alkyl;

$R^7$ is H; and $R^8$ is selected from pyridinyl, imidazolyl, thiazolyl, pyrazinyl, pyrimidinyl, oxazolyl, isoxazolyl, isothiazolyl, and pyrazolyl, each of which is optionally substituted with $R^{Cy}$.

In some embodiments, the compound of Formula (I) has formula:

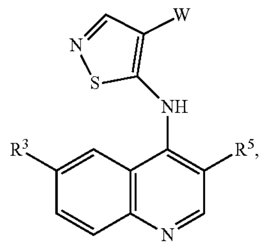

or a pharmaceutically acceptable salt thereof.

In some embodiments, the compound of Formula (I) has formula:

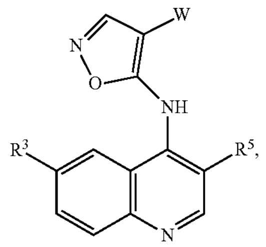

or a pharmaceutically acceptable salt thereof.

In some embodiments, the compound of Formula (I) has formula:

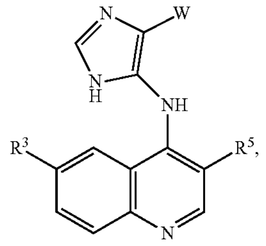

or a pharmaceutically acceptable salt thereof.

In some embodiments, the compound of Formula (I) has formula:

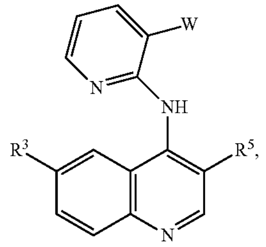

or a pharmaceutically acceptable salt thereof.

In some embodiments, the compound of Formula (I) has formula:

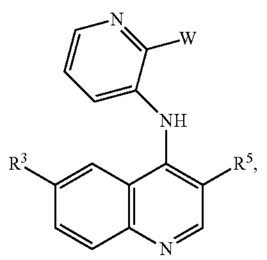

or a pharmaceutically acceptable salt thereof.

In some embodiments, the compound of Formula (I) has formula:

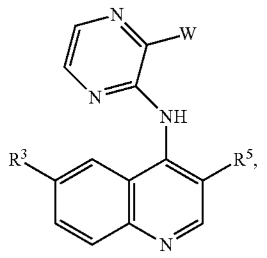

or a pharmaceutically acceptable salt thereof.

In some embodiments, the compound of Formula (I) has formula:

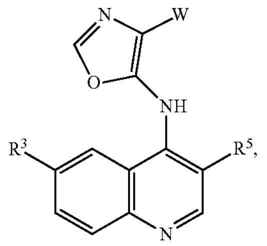

or a pharmaceutically acceptable salt thereof.

In some embodiments, the compound of Formula (I) has formula:

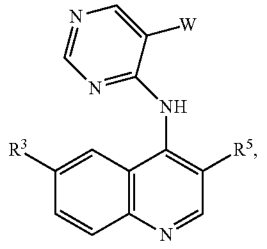

or a pharmaceutically acceptable salt thereof.

In some embodiments, the compound of Formula (I) has formula:

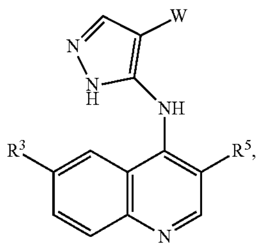

or a pharmaceutically acceptable salt thereof.

In some embodiments, the compound of Formula (I) has formula:

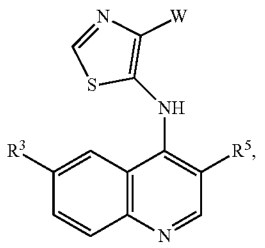

or a pharmaceutically acceptable salt thereof.

In some embodiments:

$R^3$ and $R^5$ are each independently selected from $Cy^1$, halo, CN, $OR^{a1}$, $C(O)NR^{c1}R^{d1}$, $C(O)OR^{a1}$, and $S(O)_2NR^{c1}R^{d1}$;

$Cy^1$ is 5-10 membered heteroaryl, optionally substituted with $R^{Cy}$;

$R^{a1}$ is selected from H, $C_{1-6}$ alkyl, $C_{1-4}$ haloalkyl, 5-10 membered heteroaryl, and 4-10 membered heterocycloalkyl; and $R^{c1}$ and $R^{d1}$ are each independently selected from H and $C_{1-6}$ alkyl; or $R^{c1}$ and $R^{d1}$ together with the N atom to which they are attached form a 4-7 membered heterocycloalkyl, which is optionally substituted with $R^g$.

In some embodiments:

$R^3$ is $C_{1-6}$ haloalkoxy, $R^5$ is $C(O)OR^{a1}$, and $R^{a1}$ is selected from H and $C_{1-6}$ alkyl.

In some embodiments, $R^{Cy}$ is selected from halo, CN, $NO_2$, $C_{1-6}$ alkyl, $C_{1-6}$ haloalkyl, $OR^{a2}$, $C(O)R^{b2}$, $C(O)NR^{c2}R^{d2}$, $C(O)OR^{a2}$, wherein said $C_{1-6}$ alkyl is optionally substituted with 1, 2, or 3 substituents independently selected from halo, CN, $NO_2$, $OR^{a2}$, $C(O)R^{b2}$, $C(O)NR^{c2}R^{d2}$, $C(O)OR^{a2}$, and $NR^{c2}R^{d2}$.

In some embodiments, $R^{Cy}$ i selected from halo, CN, $NO_2$, $C_{1-6}$ alkyl, $C_{1-6}$ haloalkyl, $C_{1-6}$ alkoxy, and $C_{1-6}$ haloalkoxy.

In some embodiments, $R^{a2}$ is selected from H, $C_{1-6}$ alkyl, and $C_{1-4}$ haloalkyl.

In some embodiments, W is $C(O)OR^{a2}$.

In some embodiments, W is C(O)OH.

In some embodiments, W is $C(O)OR^{a2}$, and $R^{a2}$ is $C_{1-6}$ alkyl.

In some embodiments, W is a carboxylic acid bioisostere.

In some embodiments, the carboxylic acid bioisostere is selected from a moiety of any one of the following formulae:

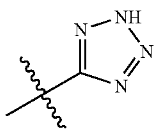
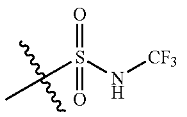
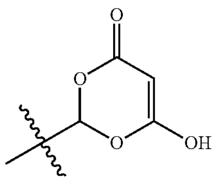
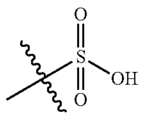
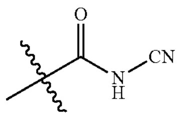
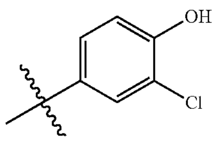
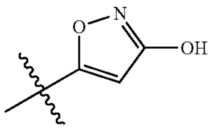
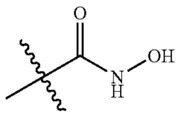
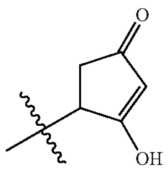

In some embodiments, the carboxylic acid bioisostere is selected from $C(O)NHC_{6-10}$aryl, $NHC(O)C_{1-3}$ hydroxyalkyl, $CH_2CN$, $CH_2C_{6-10}$aryl, $C(O)CH_2CN$, $NHS(O)_2C_{6-10}$aryl, $S(O)_2C_{1-6}$ alkyl, $C(O)C_{1-3}$ alkyl, $CH_2C(O)NH_2$, $OCH_2C_{6-10}$aryl, $NHC(O)C_{6-10}$aryl, and $NHC(O)OC_{1-6}$ alkyl. In some embodiments, the carboxylic acid bioisostere is not any one of the following groups: $C(O)NHC_{6-10}$aryl, $NHC(O)C_{1-3}$ hydroxyalkyl, $CH_2CN$, $CH_2C_{6-10}$aryl, $C(O)CH_2CN$, $NHS(O)_2C_{6-10}$aryl, $S(O)_2C_{1-6}$ alkyl, $C(O)C_{1-3}$ alkyl, $CH_2C(O)NH_2$, $OCH_2C_{6-10}$aryl, $NHC(O)C_{6-10}$aryl, and $NHC(O)OC_{1-6}$ alkyl.

In some embodiments, the compound of Formula (I) is selected from any one of the following compounds:

1A

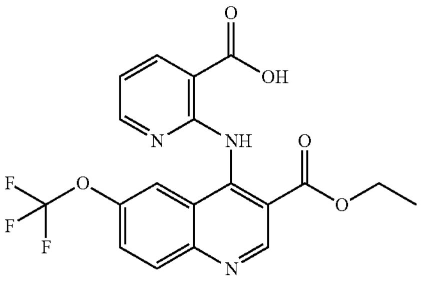

9

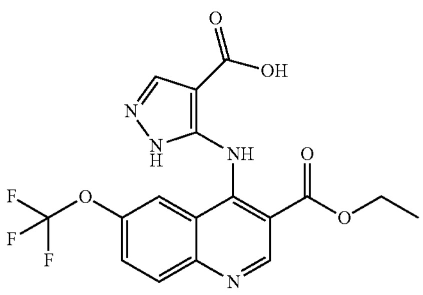

-continued

3

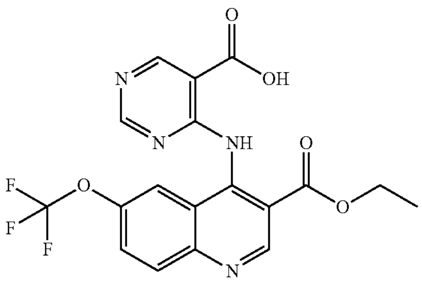

8

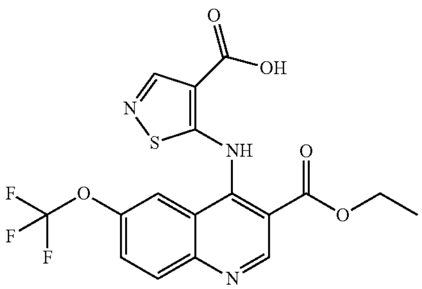

28A

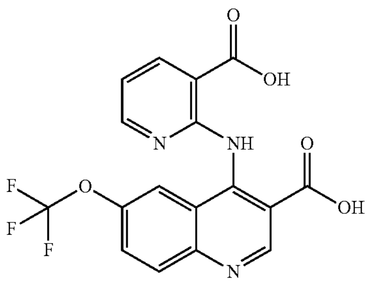

7

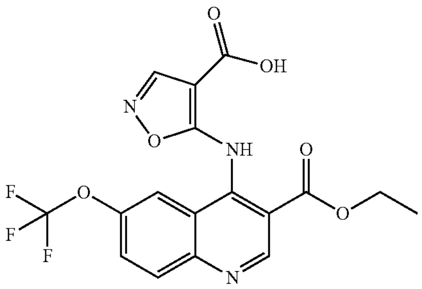

2

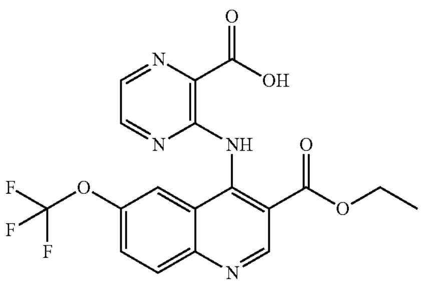

-continued
6
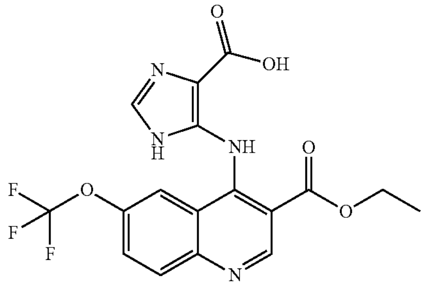
5A
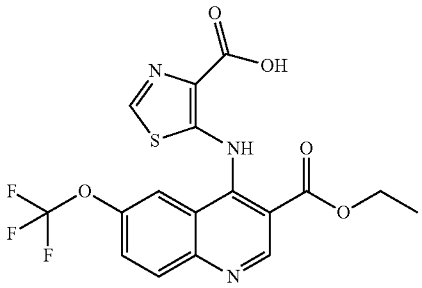
4
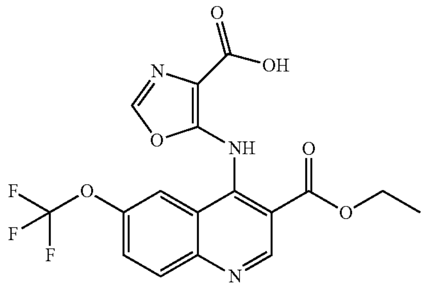
33A
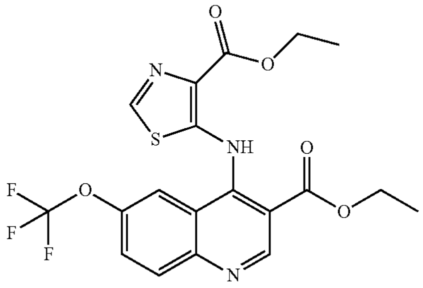
83A-INT
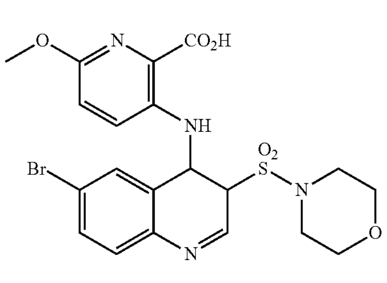
or a pharmaceutically acceptable salt thereof.
In some embodiments, the compound of Formula (I) is selected from any one of the following compounds:
1A
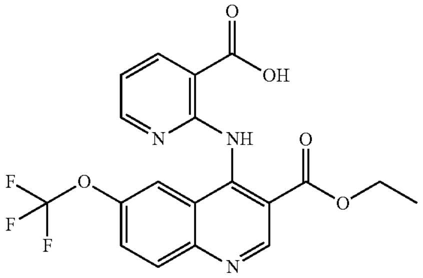
9
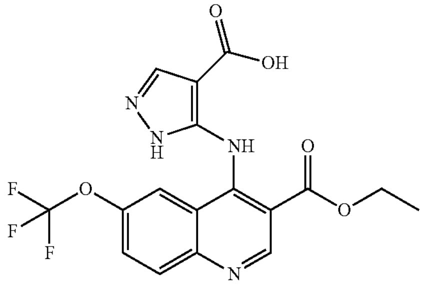
3
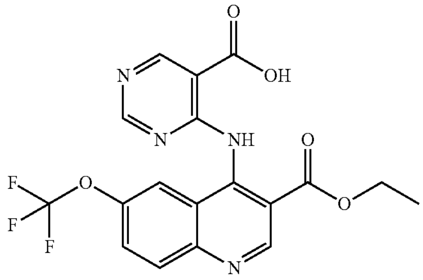
8
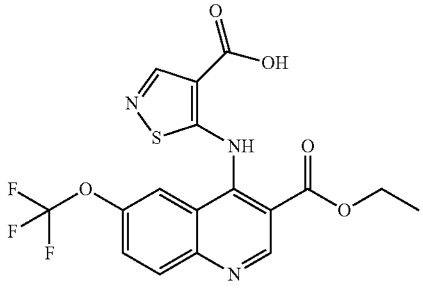
28A
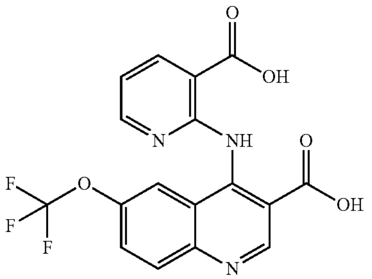

-continued
7
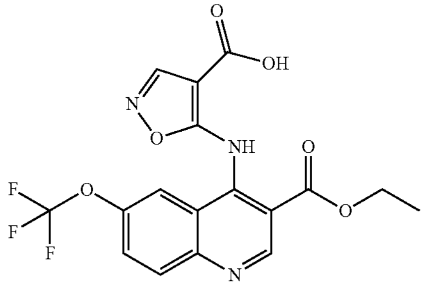
2
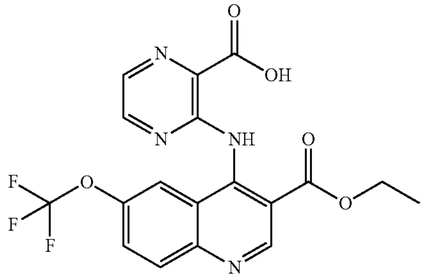
6
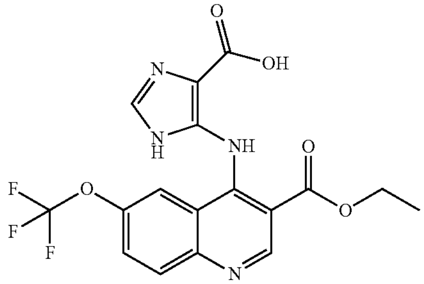
5A
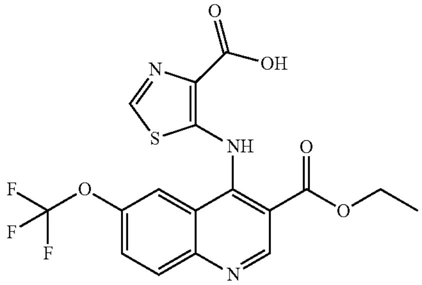
4
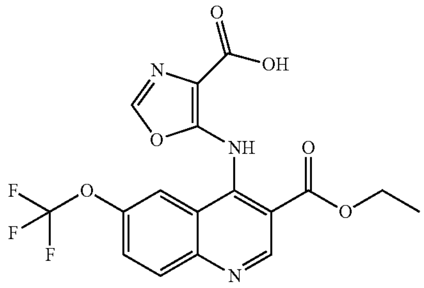
-continued
33A
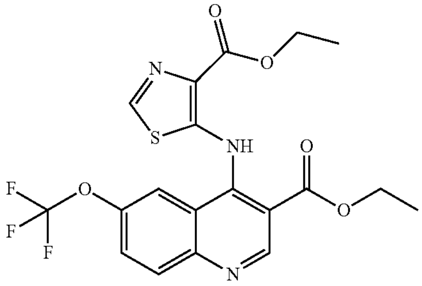
or a pharmaceutically acceptable salt thereof.
In some embodiments, the compound of Formula (I) is selected from any one of the following compounds:
106A
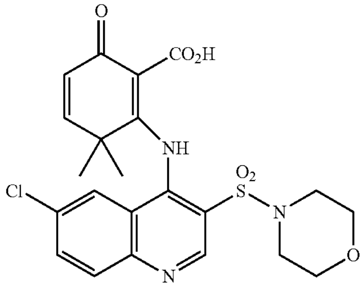
105A
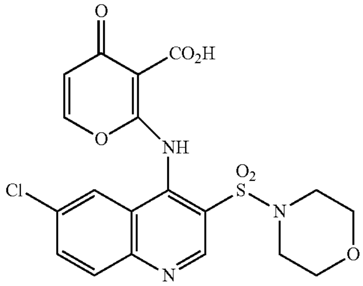
104A
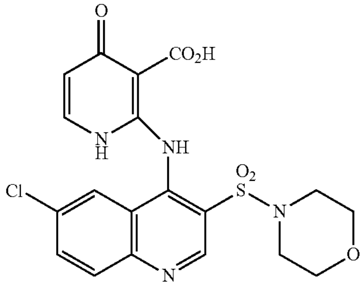
83A
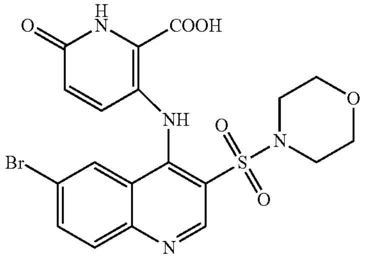

-continued

84A

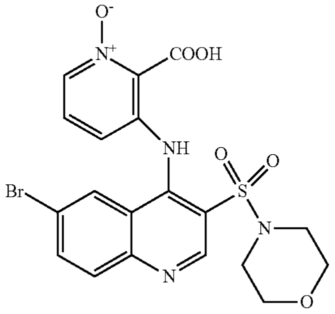

or a pharmaceutically acceptable salt thereof.

In some embodiments, $R^5$ and $R^8$, together with the atoms to which they are attached, form a 5-10 membered heteroaryl ring, which is substituted with 1, 2, or 3 substituents independently selected from $R^{Cy1}$.

In some embodiments, $R^5$ and $R^8$, together with the atoms to which they are attached, form a 4-7 membered heterocycloalkyl ring, which is substituted with 1, 2, or 3 substituents independently selected from $R^{Cy1}$.

In some embodiments, $R^{Cy1}$ is selected from halo, CN, $NO_2$, $C_{1-6}$ alkyl, $C_{1-6}$ haloalkyl, $OR^{a3}$, $C(O)R^{b3}$, $C(O)NR^{c3}R^{d3}$, $C(O)OR^{a3}$, and $NR^{c3}R^{d3}$; wherein said $C_{1-6}$ alkyl is optionally substituted with 1, 2, or 3 substituents independently selected from halo, CN, $NO_2$, $OR^{a3}$, $C(O)R^{b3}$, $C(O)NR^{c3}R^{d3}$, $C(O)OR^{a3}$, and $NR^{c3}R^{d3}$.

In some embodiments, $R^{Cy1}$ is selected from halo, CN, $NO_2$, $C_{1-6}$ alkyl, $C_{1-6}$ haloalkyl, $C_{1-6}$ alkoxy, $C_{1-6}$ haloalkoxy, and C(O)OH.

In some embodiments, any two $R^{Cy1}$ together with the atoms to which they are attached, form a 5-10 membered heteroaryl ring, which is substituted with 1, 2, or 3 substituents independently selected from $R^{Cy2}$.

In some embodiments, any two $R^{Cy1}$ together with the atoms to which they are attached, form a 4-7 membered heterocycloalkyl ring, which is optionally substituted with 1, 2, or 3 substituents independently selected from $R^{Cy2}$.

In some embodiments, $R^7$ and $R^{Cy1}$, together with the atoms to which they are attached, form a 5-10 membered heteroaryl ring, which is optionally substituted with 1, 2, or 3 substituents independently selected from $R^{Cy2}$.

In some embodiments, $R^7$ and $R^{Cy1}$, together with the atoms to which they are attached, form a 4-7 membered heterocycloalkyl ring, which is optionally substituted with 1, 2, or 3 substituents independently selected from $R^{Cy2}$.

In some embodiments, $R^{Cy2}$ is selected from halo, CN, $NO_2$, $C_{1-6}$ alkyl, $C_{1-6}$ haloalkyl, $OR^{a4}$, $C(O)NR^{c4}R^{d4}$, $C(O)OR^{a4}$, and $NR^{c4}R^{d4}$, wherein said $C_{1-6}$ alkyl is optionally substituted with 1, 2, or 3 substituents independently selected from halo, CN, $NO_2$, $OR^{a4}$, $C(O)NR^{c4}R^{d4}$, $C(O)OR^{a4}$, and $NR^{c4}R^{d4}$.

In some embodiments, $R^{Cy2}$ is $C(O)OR^{a4}$. In some embodiments, $R^{a4}$ is selected from H, $C_{1-6}$ alkyl, and $C_{1-4}$ haloalkyl. In some embodiments, $R^{a4}$ is selected from H and $C_{1-6}$ alkyl. In some embodiments, $R^{Cy2}$ is C(O)OH.

In some embodiments, $R^1$, $R^2$, $R^3$, $R^4$, and $R^6$ are each independently selected from H, $Cy^1$, halo, CN, $OR^{a1}$, $C(O)NR^{c1}R^{d1}$, $C(O)OR^{a1}$, and $S(O)_2NR^{c1}R^{d1}$.

In some embodiments:

$R^1$, $R^2$, $R^4$, and $R^6$ are each H; and $R^3$ is selected from $Cy^1$, halo, CN, $OR^{a1}$, $C(O)NR^{c1}R^{d1}$, $C(O)OR^{a1}$, and $S(O)_2NR^{c1}R^{d1}$. In some embodiments, $R^3$ is selected from $Cy^1$, $OR^{a1}$, $C(O)NR^{c1}R^{d1}$, and halo. In some embodiments, $R^3$ is $C_{1-6}$ haloalkoxy.

In some embodiments, the compound of Formula (I) has formula:

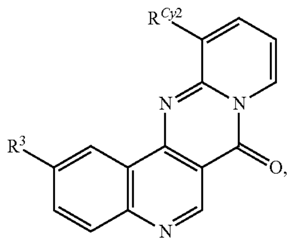

or a pharmaceutically acceptable salt thereof.

In some embodiments, the compound of Formula (I) has formula:

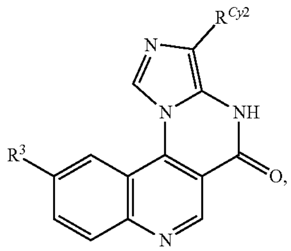

or a pharmaceutically acceptable salt thereof.

In some embodiments, the compound of Formula (I) has formula:

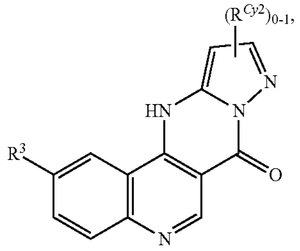

or a pharmaceutically acceptable salt thereof.

In some embodiments, the compound of Formula (I) has formula:

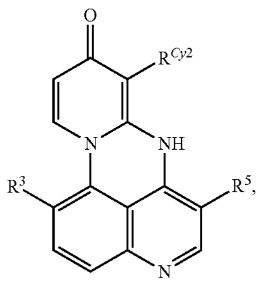

or a pharmaceutically acceptable salt thereof.

In some embodiments:

$R^3$ is selected from $Cy^1$, halo, CN, $OR^{a1}$, $C(O)NR^{c1}R^{d1}$, $C(O)OR^{a1}$, and $S(O)_2NR^{c1}R^{d1}$;

$R^{Cy2}$ is selected from halo, CN, $NO_2$, $C_{1-6}$ alkyl, $C_{1-6}$ haloalkyl, $OR^{a4}$, $C(O)NR^{c4}R^{d4}$, $C(O)OR^{a4}$, and $NR^{c4}R^{d4}$, wherein said $C_{1-6}$ alkyl is optionally substituted with 1, 2, or 3 substituents independently selected from halo, CN, $NO_2$, $OR^{a4}$, $C(O)NR^{c4}R^{d4}$, $C(O)OR^{a4}$, and $NR^{c4}R^{d4}$; and $R^{a4}$ is selected from H and $C_{1-6}$ alkyl.

In some embodiments:

$R^3$ is selected from $Cy^1$, $OR^{a1}$, $C(O)NR^{c1}R^{d1}$, and halo;

$R^{Cy2}$ is $C(O)OR^{a4}$; and $R^{a4}$ is selected from H and $C_{1-6}$ alkyl.

In some embodiments:

$R^3$ is $C_{1-6}$ haloalkoxy;

$R^{Cy2}$ is $C(O)OR^{a4}$; and $R^{a4}$ is selected from H and $C_{1-6}$ alkyl.

In some embodiments, the compound of Formula (I) is selected from any one of the following compounds:

31A

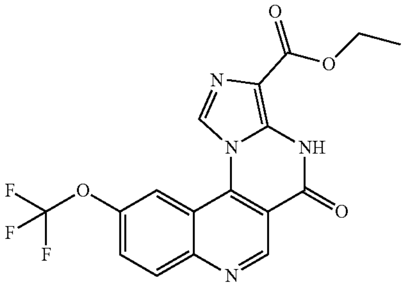

30A

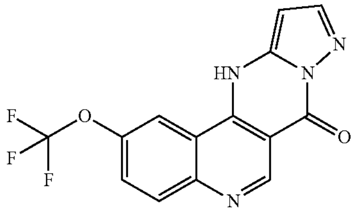

27A

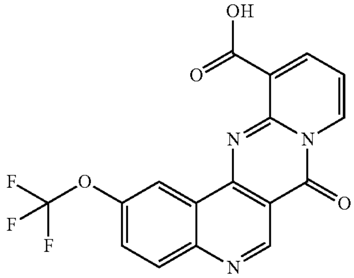

113A

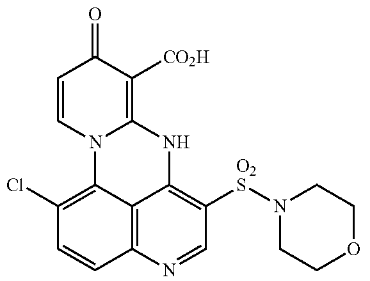

or a pharmaceutically acceptable salt thereof.

In some embodiments, the compound of Formula (I) is selected from any one of the following compounds:

31A

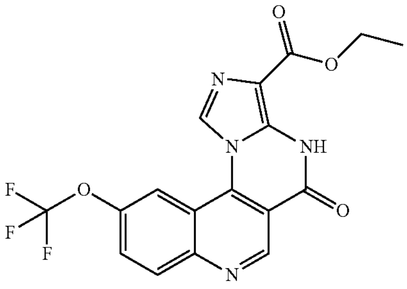

30A

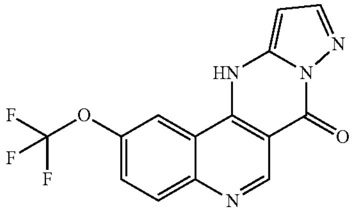

27A

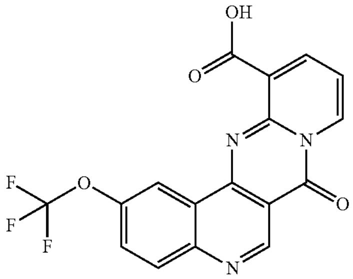

or a pharmaceutically acceptable salt thereof.

In some embodiments, the present disclosure provides a compound of Formula (II)

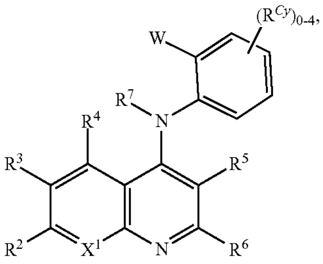

or a pharmaceutically acceptable salt thereof, wherein:

$X^1$ is selected from N and $CR^1$;

$R^1$, $R^2$, $R^3$, $R^4$, $R^5$, and $R^6$ are each independently selected from H, $C_{1-6}$ alkyl, $C_{2-6}$ alkenyl, $C_{2-6}$ alkynyl, $C_{1-4}$ haloalkyl, $Cy^1$, halo, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2R^{b1}$, $S(O)R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, 3, 4, or 5 substituents independently selected from $Cy^1$, halo, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2R^{b1}$, $S(O)_2R^{b1}$, and $S(O)_2NR^{c1}R^{d1}$;

each $Cy^1$ is independently selected from $C_{6-10}$ aryl, 5-10 membered heteroaryl, and 4-7 membered heterocycloalkyl, each of which is optionally substituted with 1, 2, or 3 substituents independently selected from $R^{Cy}$;

$R^7$ is selected from H, $C_{1-3}$ alkyl, $C(O)C_{1-6}$ alkyl, $C(O)OR^{a1}$, $S(O)_2NR^{c1}R^{d1}$ and phenyl, wherein said phenyl is optionally substituted with halo, CN, $OR^{a1}$, $SR^{a1}$, or $NR^{c1}R^{d1}$;

W is a carboxylic acid bioisostere;

$R^{Cy}$ is selected from halo, CN, $NO_2$, $C_{1-6}$ alkyl, $C_{1-6}$ haloalkyl, $C_{2-6}$ alkenyl, $C_{2-6}$ alkynyl, $OR^{a2}$, $C(O)R^{b2}$, $C(O)NR^{c2}R^{d2}$, $NR^{c2}R^{d2}$, $NR^{c2}C(O)R^{b2}$, $NR^{c2}C(O)OR^{a2}$, $NR^{c2}S(O)_2R^{b2}$, $S(O)_2R^{b2}$, and $S(O)_2NR^{c2}R^{d2}$; wherein said $C_{1-6}$ alkyl, $C_{2-6}$ alkenyl, and $C_{2-6}$ alkynyl are each optionally substituted with 1, 2, or 3 substituents independently selected from halo, CN, $NO_2$, $OR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$, $NR^{c2}C(O)OR^{a2}$, $NR^{c2}S(O)_2R^{b2}$, $S(O)_2R^{b2}$, and $S(O)_2NR^{c2}R^{d2}$;

each $R^{a1}$, $R^{b1}$, $R^{c1}$, $R^{d1}$, $R^{a2}$, $R^{b2}$, $R^{c2}$, and $R^{d2}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$;

or any $R^{c2}$ and $R^{d2}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments:

$R^1$, $R^2$, $R^3$, $R^4$, $R^5$, and $R^6$ are each independently selected from H, $C_{1-6}$ alkyl, $C_{2-6}$ alkenyl, $C_{2-6}$ alkynyl, $C_{1-4}$ haloalkyl, $Cy^1$, halo, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, 3, 4, or 5 substituents independently selected from $Cy^1$, halo, CN, $NO_2$, $OR^{a1}$, $SR^{a1}$, $C(O)R^{b1}$, $C(O)NR^{c1}R^{c1}$, $C(O)OR^{a1}$, $NR^{c1}R^{d1}$, $NR^{c1}C(O)R^{b1}$, $NR^{c1}S(O)_2R^{b1}$, and $S(O)_2NR^{c1}R^{d1}$; and $R^7$ is selected from H and $C_{1-3}$ alkyl.

In some embodiments, $X^1$ is N.

In some embodiments, $X^1$ is $CR^1$.

In some embodiments, $R^1$, $R^2$, $R^3$, $R^4$, $R^5$, and $R^6$ are each independently selected from H, $Cy^1$, halo, CN, $OR^{a1}$, $C(O)NR^{c1}R^{d1}$, $C(O)OR^{a1}$, and $S(O)_2NR^{c1}R^{d1}$.

In some embodiments, at least one, at least two, or at least three of $R^1$, $R^2$, $R^3$, $R^4$, $R^5$, and $R^6$ are H. In some embodiments, at least one of $R^1$, $R^2$, $R^3$, $R^4$, $R^5$, and $R^6$ is $Cy^1$. In some embodiments, at least one of $R^1$, $R^2$, $R^3$, $R^4$, $R^5$, and $R^6$ is halo. In some embodiments, at least one of $R^1$, $R^2$, $R^3$, $R^4$, $R^5$, and $R^6$ is CN. In some embodiments, at least one of $R^1$, $R^2$, $R^3$, $R^4$, $R^5$, and $R^6$ is $OR^{a1}$. In some embodiments, at least one of $R^1$, $R^2$, $R^3$, $R^4$, $R^5$, and $R^6$ is $C(O)NR^{c1}R^{d1}$. In some embodiments, at least one of $R^1$, $R^2$, $R^3$, $R^4$, $R^5$, and $R^6$ is $C(O)OR^{a1}$. In some embodiments, at least one of $R^1$, $R^2$, $R^3$, $R^4$, $R^5$, and $R^6$ is $S(O)_2NR^{c1}R^{d1}$.

In some embodiments:

$R^1$, $R^2$, $R^4$, and $R^6$ are each H, and $R^3$ and $R^5$ are each independently selected from $Cy^1$, halo, CN, $OR^{a1}$, $C(O)NR^{c1}R^{d1}$, $C(O)OR^{a1}$, and $S(O)_2NR^{c1}R^{d1}$.

In some embodiments:

$R^1$, $R^4$, and $R^6$ are each H, $R^2$ is selected from H, $Cy^1$, $OR^{a1}$, $C(O)NR^{c1}R^{d1}$, and halo, $R^3$ is selected from $Cy^1$, $OR^{a1}$, $C(O)NR^{c1}R^{d1}$, and halo, and $R^5$ is selected from $Cy^1$, $C(O)OR^{a1}$, $C(O)NR^{c1}R^{d1}$, $S(O)_2NR^{c1}R^{d1}$, and CN.

In some embodiments:

$R^1$, $R^2$, $R^4$, and $R^6$ are each H, $R^3$ is selected from $Cy^1$, $OR^{a1}$, $C(O)NR^{c1}R^{d1}$, and halo, and $R^5$ is selected from $Cy^1$, $C(O)OR^{a1}$, $C(O)NR^{c1}R^{d1}$, $S(O)_2NR^{c1}R^{d1}$, and CN.

In some embodiments, $R^3$ is halo. In some embodiments, $R^3$ is $Cy^1$. In some embodiments, $R^3$ is $OR^{a1}$. In some embodiments, $R^3$ is $C(O)NR^{c1}R^{d1}$. In some embodiments, $R^5$ is $Cy^1$. In some embodiments, $R^5$ is $C(O)OR^{a1}$. In some embodiments, $R^5$ is $C(O)NR^{c1}R^{d1}$. In some embodiments, $R^5$ is $S(O)_2NR^{c1}R^{d1}$. In some embodiments, $R^5$ is CN.

In some embodiments, $R^3$ is $OR^{a1}$ and $R^5$ is $C(O)OR^{a1}$. In some embodiments, $R^3$ is $OR^{a1}$ and $R^5$ is $C(O)NR^{c1}R^{d1}$. In some embodiments, $R^3$ is $C_{1-6}$ haloalkoxy and $R^5$ is $C(O)OR^{a1}$. In some embodiments, $R^3$ is $C_{1-6}$ haloalkoxy and $R^5$ is $C(O)NR^{c1}R^{d1}$.

In some embodiments:

$R^2$ is selected from H and $OR^{a1}$;

$R^3$ is selected from $C_{1-6}$ alkoxy and $C_{1-6}$ haloalkoxy; and $R^5$ is $C(O)OR^{a1}$.

In some embodiments, $Cy^1$ is selected from $C_{6-10}$ aryl and 5-10 membered heteroaryl, each of which is optionally substituted with 1 or 2 substituents independently selected from $R^{Cy}$.

In some embodiments, $Cy^1$ is $C_{6-10}$ aryl, optionally substituted with $R^{Cy}$. In some embodiments, $Cy^1$ is 5-10 membered heteroaryl, optionally substituted with $R^{Cy}$. In some embodiments, $Cy^1$ is selected from indolyl and isoxazolyl, each of which is optionally substituted with $R^{Cy}$.

In some embodiments, $R^{a1}$ is selected from H, $C_{1-6}$ alkyl, $C_{1-4}$ haloalkyl, 5-10 membered heteroaryl, and 4-10 membered heterocycloalkyl.

In some embodiments, $R^{a1}$ is H. In some embodiments, $R^{a1}$ is $C_{1-6}$ alkyl. In some embodiments, $R^{a1}$ is $C_{1-4}$ haloalkyl. In some embodiments, $R^{a1}$ is 5-10 membered heteroaryl (e.g., indolyl, such as indol-5-yl or indol-4-yl). In some embodiments, $R^{a1}$ is 4-10 membered heterocycloalkyl (e.g., piperidinyl).

In some embodiments, $R^{c1}$ and $R^{d1}$ are each independently selected from H and $C_{1-6}$ alkyl. In some embodiments, $R^{c1}$ and $R^{d1}$ are both H. In some embodiments, at least one of $R^{c1}$ and $R^{d1}$ is not H. In some embodiments, $R^{c1}$ is H and $R^{d1}$ is $C_{1-6}$ alkyl. In some embodiments, $R^{c1}$ and $R^{d1}$ are both $C_{1-6}$ alkyl.

In some embodiments, $R^{c1}$ and $R^{d1}$ together with the N atom to which they are attached form a 4-7 membered heterocycloalkyl, which is optionally substituted with $R^g$. In some embodiments, $R^{c1}$ and $R^{d1}$ together with the N atom to which they are attached form piperazinyl or morpholinyl, each of which is optionally substituted with $R^g$.

In some embodiments, $R^7$ is H. In some embodiments, $R^7$ is $C_{1-3}$ alkyl.

In some embodiments, $R^{Cy}$ is selected from halo, CN, $NO_2$, $C_{1-6}$ alkyl, $C_{1-6}$ haloalkyl, $OR^{a2}$, $C(O)R^{b2}$, $C(O)NR^{c2}R^{d2}$, $C(O)OR^{a2}$, and $NR^{c2}R^{d2}$, wherein said $C_{1-6}$ alkyl is optionally substituted with 1, 2, or 3 substituents independently selected from halo, CN, $NO_2$, $OR^{a2}$, $C(O)R^{b2}$, $C(O)NR^{c2}R^{d2}$, $C(O)OR^{a2}$, and $NR^{c2}R^{d2}$.

In some embodiments, $R^{Cy}$ is selected from halo, CN, $NO_2$, $C_{1-6}$ alkyl, $C_{1-6}$ haloalkyl, $C_{1-6}$ alkoxy, and $C_{1-6}$ haloalkoxy.

In some embodiments, $R^{a2}$ is selected from H, $C_{1-6}$ alkyl, and $C_{1-4}$ haloalkyl.

In some embodiments:

$R^1$, $R^2$, $R^3$, $R^4$, $R^5$, and $R^6$ are each independently selected from H, $Cy^1$, halo, CN, $OR^{a1}$, $C(O)NR^{c1}R^{d1}$, $C(O)OR^{a1}$, and $S(O)_2NR^{c1}R^{d1}$;

$Cy^1$ is selected from $C_{6-10}$ aryl and 5-10 membered heteroaryl, each of which is optionally substituted with 1 or 2 substituents independently selected from $R^{Cy}$;

$R^{a1}$ is selected from H, $C_{1-6}$ alkyl, $C_{1-4}$ haloalkyl, 5-10 membered heteroaryl, and 4-10 membered heterocycloalkyl;

$R^{c1}$ and $R^{d1}$ are each independently selected from H and $C_{1-6}$ alkyl; or $R^{c1}$ and $R^{d1}$ together with the N atom to which they are attached form a 4-7 membered heterocycloalkyl, which is optionally substituted with $R^8$; and $R^7$ is H.

In some embodiments:

$R^1$, $R^2$, $R^4$, and $R^6$ are each H;

$R^3$ and $R^5$ are each independently selected from $Cy^1$, halo, CN, $OR^{a1}$, $C(O)NR^{c1}R^{d1}$, $C(O)OR^{a1}$, and $S(O)_2NR^{c1}R^{d1}$;

$Cy^1$ is 5-10 membered heteroaryl, optionally substituted with $R^{Cy}$ $R^{a1}$ is selected from H, $C_{1-6}$ alkyl, $C_{1-4}$ haloalkyl, 5-10 membered heteroaryl, and 4-10 membered heterocycloalkyl;

$R^{c1}$ and $R^{d2}$ are each independently selected from H and $C_{1-6}$ alkyl; or $R^{c1}$ and $R^{d1}$ together with the N atom to which they are attached form a 4-7 membered heterocycloalkyl, which is optionally substituted with $R^g$; and $R^7$ is H.

In some embodiments:

$R^1$, $R^2$, $R^4$, and $R^6$ are each H, $R^3$ is $C_{1-6}$ haloalkoxy, $R^5$ is $C(O)OR^{a1}$, $R^{a1}$ is selected from H and $C_{1-6}$ alkyl; and $R^7$ is H.

In some embodiments, W is selected from any one of the following moieties:

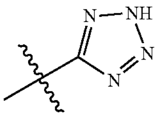
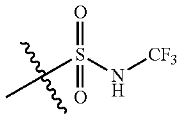
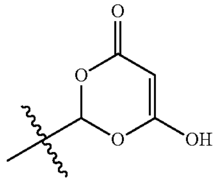
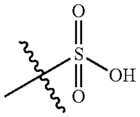
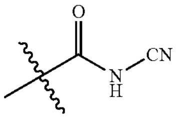
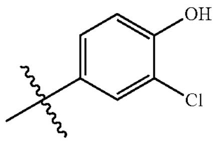
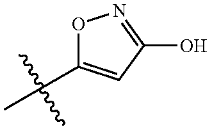
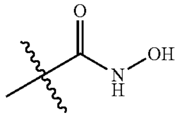
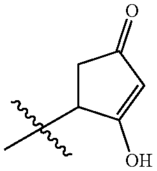

In some embodiments, the compound of Formula (II) is selected from any one of the following compounds:

10A

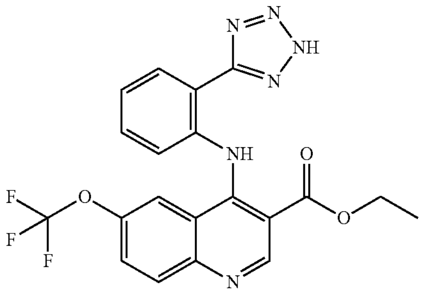

11

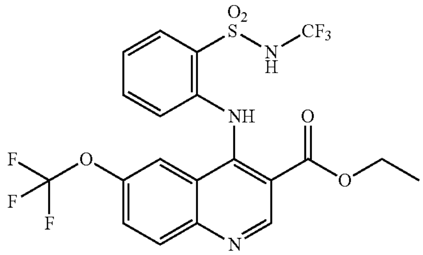

-continued

34A

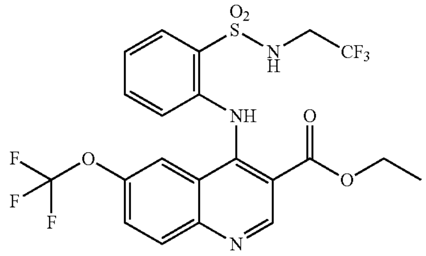

or a pharmaceutically acceptable salt thereof.

In some embodiments, the compound of Formula (II) is selected from any one of the following compounds:

10A

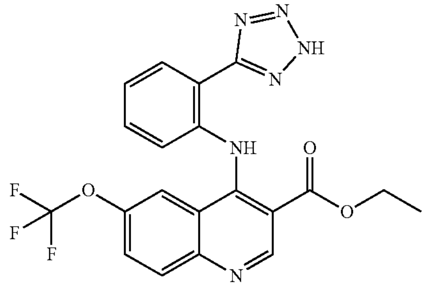

11

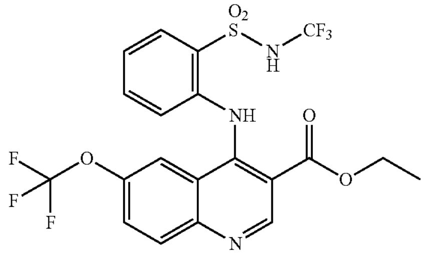

or a pharmaceutically acceptable salt thereof.

In some embodiments, the present disclosure provides a compound of Formula (III):

(III)

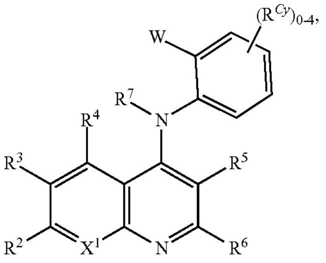

or a pharmaceutically acceptable salt thereof, wherein:

$X^1$ is selected from N and $CR^1$;

$R^1$, $R^2$, $R^3$, $R^4$, and $R^6$ are each independently selected from H, $C_{1-6}$ alkyl, $C_{2-6}$ alkenyl, $C_{2-6}$ alkynyl, $C_{1-4}$ haloalkyl, $Cy^1$, halo, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2R^{b1}$, $S(O)R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, 3, 4, or 5 substituents independently selected from $Cy^1$, halo, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2R^{b1}$, $S(O)_2R^{b1}$, and $S(O)_2NR^{c1}R^{d1}$;

$R^5$ is selected from $C(O)NR^{c1}R^{d1}$, $S(O)_2NR^{c1}R^{d1}$, and $Cy^1$;

each $Cy^1$ is independently selected from $C_{6-10}$ aryl, $C_{3-10}$ cycloalkyl, 5-10 membered heteroaryl, and 4-7 membered heterocycloalkyl, each of which is optionally substituted with 1, 2, or 3 substituents independently selected from $R^{Cy}$;

$R^7$ is selected from H, $C_{1-3}$ alkyl, $C(O)C_{1-6}$ alkyl, $C(O)OR^{a1}$, $S(O)_2NR^{c1}R^{d1}$, and phenyl, wherein said phenyl is optionally substituted with halo, CN, $OR^{a1}$, $SR^{a1}$, or $NR^{c1}R^{d1}$;

W is selected from $C(O)OR^{a2}$ and a carboxylic acid bioisostere;

$R^{Cy}$ is selected from halo, CN, $NO_2$, $C_{1-6}$ alkyl, $C_{1-6}$ haloalkyl, $C_{2-6}$ alkenyl, $C_{2-6}$ alkynyl, $C_{3-10}$ cycloalkyl, 5-10 membered heteroaryl, 4-6 membered heterocycloalkyl, $OR^{a2}$, $C(O)R^{b2}$, $C(O)OR^{a2}$, $C(O)NR^{c2}R^{d2}$, $C(O)NR^{c1}S(O)_2R^{b2}$, $NR^{c2}R^{d2}$, $NR^{c2}C(O)R^{b2}$, $NR^{c2}C(O)OR^{a2}$, $NR^{c2}S(O)_2R^{b2}$, $OC(O)R^{b1}$, $S(O)_2R^{b2}$, and $S(O)_2NR^{c2}R^{d2}$; wherein said $C_{1-6}$ alkyl, $C_{2-6}$ alkenyl, $C_{2-6}$ alkynyl, $C_{3-10}$ cycloalkyl, and 4-6 membered heterocycloalkyl are each optionally substituted with 1, 2, or 3 substituents independently selected from halo, CN, $NO_2$, $OR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$, $NR^{c2}C(O)OR^{a2}$, $NR^{c2}S(O)_2R^{b2}$, $S(O)_2R^{b2}$, and $S(O)_2NR^{c2}R^{d2}$;

each $R^{a1}$, $R^{b1}$, $R^{c1}$, $R^{d1}$, $R^{a2}$, $R^{b2}$, $R^{c2}$, and $R^{d2}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-10 membered heterocycloalkyl or 5-10 membered heteroaryl, each of which is optionally substituted with 1, 2, or 3 substituents independently selected from W;

or any $R^{c2}$ and $R^{d2}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{6-10}$ aryl-$C_{1-6}$ alkoxycarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments:

each $Cy^1$ is independently selected from $C_{6-10}$ aryl, 5-10 membered heteroaryl, and 4-7 membered heterocycloalkyl, each of which is optionally substituted with 1, 2, or 3 substituents independently selected from $R^{Cy}$;

$R^{Cy}$ is selected from halo, CN, $NO_2$, $C_{1-6}$ alkyl, $C_{1-6}$ haloalkyl, $C_{2-6}$ alkenyl, $C_{2-6}$ alkynyl, $OR^{a2}$, $C(O)R^{b2}$, $C(O)OR^{a2}$, $C(O)NR^{c2}R^{d2}$, $NR^{c2}R^{d2}$, $NR^{c2}C(O)R^{b2}$, $NR^{c2}C(O)OR^{a2}$, $NR^{c2}S(O)_2R^{b2}$, $S(O)_2R^{b2}$, and $S(O)_2NR^{c2}R^{d2}$; wherein said $C_{1-6}$ alkyl, $C_{2-6}$ alkenyl, $C_{2-6}$ alkynyl, are each optionally substituted with 1, 2, or 3 substituents independently selected from halo, CN, $NO_2$, $OR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$, $NR^{c2}C(O)OR^{a2}$, $NR^{v}$ $S(O)_2R^{b2}$, $S(O)_2R^{b2}$, and $S(O)_2NR^{c2}R^{d2}$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl) aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments:

$R^1$, $R^2$, $R^3$, $R^4$, and $R^6$ are each independently selected from H, $C_{1-6}$ alkyl, $C_{2-6}$ alkenyl, $C_{2-6}$ alkynyl, $C_{1-4}$ haloalkyl, $Cy^1$, halo, CN, $NO_2$, $OR^{a1}$ $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, 3, 4, or 5 substituents independently selected from $Cy^1$, halo, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2R^{b1}$, $S(O)_2R^{b1}$, and $S(O)_2NR^{c1}R^{d1}$; and $R^7$ is selected from H and $C_{1-3}$ alkyl.

In some embodiments, $X^1$ is N.

In some embodiments, $X^1$ is $CR^1$.

In some embodiments, $R^1$, $R^2$, $R^3$, $R^4$, and $R^6$ are each independently selected from H, $Cy^1$, halo, CN, $OR^{a1}$, C(O) $NR^{c1}R^{d1}$, $C(O)OR^{a1}$, and $S(O)_2NR^{c1}R^{d1}$.

In some embodiments:

$R^1$, $R^4$, and $R^6$ are each H, $R^2$ is selected from H, $Cy^1$, halo, CN, $OR^{a1}$, C(O) $NR^{c1}R^{d1}$, $C(O)OR^{a1}$, and $S(O)_2NR^{c1}R^{d1}$, and $R^3$ is selected from $Cy^1$, halo, CN, $OR^{a1}$, $C(O)NR^{c1}R^{D1}$, $C(O)OR^{a1}$, and $S(O)_2NR^{c1}R^{d1}$.

In some embodiments:

$R^1$, $R^4$, and $R^6$ are each H;

$R^2$ is selected from H and $OR^{a1}$; and $R^3$ is selected from $Cy^1$, $OR^{a1}$, and halo.

In some embodiments, at least one, at least two, or at least three of $R^1$, $R^2$, $R^3$, $R^4$, and $R^6$ are H. In some embodiments, at least one of $R^1$, $R^2$, $R^3$, $R^4$, and $R^6$ is $Cy^1$. In some embodiments, at least one of $R^1$, $R^2$, $R^3$, $R^4$, and $R^6$ is halo. In some embodiments, at least one of $R^1$, $R^2$, $R^3$, $R^4$, and $R^6$ is CN. In some embodiments, at least one of $R^1$, $R^2$, $R^3$, $R^4$, and $R^6$ is $OR^{a1}$. In some embodiments, at least one of $R^1$, $R^2$, $R^3$, $R^4$, and $R^6$ is $C(O)NR^{c1}R^{d1}$. In some embodiments, at least one of $R^1$, $R^2$, $R^3$, $R^4$, and $R^6$ is $C(O)OR^{a1}$. In some embodiments, at least one of $R^1$, $R^2$, $R^3$, $R^4$, and $R^6$ is $S(O)_2NR^{c1}R^{d1}$.

In some embodiments:

$R^1$, $R^2$, $R^4$, and $R^6$ are each H, and $R^3$ is selected from $Cy^1$, halo, CN, $OR^{a1}$, $C(O)NR^{c1}R^{d1}$, $C(O)OR^{a1}$, and $S(O)_2NR^{c1}R^{d1}$.

In some embodiments, $R^3$ is selected from $Cy^1$, $OR^{a1}$, $C(O)NR^{c1}R^{d1}$, and halo.

In some embodiments:

$R^2$ is selected from H and $OR^{a1}$; and $R^3$ is selected from $C_{1-6}$ alkoxy and $C_{1-6}$ haloalkoxy.

In some embodiments, $R^3$ is $C_{1-6}$ haloalkoxy. In some embodiments, $R^3$ is halo. In some embodiments, $R^3$ is $Cy^1$. In some embodiments, $R^3$ is $OR^{a1}$. In some embodiments, $R^3$ is $C(O)NR^{c1}R^{d1}$.

In some embodiments, $R^5$ is $Cy^1$. In some embodiments, $R^5$ is $C(O)NR^{c1}R^{d1}$. In some embodiments, $R^5$ is $S(O)_2NR^{c1}R^{d1}$.

In some embodiments, $R^3$ is $OR^{a1}$ and $R^5$ is C(O) $NR^{c1}R^{d1}$. In some embodiments, $R^3$ is $OR^{a1}$ and $R^5$ is $Cy^1$. In some embodiments, $R^3$ is $OR^{a1}$ and $R^5$ is $S(O)_2NR^{c1}R^{d1}$.

In some embodiments, $R^3$ is $C_{1-6}$ haloalkoxy and $R^5$ is $C(O)NR^{c1}R^{d1}$. In some embodiments, $R^3$ is $C_{1-6}$ haloalkoxy and $R^5$ is $Cy^1$. In some embodiments, $R^3$ is $C_{1-6}$ haloalkoxy and $R^5$ is $S(O)_2NR^{c1}R^{d1}$.

In some embodiments, $Cy^1$ is selected from $C_{6-10}$ aryl and 5-10 membered heteroaryl, each of which is optionally substituted with 1 or 2 substituents independently selected from $R^{Cy}$.

In some embodiments, $Cy^1$ is selected from $C_{6-10}$ aryl, optionally substituted with $R^{Cy}$. In some embodiments, $Cy^1$ is 5-10 membered heteroaryl, optionally substituted with $R^{Cy}$. In some embodiments, $Cy^1$ is selected from indolyl and isoxazolyl, each of which is optionally substituted with $R^{Cy}$.

In some embodiments, $R^{a1}$ is selected from H, $C_{1-6}$ alkyl, $C_{1-4}$ haloalkyl, 5-10 membered heteroaryl, and 4-10 membered heterocycloalkyl.

In some embodiments, $R^{a1}$ is H. In some embodiments, $R^{a1}$ is $C_{1-6}$ alkyl. In some embodiments, $R^{a1}$ is $C_{1-4}$ haloalkyl. In some embodiments, $R^{a1}$ is 5-10 membered heteroaryl (e.g., indolyl, such as indol-5-yl or indol-4-yl). In some embodiments, $R^{a1}$ is 4-10 membered heterocycloalkyl (e.g., piperidinyl).

In some embodiments, $R^{c1}$ and $R^{d1}$ are each independently selected from H and $C_{1-6}$ alkyl. In some embodiments, $R^{c1}$ and $R^{d1}$ are both H. In some embodiments, at least one of $R^{c1}$ and $R^{d1}$ is not H. In some embodiments, $R^{c1}$ is H and $R^{d1}$ is $C_{1-6}$ alkyl. In some embodiments, $R^{c1}$ and $R^{d1}$ are both $C_{1-6}$ alkyl.

In some embodiments, $R^{c1}$ and $R^{d1}$ together with the N atom to which they are attached form a 4-7 membered heterocycloalkyl, which is optionally substituted with $R^g$. In some embodiments, $R^{c1}$ and $R^{d1}$ together with the N atom to which they are attached form piperazinyl or morpholinyl, each of which is optionally substituted with $R^g$.

In some embodiments, $R^{c1}$ and $R^{d1}$ together with the N atom to which they are attached form a 4-10 membered heterocycloalkyl. In some embodiments, $R^{c1}$ and $R^{d1}$ together with the N atom to which they are attached form a 5-10 membered heteroaryl.

In some embodiments, $R^7$ is H. In some embodiments, $R^7$ is $C_{1-3}$ alkyl.

In some embodiments, $R^{Cy}$ is selected from halo, CN, $NO_2$, $C_{1-6}$ alkyl, $C_{1-6}$ haloalkyl, $OR^{a2}$, $C(O)R^{b2}$, $C(O)NR^{c}R^{d2}$, $C(O)OR^{a2}$, and $NR^{c2}R^{d2}$ wherein said $C_{1-6}$ alkyl is optionally substituted with 1, 2, or 3 substituents independently selected from halo, CN, $NO_2$, $OR^{a2}$, $C(O)R^{b2}$, $C(O)NR^{c2}R^{d2}$, $C(O)OR^{a2}$, and $NR^{c2}R^{d2}$.

In some embodiments, $R^{Cy}$ is selected from halo, CN, $C_{1-6}$ alkyl, $C_{1-6}$ haloalkyl, 5-10 membered heteroaryl, 4-6 membered heterocycloalkyl, $OR^{a2}$, $C(O)OR^{a2}$, $C(O)NR^{c2}R^{d2}$, $C(O)NR^{c1}S(O)_2R^{b2}$, $NR^{c2}R^{d2}$, $NR^{c2}C(O)R^{b2}$, $OC(O)R^{b1}$, and $S(O)_2R^{b2}$; wherein said $C_{1-6}$ alkyl is optionally substituted with $OR^{a2}$ or $NR^{c2}R^{d2}$.

In some embodiments, $R^{Cy}$ is selected from halo, CN, $NO_2$, $C_{1-6}$ alkyl, $C_{1-6}$ haloalkyl, $C_{1-6}$ alkoxy, and $C_{1-6}$ haloalkoxy.

In some embodiments, $R^{a2}$ is selected from H, $C_{1-6}$ alkyl, and $C_{1-4}$ haloalkyl.

In some embodiments, $R^{a2}$ is selected from H and $C_{1-6}$ alkyl.

In some embodiments, W is $C(O)OR^{a2}$.

In some embodiments, W is selected from any one of the following moieties:

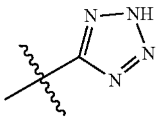

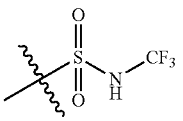

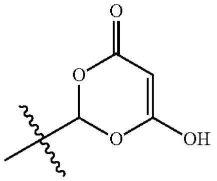

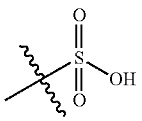

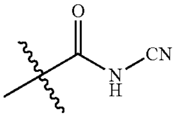

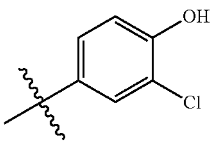

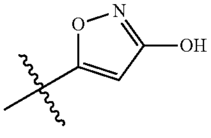

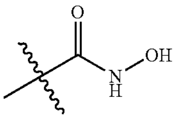

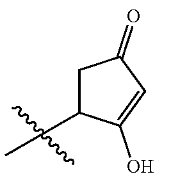

In some embodiments, the compound of Formula (III) is selected from any one of the following compounds:

13A

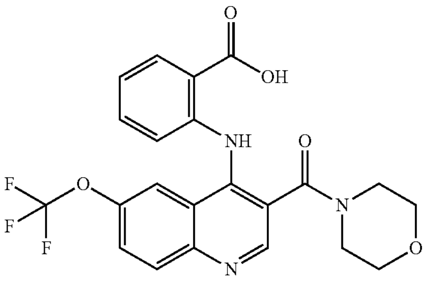

14A

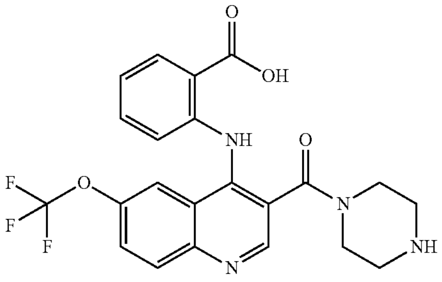

12A

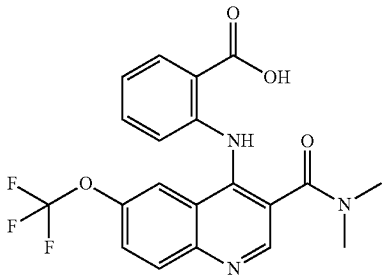

16A

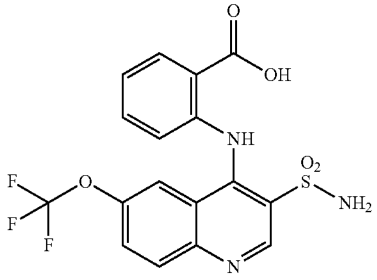

17A

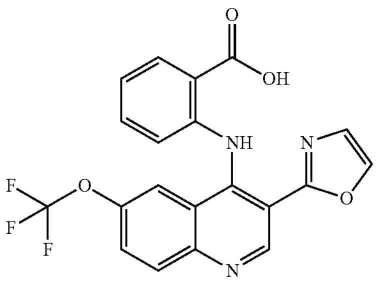

-continued
53A
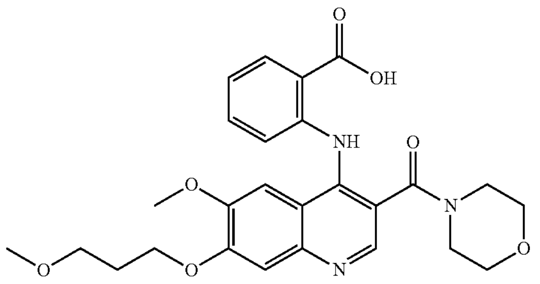
57A
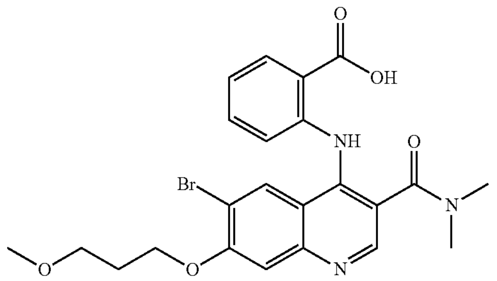
58A
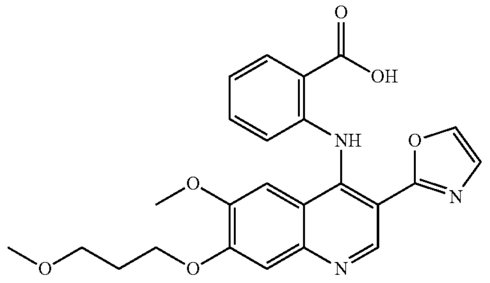
61A
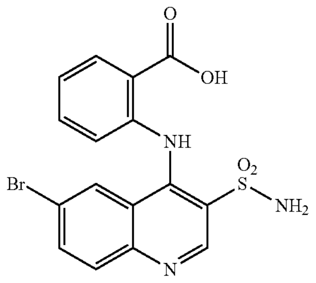
63A
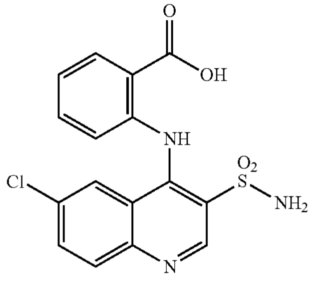
-continued
64A
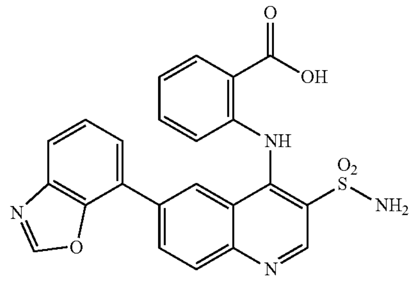
70A
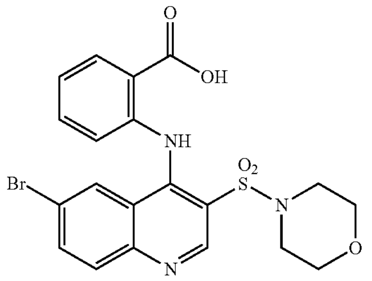
78A
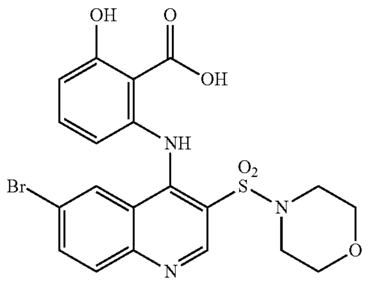
78A-BR
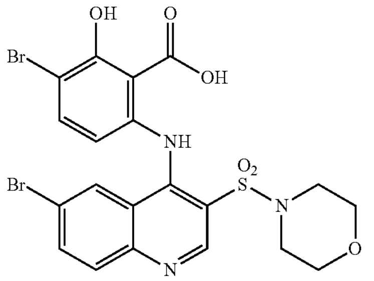
78A-INT
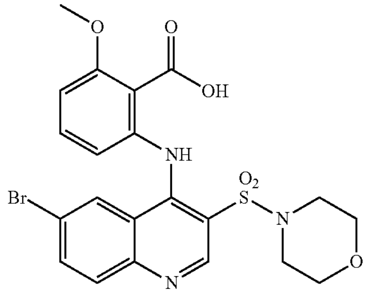

-continued
79A
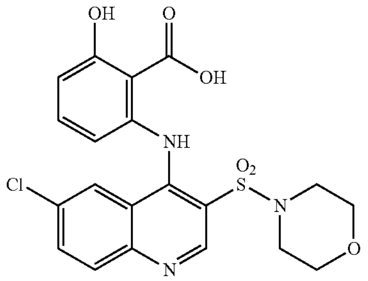
79A-INT
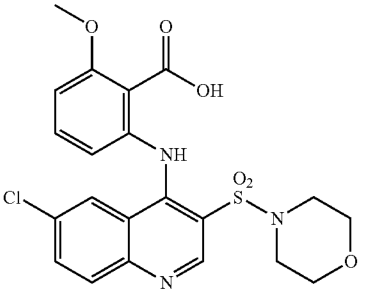
80A
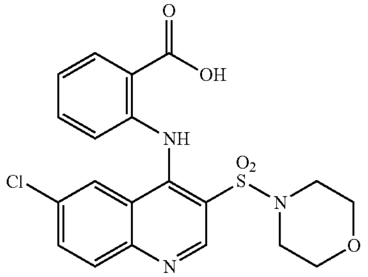
81A
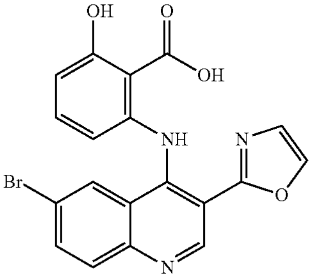
81A-INT
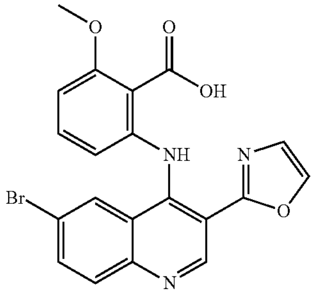
-continued
82A
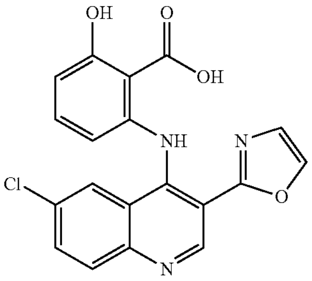
85A
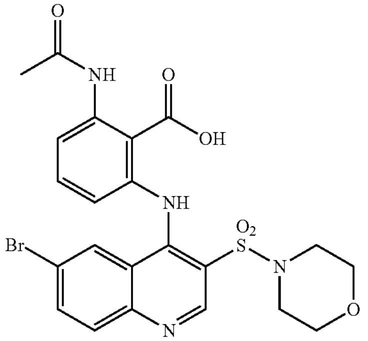
85A-BP
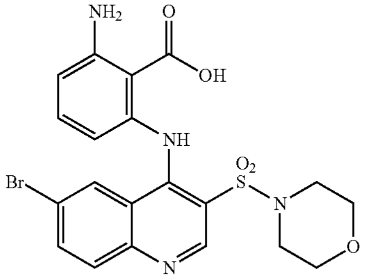
86A
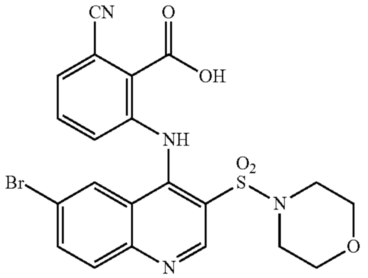
93A
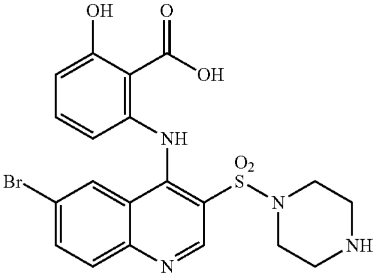

-continued
93A-INT
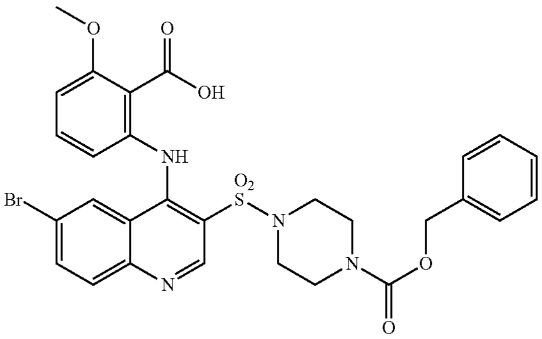
In some embodiments, the compound of Formula (III) is selected from any one of the following compounds:
13A
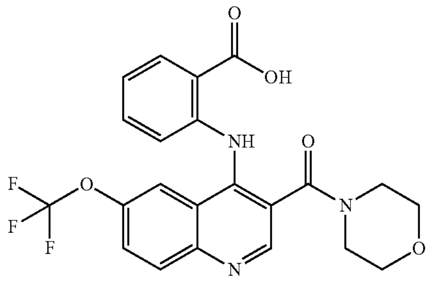
14A
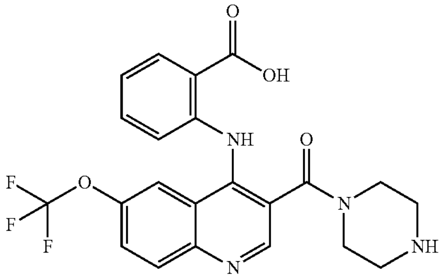
12A
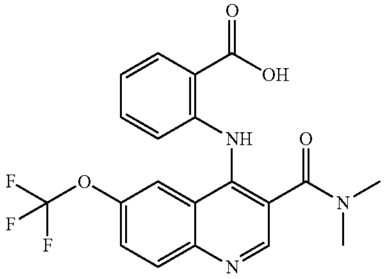
16A
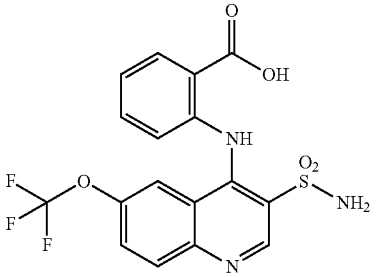
-continued
17A
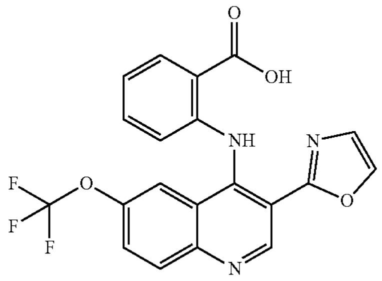
or a pharmaceutically acceptable salt thereof.
In some embodiments, wherein the compound of Formula (III) is selected from any one of the following compounds:
87A
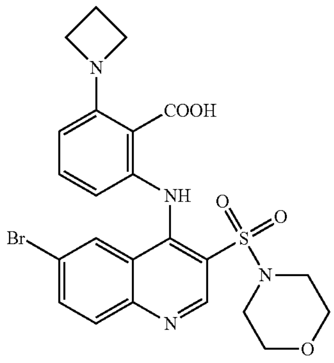
96A
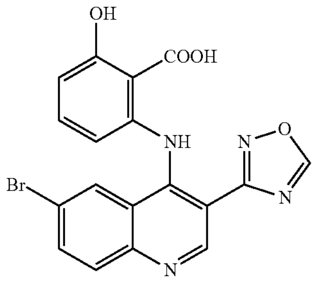
97A
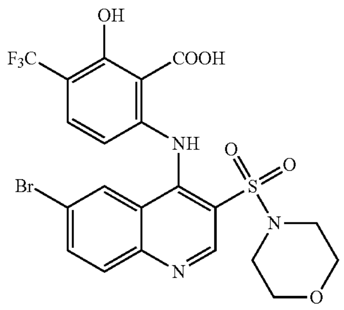

-continued
88A
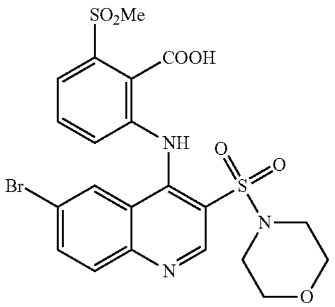
89A
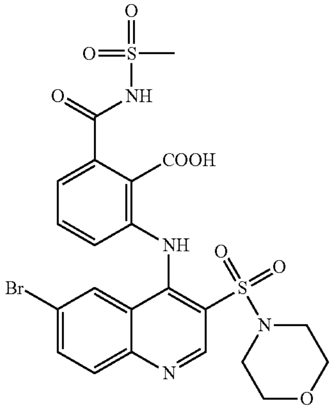
90A
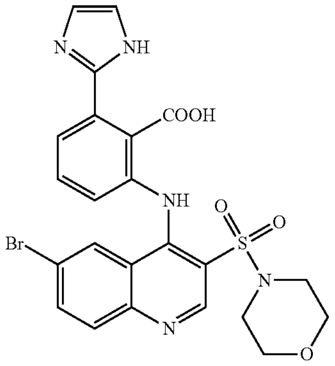
91A
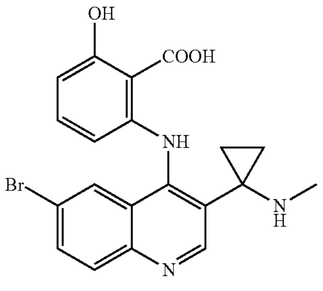
-continued
94A
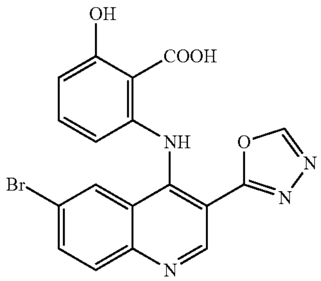
95A
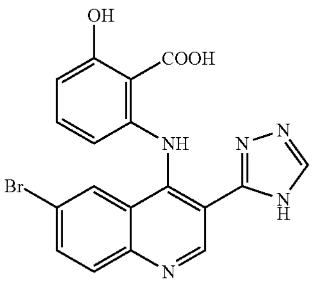
92A
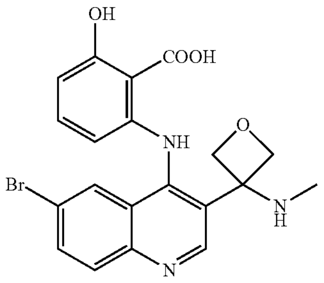
98A
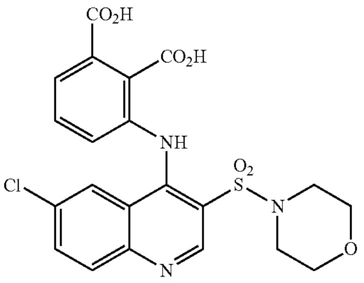
99A
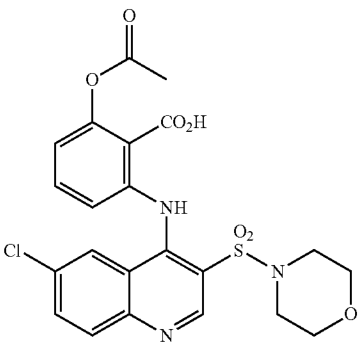

-continued
100A
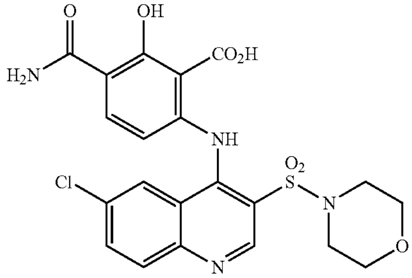
101A
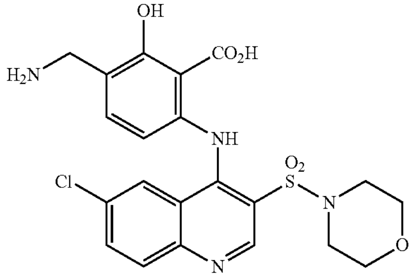
102A
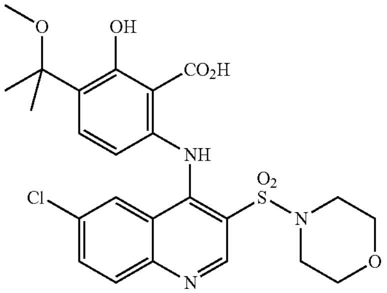
103A
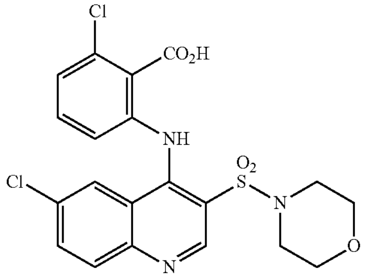
107A
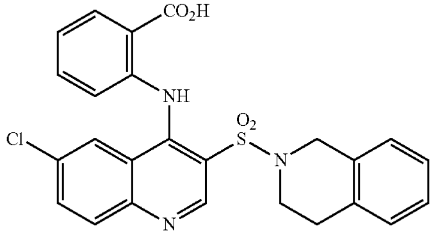
108A
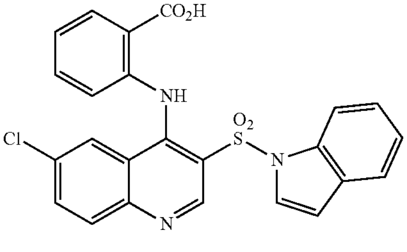
-continued
109A
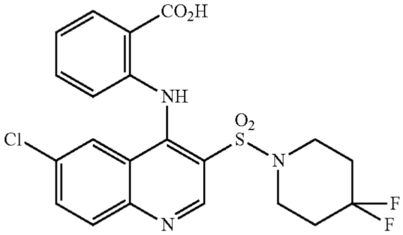
110A
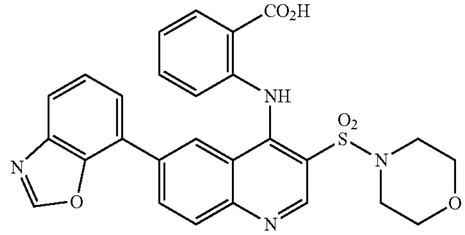
111A
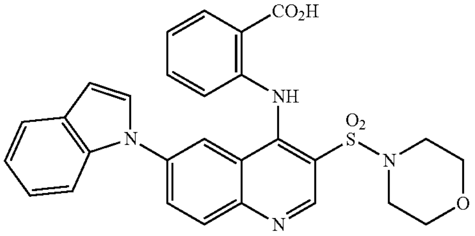
112A
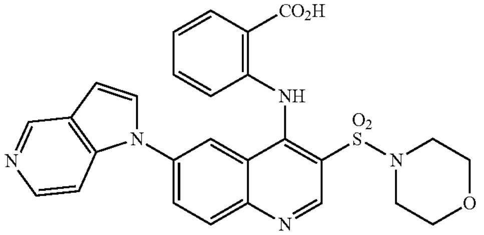
114A
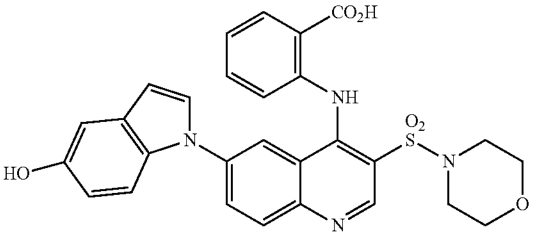
115A
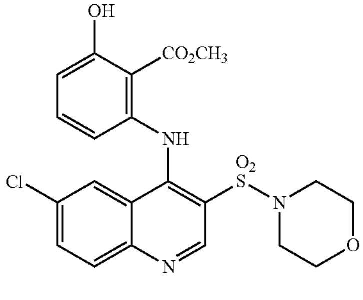

-continued

118A

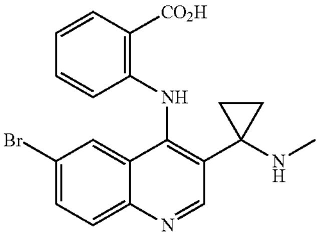

119A

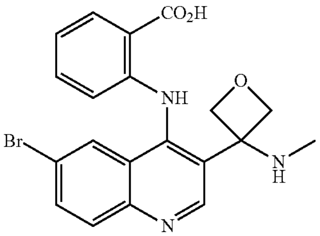

120A

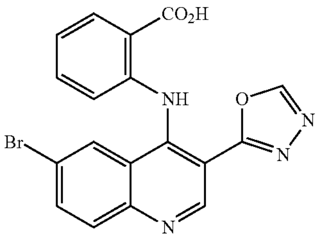

121A

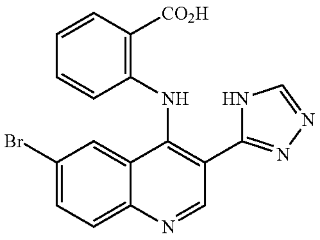

122A

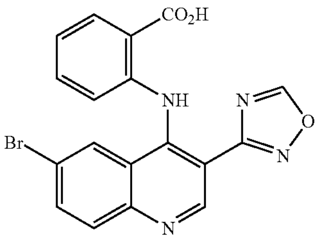

123A

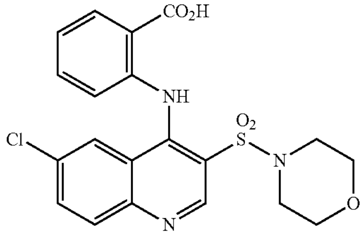

or a pharmaceutically acceptable salt thereof.

In some embodiments, the present disclosure provides a compound of Formula (IV):

(IV)

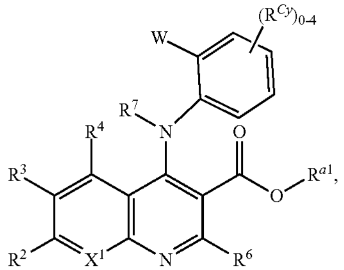

or a pharmaceutically acceptable salt thereof, wherein:

$X^1$ is selected from N and $CR^1$;

$R^1$, $R^2$, $R^4$, and $R^6$ are each independently selected from H, $C_{1-6}$ alkyl, $C_{2-6}$ alkenyl, $C_{2-6}$ alkynyl, $C_{1-4}$ haloalkyl, $Cy^1$, halo, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2R^{b1}$, $S(O)_2R^{b1}$ and $S(O)_2NR^{c1}R^{d1}$; wherein said $C_{1-6}$ alkyl, $C_{2-6}$ alkenyl, and $C_{2-6}$ alkynyl are each optionally substituted with 1, 2, 3, 4, or 5 substituents independently selected from $Cy^1$, halo, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}$ $S(O)_2R^{b1}$, $S(O)_2R^{b1}$, and $S(O)_2NR^{c1}R^{d1}$;

$R^3$ is selected from $C(O)Cy^1$, $OCy^1$, and $Cy^1$;

each $Cy^1$ is independently selected from 5-10 membered heteroaryl and 4-7 membered heterocycloalkyl, each of which is optionally substituted with 1, 2, or 3 substituents independently selected from $R^{Cy}$;

$R^7$ is selected from H and $C_{1-3}$ alkyl;

W is selected from $C(O)OR^{a2}$ and a carboxylic acid bioisostere;

$R^{Cy}$ is selected from halo, CN, $NO_2$, $C_{1-6}$ alkyl, $C_{1-6}$ haloalkyl, $C_{2-6}$ alkenyl, $C_{2-6}$ alkynyl, $OR^{a2}$, $C(O)R^{b2}$, $C(O)OR^{a2}$, $C(O)NR^{c2}R^{d2}$, $NR^{c2}R^{d2}$, $NR^{c2}C(O)R^{b2}$, $NR^{c2}C(O)OR^{a2}NR^{c2}S(O)_2R^{b2}$, $S(O)_2R^{b2}$, and $S(O)_2NR^{c2}R^{d2}$; wherein said $C_{1-6}$ alkyl, $C_{2-6}$ alkenyl, and $C_{2-6}$ alkynyl are each optionally substituted with 1, 2, or 3 substituents independently selected from halo, CN, $NO_2$, $OR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$, $NR^{c2}C(O)OR^{a2}$, $NR^{c2}$ $S(O)_2R^{b2}$, $S(O)_2R^{b2}$, and $S(O)_2NR^{c2}R^{d2}$;

each $R^{a1}$, $R^{b1}$, $R^{c1}$, $R^{d1}$, $R^{a2}$, $R^{b2}$, $R^{c2}$, and $R^{d2}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$;

or any $R^{c2}$ and $R^{d2}$ together with the N atom to which they are attached form a 4-7 membered heterocycloalkyl, which is optionally substituted with 1, 2, or 3 substituents independently selected from $R^g$;

each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl) aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, $X^1$ is N.

In some embodiments, $X^1$ is $CR^1$.

In some embodiments, $R^1$, $R^2$, $R^4$, and $R^6$ are each independently selected from H, $Cy^1$, halo, CN, $OR^{a1}$, C(O)$NR^{c1}R^{d1}$, C(O)$OR^{a1}$, and $S(O)_2NR^{c1}R^{d1}$.

In some embodiments, at least one, at least two, or at least three of $R^1$, $R^2$, $R^4$, and $R^6$ are H. In some embodiments, at least one of $R^1$, $R^2$, $R^4$, and $R^6$ is $Cy^1$. In some embodiments, at least one of $R^1$, $R^2$, $R^4$, and $R^6$ is halo. In some embodiments, at least one $R^1$, $R^2$, $R^4$, and $R^6$ is CN. In some embodiments, at least one of $R^1$, $R^2$, $R^4$, and $R^6$ is $OR^{a1}$. In some embodiments, at least one of $R^1$, $R^2$, $R^4$, and $R^6$ is C(O)$NR^{c1}R^{d1}$. In some embodiments, at least one of $R^1$, $R^2$, $R^4$, and $R^6$ is C(O)$OR^{a1}$. In some embodiments, at least one of $R^1$, $R^2$, $R^4$, and $R^6$ is $S(O)_2NR^{c1}R^{d1}$. In some embodiments, $R^1$, $R^2$, $R^4$, and $R^6$ are each H.

In some embodiments, $R^3$ is C(O)$Cy^1$. In some embodiments, $R^3$ is $OCy^1$. In some embodiments, $R^3$ is $Cy^1$.

In some embodiments, $Cy^1$ is 5-10 membered heteroaryl, optionally substituted with $R^{Cy}$. In some embodiments, $Cy^1$ is indolyl, optionally substituted with $R^{Cy}$.

In some embodiments, $Cy^1$ is 4-7 membered heterocycloalkyl, optionally substituted with $R^{Cy}$. In some embodiments, $Cy^1$ is selected from piperidine and piperazine, each of which is optionally substituted with $R^{Cy}$.

In some embodiments, $R^{a1}$ is selected from H, $C_{1-6}$ alkyl, $C_{1-4}$ haloalkyl, 5-10 membered heteroaryl, and 4-10 membered heterocycloalkyl. In some embodiments, $R^{a1}$ is selected from H and $C_{1-6}$ alkyl. In some embodiments, $R^{a1}$ is H. In some embodiments, $R^{a1}$ is $C_{1-6}$ alkyl. In some embodiments, $R^{a1}$ is $C_{1-4}$ haloalkyl. In some embodiments, $R^{a1}$ is 5-10 membered heteroaryl (e.g., indolyl, such as indol-5-yl or indol-4-yl). In some embodiments, $R^{a1}$ is 4-10 membered heterocycloalkyl (e.g., piperidinyl).

In some embodiments, $R^{c1}$ and $R^{d1}$ are each independently selected from H and $C_{1-6}$ alkyl. In some embodiments, $R^{c1}$ and $R^{d1}$ are both H. In some embodiments, at least one of $R^{c1}$ and $R^{d1}$ is not H. In some embodiments, $R^{c1}$ is H and $R^{d1}$ is $C_{1-6}$ alkyl. In some embodiments, $R^{c1}$ and $R^{d1}$ are both $C_{1-6}$ alkyl.

In some embodiments, $R^{c1}$ and $R^{d1}$ together with the N atom to which they are attached form a 4-7 membered heterocycloalkyl, which is optionally substituted with $R^g$. In some embodiments, $R^{c1}$ and $R^{d1}$ together with the N atom to which they are attached form piperazinyl or morpholinyl, each of which is optionally substituted with $R^g$.

In some embodiments, $R^{Cy}$ is selected from halo, CN, $NO_2$, $C_{1-6}$ alkyl, $C_{1-6}$ haloalkyl, $OR^{a2}$, C(O)$R^{b2}$, C(O)$NR^{c2}R^{d2}$, C(O)$OR^{a2}$, and $NR^{c2}R^{d2}$, wherein said $C_{1-6}$ alkyl is optionally substituted with 1, 2, or 3 substituents independently selected from halo, CN, $NO_2$, $OR^{a2}$, C(O)$R^{b2}$, C(O)$NR^{c2}R^{d2}$, C(O)$OR^{a2}$, and $NR^{c2}R^{d2}$. In some embodiments, $R^{Cy}$ is selected from halo, OH, CN, $NO_2$, $C_{1-6}$ alkyl, $C_{1-6}$ haloalkyl, $C_{1-6}$ alkoxy, and $C_{1-6}$ haloalkoxy. In some embodiments, $R^{Cy}$ is $OR^{a2}$. In some embodiments, $R^{Cy}$ is OH.

In some embodiments, $R^7$ is H. In some embodiments, $R^7$ is $C_{1-3}$ alkyl. In some embodiments, W is C(O)$OR^{a2}$. In some embodiments, $R^{a2}$ is selected from H and $C_{1-6}$ alkyl. In some embodiments, W is C(O)OH. In some embodiments, W is selected from any one of the following moieties:

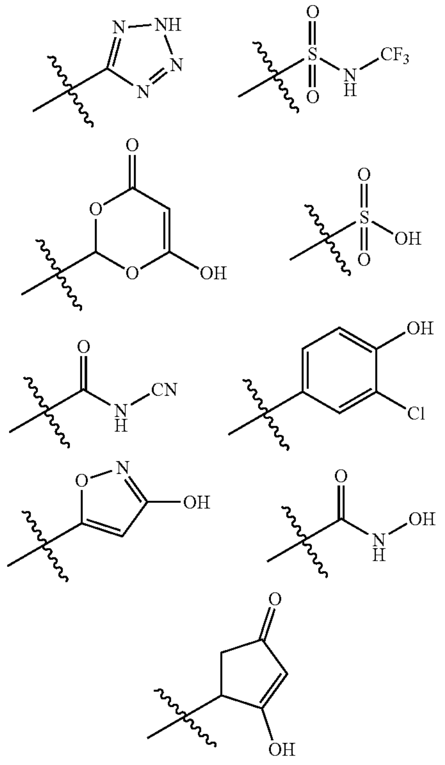

In some embodiments, the compound of Formula (IV) is selected from any one of the following compounds:

23A

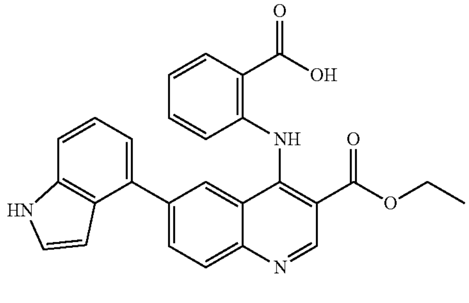

-continued
18A
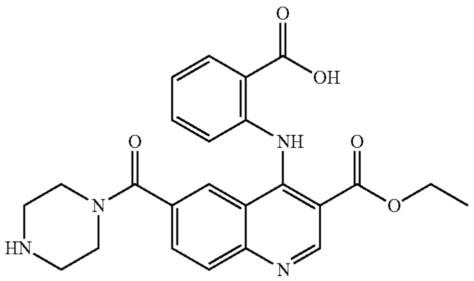
29A
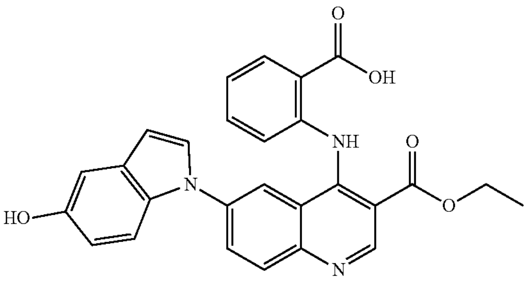
19A
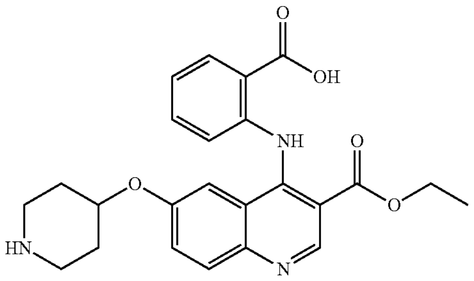
20
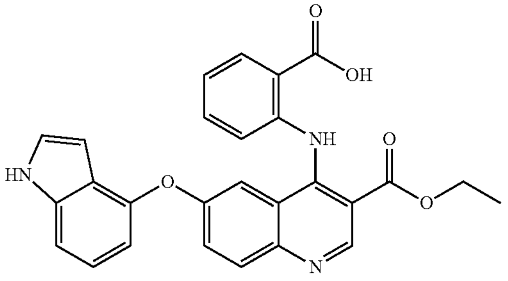
21
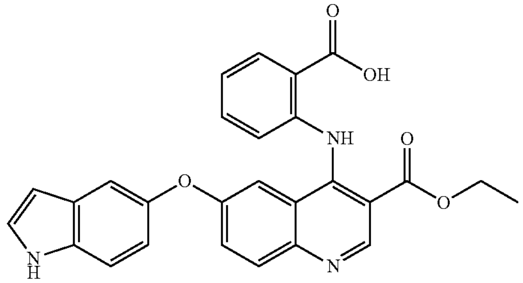
or a pharmaceutically acceptable salt thereof.
In some embodiments, the present disclosure provides a compound selected from any one of the following compounds:
26A
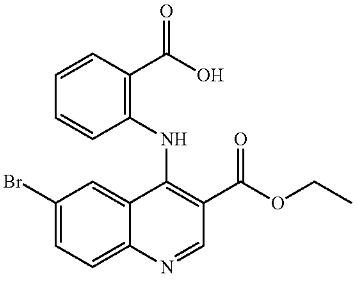
25A
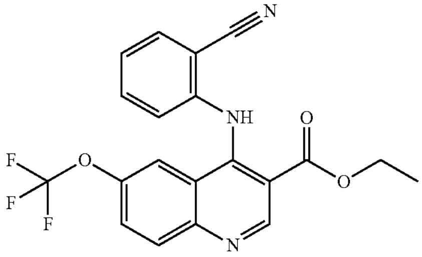
24
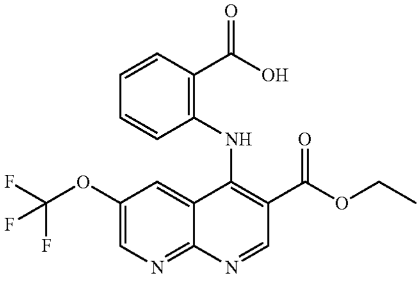
or a pharmaceutically acceptable salt thereof.
In some embodiments, the present disclosure provides a compound selected from any one of the following compounds:
15A
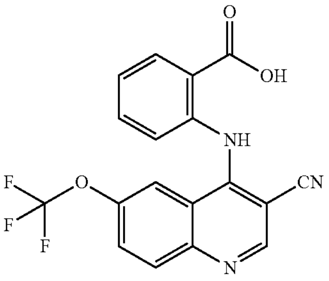
26A
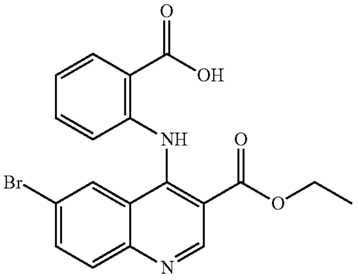

-continued

25A

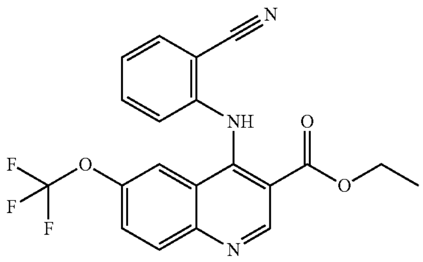

24

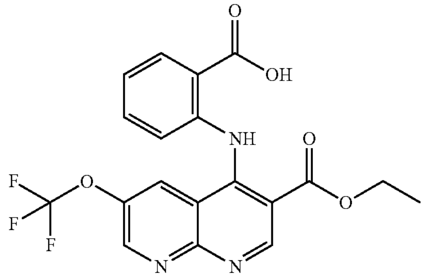

or a pharmaceutically acceptable salt thereof.

In some embodiments, the present disclosure provides a compounds of Formula (V):

(V)

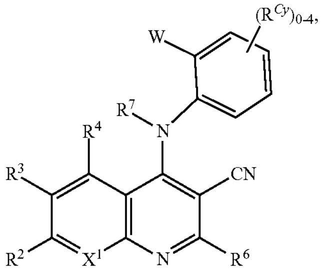

or a pharmaceutically acceptable salt thereof, wherein:

$X^1$ is selected from N and $CR^1$;

$R^1$, $R^2$, $R^3$, $R^4$, and $R^6$ are each independently selected from H, $C_{1-6}$ alkyl, $C_{2-6}$ alkenyl, $C_{2-6}$ alkynyl, $C_{1-4}$ haloalkyl, C(O)$Cy^1$, O$Cy^1$, $Cy^1$, halo, CN, $NO_2$, $OR^{a1}$, $SR^{a1}$, C(O)$R^{b1}$, C(O)$NR^{c1}R^{d1}$, C(O)$OR^{a1}$, $NR^{c1}R^{d1}$, $NR^{c1}C(O)R^{b1}$, $NR^{c1}S(O)_2R^{b1}$, $S(O)_2R^{b1}$, $S(O)_2NR^{c1}R^{d1}$; wherein said $C_{1-6}$ alkyl, $C_{2-6}$ alkenyl, and $C_{2-6}$ alkynyl are each optionally substituted with 1, 2, 3, 4, or 5 substituents independently selected from $Cy^1$, halo, CN, $NO_2$, $OR^{a1}$, $SR^{a1}$, C(O)$R^{b1}$, C(O)$NR^{c1}R^{d1}$, C(O)$OR^{a1}$, $NR^{c1}R^{d1}$, $NR^{c1}C(O)R^{b1}$, $NR^{c1}S(O)_2R^{b1}$, $S(O)_2R^{b1}$, and $S(O)_2NR^{c1}R^{d1}$;

each $Cy^1$ is independently selected from 5-10 membered heteroaryl and 4-7 membered heterocycloalkyl, each of which is optionally substituted with 1, 2, or 3 substituents independently selected from $R^{Cy}$;

$R^7$ is selected from H and $C_{1-3}$ alkyl;

or $R^7$ and the phenyl group together with the N atom to which they are attached form a 5-10 membered heteroaryl ring or a 4-7 membered heterocycloalkyl ring, each of which is optionally substituted with 1, 2, or 3 substituents independently selected from W and $R^{Cy}$;

W is selected from C(O)$OR^{a2}$ and a carboxylic acid bioisostere;

$R^{Cy}$ is selected from halo, CN, $NO_2$, $C_{1-6}$ alkyl, $C_{1-6}$ haloalkyl, $C_{2-6}$ alkenyl, $C_{2-6}$ alkynyl, $OR^{a2}$, C(O)$R^{b2}$, C(O)$OR^{a2}$, C(O)$NR^{c2}R^{d2}$, $NR^{c2}R^{d2}$, $NR^{c2}C(O)R^{b2}$, $NR^{c2}C(O)OR^{a2}$, $NR^{c2}S(O)_2R^{b2}$, $S(O)_2R^{b2}$, and $S(O)_2NR^{c2}R^{d2}$; wherein said $C_{1-6}$ alkyl, $C_{2-6}$ alkenyl, and $C_{2-6}$ alkynyl are each optionally substituted with 1, 2, or 3 substituents independently selected from halo, CN, $NO_2$, $OR^{a2}$, C(O)$R^{b2}$, C(O)$NR^{c2}R^{d2}$, C(O)$OR^{a2}$, $NR^{c2}R^{d2}$, $NR^{c2}C(O)R^{b2}$, $NR^{c2}C(O)OR^{a2}$, $NR^{c2}S(O)_2R^{b2}$, $S(O)_2R^{b2}$, and $S(O)_2NR^{c2}R^{d2}$;

each $R^{a1}$, $R^{b1}$, $R^{c1}$, $R^{d1}$, $R^{a2}$, $R^{b2}$, $R^{c2}$, and $R^{d2}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$;

or any $R^{c2}$ and $R^{d2}$ together with the N atom to which they are attached form a 4-7 membered heterocycloalkyl, which is optionally substituted with 1, 2, or 3 substituents independently selected from $R^g$;

each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl) aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, $R^1$, $R^2$, $R^3$, $R^4$, and $R^6$ are each independently selected from H, $Cy^1$, halo, CN, $OR^{a1}$, C(O)$NR^{c1}R^{d1}$, C(O)$OR^{a1}$, and $S(O)_2NR^{c1}R^{d1}$.

In some embodiments:

$R^1$, $R^4$, and $R^6$ are each H;

$R^2$ is selected from H and $OR^{a1}$; and $R^3$ is selected from $Cy^1$ and $OR^{a1}$.

In some embodiments, $R^{a1}$ is selected from $C_{1-6}$ alkyl and $C_{1-6}$ haloalkyl.

In some embodiments, $R^7$ is H.

In some embodiments, W is C(O)$OR^{a2}$.

In some embodiments, $R^{a2}$ is selected from H and $C_{1-6}$ alkyl.

In some embodiments, W is a carboxylic acid bioisostere selected from any one of the following moieties:

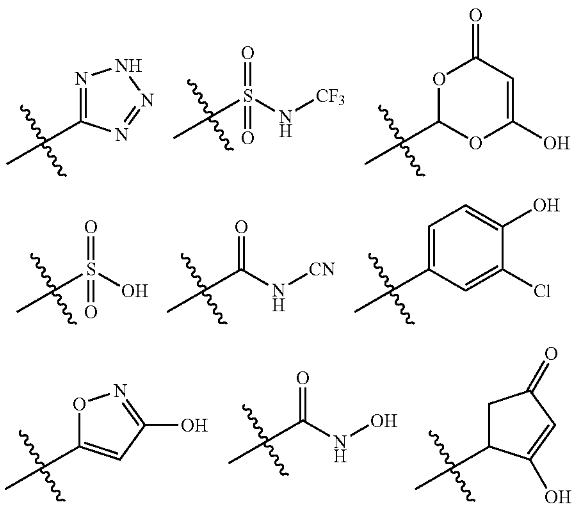

or a pharmaceutically acceptable salt thereof.

In some embodiments, the compound of Formula (V) is selected from any one of the following compounds:

15A

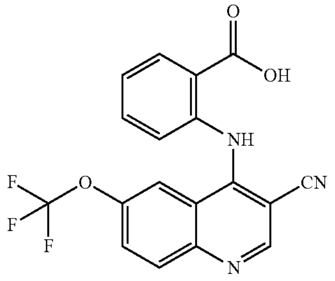

54A

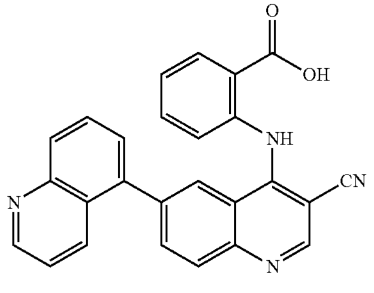

51A

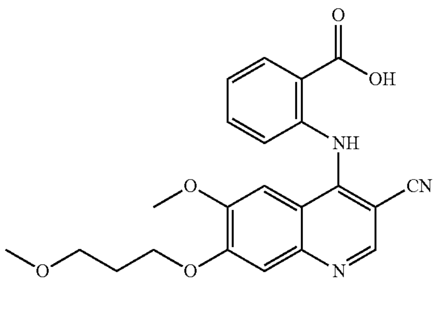

-continued

55A

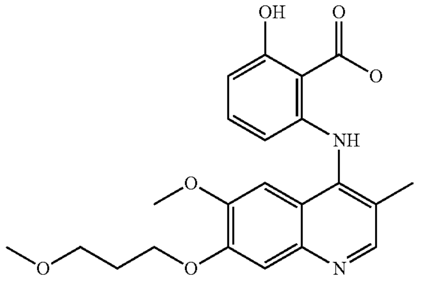

56A

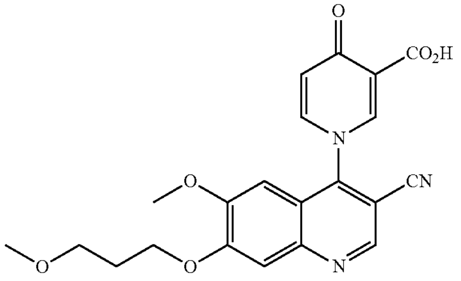

or a pharmaceutically acceptable salt thereof.

As used herein, the term "pharmaceutically acceptable salt" refers to a salt that is formed between an acid and a basic group of the compound, such as an amino functional group, or between a base and an acidic group of the compound, such as a carboxyl functional group. In some embodiments, the compound is a pharmaceutically acceptable acid addition salt. In some embodiments, acids commonly employed to form pharmaceutically acceptable salts of the therapeutic compounds described herein include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

In some embodiments, bases commonly employed to form pharmaceutically acceptable salts of the therapeutic compounds described herein include hydroxides of alkali metals, including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—(C1-C6)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

In some embodiments, the compound of Formulae (I)-(IV), or a pharmaceutically acceptable salt thereof, is substantially isolated.

Methods of Making

Compounds of any one of Formulae disclosed herein, including salts thereof, can be prepared using known organic synthesis techniques and can be synthesized according to any of numerous possible synthetic routes. A person skilled in the art knows how to select and implement appropriate synthetic protocols, and appreciates that a broad repertoire of synthetic organic reactions is available to be potentially employed in synthesizing compounds provided herein.

Suitable synthetic methods of starting materials, intermediates and products can be identified by reference to the literature, including reference sources such as: *Advances in Heterocyclic Chemistry*, Vols. 1-107 (Elsevier, 1963-2012); *Journal of Heterocyclic Chemistry* Vols. 1-49 (Journal of Heterocyclic Chemistry, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, $2^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure,* 6th Ed. (Wiley, 2007); Trost et al. (Ed.), *Comprehensive Organic Synthesis* (Pergamon Press, 1991).

The reactions for preparing the compounds provided herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of the compounds provided herein can involve the protection and deprotection of various chemical groups. The need for protection and deprotection, and the selection of appropriate protecting groups, can be readily determined by one skilled in the art. The chemistry of protecting groups can be found, for example, in P. G. M. Wuts and T. W. Greene, *Protective Groups in Organic Synthesis,* 4th Ed., Wiley & Sons, Inc., New York (2006).

Methods of Use

Modulation of Telomerase RNA Component (TERC)

Telomerase has been a therapeutic target of great interest for over two decades, based on its activity in numerous cancers. The telomerase RNA component (TERC) contains a box H/ACA domain at its 3' end, a motif that is functionally separable from the template domain and dispensable for telomerase activity in vitro. In vivo, the H/ACA motif is bound by a heterotrimer of dyskerin, NOP10, and NHP2 which stabilize TERC, and also by TCAB1, which is responsible for localizing the telomerase complex to Cajal bodies (I-Venteicher, A. S. et al. A human telomerase holoenzyme protein required for Cajal body localization and telomere synthesis. Science 323, 644-8 (2009)). Disruption of any of these interactions can also compromise telomere maintenance and cause telomere disease (Mitchell, J. R., Wood, E. & Collins, K. A telomerase component is defective in the human disease dyskeratosis congenita. Nature 402, 551-5 (1999); Vulliamy, T. et al. Mutations in the telomerase component NHP2 cause the premature ageing syndrome dyskeratosis congenita. Proceedings of the National Academy of Sciences of the United States of America 105, 8073-8 (2008); Walne, A. J. et al. Genetic heterogeneity in autosomal recessive dyskeratosis congenita with one subtype due to mutations in the telomerase-associated protein NOP10. Human molecular genetics 16, 1619-29 (2007)). The H/ACA motif serve as guides for pseudouridylation of other RNAs by dyskerin (Kiss, T., Fayet-Lebaron, E. & Jady, B. E. Box H/ACA small ribonucleoproteins. Molecular cell 37, 597-606 (2010)).

Increasing telomerase activity can be beneficial in several degenerative and age-related disorders. Conversely, inhibiting telomerase activity would be of significant utility for the treatment of cancer and disorders in which hyper-proliferative cells depend on telomerase for self-renewal.

Modulation of Poly(A) Specific Ribonuclease (PARN)

PARN is known as a 3'-5' exoribonuclease responsible for degradation of the poly(A) tails of eukaryotic mRNAs, which is a rate-limiting step in mRNA turnover (Korner, C. G. & Wahle, E. Poly(A) tail shortening by a mammalian poly(A)-specific 3'-exoribonuclease. The Journal of biological chemistry 272, 10448-56 (1997)). PARN is stimulated by presence of a m7G-cap, and requires a minimal substrate of adenosine di- or tri-nucleotides—in other words, oligo(A) rather than strictly poly(A). PARN is a widely-expressed cap-dependent, poly(A) deadenylase with a canonical role in regulating global mRNA levels during development, and additional, more specialized functions including end-trimming of the Dicer-independent microRNA (miR)-451 and deadenylation of small nucleolar (sno)RNAs. PARN loss-of-function mutations are implicated in idiopathic pulmonary fibrosis and dyskeratosis congenita. The disclosure provides methods and agents that modulate the to level or activity of human PARN. The nucleotide sequence of human PARN is NM_002582 and the amino acid sequence of PARN is 095453 (Table 1). Variants of the nucleotide sequence and the amino acid sequence are also shown in Table 1.

TABLE 1

Accession numbers for genes, RNA and proteins

| Gene | Ensembl Gene ID | Nucleotide sequence(s) and variants therein (RefSeq unless otherwise indicated) | Protein ID(S) and variants therein (Uniprot unless otherwise indicated) |
|---|---|---|---|
| TERC | ENSG00000270141 | NR_001566 | N/A |
| PARN | ENSG00000140694 | NM_002582 | O95453 |

TABLE 1-continued

| Accession numbers for genes, RNA and proteins | | | |
|---|---|---|---|
| Gene | Ensembl Gene ID | Nucleotide sequence(s) and variants therein (RefSeq unless otherwise indicated) | Protein ID(S) and variants therein (Uniprot unless otherwise indicated) |
| | | NM_001242992 | |
| | | NM_001134477 | |
| TRF4-2 a.k.a. PAPD5 | ENSG00000121274 | NM_001040284 | Q8NDFB |
| | | NM_001040285 | H3BQMO |
| | | FR872509.1 (GenBank) | CCB84642.1 (GenBank) |

PAP Associated Domain Containing 5 (PAPD5)

PAPD5, also known as Topoisomerase-Related Function Protein 4-2 (TRF4-2), also known as TUT3, also known as GLD4, also known as TENT4B, is one of the seven members of the family of noncanonical poly(A) polymerases in human cells. PAPD5 has been shown to act as a polyadenylase on abnormal pre-ribosomal RNAs in vivo in a manner analogous to degradation-mediating polyadenylation by the non-canonical poly(A) polymerase Trf4p in yeast. PAPD5 is also involved in the uridylation-dependent degradation of histone mRNAs.

Both PARN and PAPD5 are involved in the 3'-end maturation of the telomerase RNA component (TERC). Patient cells, fibroblast cells as well as converted fibroblasts (I-IPS cells) in which PARN is disrupted show decreased levels of TERC which can be restored by decreasing levels or activities of PAPD5. Deep sequencing of TERC RNA 3' termini or ends, reveals that PARN and PAPD5 are critically important for processing of post-transcriptionally acquired oligo (A) tails that target nuclear RNAs for degradation. Diminished TERC levels and the increased oligo(A) forms of TERC are normalized by restoring PARN or inhibiting PAPD5. The disclosure reveals PARN and PAPD5 as important players in the regulation and biogenesis of TERC (FIG. 1). FIG. 1 shows 3' ends of nascent TERC RNA are subject to PAPD5-mediated oligo-adenylation, which targets transcripts for degradation by the exosome. PARN counteracts the degradation pathway by removing oligo(A) tails and/or trimming genomically-encoded bases (green) of nascent TERC to yield a mature 3' end. Mature TERC is protected from further oligo-adenylation and exonucleolytic processing, possibly by the dyskerin/NOP10/NHP2/GAR1 complex, and assembles into the telomerase holoenzyme to maintain telomeres. PARN deficiency tips the balance in favor of degradation, leading to reduced TERC levels and telomere dysfunction. Thus, the disclosure also provides compounds and methods that modulate the level or activity of human PAPD5. The nucleotide sequence of human PAPD5 used is FR872509.1, and the amino acid sequence is CCB84642.1 (Table 1). Variants of the nucleotide sequence and the amino acid sequence are also shown in Table 1. The amino acid sequence of PAPD5 used is shown below:

```
PAPD5 (TRF4-2) (CCB84642.1)
                                          (SEQ ID NO: 1)
MYRSGERLLG SHALPAEQRD FLPLETTNNN NNHHQPGAWA

RRAGSSASSP PSASSSPHPS

AAVPAADPAD SASGSSNKRK RDNKASTYGL NYSLLQPSGG
```

-continued

```
RAAGGGRADG GGVVYSGTPW

KRRNYNQGVV GLHEEISDFY EYMSPRPEEE KMRMEVVNRI

ESVIKELWPS ADVQIFGSFK

TGLYLPTSDI DLVVFGKWEN LPLWTLEEAL RKHKVADEDS

VKVLDKATVP IIKLTDSFTE

VKVDISFNVQ NGVRAADLIK DFTKKYPVLP YLVLVLKQFL

LQRDLNEVFT GGIGSYSLFL MAVSFLQLHP REDACIPNTN

YGVLLIEFFE LYGRHFNYLK TGIRIKDGGS YVAKDEVQKN

MLDGYRPSML YIEDPLQPGN DVGRSSYGAM QVKQAFDYAY

VVLSHAVSPI AKYYPNNETE

SILGRIIRVT DEVATYRDWI SKQWGLKNRP EPSCNGNGVT

LIVDTQQLDK CNNNLSEENE

ALGKCRSKTS ESLSKHSSNS SSGPVSSSSA TQSSSSDVDS

DATPCKTPKQ LLCRPSTGNR

VGSQDVSLES SQAVGKMQST QTTNTSNSTN KSQHGSARLF

RSSSKGFQGT TQTSHGSLMT

NKQHQGKSNN QYYHGKKRKH KRDAPLSDLC R
```

Figure 2:
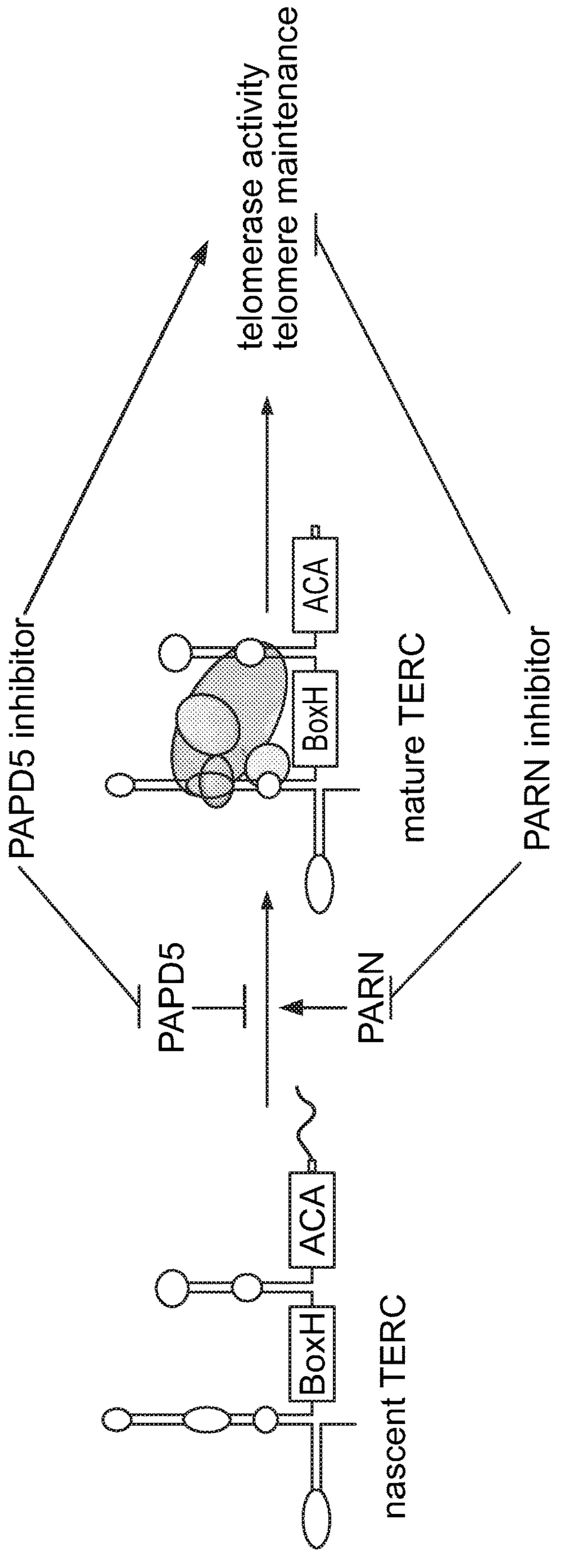
FIG. 2 is a schematic diagram showing an exemplary model of reciprocal regulation of TERC maturation by PARN and PAPD5.
Figure 3:
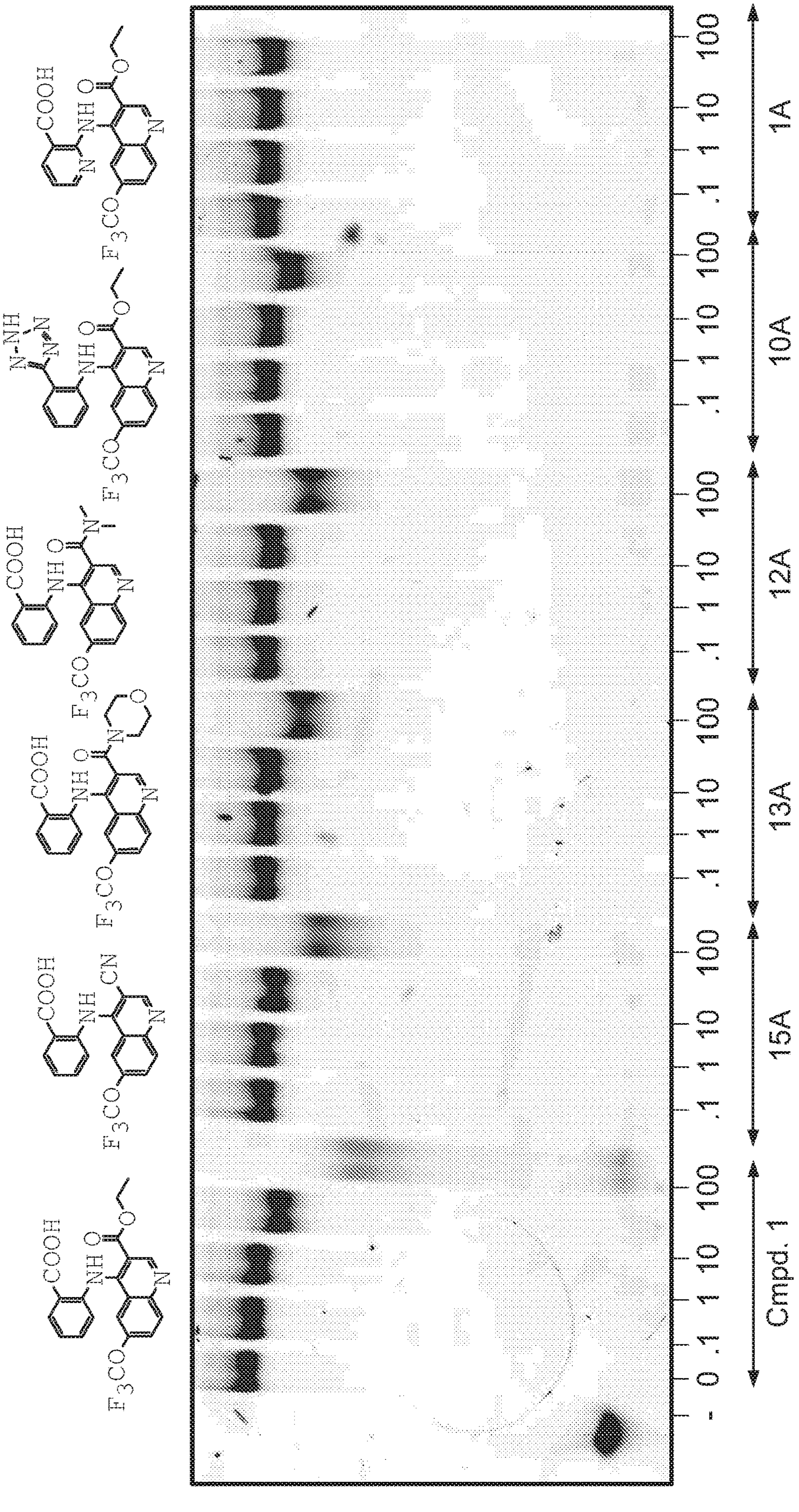
FIG. 3 contains results of RNA oligo-adenylation assay for compounds 15A, 13A, 12A, 10A, and 1A.
Figure 4:
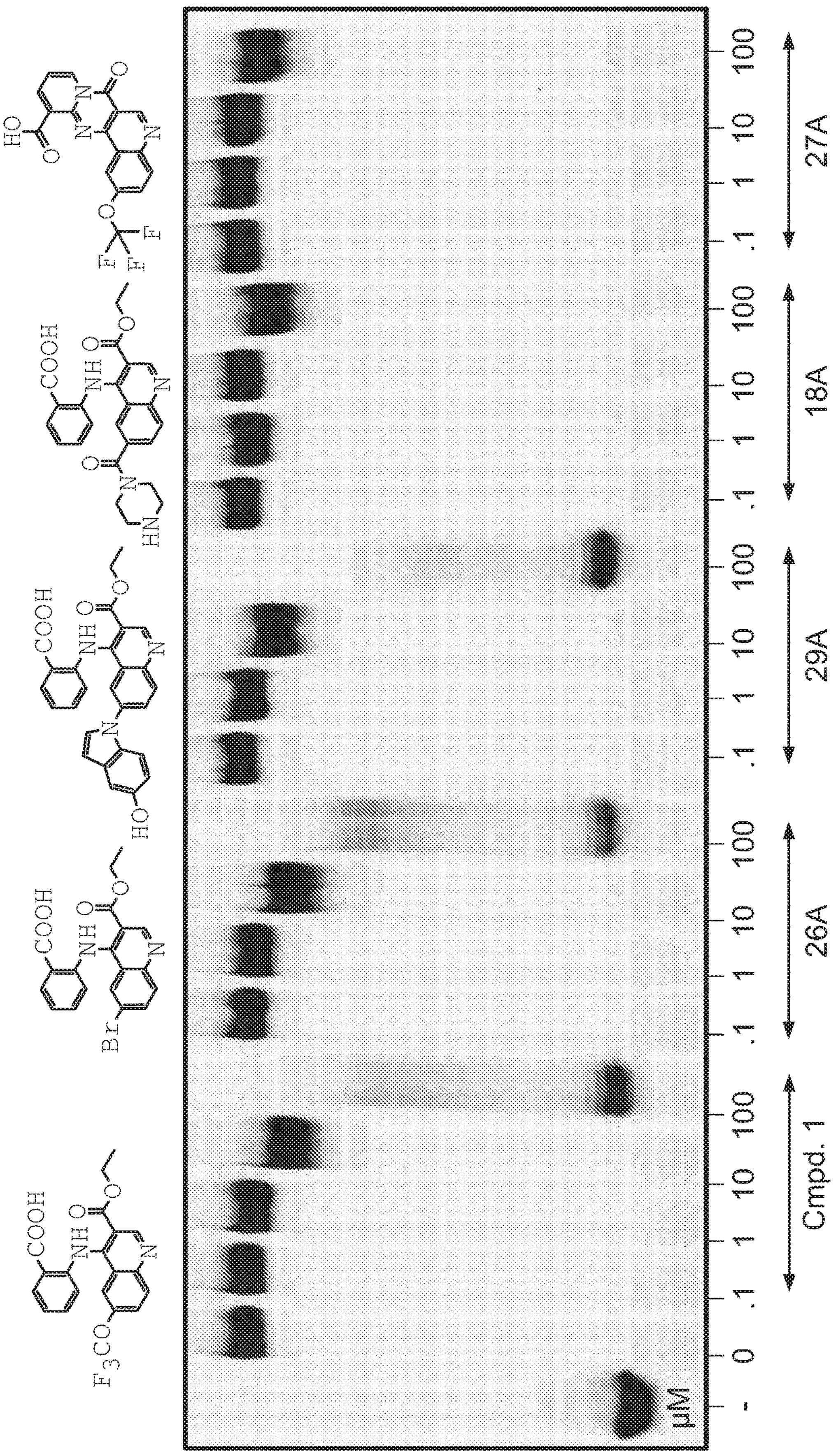
FIG. 4 contains results of RNA oligo-adenylation assay for compounds 26A, 29A, 18A, and 27A.
Figure 5:
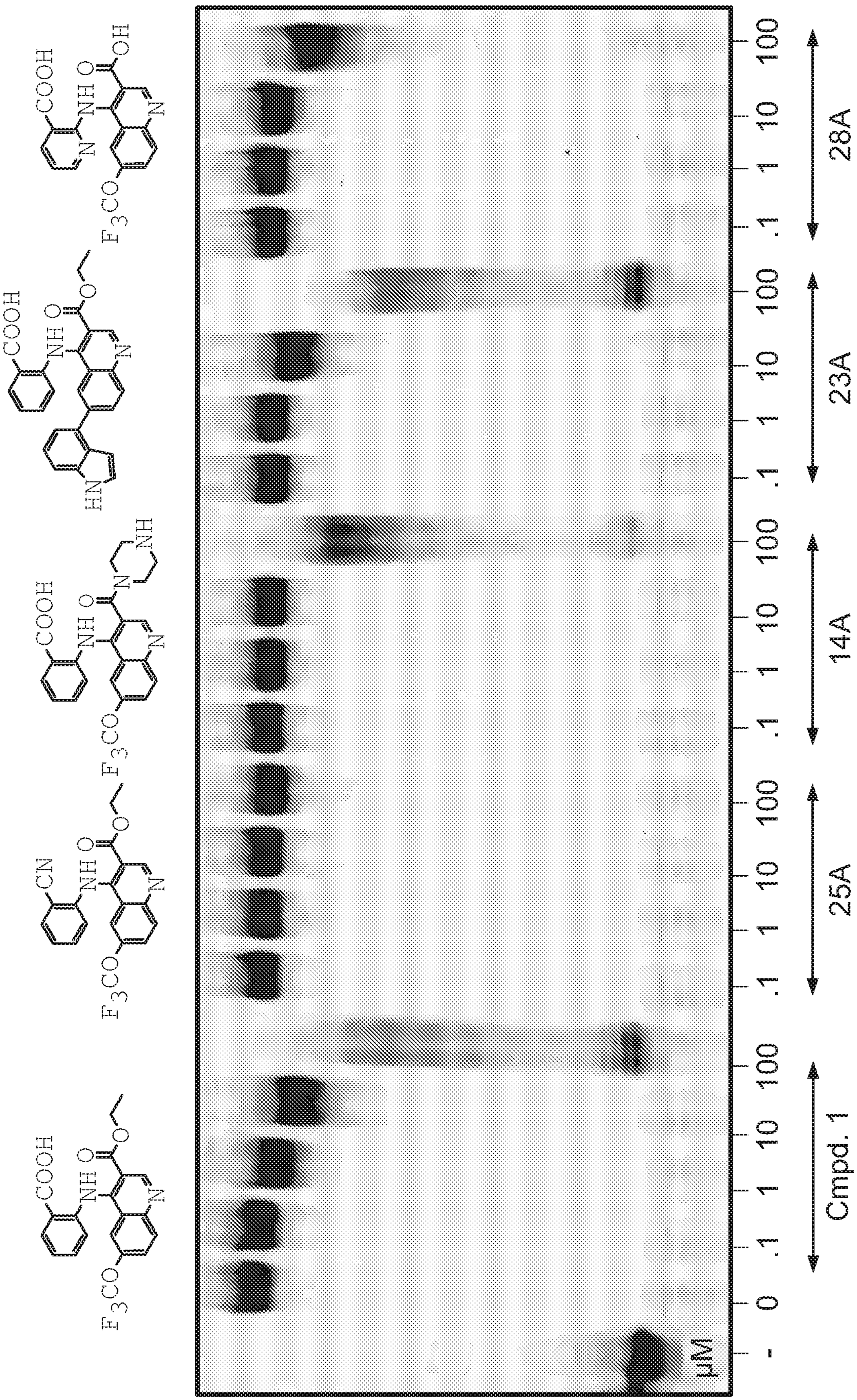
FIG. 5 contains results of RNA oligo-adenylation assay for compounds 25A, 14A, 23A, and 28A.
Figure 6:
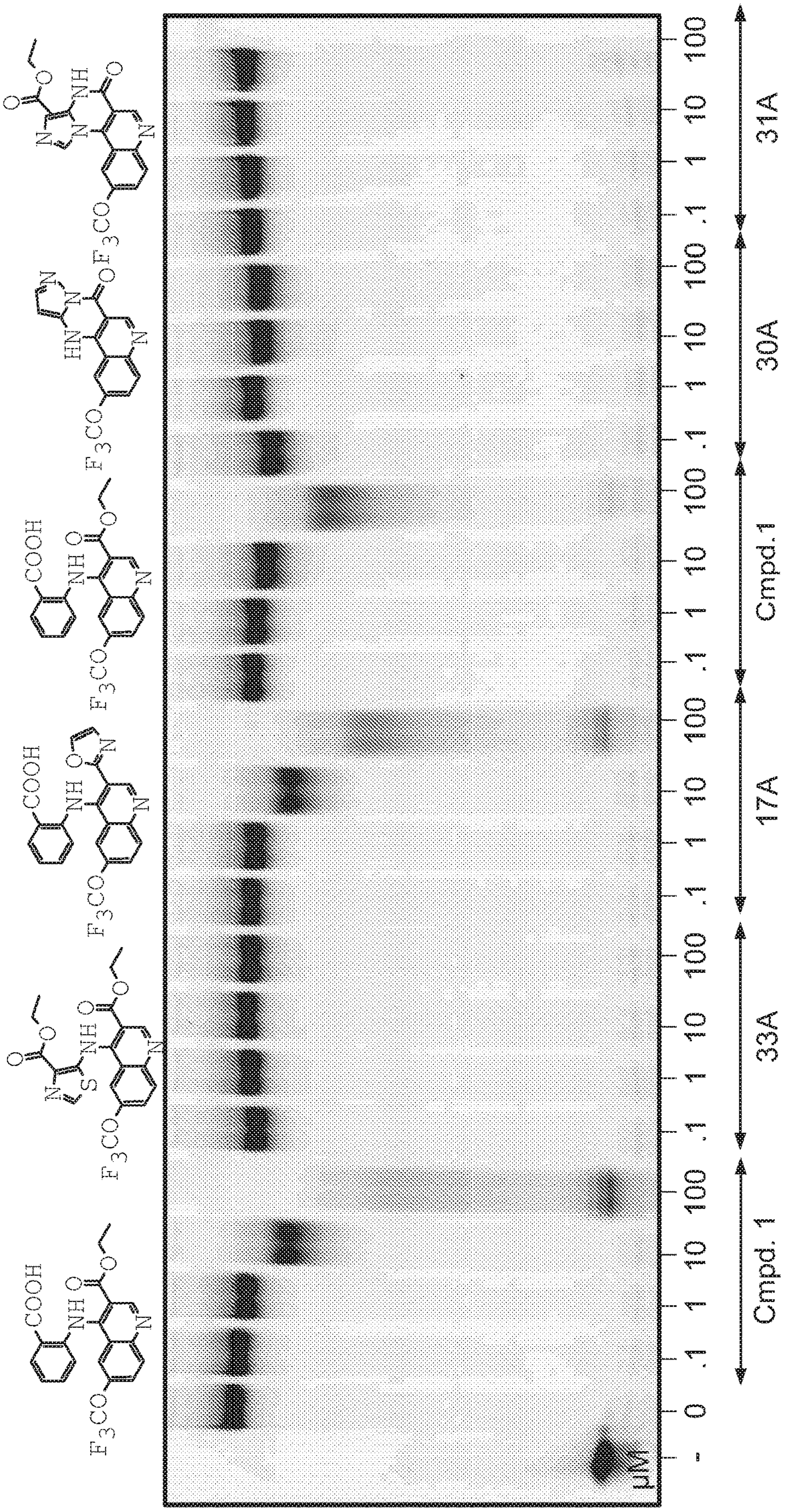
FIG. 6 contains results of RNA oligo-adenylation assay for compounds 33A, 17A, 30A, and 31A.
Figure 7:
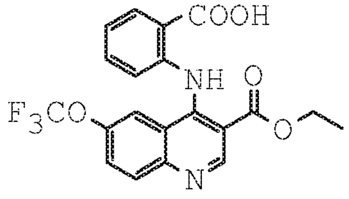
FIG. 7 contains images showing results of RNA oligo-adenylation assay for compounds 1 and 34A.
Figure 7:
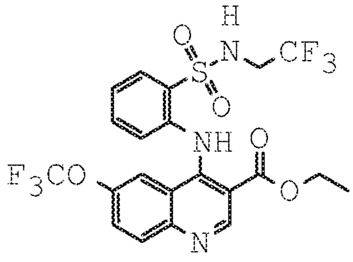
Figure 7:
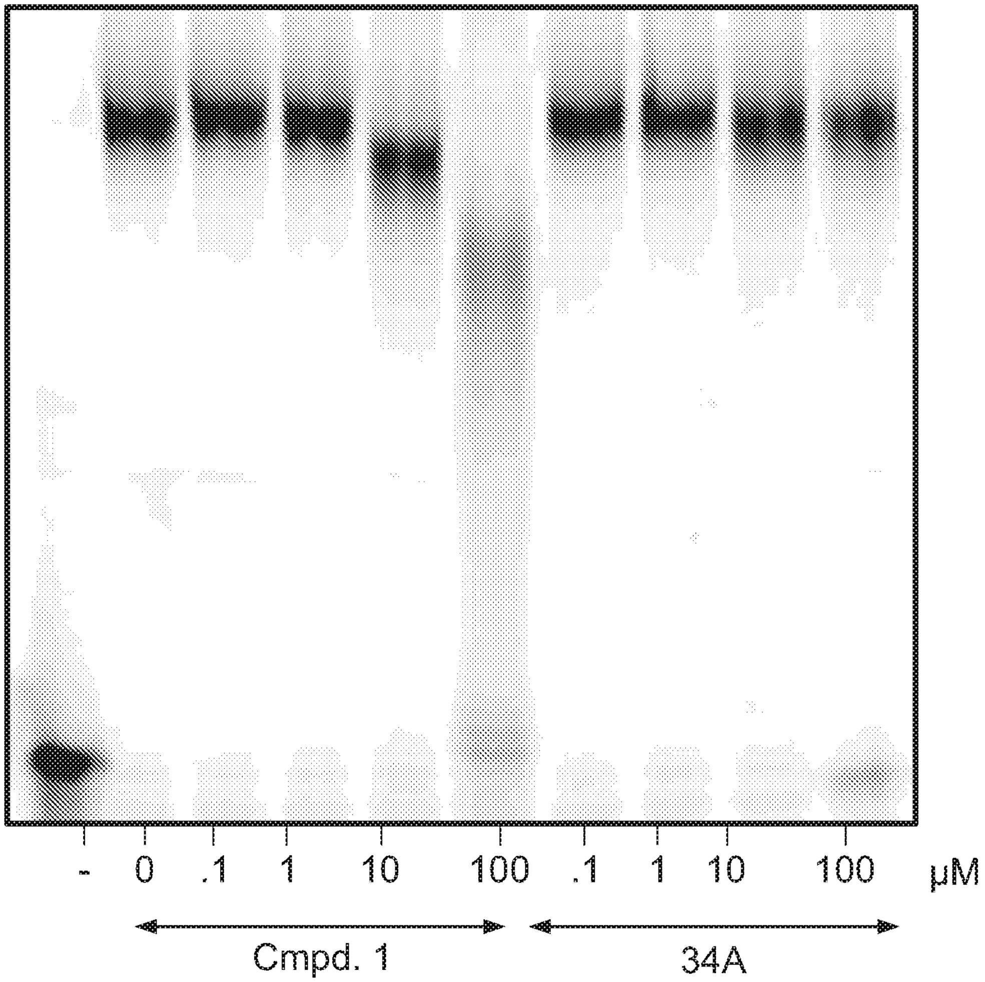
Figure 8:
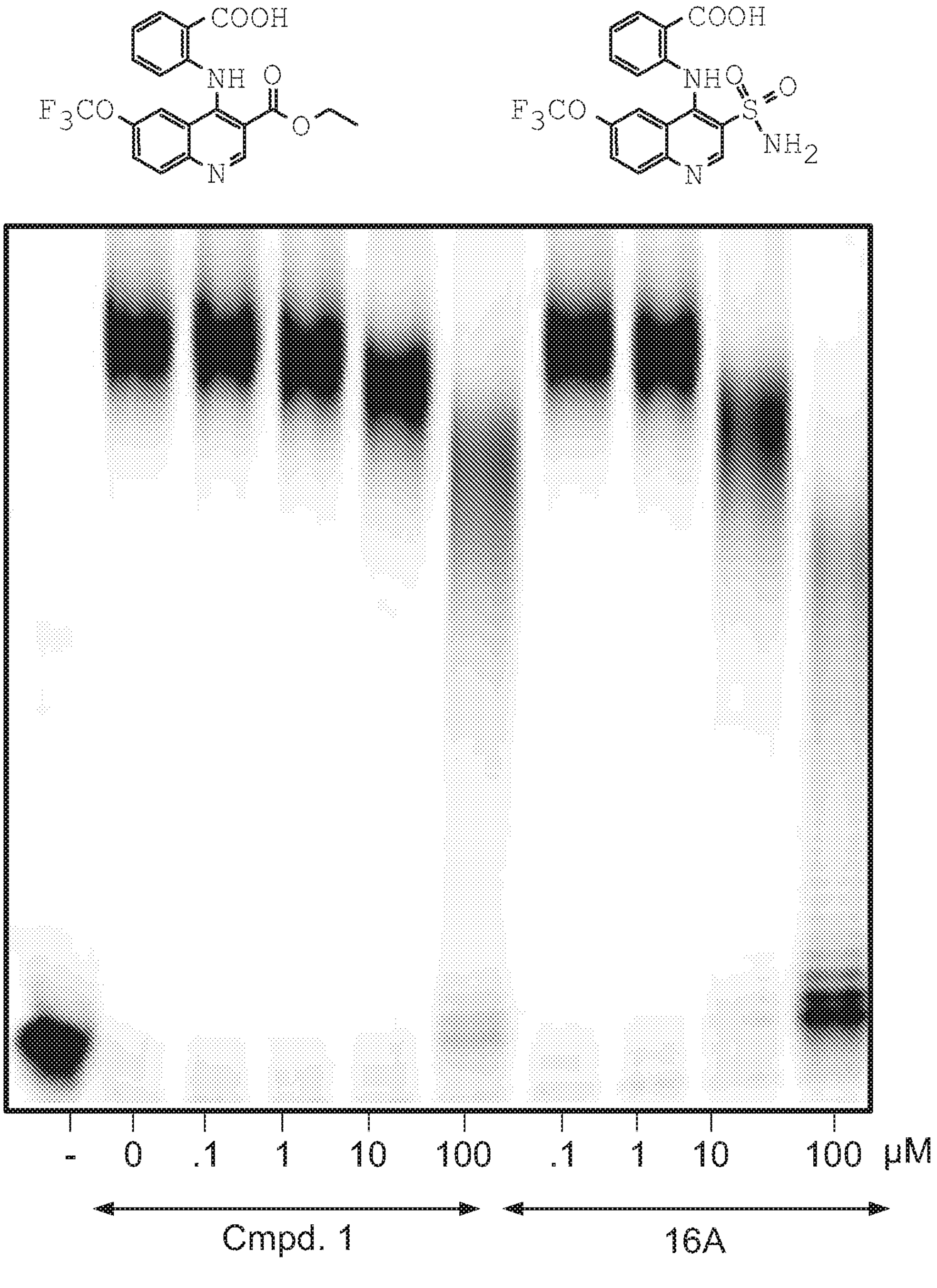
FIG. 8 contains images showing results of RNA oligo-adenylation assay for compounds 1 and 16A.
Figure 9:
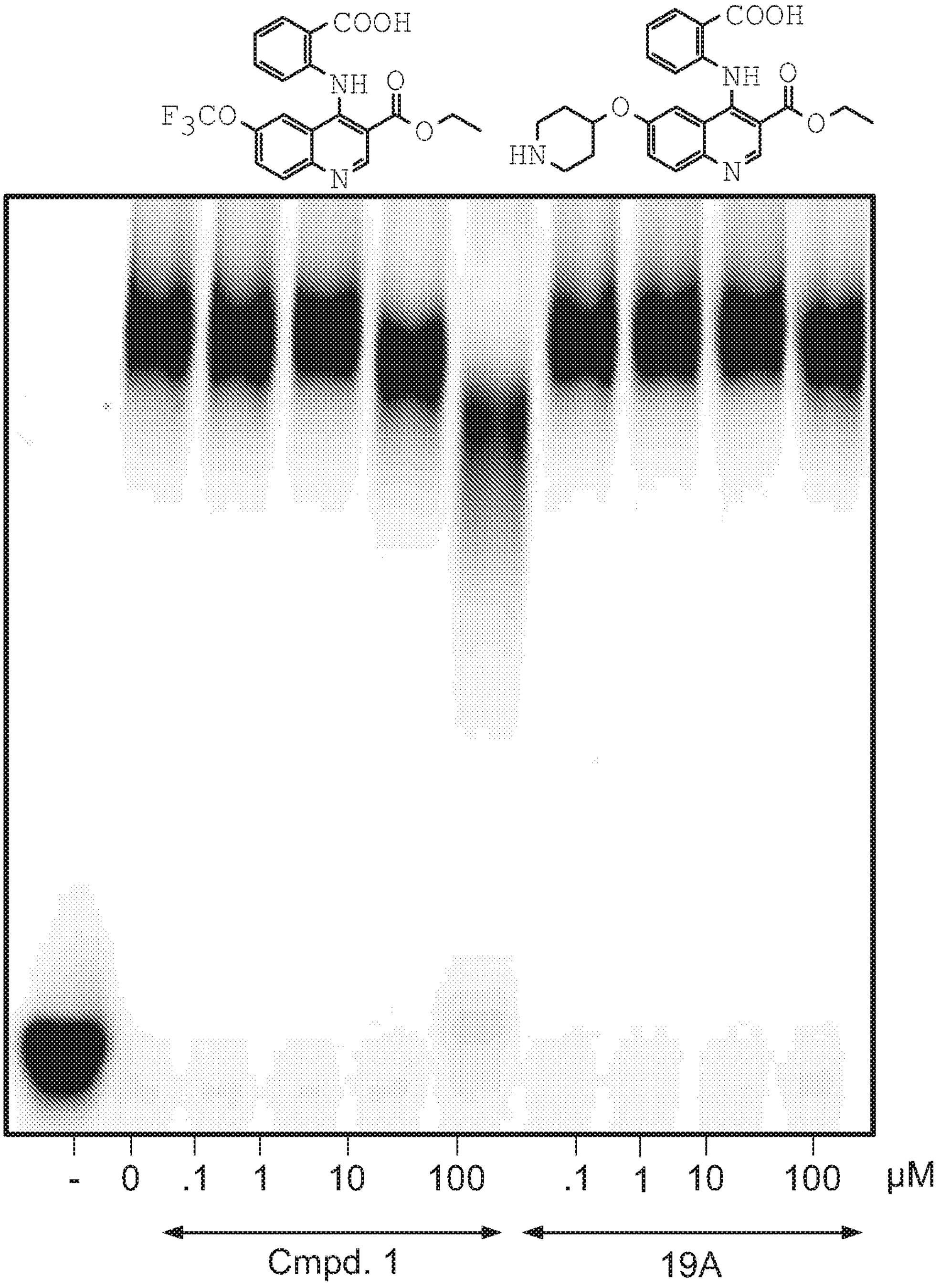
FIG. 9 contains images showing results of RNA oligo-adenylation assay for compounds 1 and 19A.
Figure 10:
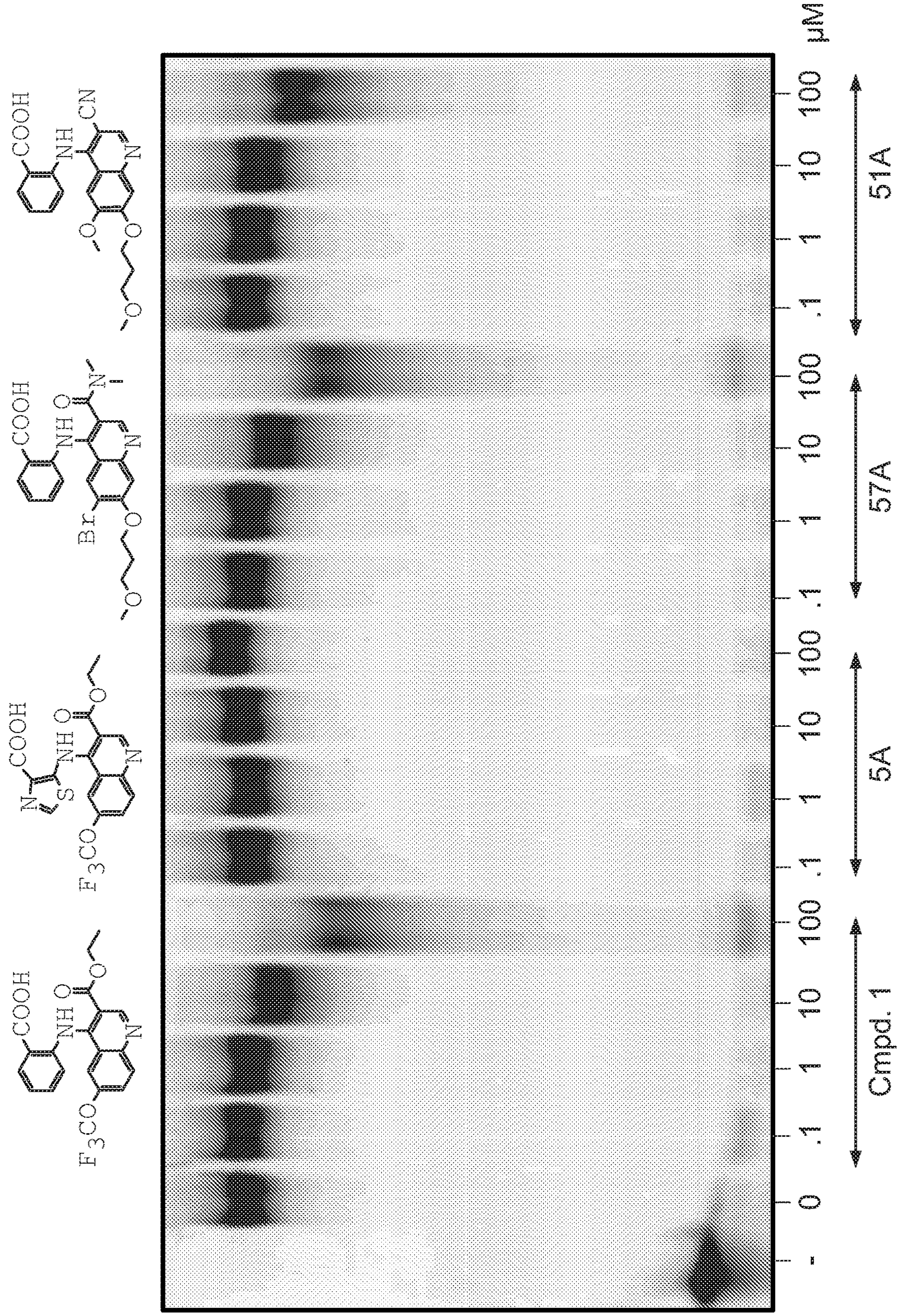
FIG. 10 contains images showing results of RNA oligo-adenylation assay for compounds 1, 5A, 57A, and MA.
Figure 11:
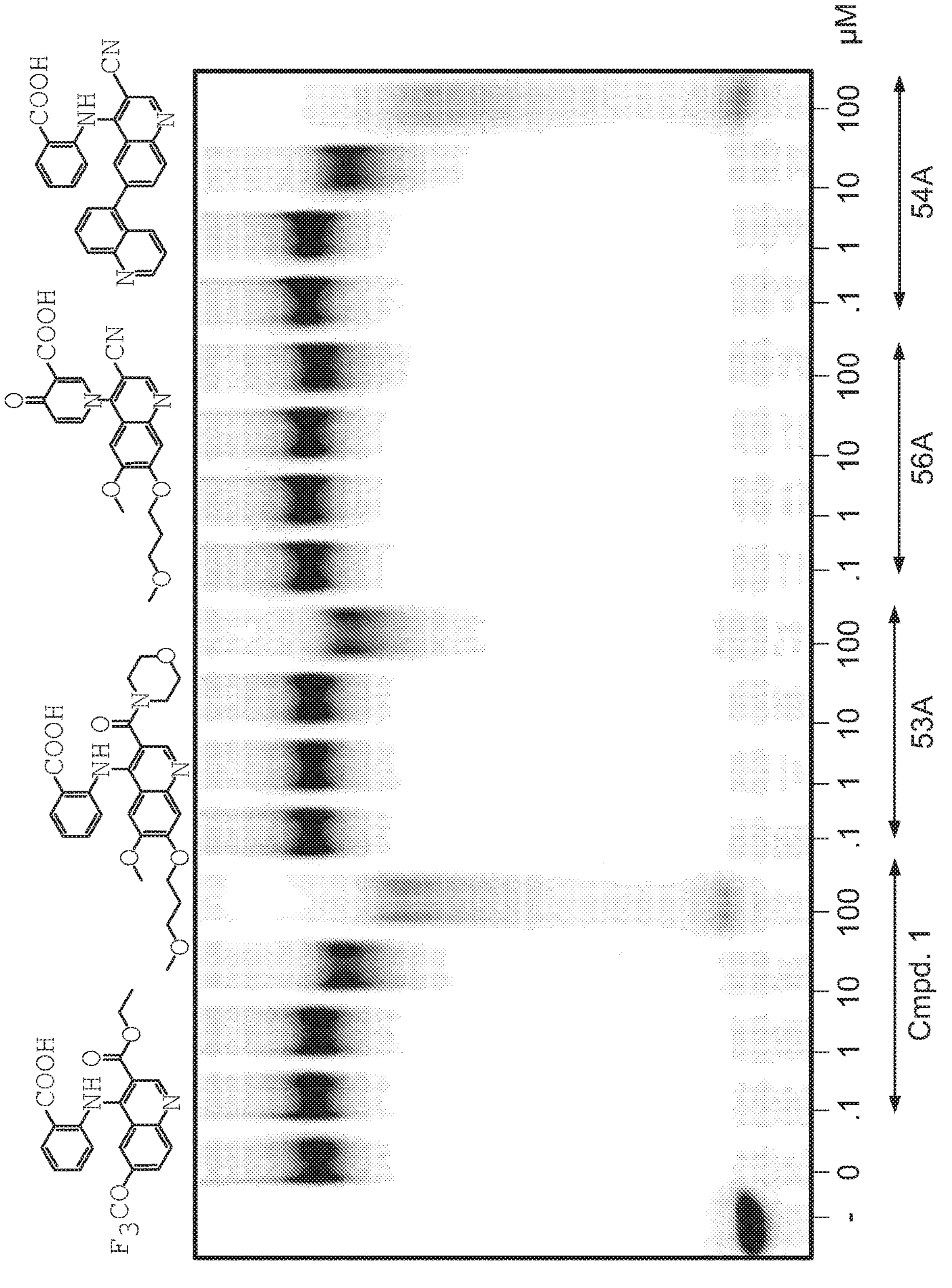
FIG. 11 contains images showing results of RNA oligo-adenylation assay for compounds 1, 53A, 56A, and 54A.
Figure 12:
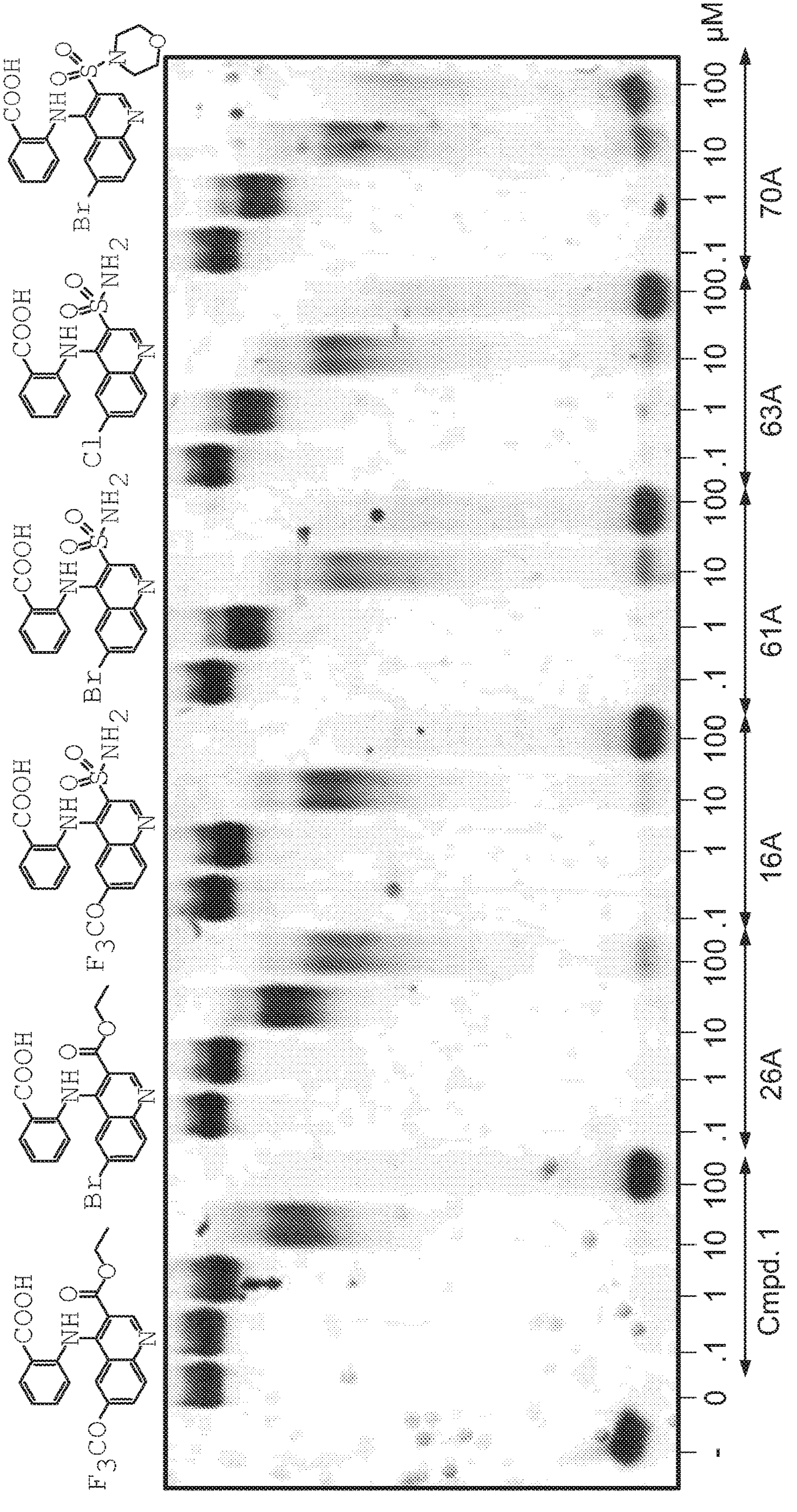
FIG. 12 contains images showing results of RNA oligo-adenylation assay for compounds 1, 26A, 16A, 61A, 63A, and 70A.
Figure 13:
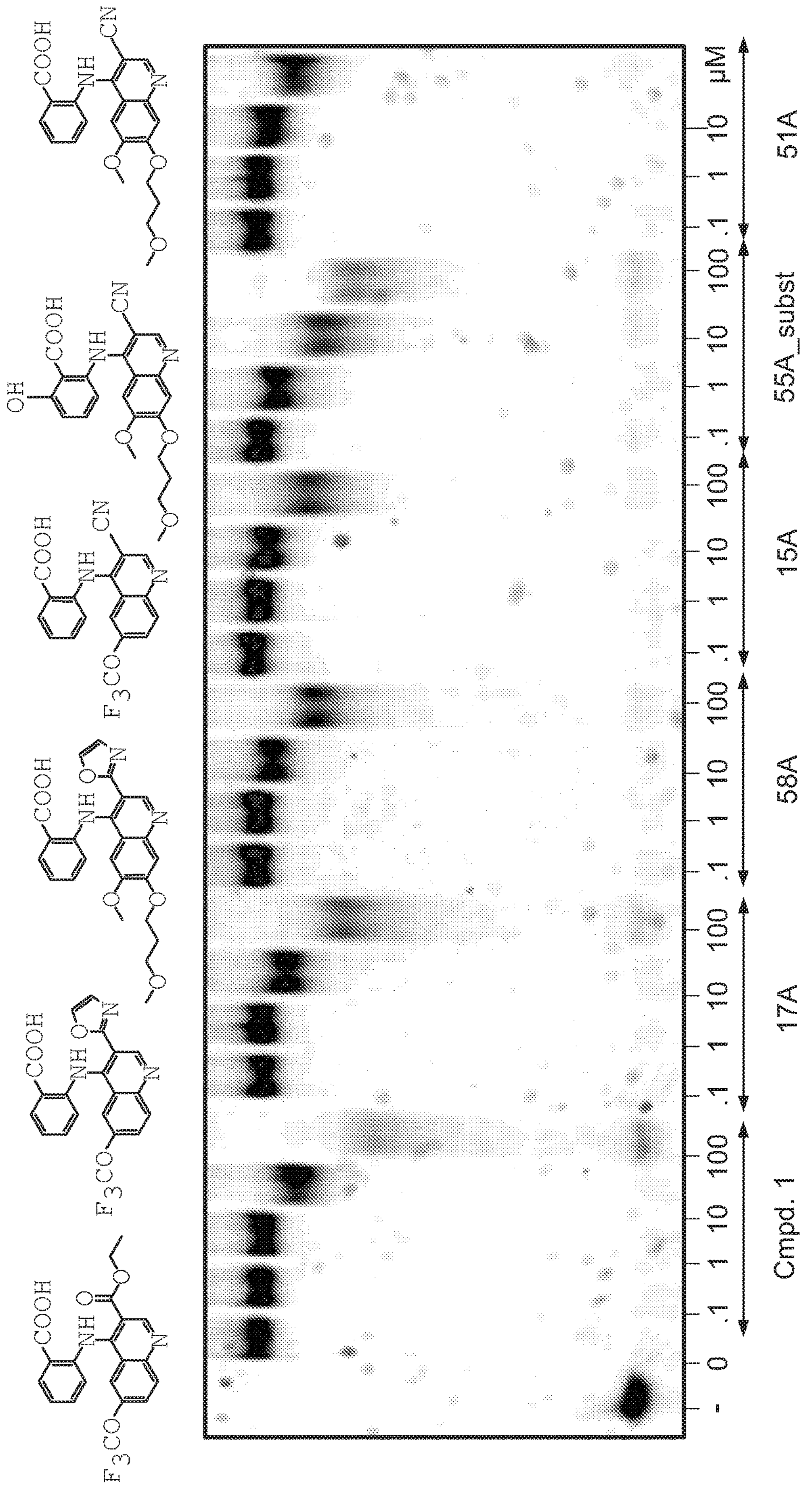
FIG. 13 contains images showing results of RNA oligo-adenylation assay for compounds 1, 17A, 16A, 58A, 15A, 55A, and 51A.
Figure 14:
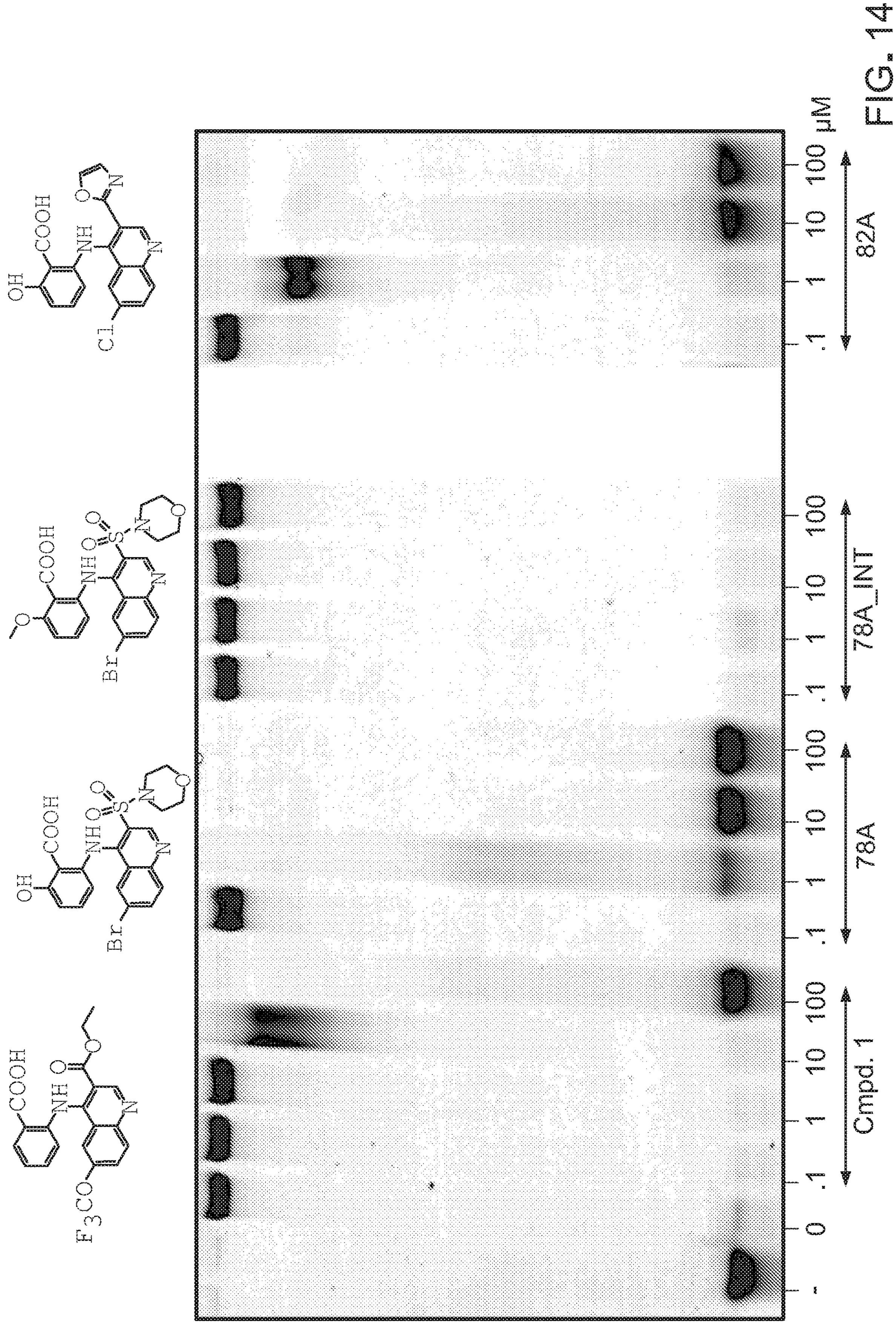
FIG. 14 contains images showing results of RNA oligo-adenylation assay for compounds 1, 78A, 78A-INT, 82A.
Figure 15:
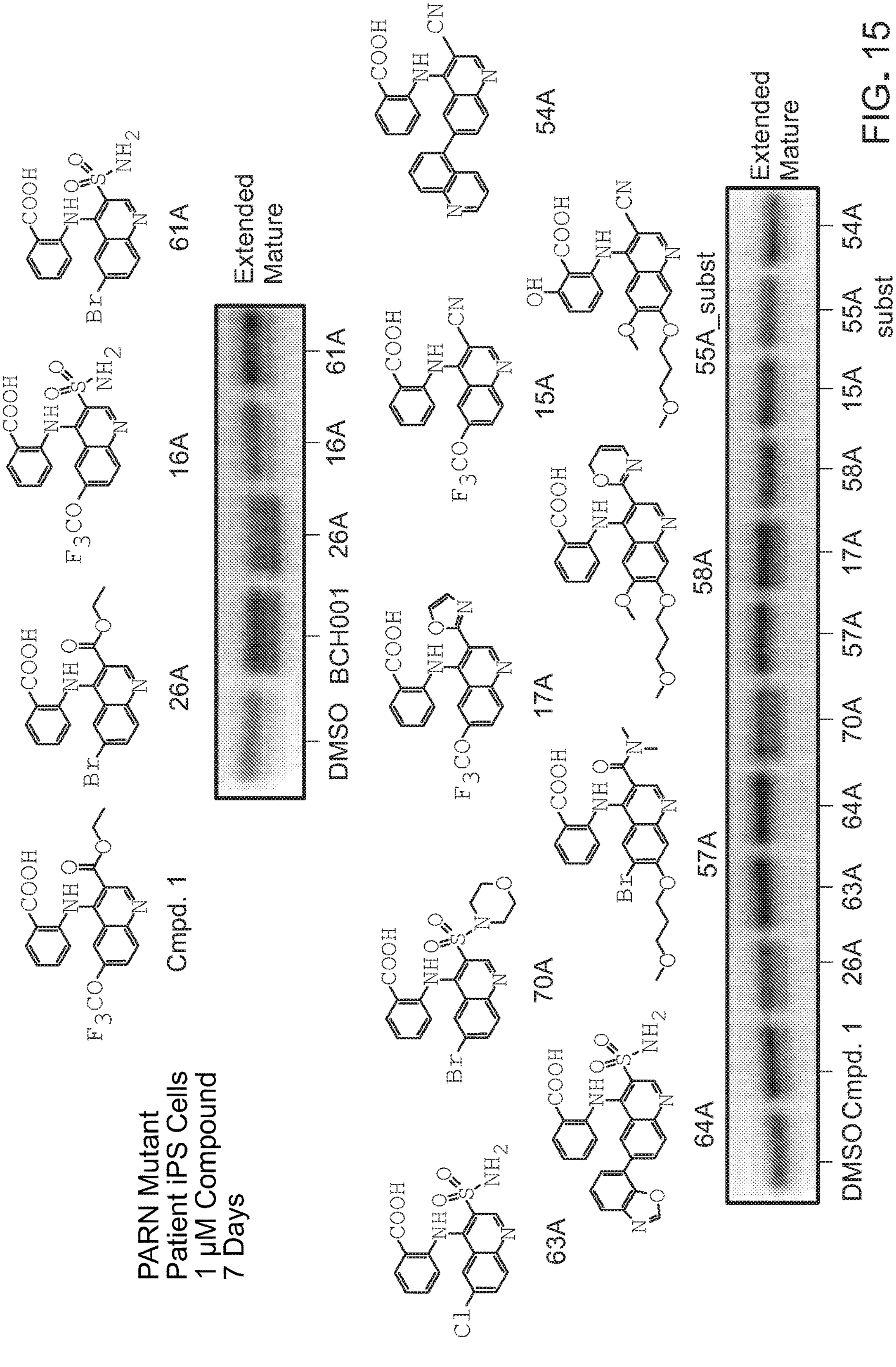
FIG. 15 contains images showing effect of compounds 1, 26A, 16A, 61A, 63A, 64A, 70A, 57A, 17A, 58A, 15A, 55A, and 54A on rapid amplification of TERC cDNA ends.
Figure 16:
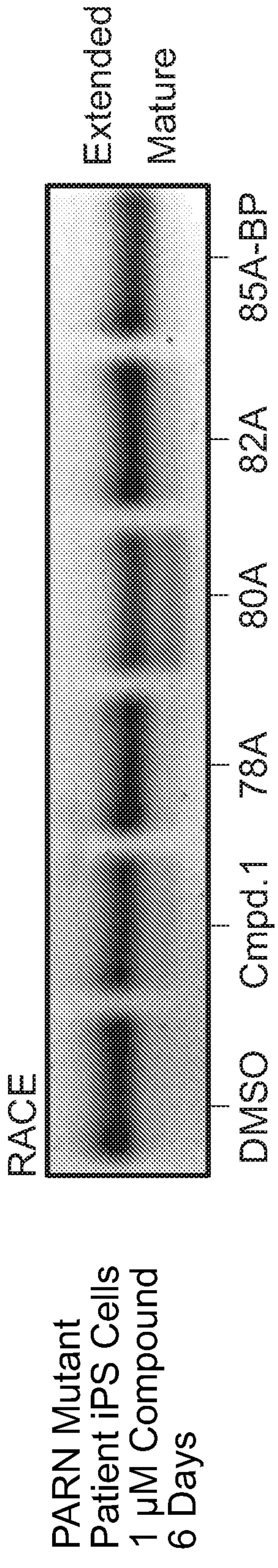
FIG. 16 contains images showing effect of compounds 1, 78A, 80A, 82A, and 85A-BP on rapid amplification of TERC cDNA ends.
Figure 17:
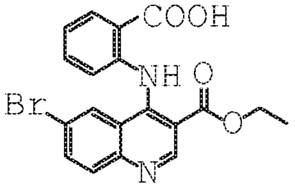
FIG. 17 contains images of northern blots showing effect of compounds 1, 26A, 16A, and 61A on TERC RNA steady state levels.
Figure 17:
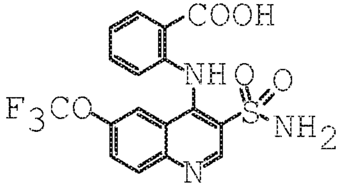
Figure 17:
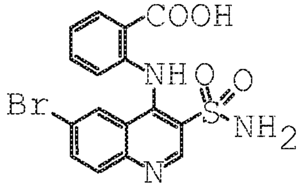
Figure 17:
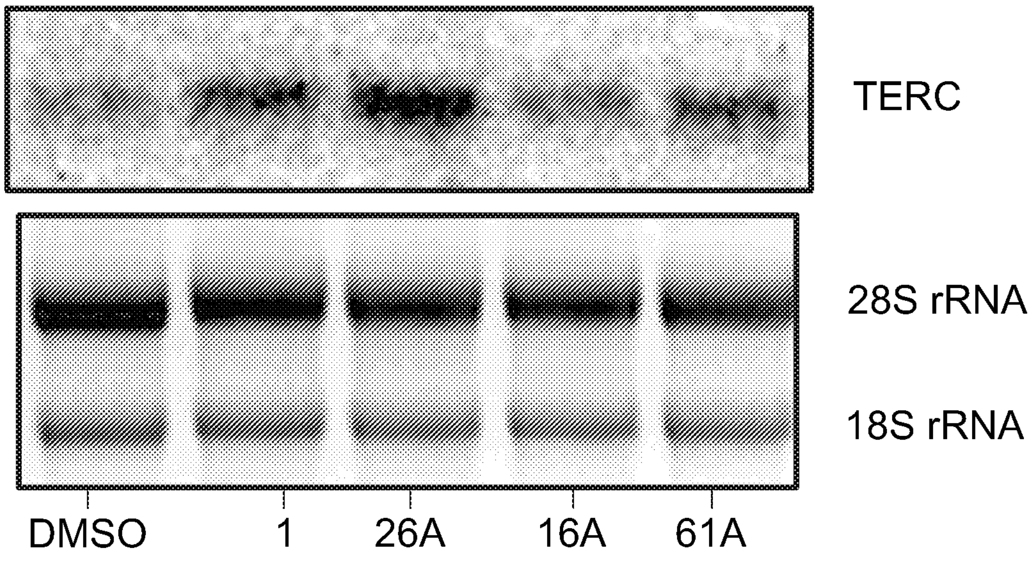
Figure 18:
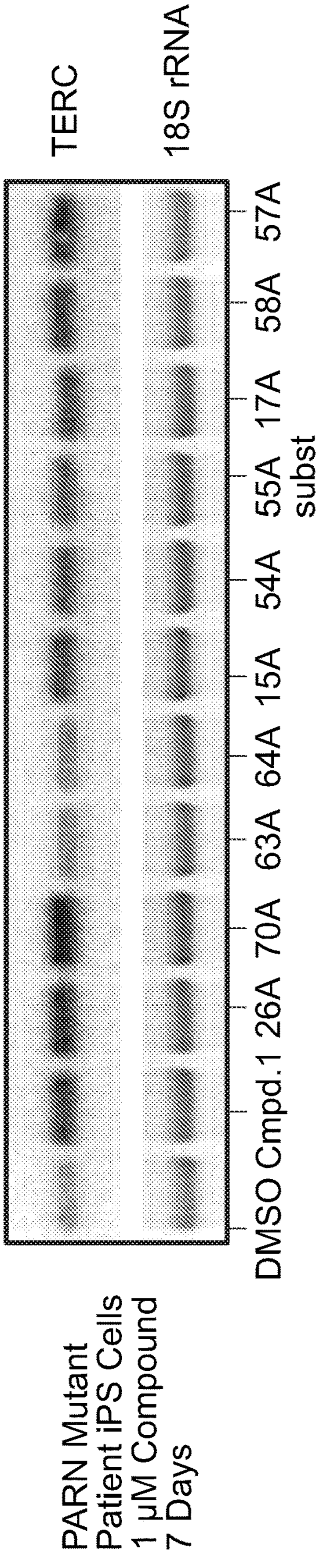
FIG. 18 contains images of northern blots showing effect of compounds 1, 26A, 70A, 63A, 64A, 15A, 55A, 17A, 58A, and 57A on TERC RNA steady state levels.
Figure 19:
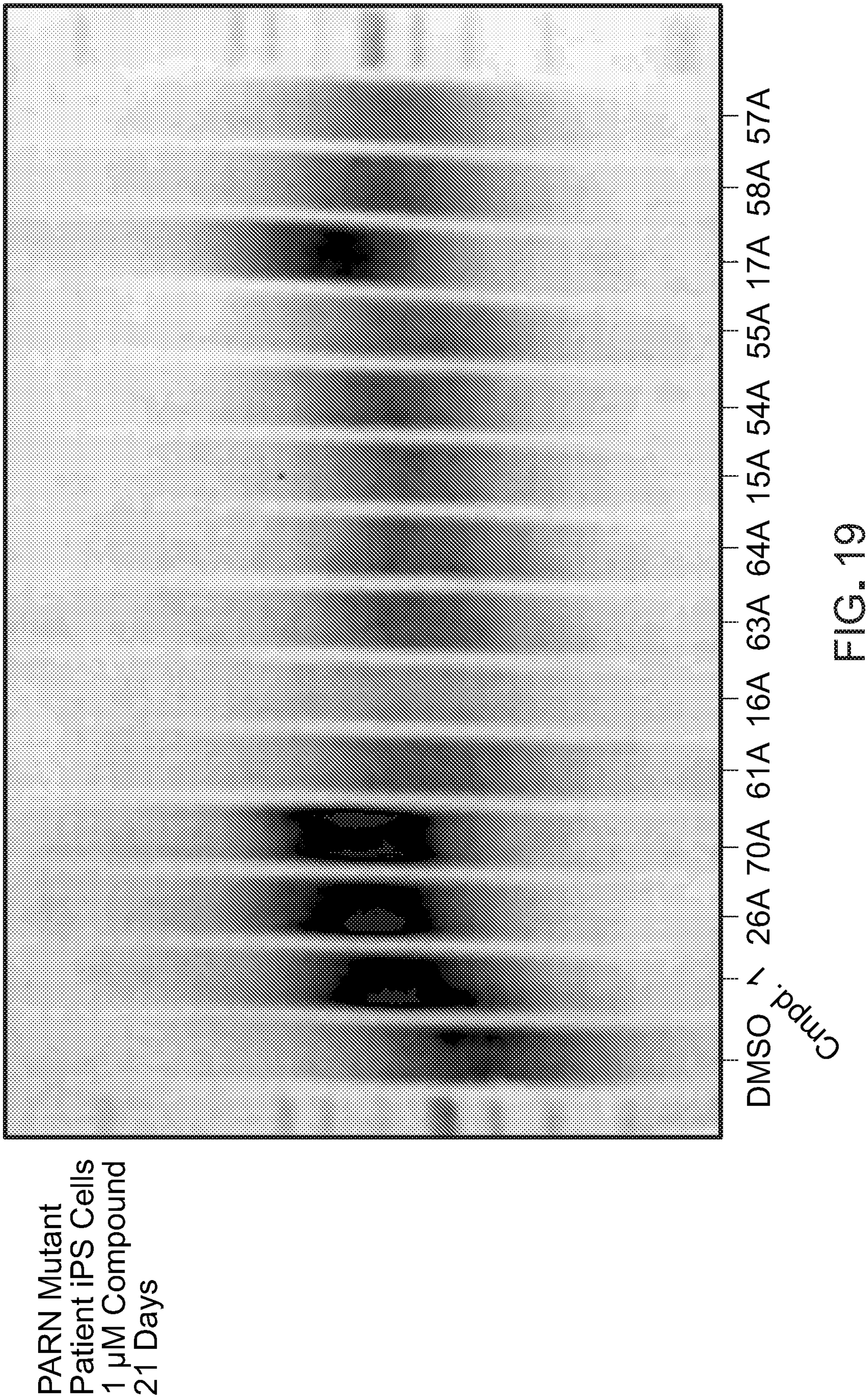
FIG. 19 contains images showing results of effect of compounds 1, 26A, 70A, 61A, 16A, 63A, 64A, 15A, 54A, 55A, 17A, 58A, and 57A on telomere length.
Figure 20:
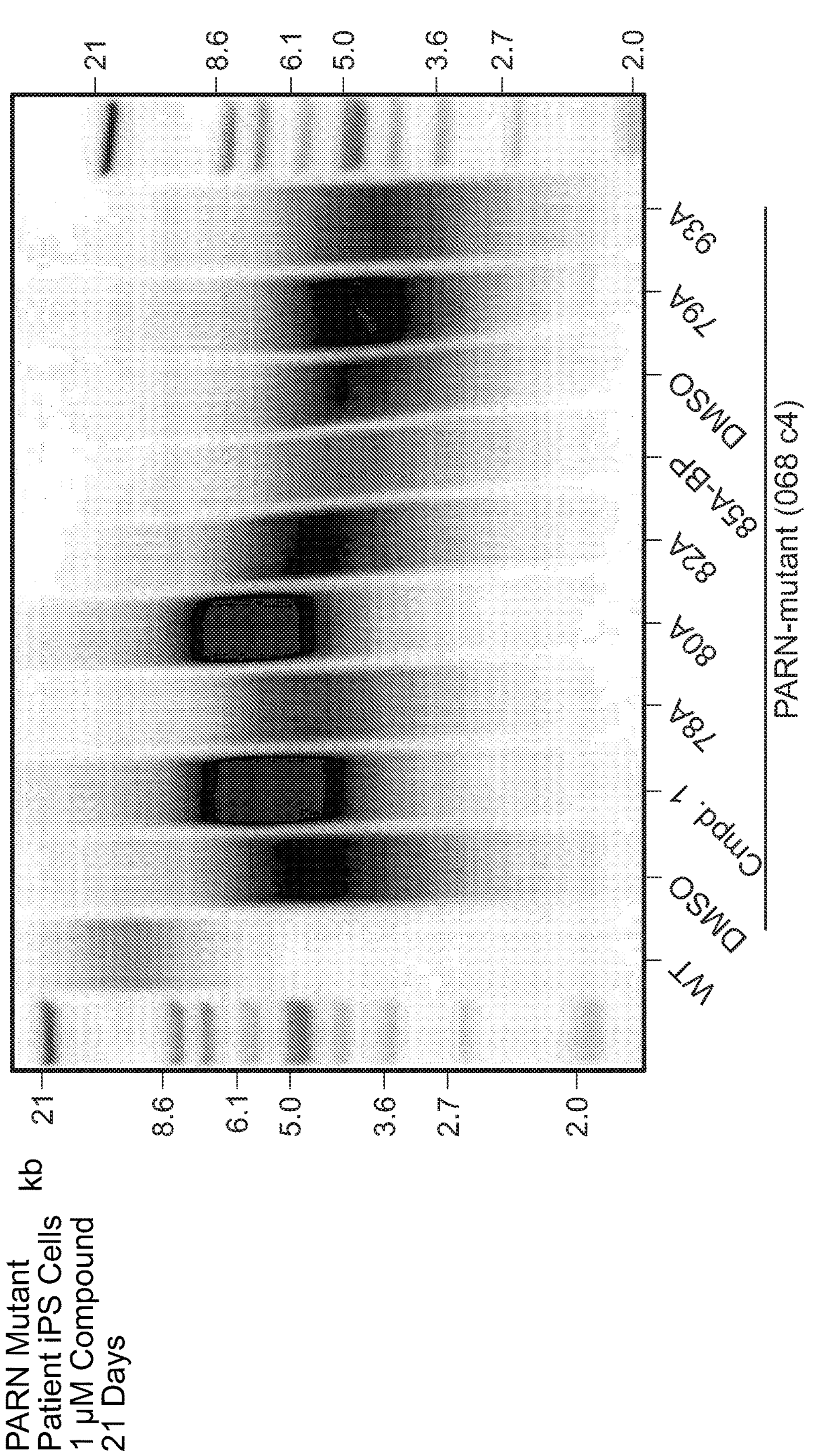
FIG. 20 contains images showing results of effect of compounds 1, 78A, 80A, 82A, 85A-BP, 79A, and 93A on telomere length.

FIG. 2 is a diagram demonstrating the reciprocal regulation of TERC levels by PAPD5 and PARN, and the potential for therapeutic manipulation of telomerase in degenerative or malignant disorders. As shown in FIG. 2, a PAPD5 inhibitor can inhibit PAPD5-mediated oligo-adenylation, which targets nascent TERC RNA for degradation by the exosome, thus increases the level or activity of TERC. In contrast, as PARN counteracts the degradation pathway by removing oligo(A) tails and/or trimming genomically-encoded bases of nascent TERC to yield a mature 3' end, PARN inhibitor will decrease the level or activity of TERC. In addition, increasing the level or activity of PARN can increase the level or activity of TERC, and increasing the level or activity of PAPD5 can decrease the level or activity of TERC.

In one aspect, the present disclosure provides compounds and associated methods of modulating TERC levels in cells. The cells can be, e.g., primary human cells, stem cells, induced pluripotent cells, fibroblasts, etc. In some embodiments, the cells are within a subject (e.g., a human subject). Therefore, the present disclosure provides methods modulating TERC levels in cells in vivo. In some embodiments, the cells can be isolated from a sample obtained from the subject, e.g., the cells can be derived from any part of the body including, but not limited to, skin, blood, and bone marrow. The cells can also be cultured in vitro using routine methods with commercially available cell reagents (e.g., cell culture media). In some embodiments, the cells are obtained from a subject, having a telomere disease, being at risk of developing a telomere disease, or being suspected of having a telomere disease. In some embodiments, the subject has no overt symptoms.

The level or activity of TERC can be determined by various means, e.g., by determining the size of telomere in the cell, by determining the stability of TERC, by determining the amount of RNA, by measuring the activity of telomerase function, and/or by measuring oligo-adenylated (oligo(A)) forms of TERC. TERC stability can be assessed, e.g., by measuring the TERC decay rates. Oligo-adenylated (oligo(A)) forms of TERC can be measured, e.g., using rapid amplification of cDNA ends (RACE) coupled with targeted deep sequencing (e.g., at the TERC 3' end) to detect oligo-adenylated (oligo(A)) forms of TERC. The size of a telomere can be measured, e.g., using Flow-fluorescent in-situ hybridization (Flow-FISH) technique.

In some embodiments, the modulation of endogenous TERC is performed. Such methods can include, e.g., altering telomerase activity, e.g., increasing or decreasing telomerase activity. The methods can involve reducing RNA expression in cells, e.g., non-coding RNA in TERC. Telomerase activity can be, e.g., regulated by modulating TERC levels by contacting cells with test compounds known to modulate protein synthesis. The methods may involve targeting post-processing activity of the endogenous TERC locus. These methods involve manipulating TERC including identifying subjects with genetic mutation (e.g., mutation in PARN), isolating cells (e.g., fibroblast), and treating cells with agents that modulate TERC levels. The methods may also involve manipulating TERC including identifying subjects with genetic mutation (e.g., mutation in PARN) and treating the subject with agents that modulate TERC levels. Subject with genetic mutation (e.g., PARN mutation) may be identified by any diagnostic means generally known in the art for that purpose.

The present disclosure shows that TERC levels are modulated at the post-transcriptional level. Thus, in one aspect, methods of modulating the level or activity of TERC involve modulating the level or activity of PARN and PAPD5.

In some embodiments, the methods involve an agent that modulates the level or activity of PARN, thereby altering the level or activity of TERC. In some cases, the agent increases the level or activity of PARN. Alternatively, the agent decreases the level or activity of PARN. In some embodiments, the methods involve an agent that modulates the level or activity of PAPD5, thereby altering the level or activity of TERC. In some embodiments, the agent increases the level or activity of PAPD5. Alternatively, the agent decreases the level or activity of PAPD5 (e.g., PAPD5 inhibitors). In some embodiments, the agent is any one of compounds described herein.

Accordingly, the present application provides compounds that modulate TERC levels and are thus useful in treating a broad array of telomere diseases or disorders associated with telomerase dysfunction, e.g., dyskeratosis congenita, aplastic anemia, pulmonary fibrosis, idiopathic pulmonary fibrosis, hematological disorder, hepatic disease (e.g., chronic liver disease), and cancer, e.g., hematological cancer and hepatocarcinoma, etc.

In some embodiments, in order to successfully treat a telomere disease, a therapeutic agent has to selectively inhibit PAPD5, while not inhibiting PARN or other polynucleotide polymerases. A PAPD5 inhibitor that is not selective and concurrently inhibits other polymerases, may not be useful in treating telomere diseases; that is, the fact that a compound is a PAPD5 inhibitor (e.g., non-selective inhibitor) is not indicative of its usefulness in prevention and treatment of telomere diseases. The selectivity to PAPD5 as opposed to other polymerases is required for potency. In some embodiments, the compounds of the present application are selective and specific inhibitors of PAPD5 and do not inhibit PARN or other polymerases. In some embodiments, it was surprisingly discovered that in order to successfully treat a telomere disease, a therapeutic agent has to be a selective inhibitor of PAPD5. In other words, a successful therapeutic agent has to inhibit PAPD5 while not substantially inhibiting PARN and/or other polynucleotide polymerases. In some embodiments, a PAPD5 inhibitor that is not selective to PAPD5 and concurrently inhibits other polymerases, may not be useful in treating telomere diseases; that is, the fact that a compound is a PAPD5 inhibitor (e.g., non-selective inhibitor) is not indicative of its usefulness in prevention and treatment of telomere diseases. The selectivity to PAPD5 as opposed to other polymerases is required for potency. In some embodiments, the compounds of the present application are selective and specific inhibitors of PAPD5 and do not substantially inhibit PARN or other polymerases.

Telomere Diseases

Telomere diseases or disorders associated with telomerase dysfunction are typically associated with changes in the size of telomere. Many proteins and RNA components are involved in the telomere regulatory pathway, including TERC, PARN and PAPD5 (also known as TRF4-2). FIGS. 1 and 2 show how these proteins or RNA components work in the regulatory pathway and how they are related to telomere diseases.

Among these telomere diseases is dyskeratosis congenita (DC), which is a rare, progressive bone marrow failure syndrome characterized by the triad of reticulated skin hyperpigmentation, nail dystrophy, and oral leukoplakia. Early mortality is often associated with bone marrow failure, infections, fatal pulmonary complications, or malignancy. Short-term treatment options for bone marrow failure in patients include anabolic steroids (e.g., oxymetholone), granulocyte macrophage colony-stimulating factor, granulocyte colony-stimulating factor, and erythropoietin. Other treatments include hematopoietic stem cell transplantation (SCT).

Idiopathic pulmonary fibrosis is a chronic and μLtimately fatal disease characterized by a progressive decline in lung function. In some appropriate cases, the following agents are used to treat idiopathic pulmonary fibrosis: nintedanib, a tyrosine kinase inhibitor that targets multiple tyrosine kinases, including vascular endothelial growth factor, fibroblast growth factor, and PDGF receptors; and pirfenidone. Other treatments include lung transplantation. In some cases, lung transplantation for idiopathic pulmonary fibrosis (I-IPF) has been shown to confer a survival benefit over medical therapy.

Generally, a method of treating a telomere disease includes administering a therapeutically effective amount of a compound described herein, to a subject who is in need of, or who has been determined to be in need of, such treatment.

Cancer

The present disclosure also provides compounds, compositions, and methods for treating pre-leukemic conditions, pre-cancerous conditions, dysplasia and/or cancers. Pre-leukemic conditions include, e.g., Myelodysplastic syndrome, and smoldering leukemia. Dysplasia refers to an abnormality of development or an epithelial anomaly of growth and differentiation, including e.g., hip dysplasia, fibrous dysplasia, and renal dysplasia, Myelodysplastic syndromes, and dysplasia of blood-forming cells.

A precancerous condition or premalignant condition is a state of disordered morphology of cells that is associated with an increased risk of cancer. If left untreated, these conditions may lead to cancer. Such conditions are can be dysplasia or benign neoplasia.

As used herein, the term "cancer" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. The term "tumor" as used herein refers to cancerous cells, e.g., a mass of cancerous cells.

Many cancer cells have abnormal telomeres. Thus, treatments described herein (e.g., PAPD5 inhibitors) can also be used to treat cancers. Cancers that can be treated or diagnosed using the methods described herein include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

In some embodiments, the methods described herein are used for treating or diagnosing a carcinoma in a subject. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the cancer is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation. Cancers treatable using the methods described herein are cancers that have increased levels of TERC, an increased expression of genes such as TERC and/or TERT, or increased activity of a telomerase relative to normal tissues or to other cancers of the same tissues.

In some embodiments, the tumor cells isolated from subjects diagnosed with cancer can be used to screen test for compounds that alter TERC levels. In some embodiments, the tumor cells can be used to screen test compounds that alter the expressive or activity of PARN or PAPD5. The cancer cells used in the methods can be, e.g., cancer stem cells. Such methods can be used to screen a library of test compounds, e.g., compounds that alter or change expression of protein or RNA of telomere-associated genes (e.g., TERC, PARN, PAPD5/PAPD5).

In some embodiments, agents that decrease the level or activity of TERC (e.g., PANR inhibitors) are used to treat cancer. In some embodiments, these agents are used in combination with other cancer treatments, e.g., chemotherapies, surgery, or radiotherapy.

Aging

Telomeres shorten over the human life span. In large population based studies, short or shortening telomeres are associated with numerous diseases. Thus, telomeres have an important role in the aging process, and can contribute to various diseases. The role of telomeres as a contributory and interactive factor in aging, disease risks, and protection is described, e.g., in Blackburn, Elizabeth H., Elissa S. Epel, and Jue Lin. "Human telomere biology: A contributory and interactive factor in aging, disease risks, and protection," Science 350.6265 (2015): 1193-1198, which is incorporated by reference in its entirety.

Telomere attrition is also a major driver of the senescence associated response. In proliferating human cells, progressive telomere erosion µLtimately exposes an uncapped free double-stranded chromosome end, triggering a permanent DNA damage response (DDR). The permanent DNA damage response has a profound impact on cell functions. For example, the damage sensor ataxia telangiectasia mutated (ATM) is recruited to uncapped telomeres, leading to the stabilization of tumor suppressor protein 53 (p53) and upregulation of the p53 transcriptional target p21. In turn, p21 prevents cyclin-dependent kinase 2 (CDK2)-mediated inactivation of RB, subsequently preventing entry into the S phase of the cell cycle. Cellular senescence contributes to various age-related diseases, e.g., glaucoma, cataracts, diabetic pancreas, type 2 diabetes mellitus, atherosclerosis, osteoarthritis, inflammation, atherosclerosis, diabetic fat, cancer, pulmonary fibrosis, and liver fibrosis, etc. The permanent DNA damage response and age-related diseases are described, e.g., in Childs, Bennett G., et al. "Cellular senescence in aging and age-related disease: from mechanisms to therapy." Nature medicine 21.12 (2015): 1424, which is incorporated herein by reference in its entirety.

As used herein, the term "aging" refers to degeneration of organs and tissues over time, in part due to inadequate replicative capacity in stem cells that regenerate tissues over time. Aging may be due to natural disease processes that occur over time, or those that are driven by cell intrinsic or extrinsic pressures that accelerate cellular replication and repair. Such pressures include natural chemical, mechanical, and radiation exposure; biological agents such as bacteria, viruses, fungus, and toxins; autoimmunity, medications, chemotherapy, therapeutic radiation, cellular therapy. As the telomere is an important factor in aging and disease development, the methods described herein can be used for treating, mitigating, or minimizing the risk of, a disorder associated with aging (and/or one or more symptoms of a disorder associated with aging) in a subject. The methods include the step of identifying a subject as having, or being at risk of a disorder associated with aging; and administering a pharmaceutical composition to the subject. In some embodiments, the pharmaceutical composition includes an agent that alters the level or activity of TERC, e.g., increase the level or activity of TERC.

As used herein, the term "disorders associated with aging" or "age-related diseases" refers to disorders that are associated with the ageing process. Exemplary disorders include, e.g., macular degeneration, diabetes mellitus (e.g., type 2 diabetes), osteoarthritis, rheumatoid arthritis, sarcopenia, cardiovascular diseases such as hypertension, atherosclerosis, coronary artery disease, ischemia/reperfusion injury, cancer, premature death, as well as age-related decline in cognitive function, cardiopulmonary function, muscle strength, vision, and hearing.

The disorder associated with aging can also be a degenerative disorder, e.g., a neurodegenerative disorder. Degenerative disorders that can be treated or diagnosed using the methods described herein include those of various organ systems, such as those affecting brain, heart, lung, liver, muscles, bones, blood, gastrointestinal and genito-urinary tracts. In some embodiments, degenerative disorders are those that have shortened telomeres, decreased levels of TERC, and/or decreased levels of telomerase relative to normal tissues. In some embodiments, the degenerative disorder is a neurodegenerative disorder. Exemplary neurodegenerative disorders include Motor Neuron Disease, Creutzfeldt-Jakob disease, Machado-Joseph disease, Spinocerebellar ataxia, Multiple sclerosis (MS), Parkinson's disease, Alzheimer's disease, Huntington's disease, hearing and balance impairments, ataxias, epilepsy, mood disorders such as schizophrenia, bipolar disorder, and depression, dementia, Pick's Disease, stroke, CNS hypoxia, cerebral senility, and neural injury such as head trauma. Recent studies have shown the association between shorter telomeres and Alzheimer's disease. The relationship between telomere length shortening and Alzheimer's disease is described., e.g., in Zhan, Yiqiang, et al. "Telomere length shortening and Alzheimer disease—a Mendelian Randomization Study," JAMA neurology 72.10 (2015): 1202-1203, which is incorporated by reference in its entirety. In some embodiments, the neurodegenerative disorder is dementia, e.g., Alzheimer's disease.

It has also been determined that there an inverse association between leucocyte telomere length and risk of coronary heart disease. This relationship is described, e.g., in Haycock, Philip C., et al. "Leucocyte telomere length and risk of cardiovascular disease: systematic review and meta-analysis." (2014): g4227; and Codd, Veryan, et al. "Identification of seven loci affecting mean telomere length and their association with disease." Nature genetics 45.4 (2013): 422-427; each of which is incorporated by reference in its entirety. Thus, there is strong evidence for a causal role of telomere-length variation in cardiovascular disease (CVD), or coronary artery disease (CAD). In some embodiments, the disorder is a cardiovascular disease (CVD), and/or coronary artery disease (CAD), and the present disclosure provides methods of treating, mitigating, or minimizing the risk of, these disorders. In some cases, the disorder is an atherosclerotic cardiovascular disease.

Furthermore, a meta-analysis of 5759 cases and 6518 controls indicated that shortened telomere length was significantly associated with type 2 diabetes mellitus risk. The relationship between telomere length and type 2 diabetes mellitus is described, e.g., in Zhao, Jinzhao, et al. "Association between telomere length and type 2 diabetes mellitus: a meta-analysis." PLoS One 8.11 (2013): e79993, which is incorporated by reference in its entirety. In some embodiments, the disorder is a metabolic disorder, e.g., type 2 diabetes mellitus.

In some embodiments, aged cells can be used to screen test compounds that alter the expressive or activity of PARN or PAPD5. The aged cells used in the methods can be, e.g., those with genetic lesions in telomere biology genes, those isolated from elderly subjects, or those that undergo numerous rounds of replication in the lab. Such methods can be used to screen a library of test compounds, e.g., compounds that alter or change expression of protein or RNA of telomere-associated genes (e.g., TERC, PARN, PAPD5/PAPD5). Exemplary methods of screening and screening techniques are described herein.

In some embodiments, agents that increase the level or activity of TERC (e.g., PAPD5/PAPD5 inhibitors) are used to treat age-related degenerative disorders due to natural causes or environmental causes. In some embodiments, these agents are used in combination with other treatments.

Viral Infections

The hepatitis B virus (HBV) is an enveloped, partially double-stranded D A virus. The compact 3.2 kb HBV genome consists of four overlapping open reading frames (ORF), which encode for the core, polymerase (Pol), envelope and X-proteins. The Pol ORF is the longest and the envelope ORF is located within it, while the X and core ORFs overlap with the Pol ORF. The lifecycle of HBV has two main events: 1) generation of closed circular DNA (cccDNA) from relaxed circular (RC DNA), and 2) reverse transcription of pregenomic RNA (pgRNA) to produce RC DNA. Prior to the infection of host cells, the HBV genome exists within the virion as RC DNA. It has been determined that HBV virions arc able to gain entry into host cells by non-specifically binding to the negatively charged proteoglycans present on the surface of human hepatocytes (Schulze, A., P. Gripon & S. Urban. Hepatology, 46. (2007). 1759-68) and via the specific binding of HBV surface antigens (HBsAg) to the hepatocyte sodium-taurocholate cotransporting polypeptide (NTCP) receptor (Yan, H. et al. J Virol, 87, (2013), 7977-91). Once the virion has entered the cell, the viral cores and the encapsidated RC DNA are transported by host factors, via a nuclear localization signal, into the nucleus through the Impf3/Impa nuclear transport receptors. Inside the nucleus, host DNA repair enzymes convert the RC DNA into cccDNA. cccDNA acts as the template for all viral mRNAs and as such, is responsible for HBV persistence in infected individuals. The transcripts produced from cccDNA are grouped into two categories; Pregenomic RNA (pgRNA) and subgenomic RNA. Subgenomic transcripts encode for the three envelopes (L, M and S) and X proteins, and pgRNA encodes for Pre-Core, Core, and Pol proteins (Quasdorff, M. & U. Protzcr. J Viral Hepat, 1 7, (2010), 527-36). Inhibition of HBV gene expression or HBV RNA synthesis leads to the inhibit ion of HBV viral replication and antigens production (Mao, R. et al. PLoS Pathog, 9, (2013), e1003494; Mao, R. et al. J Virol, 85, (2011), 1048-57). For instance, IFN-a was shown to inhibit HBV replication and viral HBsAg production by decreasing the transcription of pgRNA and subgenomic RNA from the HBV covalently closed circular DNA (cccDNA) minichromosome. (Belloni, L. et al. J Clin Invest, 122, (2012), 529-37; Mao, R. et al. J Virol, 85, (2011), 1048-57). All HBV viral mRNAs are capped and polyadenylated and then exported to the cytoplasm for translation. In the cytoplasm, the assembly of new virons is initiated and nascent pgRNA is packaged with viral Pol so that reverse transcription of pgRNA, via a single stranded DNA intermediate, into RC DNA can commence. The mature nucleocapsids containing RC DNA are enveloped with cellular lipids and viral L, M, and S proteins and then the infectious HBV particles are then released by budding at the intracellular membrane (Locarnini, S. Semin Liver Dis, (2005), 25 Suppl 1, 9-1 9). Interestingly, non-infectious particles are also produced that greatly outnumber the infectious virions. These empty, enveloped particles (L, M and S) are referred to as subviral particles. Importantly, since subviral particles share the same envelope proteins and as infectious particles, it has been surmised that they act as decoys to the host immune system and have been used for HBV vaccines. The S, M, and L envelope proteins are expressed from a single ORF that contains three different start codons. All three proteins share a 226aa sequence, the S-domain, at their C-termini. M and L have additional pre-S domains, Pre-S2 and Pre-S2 and Pre-S1, respectively. However, it is the S-domain that has the HBsAg epitope (Lambert, C. & R. Prangc. Virol J, (2007), 4, 45).

The control of viral infection needs a tight surveillance of the host innate immune system which could respond within minutes to hours after infect ion to impact on the initial growth of the virus and limit the development of a chronic and persistent infection. Despite the available current treatments based on IFN and nucleos(t)ide analogues, the Hepatitis B virus (HBV) infection remains a major health problem worldwide which concerns an estimated 350 million chronic carriers who have a higher risk of liver cirrhosis and hepatocellular carcinoma.

The secretion of antiviral cytokines in response to HBV infection by the hepatocytes and/or the intra-hepatic immune cells plays a central role in the viral clearance of infected liver.

However, chronically infected patients only display a weak immune response due to various escape strategies adopted by the virus to counteract the host cell recognition systems and the subsequent antiviral responses.

Many observations showed that several HBV viral proteins could counteract the initial host cellular response by interfering with the viral recognition signaling system and subsequently the interferon (IFN) antiviral activity. Among these, the excessive secretion of HBV empty subviral particles (SVPs, HBsAg) may participate to the maintenance of the immunological tolerant state observed in chronically infected patients (CHB). The persistent exposure to HBsAg and other viral antigens can lead to HBV-specific T-cell deletion o to progressive functional impairment (Kondo et al. Journal of Immunology (1993), 150, 4659 4671; Kondo et al. Journal of Medical Virology (2004), 74, 425 433; Fisicaro et al. Gastroenterology, (2010), 138, 682-93;). Moreover HBsAg has been reported to suppress the function of immune cells such as monocytes, dendritic cells (DCs) and natural killer (NK) cells by direct interaction (Op den Brouw et al. Immunology, (2009b), 1 26, 280-9; Woltman et al. PLoS One, (2011), 6, e15324; Shi et al. J Viral Hepat. (2012). 19, c26-33; Kondo et al. ISRN Gastroenterology, (2013), Article ID 935295).

HBsAg quantification is a significant bio marker for prognosis and treatment response in chronic hepatitis B. However the achievement of HBsAg loss and seroconversion is rarely observed in chronically infected patients but remains the pttimate goal of therapy. Current therapy such as Nucleos(t)ide analogues are molecules that inhibit HBV DA synthesis but are not directed at reducing HBsAg level. Nucleos(t)ide analogs, even with prolonged therapy, have demonstrated rates of HBsAg clearance comparable to those observed naturally (between −1%-2%) (Janssen et al. Lancet, (2005), 365, 123-9; Marcellin et al. N. Engl. J Med., (2004), 351, 1206-17; Buster et al. Hepatology, (2007), 46, 388-94). Therefore, targeting HBsAg together with HBV DNA levels in CHB patients may significantly improve CHB patient immune reactivation and remission (Wieland, S. F. & F. V. Chisari. J Virol, (2005), 79, 9369-80; Kumar et al. J Virol, (2011), 85, 987-95; Woltman et al. PLoS One, (2011), 6, e15324; Opden Brouw et al. Immunology, (2009b), 126, 280-9).

The compounds of the present disclosure are inhibitors of virion production and inhibitors of production and secretion of surface proteins HBsAg and HBeAg. The compounds reduce effective HBV RNA production at the transcriptional or post-transcriptional levels, such as the result of accelerated viral RNA degradation in the cell. In the alternative, the compounds of the present disclosure inhibit initiation of viral transcription. In sum, the compounds reduce overall levels of HBV RNA, especially HBsAg mRNA, and viral surface proteins. HBsAg may suppress immune reactions against virus or virus infected cells, and high level of HBsAg is thought to be responsible for T cell exhaustion and depletion. Disappearance of HBsAg followed by the emergence of anti-HBsAg antibodies results in a sustained virological response to HBV, which is regarded as a sign of a functional cure.

In some embodiments, the compounds may modulate any of the molecular mechanisms described, for example, in Zhou et al., Antiviral Research 149 (2018) 191-201, which is incorporated herein by reference in its entirety. In some embodiments, the compounds may modulate any of the physiological or molecular mechanisms described, for example, in Mueller et al., Journal of Hepatology 68 (2018) 412-420, which is incorporated herein by reference in its entirety. For example, the compounds of the present disclosure induce HBV RNA degradation (degradation of HBV pgRNA and HBsAg mRNA occurs in the hepatocyte nucleus and requires de novo synthesis of host proteins).

In some embodiments, the compounds of the present disclosure are useful in inhibiting of HBsAg production or secretion, in inhibiting HBV DNA production, and/or in treating or preventing hepatitis B virus (HBV) infection (acute, fulminant, or chronic) in a subject. In some embodiments, the subject is in need of such treatment or prevention (e.g., prior to the administration of the compound of the present disclosure, the subject is diagnosed as having HBV infection by a treating physician).

Additional Uses

In some embodiments, the compound of the present disclosure modulates RNAs whose transcription, post-transcriptional processing, stability, steady state levels or function are altered due to acquired or genetic defects in one or more of any cellular pathways. In some embodiments, these include non-coding RNAs (ncRNAs) that are members of the small nucleolar RNA (snoRNA), small Cajal body RNA (scaRNA), small nuclear RNA (snRNA), ribosomal RNA (rRNA), Y RNA, transfer RNA (tRNA), microRNA (miRNA), PIWI-interacting RNA (piRNA) or long non-coding RNA (lncRNA) families. The compounds may also by useful for modulating non-coding RNAs in a cell (e.g. scaRNA13, scaRNA8), and concomitantly for preventing and treating the associated disease and conditions. In some embodiments, these also include those ncRNAs affected by any of the molecular mechanisms described, for example, in Lardelli et al, Nature Genetics, 49(3), 2017, 457-464; and in Son et al., 2018, Cell Reports 23, 888-898, including those affected by disruption of PARN or TOE1 deadenylases. As such, the compounds are useful in treating or preventing genetic and other disorders, including neurodevelopmental disorders such as pontocerebellar hypoplasia. Neurodevelopmental disorders are a group of disorders in which the development of the central nervous system is disturbed. This can include developmental brain dysfunction, which can manifest as neuropsychiatric problems or impaired motor function, learning, language or non-verbal communication. In some embodiments, a neurodevelopmental disorder is selected from attention deficit hyperactivity disorder (ADHD), reading disorder (dyslexia), writing disorder (disgraphia), calculation disorder (dyscalculia), expression disorder (ability for oral expression is substantially below the appropriate level for a child's mental age), comprehension disorder (ability for comprehension is markedly below the appropriate level for a child's mental age), mixed receptive-expressive language disorder, speech disorder (dislalia) (inability to use the sounds of speech that are developmentally appropriate), stuttering (disruption of normal fluency and temporal structure of speech), and autism spectrum disorders (persistent difficulties in social communication). In some embodiments, the present disclosure provides a method of treating an acquired or genetic disease or condition associated with alterations in RNA, the method comprising administering to the subject in need thereof a therapeutically effective amount of any one of the compounds described herein, or a pharmaceutically acceptable salt thereof, or a pharmaceutically acceptable composition comprising same. In some embodiments, the RNA comprises ncRNA (e.g., snRNA, scaRNA, snoRNA, rRNA, and miRNA). In some embodiments, the RNA is disrupted by disruption of PARN or TOE1 deadenylase. In some embodiments, the acquired or genetic disease or condition associated with alterations in RNA comprises a neurodevelopmental disorder such as pontocerebellar hypoplasia.

Because the compounds are PAPD5 inhibitors, and because these affect TERC, telomerase, telomere maintenance and stem cell self-renewal, the compounds are useful in modulating ex vivo expansion of stem cells, and also useful for allograft exhaustion, in hematopoietic or other tissues. For example, PAPD5 inhibitors may be useful for the ex vivo expansion of hematopoietic stem cells as described in Fares, et al, 2015, Science 345, 1590-1512, and Boitano, et al, 2010 329, 1345-1348, both of which are incorporated by reference herein in their entireties.

CRISPR/Cas9 (CRISPR-Associated 9)

Genome engineering and genetic modulation by the control of individual gene expression can be used in therapeutics as well. CRISPR (clustered regularly interspaced short palindromic repeats) is a family of DNA sequences found within the genomes of prokaryotic organisms such as bacteria and archaea. CRISPR/Cas RNA-guided genome targeting and gene regulation in mammalian cells (e.g., using modified bacterial CRISPR/Cas components) can be used to inhibit the expression and/or activity of genes (e.g., PAPD5).

In some embodiments, a catalytically silent Cas-9 mutant (a null nuclease) can be tethered to specified gene promoter regions and has the effect of reducing expression of those genes. In some embodiments, the Cas-9 mutant is linked to a transcription factor.

In some embodiments, the CRISPR/Cas9 genome targeting can create biallelic null mutations, thus inhibit the expression and the activity of a gene (e.g., PAPD5). Thus, in some embodiments, the PAPD5 inhibitor can be a vector that encode guide RNAs (gRNAs) that target PAPD5 for CRISPR/Cas9, wherein CRISPR/Cas9 creates null mutations in PAPD5, thereby decreasing the level and activity of PAPD5. In some embodiments, the PAPD5 inhibitor includes the CRISPR/Cas9 system and the guide RNAs. In some embodiments, the guide RNA can have the following sequences:

(SEQ ID NO: 2)
CCUCUUGUUGCUGCUGCCCG;

(SEQ ID NO: 3)
CGGAGCGAUACAUGCCGGCC;
or (SEQ ID NO: 4)
CCUCUUGUUGCUGCUGCCCG.

The CRISPR/Cas9 targeting can be used in the various methods as described herein, for example, modulating telomerase RNA component, screening, diagnosing, treating or preventing a disease or condition selected from: a disorder associated with telomere or telomerase dysfunction, a disorder associated with aging, a pre-leukemic or pre-cancerous condition, a viral infection (e.g., an HBV infection), a neurodevelopmental disorder, and an acquired or genetic disease or condition associated with alterations in RNA, etc.

Diagnosing a Subject in Need of Treatment

The present specification provides methods of diagnosing a subject in need of treatment (e.g., as having any one of telomere diseases described herein). As an example, if the level or activity of TERC, PARN, and/or PAPD5 in a subject is comparable to the level or activity of TERC, PARN, and/or PAPD5 in a subject having the telomere disease and, optionally, the subject has one or more symptoms associated with telomere disease (e.g., aplastic anemia, pulmonary fibrosis, hepatic cirrhosis), then the subject can be diagnosed as having or being at risk of developing a telomere disease.

In some embodiments, if the level or activity of TERC, PARN, and/or PAPD5 in a subject is comparable to the level or activity of TERC, PARN, and/or PAPD5 in a control subject who does not have a telomere disease, then the subject can be diagnosed as not having telomere disease or not being at risk of developing a telomere disease.

In some embodiments, the subject is determined to have or being at risk of developing a telomere disease if there is a mutation at PARN. The mutation can be a missense mutation, deletion or truncation mutation, omission of single or groups of nucleotides encoding one or several amino acids, non-coding mutation such as promoter, enhancer, or splicing mutation, or other mutations. (See, e.g., Nagpal, et al, Cell Stem Cell, 2020. The mutation can be a deletion containing part of PARN gene or the entire PARN gene. The mutation can also be a mutation at position 7 and/or 87 of PARN, e.g., the amino acid residue at position 7 is not asparagine, and/or the amino acid residue at position 87 of PARN is not serine. For example, the mutation can be a missense variant c.19A>C, resulting in a substitution of a highly conserved amino acid p.Asn7His. In some cases, the mutation is a missense mutation c.260C>T, encoding the substitution of a highly conserved amino acid, p. Ser87Leu. In some embodiments, the subject is determined to have or be at risk of developing a telomere disease if there is a mutation in DKC1. The mutation can be a missense mutation, deletion or truncation mutation, omission of single or groups of nucleotides encoding one or several amino acids, non-coding mutation such as promoter, enhancer, or splicing mutation, or other mutations. (See, e.g., Fok, et al, Blood, 2019; and Nagpal, et al, Cell Stem Cell, 2020). In some embodiments, the subject is determined to have or be at risk of developing a telomere disease if there is a mutation in any factor that regulates TERC, including NOP10, NHP2, NAF1, GAR1, TCAB1/WRAP53, ZCCHC8, and TERC itself. The mutation can be a missense mutation, deletion or truncation mutation of whole or part of the gene, omission of single or groups of amino acids. In some embodiments the subject is determined to have or be at risk of developing a telomere disease if there is a mutation in any factor that regulates telomere biology, such as TERT, TINF2, ACD/TPP1, STN1, CTC1, or POT1. The mutation can be a missense mutation, deletion or truncation mutation, omission of single or groups of nucleotides encoding one or several amino acids, non-coding mutation such as promoter, enhancer, or splicing mutation, or other mutations.

In some embodiments, a subject has no overt signs or symptoms of a telomere disease, but the level or activity of TERC, PARN or PAPD5 may be associated with the presence of a telomeres disease, then the subject has an increased risk of developing telomere disease. In some embodiments, once it has been determined that a person has telomere disease, or has an increased risk of developing telomere disease, then a treatment, e.g., with a small molecule (e.g., a PAPD5 inhibitor) or a nucleic acid encoded by a construct, as known in the art or as described herein, can be administered.

Suitable reference values can be determined using methods known in the art, e.g., using standard clinical trial methodology and statistical analysis. The reference values can have any relevant form. In some cases, the reference comprises a predetermined value for a meaningful level of PAPD5 protein, e.g., a control reference level that represents a normal level of PAPD5 protein, e.g., a level in an unaffected subject or a subject who is not at risk of developing a disease described herein, and/or a disease reference that represents a level of the proteins associated with conditions associated with telomere disease, e.g., a level in a subject having telomere disease (e.g., pulmonary fibrosis, hepatic cirrhosis or aplastic anemia). In another embodiment, the reference comprises a predetermined value for a meaningful level of PARN protein, e.g., a control reference level that represents a normal level of PARN protein, e.g., a level in an unaffected subject or a subject who is not at risk of developing a disease described herein, and/or a disease reference that represents a level of the proteins associated with conditions associated with telomere disease, e.g., a level in a subject having telomere disease (e.g., pulmonary fibrosis, hepatic cirrhosis or aplastic anemia).

The predetermined level can be a single cut-off (threshold) value, such as a median or mean, or a level that defines the boundaries of an upper or lower quartile, tertile, or other segment of a clinical trial population that is determined to be statistically different from the other segments. It can be a range of cut-off (or threshold) values, such as a confidence interval. It can be established based upon comparative groups, such as where association with risk of developing disease or presence of disease in one defined group is a fold higher, or lower, (e.g., approximately 2-fold, 4-fold, 8-fold, 16-fold or more) than the risk or presence of disease in another defined group. It can be a range, for example, where a population of subjects (e.g., control subjects) is divided equally (or unequally) into groups, such as a low-risk group, a medium-risk group and a high-risk group, or into quartiles, the lowest quartile being subjects with the lowest risk and the highest quartile being subjects with the highest risk, or into n-quantiles (i.e., n regularly spaced intervals) the lowest of the n-quantiles being subjects with the lowest risk and the highest of the n-quantiles being subjects with the highest risk.

In some embodiments, the predetermined level is a level or occurrence in the same subject, e.g., at a different time point, e.g., an earlier time point.

Subjects associated with predetermined values are typically referred to as reference subjects. For example, in some embodiments, a control reference subject does not have a disorder described herein. In some embodiments, it may be desirable that the control subject is deficient in PARN gene (e.g., Dyskeratosis Congenita), and in other embodiments, it may be desirable that a control subject has cancer. In some cases, it may be desirable that the control subject has high telomerase activity, and in other cases it may be desirable that a control subject does not have substantial telomerase activity.

In some embodiments, the level of TERC or PARN in a subject being less than or equal to a reference level of TERC or PARN is indicative of a clinical status (e.g., indicative of a disorder as described herein, e.g., telomere disease). In some embodiments, the activity of TERC or PARN in a subject being greater than or equal to the reference activity level of TERC or PARN is indicative of the absence of disease.

The predetermined value can depend upon the particular population of subjects (e.g., human subjects or animal models) selected. For example, an apparently healthy population will have a different 'normal' range of levels of TERC than will a population of subjects which have, are likely to have, or are at greater risk to have, a disorder described herein. Accordingly, the predetermined values selected may take into account the category (e.g., sex, age, health, risk, presence of other diseases) in which a subject (e.g., human subject) falls. Appropriate ranges and categories can be selected with no more than routine experimentation by those of ordinary skill in the art. In characterizing likelihood, or risk, numerous predetermined values can be established.

In some embodiments, the methods described in this disclosure involves identifying a subject as having, being at risk of developing, or suspected of having a disorder associated with telomerase dysfunction. The methods include determining the level or activity of TERC, PARN, or PAPD5 in a cell from the subject; comparing the level or activity of TERC, PARN, or PAPD5 to the reference level or reference activity of TERC, PARN, or PAPD5; and identifying the subject as having, being at risk of developing, or suspected of having a disorder associated with telomerase dysfunction if the level or activity of TERC, PARN, or PAPD5 is significantly different from the reference level or activity of TERC, PARN, or PAPD5. In some embodiments, the reference level or activity of TERC, PARN, or PAPD5 are determined by cells obtained from subjects without disorders associated with telomerase dysfunction.

The level or activity of TERC, PARN, or PAPD5 can be determined in various types of cells from a subject. The methods can include obtaining cells from a subject, and transforming these cells to induced pluripotent stem cells (I-IPS) cells, and these iPS cells can be used to determine the level or activity of TERC, PARN, or PAPD5. These cells can be, e.g., primary human cells or tumor cells. Pluripotent stem cells (I-IPS) cells can be generated from somatic cells by methods known in the art (e.g., somatic cells may be genetically reprogrammed to an embryonic stem cell-like state by being forced to express genes and factors important for maintaining the defining properties of embryonic stem cells). In some embodiments, the methods of diagnosing a subject include analyzing blood sample of the subject, or a sample of hair, urine, saliva, or feces of the subject (e.g., a subject may be diagnosed without any cell culture surgically obtained from the subject).

The subject may be one having a mutation at PARN, e.g., a deletion containing part of PARN gene or the entire PARN gene. For example, the mutation may be one wherein the amino acid residue at position 7 of PARN is not asparagine or serine. For example, the subject can have a missense variant c.19A>C, resulting in a substitution of a highly conserved amino acid p.Asn7His. The subject can have a missense mutation c.260C>T, encoding the substitution of a highly conserved amino acid, p.Ser87Leu.

Induced Pluripotent Stem Cells

Induced pluripotent stem cells (I-IPSC or iPS), are somatic cells (e.g., derived from patient skin or other cell) that have been genetically reprogrammed to an embryonic stem cell-like state by being forced to express genes and factors important for maintaining the defining properties of embryonic stem cells. These cells can be generated by methods known in the art.

It is known that mouse iPSCs demonstrate important characteristics of pluripotent stem cells, including expressing stem cell markers, forming tumors containing cells from all three germ layers, and being able to contribute to many different tissues, when injected into mouse embryos at a very early stage in development.

Human iPSCs also express stem cell markers and are capable of generating cells characteristic of all three germ layers. iPSCs can be generated from human fibroblasts and are already useful tools for drug development and modeling of diseases. Viruses are currently used to introduce the reprogramming factors into adult cells (e.g., lentiviral vectors disclosed herein), and this process can be carefully controlled and tested in cultured, isolated cells first to then treat cells (e.g., by contacting with a test compound) to express altered markers, e.g., iPSCs from tumor cells can be manipulated to differentiate or iPSCs from cardiomyocytes can be manipulated to de-differentiate.

The iPSC manipulation strategy can be applied to any cells obtained from a subject to test whether the compound can alter the level or activity of TERC, PARN, or PAPD5. The cells are contacted with test compounds (e.g., small molecules). In some embodiments, these iPSC cells can be used for screening compounds that modulate TERC. In some embodiments, the iPSC cells can be converted from patient skin fibroblasts.

Cell Expansion

The present disclosure provides methods of expanding a cell population by culturing one or more cells in the presence of compounds as disclosed herein (e.g., compounds of Formulae (I), (II), (III), or (IV)). In some embodiments, cell expansion can involve contacting the cells with an effective amount of compound of the present disclosure (e.g., PAPD5 inhibitors of Formulae (I), (II), (III), or (IV)). The PAPD5 inhibitors can decrease the level and activity of PAPD5, thereby increasing or maintaining the length of the telomere. Telomerase activity and telomere length maintenance are related to cell expansion capability. As the cell divides, the telomere length gradually shortens, eventually leading to senescence of cells. Based on the telomere theory, aging in cells is irreversible. Programmed cell cycle arrest happens in response to the telomerase activity and the total number of cell divisions cannot exceed a particular limit termed the Hayflick limit. It has been determined that maintaining telomere length during cell replication is important for cell expansion (e.g., stem cell expansion). The present disclosure provides methods of promoting cell expansion, and methods of inhibiting, slowing, or preventing cell aging.

In some embodiments, the cell is a stem cell. Stem cells can include, but are not limited to, for example, pluripotent stem cells, embryonic stem cells, hematopoietic stem cells, adipose derived stem cells, mesenchymal stem cells, umbilical cord blood stem cells, placentally derived stem cells, exfoliated tooth derived stem cells, hair follicle stem cells, or neural stem cells. In some embodiments, the cell is a peripheral blood mononuclear (PBMC) cell.

The cells can be derived from the subject with a disease or condition associated with any disorder described herein, e.g., cancer, a telomere or telomerase dysfunction, a disorder associated with aging, a pre-leukemic or pre-cancerous condition, and a neurodevelopment disorder. The cells can be isolated and derived, for example, from tissues such as pancreatic tissue, liver tissue, smooth muscle tissue, striated muscle tissue, cardiac muscle tissue, bone tissue, bone marrow tissue, bone spongy tissue, cartilage tissue, liver tissue, pancreas tissue, pancreatic ductal tissue, spleen tissue, thymus tissue, lymph nodes tissue, thyroid tissue, epidermis tissue, dermis tissue, subcutaneous tissue, heart tissue, lung tissue, vascular tissue, endothelial tissue, blood cells, bladder tissue, kidney tissue, digestive tract tissue, esophagus tissue, stomach tissue, small intestine tissue, large intestine tissue, adipose tissue, uterus tissue, eye tissue, lung tissue, testicular tissue, ovarian tissue, prostate tissue, connective tissue, endocrine tissue, or mesentery tissue.

The cells can be isolated from any mammalian organism, e.g., human, mouse, rats, dogs, or cats, by any means know to one of ordinary skill in the art. One skilled in the art can isolate embryonic or adult tissues and obtain various cells (e.g., stem cells).

The expanded cell population can be further enriched by using appropriate cell markers. For example, stem cells can be enriched by using specific stem cell markers, e.g., FLK-1, AC133, CD34, c-kit, CXCR-4, Oct-4, Rex-1, CD9, CD13, CD29, CD34, CD44, CD166, CD90, CD105, SH-3, SH-4, TRA-1-60, TRA-1-81, SSEA-4, and Sox-2. One skilled in the art can enrich a specific cell population by using antibodies known in the art against any of these cell markers. In some embodiments, expanded stem cells can be purified based on desired stem cell markers by fluorescence activated cell sorting (FACS), or magnet activated cell sorting (MACS).

The cells (e.g., stem cells) can be cultured and expanded in suitable growth media. Commonly used growth media include, but are not limited to, Iscove's modified Dulbecco's Media (IMDM) medium, McCoy's 5A medium, Dulbecco's Modified Eagle medium (DMEM), KnockOut™ Dulbecco's Modified Eagle medium (KO-DMEM), Dulbecco's Modified Eagle Medium/Nutrient Mixture F-12 (DMEM/F12), Roswell Park Memorial Institute (RPMI) medium, minimum essential medium alpha medium (α-MEM), F-12K nutrient mixture medium (Kaighn's modification, F-12K), X-vivo™ 20 medium, Stemline™ medium, StemSpan™ CC100 medium, StemSpan™ H2000 medium, MCDB 131 Medium, Basal Media Eagle (BME), Glasgow Minimum Essential medium (GMEM), Modified Eagle Medium (MEM), Opti-MEM I Reduced Serum medium, Waymouth's MB 752/1 Medium, Williams' Medium E, NCTC-109 Medium, neuroplasma medium, BGJb Medium, Brinster's BMOC-3 Medium, Connaught Medical Research Laboratories (CMRL) Medium, $CO_2$-Independent Medium, and Leibovitz's L-15 medium.

The compounds of the present disclosure (e.g., compounds of Formulae (I), (II), or (III)) can be used to expand various cell population, e.g., by adding the compound in cell culture media in a tube or plate. The concentration of the compound can be determined by, but limited to, the time of cell expansion. For example, the cells can be in culture with high concentration of the compound for a short period of time, e.g., at least or about 1 day, 2 days, 3 days, 4 days, or 5 days. In some embodiments, the cells can be cultured with a low concentration of the compound for a long period of time, e.g., at least or about 3 days, 4 days, 5 days, 6 days, 1 week, 2 weeks, 3 weeks, or 4 weeks.

In some embodiments, growth factors are also added to the growth medium to expand cells. Examples of suitable growth factors include, but are not limited to, thrombopoietin, stem cell factor, IL-1, IL-3, IL-7, flt-3 ligand, G-CSF, GM-CSF, Epo, FGF-1, FGF-2, FGF-4, FGF-20, IGF, EGF, NGF, LIF, PDGF, bone morphogenic proteins, activin-A, VEGF, forskolin, and glucocorticords. Further, one skilled in the art, using methods known in the art, can add a feeder layer to the culture medium. A feeder layer can include cells such as, placental tissue or cells thereof.

The methods described herein can also be used to produce and expand Chimeric Antigen Receptor (CAR) T-Cells. CAR-T cell therapies involve genetic modification of patient's autologous T-cells to express a CAR specific for a tumor antigen, following by ex vivo cell expansion and re-infusion back to the patient. PBMCs can be collected from a patient and cultured in the presence of the compounds as described herein (e.g., compounds of Formulae (I), (II), (III), or (IV)), with appropriate media (e.g., complete media containing 30 U/mL interleukin-2 and anti-CD3/CD28 beads). The cells can be expanded for about 3 to 14 days (e.g., about 3 to 7 days). Subsets of T cells can be sorted by FACS. Gating strategies for cell sorting can exclude other blood cells, including granulocytes, monocytes, natural killer cells, dendritic cells, and B cells. Primary T cells are then transduced by incubating cells with the CAR-expressing lentiviral vector in the culture media. In some embodiments, the culture media can be supplemented with the compounds as described herein. The transduced cells are then cultured for at least a few days (e.g., 3 days) before being used in CAR-T cell therapies.

In some embodiments, the present disclosure provides a method of expanding a cell, the method comprising culturing the cell in the presence of an effective amount of a compound as described herein (e.g., a compound of Formulae (I), (II), (III), or (IV)), or a pharmaceutically acceptable salt thereof.

In some embodiments, the cell is selected from the group consisting of: stem cell, pluripotent stem cell, hematopoietic stem cell, and embryonic stem cell.

In some embodiments, the cell is a pluripotent stem cell.

In some embodiments, the cell is a hematopoietic stem cell.

In some embodiments, the cell is an embryonic stem cell.

In some embodiments, the cell is collected from a subject with a disease or condition selected from the group consisting of a disorder associated with telomere or telomerase dysfunction, a disorder associated with aging, a pre-leukemic or pre-cancerous condition, and a neurodevelopment disorder.

In some embodiments, the method further comprises culturing the cell with a feeder layer in a medium.

In some embodiments, the cell has at least one stem cell marker selected from the group consisting of FLK-1, AC133, CD34, c-kit, CXCR-4, Oct-4, Rex-1, CD9, CD13, CD29, CD34, CD44, CD166, CD90, CD105, SH-3, SH-4, TRA-1-60, TRA-1-81, SSEA-4, and Sox-2.

In some embodiments, the stem cell marker is CD34.

In some embodiments, the method further comprising enriching stem cells by isolating CD34+ cells.

In some embodiments, the subject is a mammal.

In some embodiments, the subject is a human.

In some embodiments, the method comprises culturing the cell in a medium selected from the group consisting of Iscove's modified Dulbecco's Media (IMDM) medium, Dulbecco's Modified Eagle Medium (DMEM), Roswell Park Memorial Institute (RPMI) medium, minimum essential medium alpha medium (α-MEM), Basal Media Eagle (BME) medium, Glasgow Minimum Essential Medium (GMEM), Modified Eagle Medium (MEM), Opti-MEM I Reduced Serum medium, neuroplasma medium, $CO_2$-independent medium, and Leibovitz's L-15 medium.

In some embodiments, the cell is a Chimeric Antigen Receptor (CAR) T-Cell.

In some embodiments, the cell is a lymphocyte.

In some embodiments, the cell is a T cell, an engineered T cell, or a natural killer cell (NK).

Pharmaceutical Compositions and Formulations

The present application also provides pharmaceutical compositions comprising an effective amount of any one of the compounds disclosed herein, or a pharmaceutically acceptable salt thereof, and a pharmaceutically acceptable carrier. The pharmaceutical composition can also comprise at least one of any one of the additional therapeutic agents described herein. In certain embodiments, the application also provides pharmaceutical compositions and dosage forms comprising any one the additional therapeutic agents described herein (e.g., in a kit). The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that can be used in the pharmaceutical compositions of the present application include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

The compositions or dosage forms can contain any one of the compounds and therapeutic agents described herein in the range of 0.005% to 100% with the balance made up from the suitable pharmaceutically acceptable excipients. The contemplated compositions can contain 0.001%400% of any one of the compounds and therapeutic agents provided herein, in one embodiment 0.1-95%, in another embodiment 75-85%, in a further embodiment 20-80%, wherein the balance can be made up of any pharmaceutically acceptable excipient described herein, or any combination of these excipients.

Routes of Administration and Dosage Forms

The pharmaceutical compositions of the present application include those suitable for any acceptable route of administration. Acceptable routes of administration include, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intranasal, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral and vaginal.

Compositions and formulations described herein can conveniently be presented in a unit dosage form, e.g., tablets, capsules (e.g., hard or soft gelatin capsules), sustained release capsules, and in liposomes, and can be prepared by any methods well known in the art of pharmacy. See, for example, Remington: The Science and Practice of Pharmacy, Lippincott Williams & Wilkins, Baltimore, MD (20th ed. 2000). Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In some embodiments, any one of the compounds and therapeutic agents disclosed herein are administered orally. Compositions of the present application suitable for oral administration can be presented as discrete units such as capsules, sachets, granules or tablets each containing a predetermined amount (e.g., effective amount) of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which can beneficially increase the rate of compound absorption. In the case of tablets for oral use, carriers that are commonly used include lactose, sucrose, glucose, mannitol, and silicic acid and starches. Other acceptable excipients can include: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents can be added. Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions or infusion solutions which can contain antioxidants, buffers, bacteriostats and solutes which render the formulation isotonic with the blood of the intended recipient; and aqueous and non-aqueous sterile suspensions which can include suspending agents and thickening agents. The formulations can be presented in unit-dose or multi-dose containers, for example, sealed ampules and vials, and can be stored in a freeze dried (lyophilized) condition requiring only the addition of the sterile liquid carrier, for example water for injections, saline (e.g., 0.9% saline solution) or 5% dextrose solution, immediately prior to use. Extemporaneous injection solutions and suspensions can be prepared from sterile powders, granules and tablets. The injection solutions can be in the form, for example, of a sterile injectable aqueous or oleaginous suspension. This suspension can be formulated according to techniques known in the art using suitable dispersing or wetting agents and suspending agents. The sterile injectable preparation can also be a sterile injectable solution or suspension in a non-toxic parenterally-acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium. For this purpose, any bland fixed oil can be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant.

The pharmaceutical compositions of the present application can be administered in the form of suppositories for rectal administration. These compositions can be prepared by mixing a compound of the present application with a suitable non-irritating excipient which is solid at room temperature but liquid at the rectal temperature and therefore will melt in the rectum to release the active components. Such materials include cocoa butter, beeswax, and polyethylene glycols.

The pharmaceutical compositions of the present application can be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art. See, for example, U.S. Pat. No. 6,803,031. Additional formulations and methods for intranasal administration are found in Ilium, L., *J Pharm Pharmacol,* 56:3-17, 2004 and Ilium, L., *Eur JPharm Sci* 11:1-18, 2000.

The topical compositions of the present disclosure can be prepared and used in the form of an aerosol spray, cream, emulsion, solid, liquid, dispersion, foam, oil, gel, hydrogel, lotion, mousse, ointment, powder, patch, pomade, solution, pump spray, stick, towelette, soap, or other forms commonly employed in the art of topical administration and/or cosmetic and skin care formulation. The topical compositions can be in an emulsion form. Topical administration of the pharmaceutical compositions of the present application is especially useful when the desired treatment involves areas or organs readily accessible by topical application. In some embodiments, the topical composition comprises a combination of any one of the compounds and therapeutic agents disclosed herein, and one or more additional ingredients, carriers, excipients, or diluents including absorbents, anti-irritants, anti-acne agents, preservatives, antioxidants, coloring agents/pigments, emollients (moisturizers), emulsifiers, film-forming/holding agents, fragrances, leave-on exfoliants, prescription drugs, preservatives, scrub agents, silicones, skin-identical/repairing agents, slip agents, sunscreen actives, surfactants/detergent cleansing agents, penetration enhancers, and thickeners.

The compounds and therapeutic agents of the present application can be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polydimethylsiloxane, polycaprolactone, polyethylene glycol, polylactic acid, ethylene vinyl acetate, and mixtures thereof. The coatings can optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the present application provides an implantable drug release device impregnated with or containing a compound or a therapeutic agent, or a composition comprising a compound of the present application or a therapeutic agent, such that said compound or therapeutic agent is released from said device and is therapeutically active.

Dosages and Regimens

In the pharmaceutical compositions of the present application, a therapeutic compound is present in an effective amount (e.g., a therapeutically effective amount).

Effective doses can vary, depending on the diseases treated, the severity of the disease, the route of administration, the sex, age and general health condition of the subject, excipient usage, the possibility of co-usage with other therapeutic treatments such as use of other agents and the judgment of the treating physician.

In some embodiments, an effective amount of a therapeutic compound can range, for example, from about 0.001 mg/kg to about 500 mg/kg (e.g., from about 0.001 mg/kg to about 200 mg/kg; from about 0.01 mg/kg to about 200 mg/kg; from about 0.01 mg/kg to about 150 mg/kg; from about 0.01 mg/kg to about 100 mg/kg; from about 0.01 mg/kg to about 50 mg/kg; from about 0.01 mg/kg to about 10 mg/kg; from about 0.01 mg/kg to about 5 mg/kg; from about 0.01 mg/kg to about 1 mg/kg; from about 0.01 mg/kg to about 0.5 mg/kg; from about 0.01 mg/kg to about 0.1 mg/kg; from about 0.1 mg/kg to about 200 mg/kg; from about 0.1 mg/kg to about 150 mg/kg; from about 0.1 mg/kg to about 100 mg/kg; from about 0.1 mg/kg to about 50 mg/kg; from about 0.1 mg/kg to about 10 mg/kg; from about 0.1 mg/kg to about 5 mg/kg; from about 0.1 mg/kg to about 2 mg/kg; from about 0.1 mg/kg to about 1 mg/kg; or from about 0.1 mg/kg to about 0.5 mg/kg).

In some embodiments, an effective amount of a therapeutic compound is about 0.1 mg/kg, about 0.5 mg/kg, about 1 mg/kg, about 2 mg/kg, or about 5 mg/kg.

The foregoing dosages can be administered on a daily basis (e.g., as a single dose or as two or more divided doses, e.g., once daily, twice daily, thrice daily) or non-daily basis (e.g., every other day, every two days, every three days, once weekly, twice weekly, once every two weeks, once a month). The compounds and compositions described herein can be administered to the subject in any order. A first therapeutic agent, such as a compound of any one of the Formulae disclosed herein, can be administered prior to or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before or after), or concomitantly with the administration of a second therapeutic agent, such as an anti-cancer therapy described herein, to a subject in need of treatment. Thus, the compound of any one of the Formulae disclosed herein, or a composition containing the compound, can be administered separately, sequentially or simultaneously with the second therapeutic agent, such as a chemotherapeutic agent described herein. When the compound of any one of the Formulae disclosed herein, or a pharmaceutically acceptable salt thereof, and a second or third therapeutic agent are administered to the subject simultaneously, the therapeutic agents can be administered in a single dosage form (e.g., tablet, capsule, or a solution for injection or infusion).

Combination Therapies

In some embodiments, the compounds described here may be administered to a subject in any combination with treatments for telomere diseases that are known in the art. The combination treatment may be administered to the subject either consecutively or concomitantly with the compound of any one of the Formulae disclosed herein. When combination treatment comprises an alternative therapeutic agent, the therapeutic agent may be administered to the subject in any one of the pharmaceutical compositions described herein.

In some embodiments, the compounds of the present disclosure may be used in combination with a therapeutic agent that is useful in treating a telomere disease (e.g., a therapeutic agent that modulates the level or activity of TERC). In some embodiments, the agent useful in treating a telomere disease is a nucleic acid comprising a nucleotide sequence that encodes PARN. The agent can also be an anti-PARN antibody or anti-PARN antibody fragment. In some embodiments, the agent is an antisense molecule or a small interfering nucleic acid which is specific for a nucleic acid encoding PARN. In some embodiments, the agent is a nucleic acid comprising a nucleotide sequence that encodes PAPD5. The agent can also be an anti-PAPD5 antibody or anti-PAPD5 antibody fragment. In some embodiments, the agent is an antisense molecule or a small interfering nucleic acid which is specific for a nucleic acid encoding PAPD5. The antisense molecule described herein can be an oligonucleotide. In some cases, the agent binds to PARN or PAPD5.

In some embodiments, the therapeutic agent that is useful in treating a telomere disease is selected from adenosine analogues, aminoglycosides, and purine nucleotides, etc. In some cases, the aminoglycoside can be a member of the neomycin and kanamycin families. The aminoglycoside can be, for example, kanamycin B sulfate, pramycin sulfate, spectinomycin dihydrochloride pentahydrate, ribostamycin sulfate, sisomicin sulfate, amikacin disulfide, dihydrostreptomycin sesquisulfate, hygromycin B, netilmicin sulfate, paromomycin sulfate, kasugamycin, neomycin, gentamicin, tobramycin sulfate, streptomycin sulfate, or neomycin B, or derivatives thereof.

In some embodiments, the therapeutic agent that is useful in treating a telomere disease a nucleoside analogue, e.g., an adenosine analogue, 8-chloroadenosine (8-C1-Ado) and 8-aminoadenosine (8-amino-Ado), or the triphosphate derivative thereof, synthetic nucleoside analogue bearing a fluoroglucopyranosyl sugar moiety, benzoyl-modified cytosine or adenine, adenosine- and cytosine-based glucopyranosyl nucleoside analogue, or glucopyranosyl analogue bearing uracil, 5-fluorouracil or thymine, etc.

Adenosine analogues, aminoglycosides, and purine nucleotides are known in the art, and they are described, e.g., in Kim, Kyumin, et al. "Exosome Cofactors Connect Transcription Termination to RNA Processing by Guiding Terminated Transcripts to the Appropriate Exonuclease within the Nuclear Exosome." Journal of Biological Chemistry (2016): jbc-M116; Chen, Lisa S., et al. "Chain termination and inhibition of mammalian poly (A) polymerase by modified ATP analogues." Biochemical pharmacology 79.5 (2010): 669-677; Ren, Yan-Guo, et al. "Inhibition of Klenow DNA polymerase and poly (A)-specific ribonuclease by aminoglycosides." Rna 8.11 (2002): 1393-1400; Thuresson, Ann-Charlotte, Leif A. Kirsebom, and Anders Virtanen. "Inhibition of poly (A) polymerase by aminoglycosides." Biochimie 89.10 (2007): 1221-1227; AA Balatsos, N., et al. "Modulation of poly (A)-specific ribonuclease (PARN): current knowledge and perspectives." Current medicinal chemistry 19.28 (2012): 4838-4849; Balatsos, Nikolaos A A, Dimitrios Anastasakis, and Constantinos Stathopoulos. "Inhibition of human poly (A)-specific ribonuclease (PARN) by purine nucleotides: kinetic analysis." Journal of enzyme inhibition and medicinal chemistry 24.2 (2009): 516-523; Balatsos, Nikolaos A A, et al. "Competitive inhibition of human poly (A)-specific ribonuclease (PARN) by synthetic fluoro-pyranosyl nucleosides." Biochemistry 48.26 (2009): 6044-6051; and Balatsos, Nikolaos, et al. "Kinetic and in silico analysis of the slow-binding inhibition of human poly (A)-specific ribonuclease (PARN) by novel nucleoside analogues." Biochimie 94.1 (2012): 214-221; each of which is incorporated herein by reference in its entirety. Numerous therapeutic agents that can modulate the level or activity of PARN and/or PAPD5 are described, e.g., in WO 2017/066796, which is incorporated herein by reference in its entirety.

In some embodiments, the compounds of the present disclosure are used in combination with an anti-cancer therapy. In some embodiments, the anti-cancer therapy is selected from the group consisting of surgery, radiation therapy, chemotherapy, gene therapy, DNA therapy, viral therapy, RNA therapy, adjuvant therapy, and immunotherapy. In some embodiments, the anti-cancer therapy is selected from the group consisting of a platinum agent, mitomycin C, a poly (ADP-ribose) polymerase (PARP) inhibitor, a radioisotope, a vinca alkaloid, an antitumor alkylating agent, a monoclonal antibody and an antimetabolite. In some embodiments, the anti-cancer therapy is an ataxia telangiectasia mutated (ATM) kinase inhibitor. Suitable examples of platinum agents include cisplatin, carboplatin, oxaliplatin, satraplatin, picoplatin, nedaplatin, triplatin, and lipoplatin. Suitable examples of cytotoxic radioisotopes include $^{67}Cu$, $^{67}Ga$, $^{90}Y$, $^{131}I$, $^{177}Lu$, 186Re, $^{188}Re$, α-Particle emitter, $^{211}At$, $^{213}Bi$, $^{225}Ac$, Auger-electron emitter, $^{125}I$, $^{212}Pb$, and $^{111}$ in. Suitable examples of antitumor alkylating agents include nitrogen mustards, cyclophosphamide, mechlorethamine or mustine (HN2), uramustine or uracil mustard, melphalan, chlorambucil, ifosfamide, bendamustine, nitrosoureas, carmustine, lomustine, streptozocin, alkyl sulfonates, busulfan, thiotepa, procarbazine, altretamine, triazenes, dacarbazine, mitozolomide, and temozolomide. Suitable examples of anti-cancer monoclonal antibodies include to necitumumab, dinutuximab, nivolumab, blinatumomab, pembrolizumab, ramucirumab, obinutuzumab, adotrastuzumab emtansine, pertuzumab, brentuximab, ipilimumab, ofatumumab, catumaxomab, bevacizumab, cetuximab, tositumomab-$I^{131}$, ibritumomab tiuxetan, alemtuzumab, gemtuzumab ozogamicin, trastuzumab, and rituximab. Suitable examples of vinca alkaloids include vinblastine, vincristine, vindesine, vinorelbine, desoxyvincaminol, vincaminol, vinburnine, vincamajine, vineridine, vinburnine, and vinpocetine. Suitable examples of antimetabolites include fluorouracil, cladribine, capecitabine, mercaptopurine, pemetrexed, fludarabine, gemcitabine, hydroxyurea, methotrexate, nelarbine, clofarabine, cytarabine, decitabine, pralatrexate, floxuridine, and thioguanine.

Kits

The present disclosure also includes pharmaceutical kits useful, for example, in the treatment of disorders, diseases and conditions referred to herein, which include one or more containers containing a pharmaceutical composition comprising a therapeutically effective amount of a compound of the present disclosure. Such kits can further include, if desired, one or more of various conventional pharmaceutical kit components, such as, for example, containers with one or more pharmaceutically acceptable carriers, additional containers, etc. Instructions, either as inserts or as labels, indicating quantities of the components to be administered, guidelines for administration, and/or guidelines for mixing the components, can also be included in the kit. The kit can optionally include directions to perform a test to determine that a subject is in need of treatment with a compound of any one of Formulae (I)-(IV) as described herein, and/or any of the reagents and device(s) to perform such tests. The kit can also optionally include an additional therapeutic agent (e.g., a nucleic acid comprising a nucleotide sequence that encodes PARN or PAPD5).

Definitions

As used herein, the term "about" means "approximately" (e.g., plus or minus approximately 10% of the indicated value).

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in the present specification various aryl, heteroaryl, cycloalkyl, and heterocycloalkyl rings are described. Unless otherwise specified, these rings can be attached to the rest of the molecule at any ring member as permitted by valency. For example, the term "a pyridine ring" or "pyridinyl" may refer to a pyridin-2-yl, pyridin-3-yl, or pyridin-4-yl ring.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The term "aromatic" refers to a carbocycle or heterocycle having one or more polyunsaturated rings having aromatic character (i.e., having (4n+2) delocalized π (pi) electrons where n is an integer).

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. The substituents are independently selected, and substitution may be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms.

As used herein, "$_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkylene", employed alone or in combination with other terms, refers to a divalent alkyl linking group having n to m carbons. Examples of alkylene groups include, but are not limited to, ethan-1,1-diyl, ethan-1,2-diyl, propan-1,1, -diyl, propan-1,3-diyl, propan-1,2-diyl, butan-1,4-diyl, butan-1,3-diyl, butan-1,2-diyl, 2-methyl-propan-1,3-diyl, and the like. In some embodiments, the alkylene moiety contains 2 to 6, 2 to 4, 2 to 3, 1 to 6, 1 to 4, or 1 to 2 carbon atoms.

As used herein, the term "$C_{n-m}$ alkoxy", employed alone or in combination with other terms, refers to a group of formula —O-alkyl, wherein the alkyl group has n to m carbons. Example alkoxy groups include, but are not limited to, methoxy, ethoxy, propoxy (e.g., n-propoxy and isopropoxy), butoxy (e.g., n-butoxy and tert-butoxy), and the like. In some embodiments, the alkyl group has 1 to 6, 1 to 4, or 1 to 3 carbon atoms.

As used herein, "$C_{n-m}$ haloalkoxy" refers to a group of formula —O-haloalkyl having n to m carbon atoms. An example haloalkoxy group is $OCF_3$. In some embodiments, the haloalkoxy group is fluorinated only. In some embodiments, the alkyl group has 1 to 6, 1 to 4, or 1 to 3 carbon atoms.

As used herein, the term "amino" refers to a group of formula —$NH_2$.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms. Examples of alkylamino groups include, but are not limited to, N-methylamino, N-ethylamino, N-propylamino (e.g., N-(n-propyl)amino and N-isopropylamino), N-butylamino (e.g., N-(n-butyl)amino and N-(tert-butyl)amino), and the like.

As used herein, the term "di($C_{n-m}$-alkyl)amino" refers to a group of formula —$N(alkyl)_2$, wherein the two alkyl groups each has, independently, n to m carbon atoms. In some embodiments, each alkyl group independently has 1 to 6, 1 to 4, or 1 to 3 carbon atoms.

As used herein, the term "$C_{n-m}$ alkoxycarbonyl" refers to a group of formula —C(O)O-alkyl, wherein the alkyl group has n to m carbon atoms. In some embodiments, the alkyl group has 1 to 6, 1 to 4, or 1 to 3 carbon atoms. Examples of alkoxycarbonyl groups include, but are not limited to, methoxycarbonyl, ethoxycarbonyl, propoxycarbonyl (e.g., n-propoxycarbonyl and isopropoxycarbonyl), butoxycarbonyl (e.g., n-butoxycarbonyl and tert-butoxycarbonyl), and the like.

As used herein, the term "$C_{n-m}$ alkylcarbonyl" refers to a group of formula —C(O)-alkyl, wherein the alkyl group has n to m carbon atoms. In some embodiments, the alkyl group has 1 to 6, 1 to 4, or 1 to 3 carbon atoms. Examples of alkylcarbonyl groups include, but are not limited to, methylcarbonyl, ethylcarbonyl, propylcarbonyl (e.g., n-propylcarbonyl and isopropylcarbonyl), butylcarbonyl (e.g., n-butylcarbonyl and tert-butylcarbonyl), and the like.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonylamino" refers to a group of formula —$NHS(O)_2$-alkyl, wherein the alkyl group has n to m carbon atoms. In some embodiments, the alkyl group has 1 to 6, 1 to 4, or 1 to 3 carbon atoms.

As used herein, the term "aminosulfonyl" refers to a group of formula —$S(O)_2NH_2$.

As used herein, the term "$C_{n-m}$ alkylaminosulfonyl" refers to a group of formula —$S(O)_2NH$(alkyl), wherein the alkyl group has n to m carbon atoms. In some embodiments, the alkyl group has 1 to 6, 1 to 4, or 1 to 3 carbon atoms.

As used herein, the term "di(Cn-in alkyl)aminosulfonyl" refers to a group of formula —$S(O)_2N(alkyl)_2$, wherein each alkyl group independently has n to m carbon atoms. In some embodiments, each alkyl group has, independently, 1 to 6, 1 to 4, or 1 to 3 carbon atoms.

As used herein, the term "aminosulfonylamino" refers to a group of formula —$NHS(O)_2NH_2$.

As used herein, the term "$C_{n-m}$ alkylaminosulfonylamino" refers to a group of formula —$NHS(O)_2NH$(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonylamino" refers to a group of formula —$NHS(O)_2$ $N(alkyl)_2$, wherein each alkyl group independently has n to m carbon atoms. In some embodiments, each alkyl group has, independently, 1 to 6, 1 to 4, or 1 to 3 carbon atoms.

As used herein, the term "aminocarbonylamino", employed alone or in combination with other terms, refers to a group of formula —$NHC(O)NH_2$.

As used herein, the term "$C_{n-m}$ alkylaminocarbonylamino" refers to a group of formula —NHC(O)NH (alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminocarbonylamino" refers to a group of formula —$NHC(O)N(alkyl)_2$, wherein each alkyl group independently has n to m carbon atoms. In some embodiments, each alkyl group has, independently, 1 to 6, 1 to 4, or 1 to 3 carbon atoms.

As used herein, the term "carbamyl" to a group of formula —$C(O)NH_2$.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$-alkyl)carbamyl" refers to a group of formula —$C(O)N(alkyl)_2$, wherein the two alkyl groups each has, independently, n to m carbon atoms. In some embodiments, each alkyl group independently has 1 to 6, 1 to 4, or 1 to 3 carbon atoms.

As used herein, the term "thio" refers to a group of formula —SH.

As used herein, the term "$C_{n-m}$ alkylthio" refers to a group of formula —S-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfinyl" refers to a group of formula —S(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonyl" refers to a group of formula —$S(O)_2$-alkyl, wherein the alkyl group has n to m carbon atoms. In some embodiments, the alkyl group has 1 to 6, 1 to 4, or 1 to 3 carbon atoms.

As used herein, the term "carbonyl", employed alone or in combination with other terms, refers to a —C(═O)— group, which may also be written as C(O).

As used herein, the term "carboxy" refers to a —C(O)OH group.

As used herein, the term "cyano-$C_{1-3}$ alkyl" refers to a group of formula —($C_{1-3}$ alkylene)-CN.

As used herein, the term "HO—$C_{1-3}$ alkyl" refers to a group of formula —($C_{1-3}$ alkylene)-OH.

As used herein, "halo" refers to F, Cl, Br, or I. In some embodiments, a halo is F, Cl, or Br.

As used herein, the term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In some embodiments, aryl groups have from 6 to 10 carbon atoms. In some embodiments, the aryl group is phenyl or naphthyl.

As used herein, "cycloalkyl" refers to non-aromatic cyclic hydrocarbons including cyclized alkyl and/or alkenyl groups. Cycloalkyl groups can include mono- or polycyclic (e.g., having 2, 3 or 4 fused rings) groups and spirocycles. Ring-forming carbon atoms of a cycloalkyl group can be optionally substituted by 1 or 2 independently selected oxo or sulfide groups (e.g., C(O) or C(S)). Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, or 10 ring-forming carbons ($C_{3-10}$). In some embodiments, the cycloalkyl is a $C_{3-10}$ monocyclic or bicyclic cycloalkyl. In some embodiments, the cycloalkyl is a $C_{3-7}$ monocyclic cycloalkyl. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcamyl, adamantyl, and the like. In some embodiments, cycloalkyl is cyclopropyl, cyclobutyl, cyclopentyl, or cyclohexyl.

As used herein, "heteroaryl" refers to a monocyclic or polycyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur and oxygen. In some embodiments, any ring-forming N in a heteroaryl moiety can be an N-oxide. In some embodiments, the heteroaryl is a 5-10 membered monocyclic or bicyclic heteroaryl having 1, 2, 3 or 4 heteroatom ring members independently selected from nitrogen, sulfur and oxygen. In some embodiments, the heteroaryl is a 5-6 monocyclic heteroaryl having 1 or 2 heteroatom ring members independently selected from nitrogen, sulfur and oxygen. In some embodiments, the heteroaryl is a five-membered or six-membered heteroaryl ring. A five-membered heteroaryl ring is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl and pyridazinyl.

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, 7-, 8-, 9- or 10-membered heterocycloalkyl groups. Heterocycloalkyl groups can also include spirocycles. Example heterocycloalkyl groups include pyrrolidin-2-one, 1,3-isoxazolidin-2-one, pyranyl, tetrahydropyran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by 1 or 2 independently selected oxo or sulfido groups (e.g., C(O), S(O), C(S), or $S(O)_2$, etc.). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the cycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl is a monocyclic 4-6 membered heterocycloalkyl having 1 or 2 heteroatoms independently selected from nitrogen, oxygen, or sulfur and having one or more oxidized ring members. In some embodiments, the heterocycloalkyl is a monocyclic or bicyclic 4-10 membered heterocycloalkyl having 1, 2, 3, or 4 heteroatoms independently selected from nitrogen, oxygen, or sulfur and having one or more oxidized ring members.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

As used herein, the term "oxo" refers to an oxygen atom as a divalent substituent, forming a carbonyl group when attached to a carbon (e.g., C═O), or attached to a heteroatom forming a sulfoxide or sulfone group.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C═N double bonds, N═N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. In some embodiments, the compound has the (R)-configuration. In some embodiments, the compound has the (S)-configuration.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, enamine—imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the PAPD5 with a compound of the invention includes the administration of a compound of the present invention to an individual or patient, such as a human, having PAPD5, as well as, for example, introducing a compound of the invention into a sample containing a cellular or purified preparation containing the PAPD5.

As used herein, the term "individual", "patient", or "subject" used interchangeably, refers to any animal, including mammals, preferably mice, rats, other rodents, rabbits, dogs, cats, swine, cattle, sheep, horses, or primates, and most preferably humans.

As used herein, the phrase "effective amount" or "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein the term "treating" or "treatment" refers to 1) inhibiting the disease; for example, inhibiting a disease, condition or disorder in an individual who is experiencing or displaying the pathology or symptomatology of the disease, condition or disorder (i.e., arresting further development of the pathology and/or symptomatology), or 2) ameliorating the disease; for example, ameliorating a disease, condition or disorder in an individual who is experiencing or displaying the pathology or symptomatology of the disease, condition or disorder (i.e., reversing the pathology and/or symptomatology).

As used herein, the term "preventing" or "prevention" of a disease, condition or disorder refers to decreasing the risk of occurrence of the disease, condition or disorder in a subject or group of subjects (e.g., a subject or group of subjects predisposed to or susceptible to the disease, condition or disorder). In some embodiments, preventing a disease, condition or disorder refers to decreasing the possibility of acquiring the disease, condition or disorder and/or its associated symptoms. In some embodiments, preventing a disease, condition or disorder refers to completely or almost completely stopping the disease, condition or disorder from occurring.

EXAMPLES

Example 1

Inhibition of Recombinant PAPD5

Recombinant PAPD5 as well as catalytically inactive mutant PAPD5 (D189A, D191A) were purified for in vitro assays. An in vitro RNA polyadenylation assay using recombinant PAPD5, ATP and an oligonucleotide substrate utilized the following phenomenon: ATP utilization by PAPD5 reads out as a decreased luminescence signal produced by luciferase (KinaseGlo, Promega, Madison, WI).

0.25 μl of PAPD5 in a buffer composition at a concentration of 50 nM was added to a well of a microtitre plate (e.g., Product #3820; non-binding surface; Corning Incorporated, Corning, NY) using a Thermo MultiDrop Combi (Thermo Fisher Scientific, Waltham, MA). For positive control (e.g., wells A24: P24 in a multi-well plate), 0.5 μl of mutant PAPD5 was added at a concentration of 50 nM.

100 nl of a compound dissolved in DMSO was transferred to each well of the assay plate via pin transfer. For negative control wells, DMSO alone was added. Plates were gently vortexed for 5 seconds, then incubated for 2 hours at room temperature.

After 2 hours, 5 μl of luciferase (Promega KinaseGlo, Madison, WI) was added using a MultiDrop Combi (Thermo Fisher Scientific, Waltham, MA). The mixture was gently vortexed for 5 seconds and incubated for 10 minutes at room temperature. Plates were spun for 1 minute prior to luminescence measurements. Luminescent measurements were quantitated using a PerkinElmer EnVisioni'm plate reader.

The fold-change for 100 μM compound and 33 μM compound were calculated. For certain compounds, fold-change at 10 μM, 3.3 μM, and 1 μM concentration was also determined. The fold change is a ratio of luminescence from a sample with inhibitor compared to that with DMSO (a higher number indicates higher inhibition).

Referring to FIGS. 3-6, cmpd.1 (also referred to as 32A) is a compound having the formula:

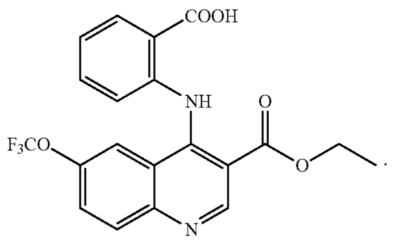 [SMILES: CCOC(=O)c1cnc2ccc(OC(F)(F)F)cc2c1Nc1ccccc1C(=O)O]

Example 2

Qualitative measure of RNA oligo-extension inhibition for the tested compounds, expressed as range from minimal activity (0) to that of compound 1 (+++), and results of a DSF binding assay (shown as shift in temperature at 100 μM of the compound) are shown in the Table 2 below.

TABLE 2

| Compound No. | Inhibition of PAPD5 RNA oligo adenylation | $\Delta T_m$ 100 μM |
|---|---|---|
| 10A | + | 1.0 |
| 13A | + | 5.6 |
| 1A | 0 | 0.4 |
| 12A | + | 6.1 |
| 15A | ++ | 8.8 |
| 26A | +++ | 11.1 |
| 27A | 0 | 2.8 |
| 14A | ++ | 1.7 |
| 23A | +++ | 4.6 |
| 25A | 0 | 0.1 |
| 18A | 0 | -0.1 |
| 28A | + | 5.5 |
| 29A | +++ | 4.9 |
| 30A | 0 | 1.7 |
| 31A | 0 | 1.8 |
| 33A | 0 | 0.7 |
| 32A | +++ | 7.9 |
| 17A | +++ | 8.4 |
| 5A | 0 | 2.3 |
| 16A | +++ | 9.6 |
| 19A | 0 | 0.6 |
| 34A | 0 | 0.3 |
| 51A | + | 7.9 |
| 53A | + | 5.2 |
| 54A | +++ | fluorescent |
| 55A | +++ | 13.9 |
| 56A | 0 | 0.4 |
| 57A | +++ | 9.8 |
| 58A | + | 8.5 |
| 61A | +++ | 11.1 |
| 63A | +++ | 9.3 |
| 64A | | 6.3 |
| 70A | +++ | 13.7 |
| 78A | +++ | 17.1 |
| 78A-BR | | fluorescent |
| 78A-INT | 0 | 1.1 |
| 79A | | |
| 79A-INT | | 0 |
| 80A | +++ | 16.4 |
| 81A | | |
| 81A-INT | | |
| 82A | +++ | 13.5 |
| 83A-INT | | |
| 85A | | 0 |
| 85A-BP | | 6.8 |
| 86A | | |
| 93A | | |
| 93A-INT | | 0 |

Example 3

Preparation of Compound 1A

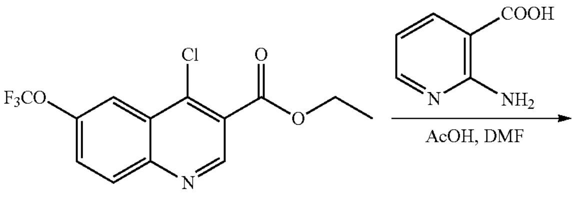

-continued

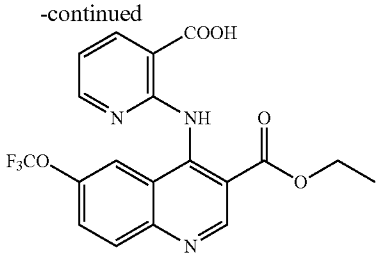

Synthesis of 2-[[3-ethoxycarbonyl-6-(trifluoromethoxy)-4-quinolyl]amino]pyridine-3-carboxylic acid: To a sealed tube was added: ethyl 4-chloro-6-(trifluoromethoxy)quinoline-3-carboxylate (100 mg, 312.83 μmol, 1 eq), AcOH (4.70 mg, 78.21 μmol, 4.47 μL, 0.25 eq) 2-aminopyridine-3-carboxylic acid (129.63 mg, 938.49 μmol, 3 eq) and DMF (4 mL). Then the sealed tube was stirred at 130° C. for 0.5 h under microwave. LCMS showed starting material remained and desired product was formed. The mixture was filtered and the filtrate was purified directly. The filtrate was purified by prep-HPLC: column: Waters Xbridge BEH C18 100×25 mm×5 μm; mobile phase: [water(10 mMNH$_4$HCO$_3$)-ACN]; B %: 20%-70%, 8 min. 2-[[3-ethoxycarbonyl-6-(trifluoromethoxy)-4-quinolyl]amino]pyridine-3-carboxylic acid (2.24 mg, 5.10 μmol, 1.63% yield, 95.96% purity) was obtained as off-white solid. $^1$H NMR (400 MHz, DMSO-d$_6$) δ=9.38 (s, 1H), 8.49 (d, J=1.6 Hz, 1H), 8.38 (d, J=1.6 Hz, 1H), 8.36 (d, J=10.8 Hz, 1H), 8.35 (s, 1H), 8.32-8.01 (m, 1H), 7.48-7.23 (m, 2H), 6.81-6.78 (m, 1H), 4.23 (1, J=6.8 Hz, 2H), 1.07 (t, J=7.2 Hz, 1H). MS $(M+H)^+$=422.0.

Example 4

Preparation of Compound 5A

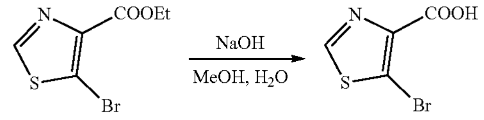 [SMILES: CCOC(=O)c1ncsc1Br ; "NaOH" ; O=C(O)c1ncsc1Br]

Step 1—Synthesis of 5-bromothiazole-4-carboxylic acid: To a stirred solution of ethyl 5-bromothiazole-4-carboxylate (3.7 g, 15.67 mmol, 1 eq) in MeOH (20 mL), THF (20 mL), H$_2$O (20 mL) was added NaOH (2 M, 23.51 mL, 3 eq). Then the mixture was stirred at 20° C. for 1 h. TLC (Petroleum ether:Ethyl acetate=20/1) showed starting material was completely consumed. The mixture was adjusted to pH=3 by adding 6N HCl, then filtered. The filter cake was dried over in vacuo. 5-bromothiazole-4-carboxylic acid (2.8 g, 13.46 mmol, 85.88% yield) was obtained as yellow solid. $^1$H NMR (400 MHz, DMSO-d6) δ=13.38 (brs, 1H), 9.14 (s, 1H).

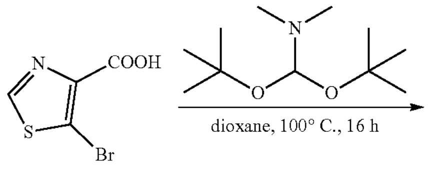

-continued

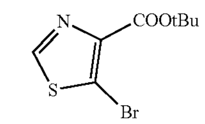

Step 2—Synthesis of 4-chloro-6-(trifluoromethoxy)quinoline-3-carbonyl chloride: To a solution of 5-bromothiazole-4-carboxylic acid (1.7 g, 8.17 mmol, 1 eq) in dioxane (20 mL) was added dropwise 1,1-ditertbutoxy-N,N-dimethyl-methanamine (1.66 g, 8.17 mmol, 1.96 mL, 1 eq), then stirred for 2 h at 100° C. TLC (Petroleum ether:Ethyl acetate=5:1, Rf=0.43) showed the reaction was complete. The mixture was concentrated in vacuo. The crude product was purified by flash column (ISCO 20 g silica, 0~10% ethyl acetate in petroleum ether, gradient over 30 min). TLC (Petroleum ether:Ethyl acetate=5:1, Rf=0.43). tert-butyl 5-bromothiazole-4-carboxylate (1.6 g, 6.06 mmol, 74.14% yield) was obtained as a yellow oil. $^1$H NMR (400 MHz, DMSO-d6) δ=8.76 (s, 1H), 1.64 (s, 9H).

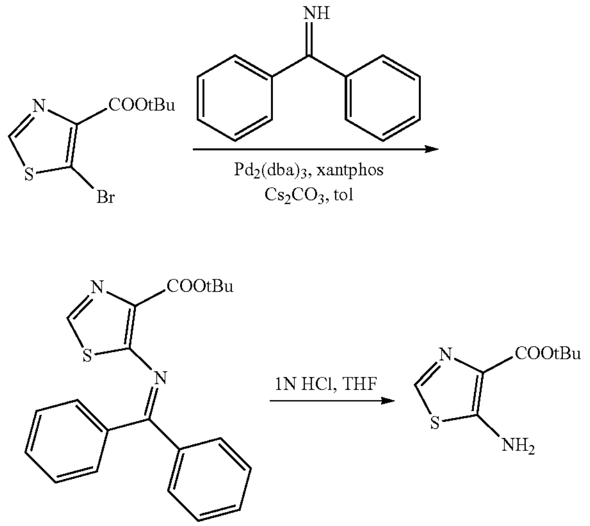

Step 3—Synthesis of tert-butyl 5-(benzhydrylideneamino)thiazole-4-carboxylate: To a stirred solution of tert-butyl 5-bromothiazole-4-carboxylate (2 g, 7.57 mmol, 1 eq) in toluene (20 mL) was added $Cs_2CO_3$ (4.93 g, 15.14 mmol, 2 eq), Xantphos (788.61 mg, 1.36 mmol, 0.18 eq), $Pd_2(dba)_3$ (346.68 mg, 378.59 μmol, 0.05 eq) and diphenylmethanimine (2.06 g, 11.36 mmol, 1.91 mL, 1.5 eq). Then the mixture was stirred at 80° C. for 16 h. TLC (Petroleum ether:Ethyl acetate=3/1) showed starting material was completely consumed and new spot was formed. The solvent was removed in vacuo to afford the residue. The residue was dissolved in ethyl acetate (30 mL), washed with water (20 mL), dried over anhydrous sodium sulfate and concentrated to afford the crude product. The crude product was purified by column chromatography ($SiO_2$, Petroleum ether/Ethyl acetate=1/0 to 10/1). tert-butyl 5-(benzhydrylideneamino) thiazole-4-carboxylate (2.3 g, 6.31 mmol, 83.35% yield) was obtained as yellow solid. $^1$H NMR (400 MHz, CHLOROFORM-d) δ=8.29 (s, 1H), 7.88-7.81 (m, 2H), 7.51-7.40 (m, 6H), 7.26-7.15 (m, 2H), 1.55 (s, 9H).

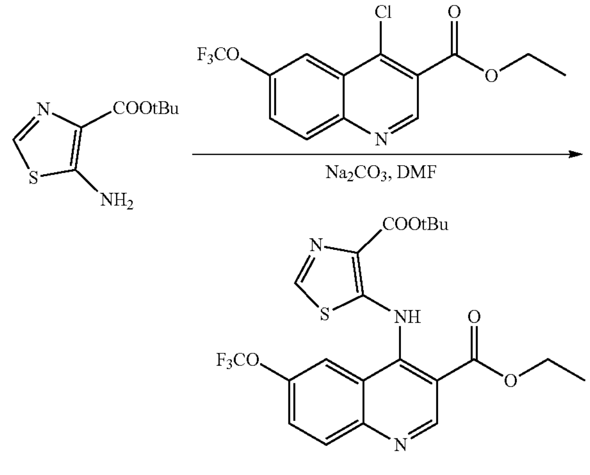

Step 4—Synthesis of tert-butyl 5-[[3-ethoxycarbonyl-6-(trifluoromethoxy)-4-quinolyl]amino]thiazole-4-carboxylate: To a stirred solution of ethyl 4-chloro-6-(trifluoromethoxy)quinoline-3-carboxylate (400 mg, 1.25 mmol, 1 eq) in DMF (5 mL) was added tert-butyl 5-aminothiazole-4-carboxylate (375.88 mg, 1.88 mmol, 1.5 eq) and $Na_2CO_3$ (265.25 mg, 2.50 mmol, 2 eq). Then the mixture was stirred at 110° C. for 5 hr. LCMS showed desired product was formed. The mixture was poured into water (20 mL), extracted with ethyl acetate (20 mL×3). The combined organic layers were dried over anhydrous sodium sulfate and concentrated to afford the crude product. The residue was purified by flash column (ISCO 10 g silica, 0-30% Ethyl acetate in Petroleum ether, gradient over 20 min). tert-butyl 5-[[3-ethoxycarbonyl-6-(trifluoromethoxy)-4-quinolyl] amino]thiazole-4-carboxylate (370 mg, 765.32 μmol, 61.16% yield) was obtained as a yellow solid. $^1$H NMR (400 MHz, CHLOROFORM-d) δ=11.24 (s, 1H), 9.37 (s, 1H), 8.18 (d, J=9.2 Hz, 1H), 8.10 (s, 1H), 7.77 (s, 1H), 7.66 (br d, J=8.0 Hz, 1H), 4.51 (q, J=7.2 Hz, 2H), 1.71 (s, 9H), 1.46 (t, J=7.2 Hz, 3H).

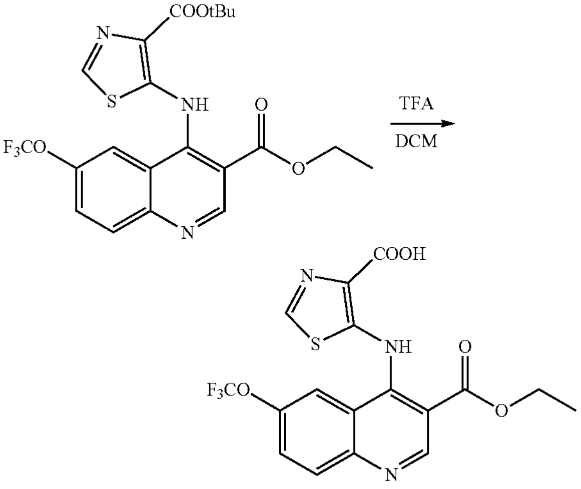

Step 5—Synthesis of 5-((3-(ethoxycarbonyl)-6-(trifluoromethoxy)quinolin-4-yl)amino)thiazole-4-carboxylic acid: To a stirred solution of tert-butyl 5-[[3-ethoxycarbonyl-6-(trifluoromethoxy)-4-quinolyl]amino]thiazole-4-carboxylate (140 mg, 289.58 μmol, 1 eq) in DCM (1 mL) was added TFA (1 mL). Then the mixture was stirred at 25° C. for 1 h. LCMS showed starting material was completely consumed and desired product was formed. DMF (3 mL) was added to the mixture. Part of TFA was removed in vacuo. The solution was purified by prep-HPLC:column: Phenomenex Luna C18 100x30 mmx5 μm; mobile phase: [water(0.1% TFA)-ACN]; B %: 10%-45%, 12 min. 5-[[3-ethoxy carbonyl-6-(trifluoromethoxy)-4-quinolyl]amino]thiazole-4-carboxylic acid (25 mg, 38.35 μmol, 13.24% yield, 83.04% purity, TFA) was obtained as yellow solid. $^1$H NMR (400 MHz, DMSO-d6) δ=8.92 (br s, 1H), 8.45 (s, 1H), 8.20-7.97 (m, 2H), 7.86 (br d, J=8.0 Hz, 1H), 4.24-4.05 (m, 2H), 1.21 (br t, J=6.9 Hz, 3H). MS $(M+H)^+$=428.0.

Example 5

Preparation of Compound 10A

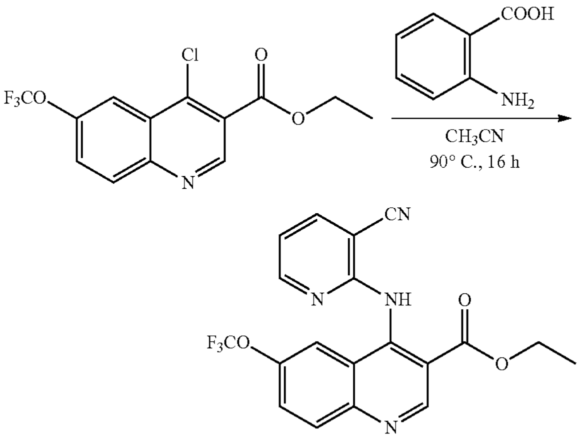

Step 1—Synthesis of ethyl 4-(2-cyanoanilino)-6-(trifluoromethoxy)quinoline-3-carboxylate: A solution of ethyl 4-chloro-6-(trifluoromethoxy)quinoline-3-carboxylate (0.2 mg, 625.66 μmol, 1 eq) and 2-aminobenzonitrile (147.83 mg, 1.25 mmol, 2.0 eq) in ACN (3 mL) was stirred at 90° C. for 16 h. LCMS showed starting material was completely consumed and desired product was formed. The mixture was concentrated to afford the crude product. The crude product was purified by flash column (ISCO 12 g silica, 0-50% ethyl acetate in petroleum ether, gradient over 20 min, 1/400 TEA) to give ethyl 4-(2-cyanoanilino)-6-(trifluoromethoxy) quinoline-3-carboxylate (0.2 g, 498.33 μmol, 79.65% yield) as yellow solid. MS $(M+H)^+$=402.0

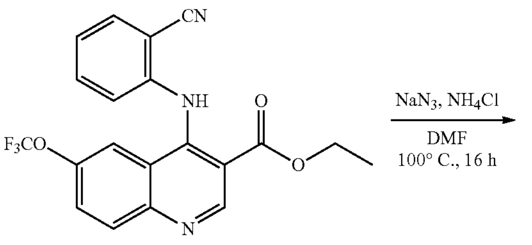

-continued

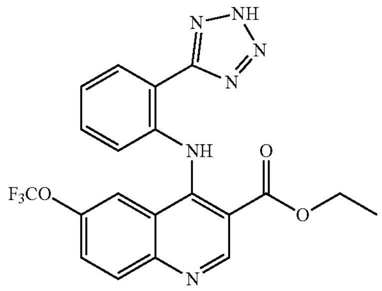

Step 2—Synthesis of ethyl 4-[2-(2H-tetrazol-5-yl)anilino]-6-(trifluoromethoxy)quinoline-3-carboxylate: To a stirred solution of ethyl 4-(2-cyanoanilino)-6-(trifluoromethoxy)quinoline-3-carboxylate (150 mg, 373.75 μmol, 1 eq) and $NH_4Cl$ (199.92 mg, 3.74 mmol, 10 eq) in DMF (2 mL) was added $NaN_3$ (121.49 mg, 1.87 mmol, 5 eq), then stirred for 14 h at 100° C. LCMS showed ~65% desired product and ~25% starting material were detected. The mixture was filtered to give filtrate. The crude product was purified by prep-HPLC (Waters Xbridge Prep OBD C18 150x40 mmx10 μm column; 10%-40% acetonitrile in an a 0.04% ammonia solution and 10 mM $NH_4HCO_3$ in water, 10 min gradient) to give ethyl 4-[2-(2H-tetrazol-5-yl)anilino]-6-(trifluoromethoxy)quinoline-3-carboxylate (34.27 mg, 75.27 μmol, 20.14% yield, 97.6% purity) as yellow solid. $^1$H NMR (400 MHz, DMSO-$d_6$) δ=10.83 (br s, 1H), 9.07 (s, 1H), 8.22-8.00 (m, 2H), 7.87-7.65 (m, 2H), 7.38-7.24 (m, 2H), 6.94 (d, J=8.1 Hz, 1H), 4.15 (br s, 2H), 1.18 (t, J=7.1 Hz, 3H). MS $(M+H)^+$=445.0.

Example 6

Preparation of Compound 12A

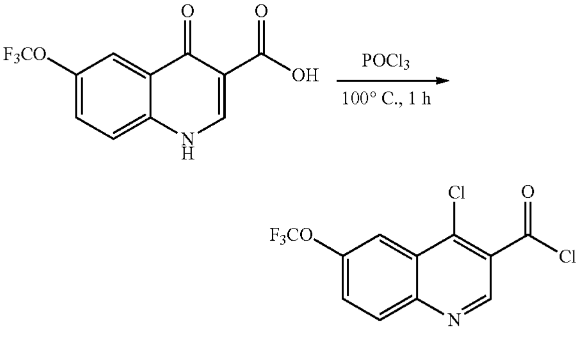

Step 1—Synthesis of 4-chloro-6-(trifluoromethoxy)quinoline-3-carbonyl chloride: A stirred solution of 4-oxo-6-(trifluoromethoxy)-1H-quinoline-3-carboxylic acid (300 mg, 1.10 mmol, 1 eq) in $POCl_3$ (3 mL) was heated to 100° C. and stirred for 1 h. LCMS showed no starting material was remained. The mixture was cooled to room temperature and concentrated in vacuo. The residual was dissolved in toluene (3 mLx2), concentrated in vacuo to dryness to give 4-chloro-6-trifluoromethoxy)quinoline-3-carbonyl chloride (335.2 mg, crude) was obtained as a brown gum.

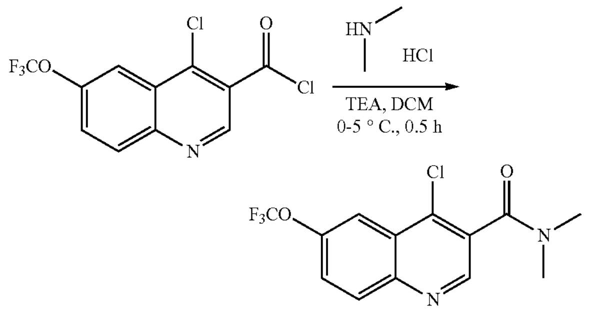

Step 2—Synthesis of methyl 4-chloro-N, N-dimethyl-6-(trifluoromethoxy)quinoline-3-carboxamide: to a solution of 4-chloro-6-(trifluoromethoxy)quinoline-3-carbonyl chloride (330 mg, 1.06 mmol, 1 eq) in DCM (3 mL) was added TEA (429.05 mg, 4.24 mmol, 590.16 μL, 4 eq) and N-methylmethanamine (77.79 mg, 954.00 μmol, 87.41 μL, 0.9 eq, HCl) at 0° C., then stirred for 0.5 h at 0° C. LCMS showed the reaction was complete. Water (3 mL) was added into the above solution, separated, extracted with DCM (5 mL×2). The combined organic layers was washed with water (3 mL), dried over $Na_2SO_4$, concentrated in vacuo to give 4-chloro-N,N-dimethyl-6-(trifluoromethoxy)quinoline-3-carboxamide (230.2 mg, crude) as brown oil. MS $(M+H)^+$=319.1.

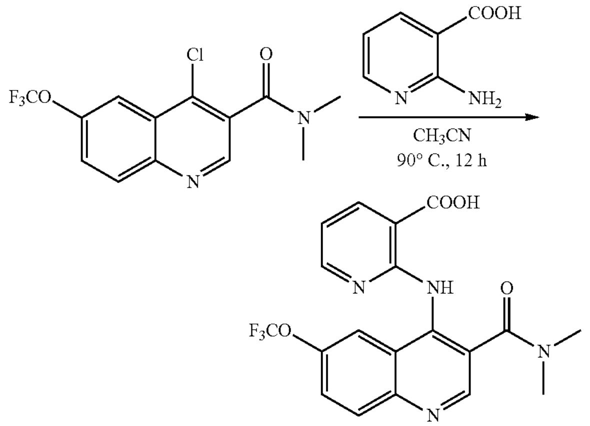

Step 3—Synthesis of 2-[[3-(dimethylcarbamoyl)-6-(trifluoromethoxy)-4-quinolyl]amino]benzoic acid: a solution of 4-chloro-N,N-dimethyl-6-(trifluoromethoxy)quinoline-3-carboxamide (110 mg, 345.18 μmol, 1 eq) and 2-aminobenzoic acid (56.80 mg, 414.21 μmol, 1.2 eq) in ACN (4 mL) was stirred for 14 h at 90° C. LCMS showed the reaction was complete, the desired product was detected. The mixture was concentrated in vacuo, dissolved in MeOH (2 mL). The crude product was purified by prep-HPLC (Waters Xbridge Prep OBD C18 150×40 mm×10 μm column; 1%-30% acetonitrile in an a 0.04% ammonia solution and 10 mM $NH_4HCO_3$ in water, 10 min gradient) to give 2-[[3-(dimethylcarbamoyl)-6-(trifluoromethoxy)-4-quinolyl]amino]benzoic acid (67.29 mg, 152.20 μmol, 44.09% yield, 94.85% purity) as yellow solid. $^1H$ NMR (400 MHz, DMSO-d6) δ=12.00 (br s, 1H), 8.68 (s, 1H), 8.13 (d, J=9.0 Hz, 1H), 8.00-7.91 (m, 2H), 7.79 (br d, J=8.8 Hz, 1H), 7.38 (br s, 1H), 7.23 (t, J=7.6 Hz, 1H), 6.90 (t, J=7.4 Hz, 1H), 6.72 (d, J=8.2 Hz, 1H), 2.72 (s, 3H), 2.56 (s, 3H). MS $(M+H)^+$=420.0

Example 7

Preparation of Compound 13A

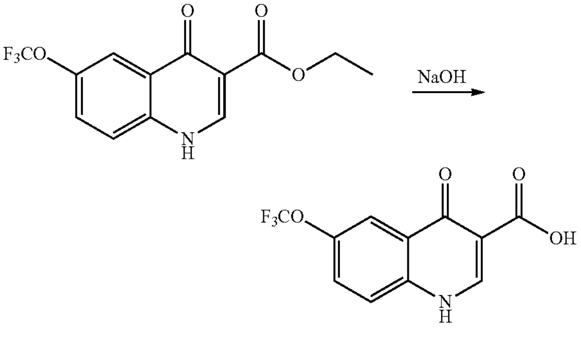

Step 1—Synthesis of 4-oxo-6-(trifluoromethoxy)-1H-quinoline-3-carboxylic acid: A suspension of ethyl 4-oxo-6-(trifluoromethoxy)-1H-quinoline-3-carboxylate (500 mg, 1.66 mmol, 1 eq) in NaOH (2M, 12.50 mL, 15.06 eq) was stirred at 90° C. for 1 h. LCMS showed starting material was completely consumed and desired product was formed. The mixture was cooled to 0° C., adjusted to pH6-7 by adding 4N HCl, then filtered. The filter cake was dried in vacuo. 4-oxo-6-(trifluoromethoxy)-1H-quinoline-3-carboxylic acid (450 mg, 1.65 mmol, 99.24% yield) was obtained as white solid. $^1H$ NMR (400 MHz, DMSO-d6) δ=8.81 (s, 1H), 8.01 (s, 1H), 7.84 (d, J=9.2 Hz, 1H), 7.64 (d, J=8.0 Hz, 1H). MS (M−H)−=271.9.

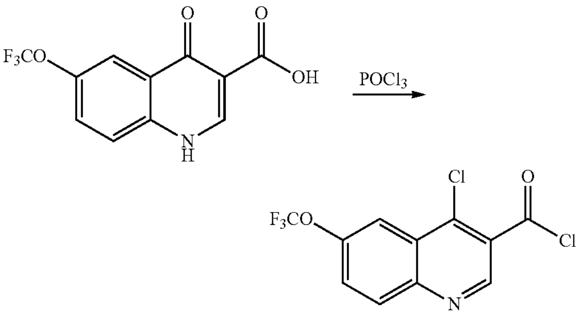

Step 2—Synthesis of 4-chloro-6-(trifluoromethoxy)quinoline-3-carbonyl chloride: A solution of 4-oxo-6-(trifluoromethoxy)-1H-quinoline-3-carboxylic acid (200 mg, 732.16 μmol, 1 eq) in $POCl_3$ (2 mL) was stirred at 100° C. for 1 h. LCMS (a sample was quenched with MeOH at low temperature) showed starting material was completely consumed and desired product was formed. The resulting solution was evaporated to dryness and the residue azeotroped with toluene (3 mL×2). 4-chloro-6-(trifluoromethoxy)quinoline-3-carbonyl chloride (200 mg, crude) was obtained as brown solid.

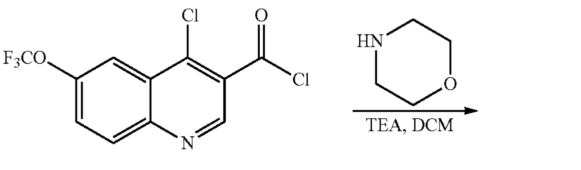

-continued

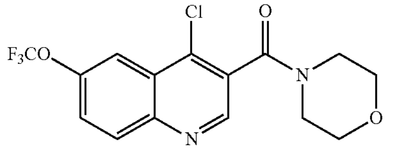

Step 3Synthesis of [4-chloro-6-(trifluoromethoxy)-3-quinolyl]-morpholino-methanone: To a stirred solution of 4-chloro-6-(trifluoromethoxy)quinoline-3-carbonyl chloride (100 mg, 322.52 μmol, 1 eq) in DCM (3 mL) was added TEA (97.91 mg, 967.57 μmol, 134.67 4, 3.0 eq) and morpholine (25.29 mg, 290.27 μmol, 25.54 μL, 0.9 eq) at 0° C. Then the mixture was stirred at 0° C. for 0.5 h. LCMS showed starting material was completely consumed and desired product was formed. The mixture was quenched with water (5 mL) at 0° C., extracted with DCM (5 mL×3). The combined organic layers were dried over anhydrous sodium sulfate and concentrated to afford the crude product. [4-chloro-6-(trifluoromethoxy)-3-quinolyl]-morpholino-methanone (90 mg, crude) was obtained as yellow solid. MS $(M+H)^+$=361.1.

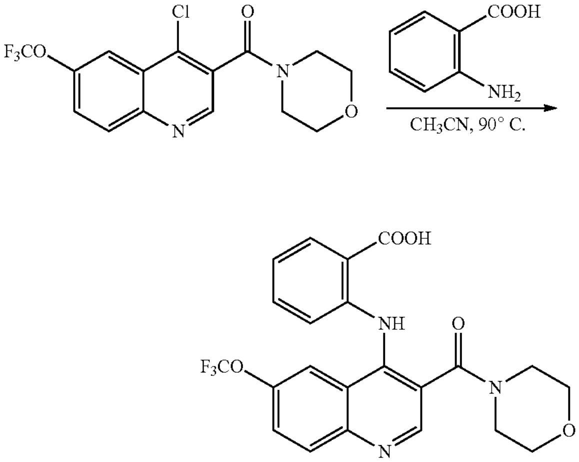

Step 4—Synthesis of 2-[[3-(morpholine-4-carbonyl)-6-(trifluoromethoxy)-4-quinolyl]amino]benzoic acid: To a stirred solution of [4-chloro-6-(trifluoromethoxy)-3-quinolyl]-morpholino-methanone (90 mg, 249.50 μmol, 1 eq) in $CH_3CN$ (3 mL) was added 2-aminobenzoic acid (47.90 mg, 349.31 μmol, 1.4 eq). Then the mixture was stirred at 90° C. for 12 h. LCMS showed starting material was completely consumed and desired product was formed. The mixture was concentrated to afford the crude product. The crude product was purified by prep-HPLC:column: Welch Xtimate C18 150×30 mm×5 μm; mobile phase: [water(10 mM $NH_4HCO_3$)-ACN]; B %: 10%-50%, 8 min. 2-[[3-(morpholine-4-carbonyl)-6-(trifluoromethoxy)-4-quinolyl]amino] benzoic acid (51.07 mg, 110.69 μmol, 44.36% yield, 100.00% purity) was obtained as yellow solid. $^1H$ NMR (400 MHz, DMSO-$d_6$) δ=13.20 (brs, 1H), 10.74 (brs, 1H), 8.78 (s, 1H), 8.19 (d, J=9.2 Hz, 1H), 8.96 (d, J=7.2 Hz, 1H), 7.93 (s, 1H), 7.83 (d, J=8.8 Hz, 1H), 7.32 (t, J=8.0 Hz, 1H), 6.95 (t, J=7.6 Hz, 1H), 6.72 (d, J=8.4 Hz, 1H), 3.85-3.23 (m, 8H). MS $(M+H)^+$=428.0.

Example 8

Preparation of Compound 14A

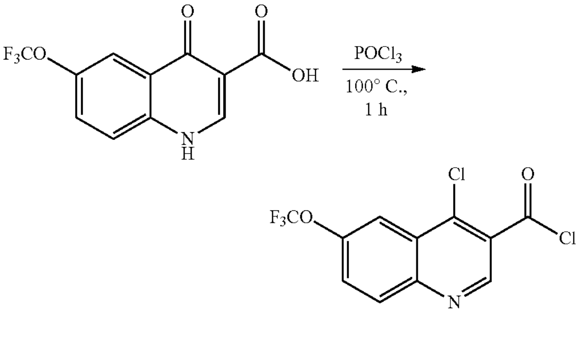

Step 1—Synthesis of 4-chloro-6-(trifluoromethoxy)quinoline-3-carbonyl chloride: A solution of 4-oxo-6-(trifluoromethoxy)-1H-quinoline-3-carboxylic acid (500 mg, 1.83 mmol, 1 eq) in $POCl_3$ (2 mL) was stirred at 100° C. for 1 h. LCMS (a sample was quenched with MeOH at low temperature) showed starting material was completely consumed and desired product was formed. The resulting solution was evaporated to dryness and the residue azeotroped with toluene (5 mL×2). 4-chloro-6-(trifluoromethoxy)quinoline-3-carbonyl chloride (500 mg, crude) was obtained as brown gum.

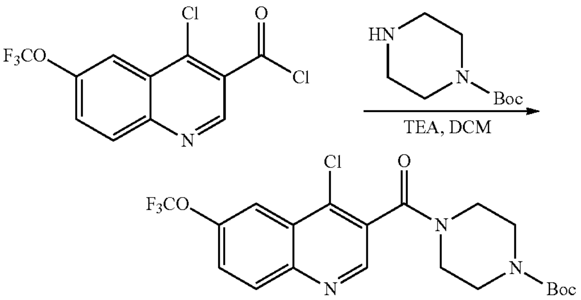

Step 2—Synthesis of tert-butyl 4-(4-chloro-6-(trifluoromethoxy)quinoline-3-carbonyl)piperazine-1-carboxylate: To a stirred solution of 4-chloro-6-(trifluoromethoxy)quinoline-3-carbonyl chloride (500 mg, 1.61 mmol, 1 eq) in DCM (7 mL) was added TEA (489.54 mg, 4.84 mmol, 673.37 μL, 3.0 eq) and tert-butyl piperazine-1-carboxylate (270.32 mg, 1.45 mmol, 0.9 eq) at 0-5° C. Then the mixture was stirred at 0-5° C. for 0.5 h. LCMS showed starting material was completely consumed and desired product was formed. The mixture was quenched with water (6 mL) at 0° C., extracted with DCM (5 mL×3). The combined organic layers were dried over anhydrous sodium sulfate and concentrated to afford the crude product. tert-butyl 4-[4-chloro-6-(trifluoromethoxy)quinoline-3-carbonyl]piperazine-1-carboxylate (630 mg, crude) was obtained as brown solid. MS $(M+H)^+$=460.1.

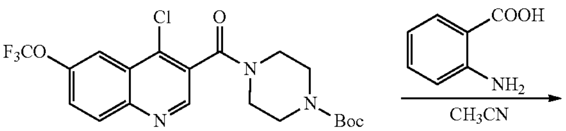

-continued

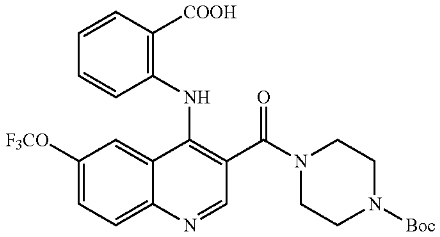

Step 3—Synthesis of 2-[[3-(4-tert-butoxycarbonylpiperazine-1-carbonyl)-6-(trifluoromethoxy)-4-quinolyl]amino] benzoic acid: A solution of tert-butyl 4-[4-chloro-6-(trifluoromethoxy)quinoline-3-carbonyl]piperazine-1-carboxylate (300 mg, 652.39 μmol, 1 eq) and 2-aminobenzoic acid (107.36 mg, 782.87 μmol, 1.2 eq) in $CH_3CN$ (5 mL) were stirred at 90° C. for 40 h. LCMS showed desired product was formed. The mixture was concentrated to afford the crude product. 2-[[3-(4-tert-butoxycarbonylpiperazine-1-carbonyl)-6-(trifluoromethoxy)-4-quinolyl]amino]benzoic acid (450 mg, crude) was obtained as brown solid. MS $(M+H)^+$=561.2.

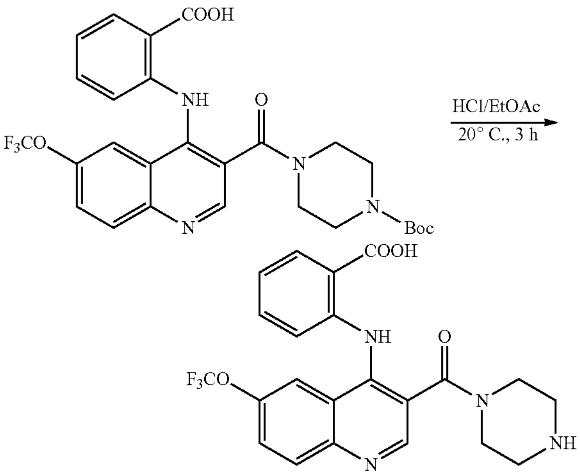

Step 4—Synthesis of 2-[[3-(piperazine-1-carbonyl)-6-(trifluoromethoxy)-4-quinolyl]amino]benzoic acid: To a stirred solution of 2-[[3-(4-tert-butoxycarbonylpiperazine-1-carbonyl)-6-(trifluoromethoxy)-4-quinolyl]amino]benzoic acid (170 mg, 303.29 μmol, 1 eq) in ethyl acetate (2 mL) was added 4N HCl/EtOAc (2 mL). Then the mixture was stirred at 20° C. for 3 h. LCMS showed starting material was completely consumed and desired product was formed. The mixture was concentrated to afford the crude product. The crude product was purified by prep-HPLC:column: Phenomenex Luna C18 150×30 mm×5 μm; mobile phase: [water (0.04% HCl)-ACN]; B %: 15%-40%, 10 min2-[[3-(piperazine-1-carbonyl)-6-(trifluoromethoxy)-4-quinolyl]amino] benzoic acid (63.81 mg, 138.30 μmol, 45.60% yield, 99.79% purity) was obtained as yellow solid. $^1$H NMR (400 MHz, Methol-$d_4$) δ=8.76 (s, 1H), 8.52 (s, 1H), 8.21 (d, J=6.4 Hz, 1H), 8.16 (d, J=9.2 Hz, 1H), 8.01 (d, J=8.8 Hz, 1H), 7.67 (t, J=8.0 Hz, 1H), 7.50 (t, J=9.2 Hz, 1H), 7.39 (d, J=8.0 Hz, 1H), 3.56-3.32 (m, 4H), 3.30-3.01 (m, 4H). MS $(M+H)^+$=461.1.

Example 9

Preparation of Compound 15A

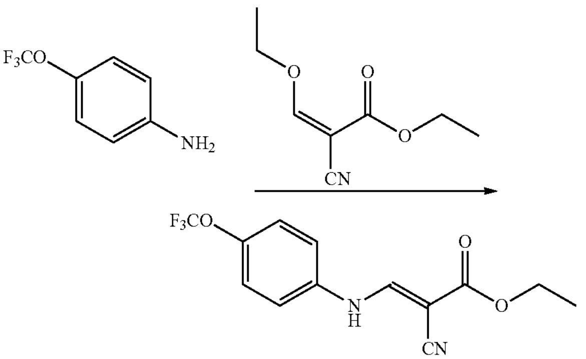

Step 1—Synthesis of ethyl-2-cyano-3-[4-(trifluoromethoxy)anilino]prop-2-enoate: To a stirred solution of 4-(trifluoromethoxy)aniline (2 g, 11.29 mmol, 1.53 mL, 1 eq) in toluene (50 mL) was added ethyl-2-cyano-3-ethoxy-prop-2-enoate (2.10 g, 12.42 mmol, 1.1 eq). Then the mixture was stirred at 110° C. for 14 h. TLC (Petroleum ether:Ethyl acetate=2/1) showed starting material was completely consumed and new spot was observed. The mixture was concentrated to afford the crude product. The crude product was triturated with MTBE (30 mL) at 20° C. for 15 min. ethyl-2-cyano-3-[4-(trifluoromethoxy)anilino]prop-2-enoate (1.7 g, 5.66 mmol, 50.15% yield) was obtained as pale yellow solid. $^1$H NMR (400 MHz,DMSO) δ=8.51-8.32 (m, 1H), 7.70-7.51 (m, 2H), 7.48-7.32 (m, 2H), 4.26-4.15 (m, 2H), 1.28-1.10 (m, 3H).

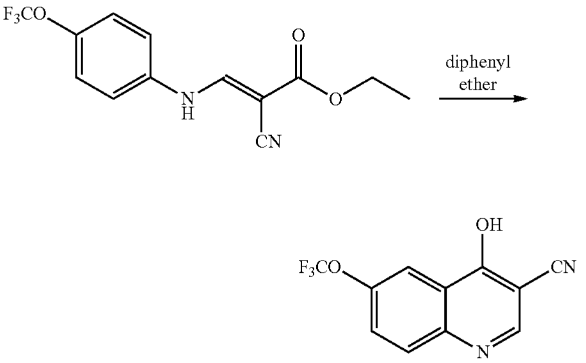

Step 2—Synthesis of 6-(trifluoromethoxy)quinolin-4-ol: A solution of ethyl-2-cyano-3-[4-(trifluoromethoxy)anilino] prop-2-enoate (500 mg, 1.67 mmol, 1 eq) in $Ph_2O$ (3 mL) was stirred at 250° C. for 12 h. TLC (Petroleum ether:Ethyl acetate=5/1) showed starting material was completely consumed and new spot was observed. The mixture (2 batches) was cooled to rt (~20° C.), MTBE (20 mL) was added, stirred for 5 min. Then filtered, the filter was washed with MTBE (3 mL×2), dried over in vacuo. 4-hydroxy-6-(trifluoromethoxy)quinoline-3-carbonitrile (0.6 g, crude) was obtained as brown solid.

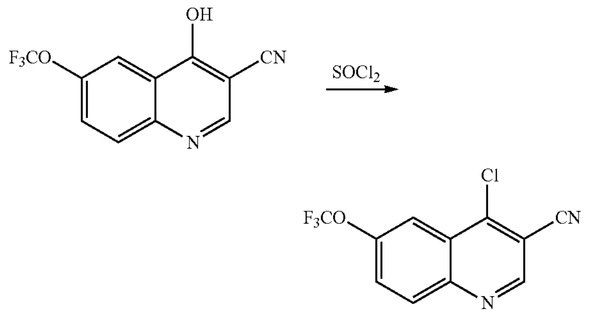

Step 3—Synthesis of 4-chloro-6-(trifluoromethoxy)quinoline-3-carbonitrile: To a suspension of 4-hydroxy-6-(trifluoromethoxy)quinoline-3-carbonitrile (200 mg, 786.89 μmol, 1 eq) in $SOCl_2$ (1 mL) was added DMF (5.75 mg, 78.69 μmol, 6.05 μL, 0.1 eq) at 0° C. Then the mixture was stirred at 20° C. for 13 h. LCMS (quenched with MeOH at low temperature) showed starting material was completely consumed and desired product was formed. The resulting solution was evaporated to dryness and the residue azeotroped with toluene (3 mL×2). 4-chloro-6-(trifluoromethoxy) quinoline-3-carbonitrile (160 mg, crude) was obtained as brown solid.

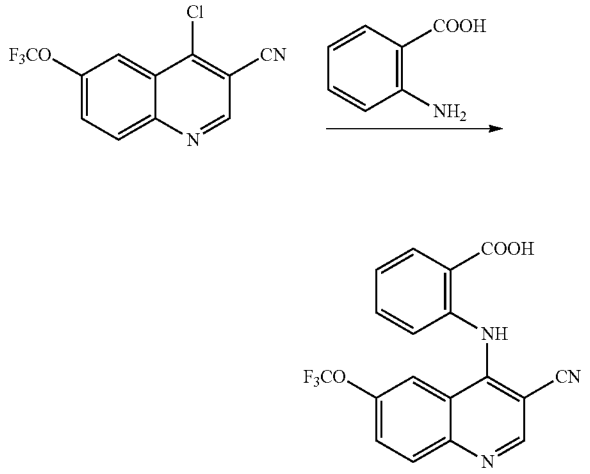

Step 4Synthesis of 2-[[3-cyano-6-(trifluoromethoxy)-4-quinolyl]amino]benzoic acid: A suspension of 4-chloro-6-(trifluoromethoxy)quinoline-3-carbonitrile (80 mg, 293.46 μmol, 1 eq) and 2-aminobenzoic acid (48.29 mg, 352.15 μmol, 1.2 eq) in $CH_3CN$ (3 mL) were stirred at 90° C. for 12 h. LCMS showed starting material was completely consumed and desired product was formed. The mixture was concentrated to afford the crude product. The crude product was purified by prep-HPLC: column: Phenomenex Luna C18 150×30 mm×5 μm; mobile phase: [water(0.04% HCl)-ACN]; B %: 30%-60%, 10 min. 2-[[3-cyano-6-(trifluoromethoxy)-4-quinolyl]amino]benzoic acid (19.62 mg, 51.29 μmol, 17.48% yield, 97.59% purity) was obtained as yellow solid. $^1H$ NMR (400 MHz, DMSO-$d_6$) δ=8.94 (s, 1H), 8.72 (s, 1H), 8.18 (d, J=8.8 Hz, 1H), 8.02 (t, J=6.4 Hz, 2H), 7.69 (t, J=7.2 Hz, 1H), 7.55-7.51 (m, 2H). MS $(M+H)^+$=428.0.

Example 10

Preparation of Compound 16A

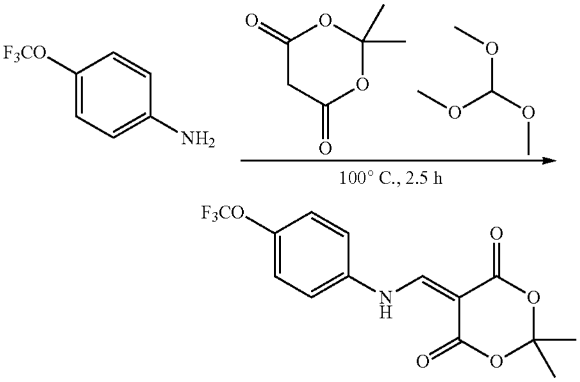

Step 1—A solution of 2,2-dimethyl-1,3-dioxane-4,6-dione (4.48 g, 31.05 mmol, 1.1 eq) and trimethoxymethane (13.30 g, 125.34 mmol, 13.74 mL, 4.44 eq) were stirred at 100° C. for 1 h, then 4-(trifluoromethoxy)aniline (5 g, 28.23 mmol, 3.82 mL, 1 eq) was added in dropwise at 100° C. over 0.5 h and stirred at 100° C. for another 1 h. TLC (Petroleum ether:Ethyl acetate=2/1) showed starting material was completely consumed and new spot was observed. The mixture was diluted with MTBE (30 ML), then filtered. The filter cake was dried in vacuo. 2,2-dimethyl-5-[[4-(trifluoromethoxy)anilino]methylene]-1,3-dioxane-4,6-dione (8 g, 24.15 mmol, 85.56% yield) was obtained as yellow solid. $^1H$ NMR (400 MHz,DMSO) δ=11.29 (brs, 1H), 8.64 (s, 1H), 7.70 (d, J=9.2 Hz, 2H), 7.42 (d, J=8.8 Hz, 2H), 1.67 (s, 6H).

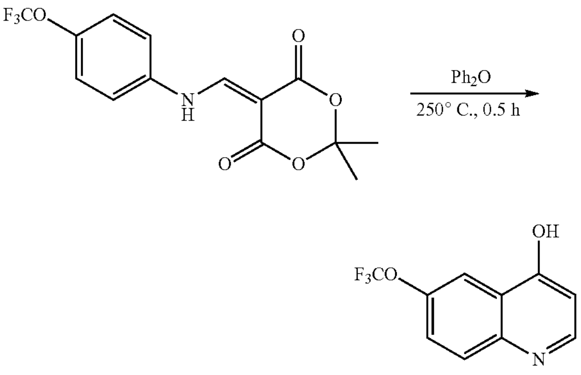

Step 2-2,2-dimethyl-5-[[4-(trifluoromethoxy)anilino] methylene]-1,3-dioxane-4,6-dione (4 g, 12.08 mmol, 1 eq) was added into $Ph_2O$ (10 mL) at 240° C., then stirred for 0.5 h at 240° C. TLC (Petroleum ether:Ethyl acetate=3:1, Rf=0.04) showed the reaction was complete. The mixture was cooled to 20° C., followed by MTBE (10 mL), then filtered to give crude product. 6-(trifluoromethoxy)quinolin-4-ol (870 mg, crude) was obtained as a brown solid. $^1H$ NMR (400 MHz, METHANOL-d4) δ=8.07 (br s, 1H), 7.97 (d, J=7.3 Hz, 1H), 7.70-7.61 (m, 1H), 7.61-7.54 (m, 1H), 6.32 (d, J=7.3 Hz, 1H), 4.89 (s, 1H).

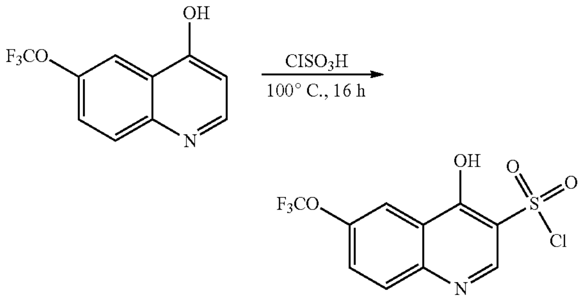

Step 3—To a stirred solution of chlorosulfonic acid (10 mL) was added 6-(trifluoromethoxy)quinolin-4-ol (1 g, 4.36 mmol, 1 eq) at 20° C. Then the mixture was heated to 100° C. and stirred at 100° C. for 16 h. LCMS showed starting material was completely consumed and new peak with the Ms of sulfonic acid. The mixture was poured onto ice (~8 g), extracted with ethyl acetate (8 mL×3). The combined organic layers were dried over anhydrous sodium sulfate and concentrated to afford the crude product. 4-hydroxy-6-(trifluoromethoxy)quinoline-3-sulfonyl chloride (1 g, 3.05 mmol, 69.94% yield) was obtained as brown solid.

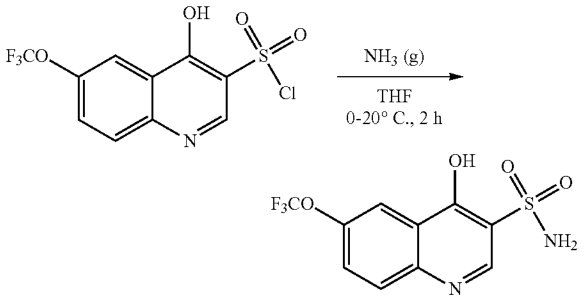

Step 4—To a stirred solution of THF (5 mL) was bubbled with $NH_3$ to pH~14 at 0° C., then 4-hydroxy-6-(trifluoromethoxy)quinoline-3-sulfonyl chloride (1 g, 3.05 mmol, 1 eq) dissolved in THF (1 mL) was added at 0° C. Then the mixture was stirred at 20° C. for 2 h. LCMS showed starting material was completely consumed and desired product was formed. The mixture was concentrated to afford the crude product. 4-hydroxy-6-(trifluoromethoxy)quinoline-3-sulfonamide (1.1 g, crude) was obtained as yellow solid.

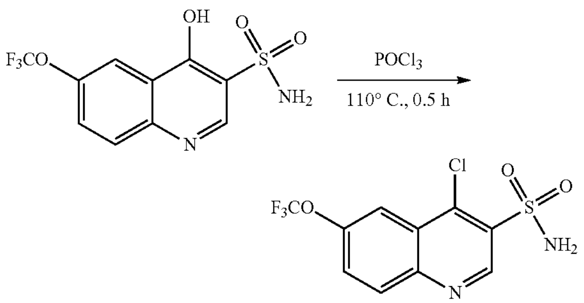

Step 5—A stirred solution of 4-hydroxy-6-(trifluoromethoxy)quinoline-3-sulfonamide (200 mg, 648.86 μmol, 1 eq) in $POCl_3$ (2 mL) was stirred at 110° C. for 0.5 h. LCMS showed starting material was completely consumed. $POCl_3$ was removed in vacuo to afford the residue. The residue was dissolved in ethyl acetate (5 mL), poured into ice water (5 mL), separated. The organic layer was dried over anhydrous sodium sulfate and concentrated to afford the crude product. 4-chloro-6-(trifluoromethoxy)quinoline-3-sulfonamide (160 mg, crude) was obtained as brown gum. MS (M−H)−=324.8.

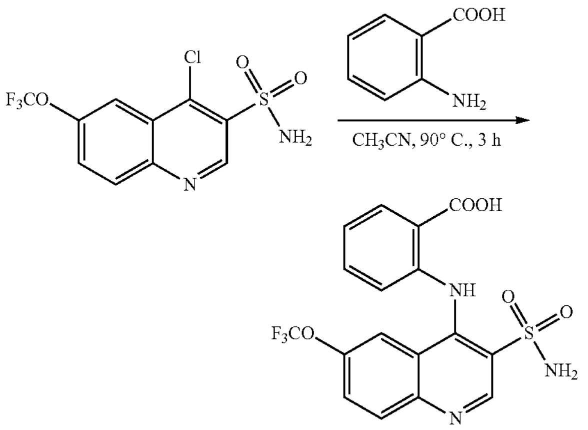

Step 6—A solution of 4-chloro-6-(trifluoromethoxy)quinoline-3-sulfonamide (200 mg, 612.22 μmol, 1 eq) and 2-aminobenzoic acid (83.96 mg, 612.22 μmol, 1 eq) in $CH_3CN$ (3 mL) were stirred at 90° C. for 3 h. LCMS showed starting material was completely consumed and desired product was formed. The mixture was concentrated in vacuo. The crude product was purified by prep-HPLC: column: Waters Xbridge BEH C18 100×25 mm×5 μm; mobile phase: [water(10 mM $NH_4HCO_3$)-ACN]; B %: 15%-45%, 8 min. 2-[[3-sulfamoyl-6-(trifluoromethoxy)-4-quinolyl]amino]benzoic acid (69.01 mg, 155.36 μmol, 25.38% yield, 96.21% purity) was obtained as yellow solid. $^1$H NMR (400 MHz, MeOH-$d_4$) δ=9.21 (s, 1H), 8.11 (d, J=9.2 Hz, 1H), 8.06 (dd, J=2.0, 8.0 Hz, 1H), 7.69 (d, J=2.0 Hz, 1H), 7.53 (s, 1H), 7.19 (t, J=2.0 Hz, 1H), 7.05 (t, J=2.0 Hz, 1H), 6.55 (d, J=7.6 Hz, 1H). MS $(M+H)^+$=428.0.

Example 11

Preparation of Compound 17A

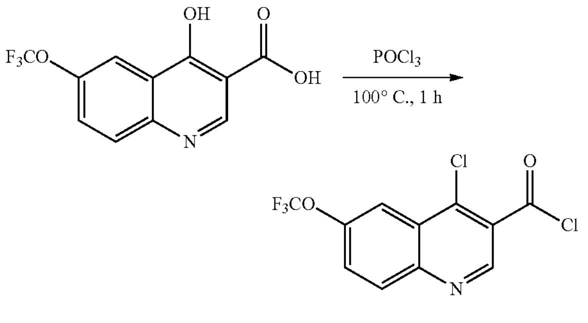

Step 1—Synthesis of 4-chloro-6-(trifluoromethoxy)quinoline-3-carbonyl chloride: A stirred solution of 4-oxo-6-(trifluoromethoxy)-1H-quinoline-3-carboxylic acid (500 mg, 1.83 mmol, 1 eq) in POCl3 (5 mL) was heated to 100° C. and stirred for 1 h. LCMS showed no starting material was remain. The mixture was cooled to room temperature and concentrated in vacuo. The residual was dissolved in toluene (3 mL×2), concentrated in vacuo to give 4-chloro-6-(trifluoromethoxy)quinoline-3-carbonyl chloride (550.6 mg, crude) as brown gum.

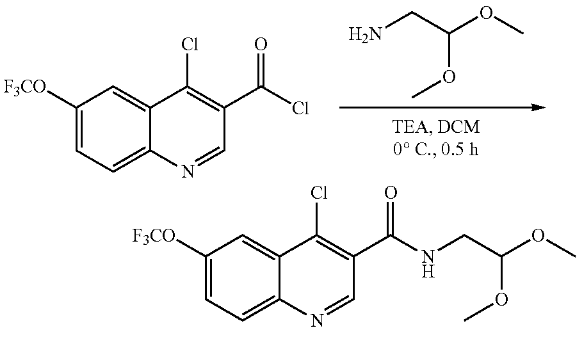

Step 2—Synthesis of 4-chloro-N-(2, 2-dimethoxyethyl)-6-(trifluoromethoxy)quinoline-3-carboxamide: A solution of 4-chloro-6-(trifluoromethoxy)quinoline-3-carbonyl chloride (550 mg, 1.77 mmol, 1 eq) in DCM (6 mL) was added TEA (538.49 mg, 5.32 mmol, 740.71 μL, 3 eq) and 2,2-dimethoxyethanamine (167.85 mg, 1.60 mmol, 173.93 μL, 0.9 eq) at 0° C., then stirred for 0.5 h at 0° C. LCMS showed the reaction was complete. Water (6 mL) was added into the above solution, separated, extracted with DCM (3 mL×2). The combined organic layers were dried over sodium sulfate, concentrated in vacuo to give 4-chloro-N-(2,2-dimethoxyethyl)-6-(trifluoromethoxy)quinoline-3-carboxamide (420.3 mg, crude) as brown solid. $^1$H NMR (400 MHz, DMSO-$d_6$) δ=8.99-8.84 (m, 2H), 8.30 (d, J=9.3 Hz, 1H), 8.16 (s, 1H), 7.95 (dd, J=1.9, 9.2 Hz, 1H), 4.55 (t, J=5.5 Hz, 1H), 3.43 (t, J=5.7 Hz, 2H), 3.34 (s, 6H). MS $(M+H)^+$=379.0

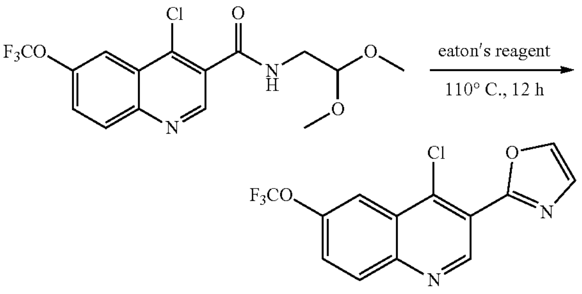

Step 3—Synthesis of 2-[4-chloro-6-(trifluoromethoxy)-3-quinolyl]Oxazole: A solution of 4-chloro-N-(2,2-dimethoxyethyl)-6-(trifluoromethoxy)quinoline-3-carboxamide (350 mg, 924.14 μmol, 1 eq) in eaton's reagent (6.08 g, 25.54 mmol, 4 mL, 27.64 eq) was stirred for 3 h at 120° C. LCMS showed the reaction was complete. The mixture was added into ice-water (5 mL), stirred for 5 mins. Ethyl acetate (5 mL) was added into the above solution, separated. The aqueous layer was extracted with\ethyl acetate (5 mL×2). The combined organic layers were dried over $Na_2SO_4$, concentrated in vacuo. The crude product was purified by flash column (ISCO 10 g silica, 0~30% ethyl acetate in petroleum ether, gradient over 30 min) to give. 2-[4-chloro-6-(trifluoromethoxy)-3-quinolyl]oxazole (55.3 mg, 175.75 μmol, 19.02% yield) as off-white solid. MS $(M+H)^+$=315.0

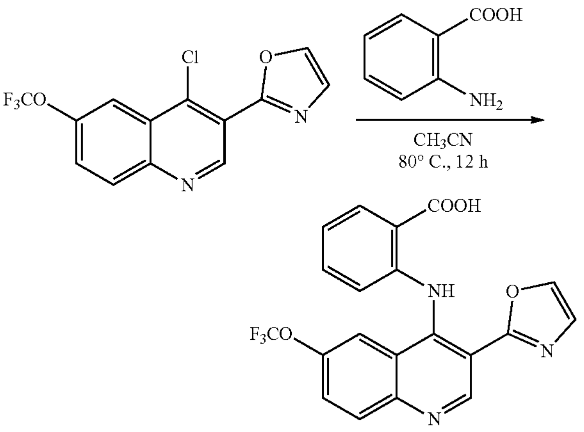

Step 4—Synthesis of 2-[[3-oxazol-2-yl-6-(trifluoromethoxy)-4-quinolyl]amino]benzoic acid: 2-aminobenzoic acid (19.18 mg, 139.84 μmol, 1.1 eq) and 2-[4-chloro-6-(trifluoromethoxy)-3-quinolyl]oxazole (40 mg, 127.13 μmol, 1 eq) were added into ACN (1 mL), then stirred for 5 h at 90° C. LCMS showed the starting material was consumed completely, desired product was detected. The mixture was filtered to give filter cake. The crude product was purified by prep-HPLC (Waters Xbridge BEH C18 100×30 mm×10 μm column; 5%-35% acetonitrile in a 10 mM $NH_4HCO_3$ in water, 10 min gradient) to give 2-[[3-oxazol-2-yl-6-(trifluoromethoxy)-4-quinolyl]amino]benzoic acid (10.3 mg, 24.55 μmol, 19.31% yield, 99.00% purity) as yellow solid. $^1$H NMR (400 MHz, DMSO-$d_6$) δ=11.40 (br s, 1H), 9.34 (s, 1H), 8.29 (s, 1H), 8.16 (d, J=9.0 Hz, 1H), 7.96 (dd, J=1.4, 7.8 Hz, 1H), 7.75 (br d, J=9.2 Hz, 1H), 7.56-7.47 (m, 2H), 7.20 (t, J=7.7 Hz, 1H), 7.01 (t, J=7.5 Hz, 1H), 6.58 (d, J=8.2 Hz, 1H). MS $(M-H)^+$=414.0.

Example 12

Preparation of Compounds 26A and 18A

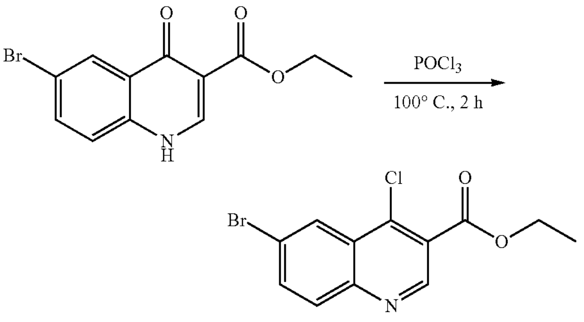

Step 1—Synthesis of ethyl 6-bromo-4-chloro-quinoline-3-carboxylate: ethyl 6-bromo-4-oxo-1H-quinoline-3-carboxylate (1.5 g, 5.07 mmol, 1.0 eq) was added into POCl3 (15 mL) at 0° C., then stirred for 3 h at 110° C. LCMS showed ~2% starting material was remained. The mixture was cooled to room temperature, concentrated in vacuo to remove excess solvents. The residual was added dropwise into a mixture of ice-water (10 mL) and ethyl acetate (10 mL), separated, extracted with ethyl acetate (10 mL×2). The combined organic layers were washed with 10% $NaHCO_3$, concentrated in vacuo. ethyl 6-bromo-4-chloro-quinoline-3-carboxylate (1.41 g, 4.48 mmol, 88.49% yield) was obtained as a off-white solid. $^1$H NMR (400 MHz, CHLOROFORM-d) δ=9.20 (s, 1H), 8.56 (d, J=2.0 Hz, 1H), 8.03 (d, J=8.8 Hz, 1H), 7.91 (dd, J=2.1, 8.9 Hz, 1H), 4.51 (q, J=7.1 Hz, 2H), 1.47 (t, J=7.1 Hz, 3H).

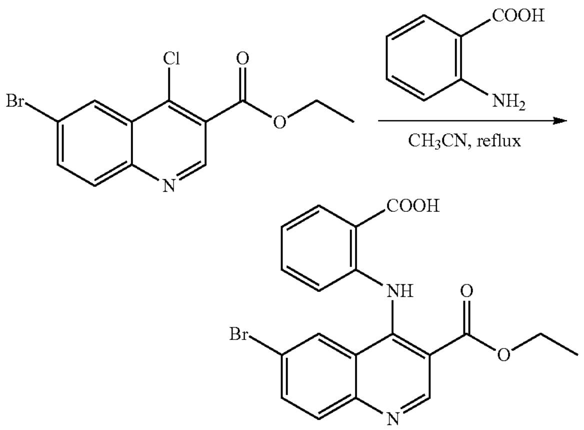

Step 2—Synthesis of 2-[(6-bromo-3-ethoxycarbonyl-4-quinolyl)amino]benzoic acid: A solution of ethyl 6-bromo-4-chloro-quinoline-3-carboxylate (200 mg, 635.80 μmol, 1 eq) and 2-aminobenzoic acid (95.91 mg, 699.39 μmol, 1.1 eq) in $CH_3CN$ (3 mL) were stirred at 90° C. for 16 h. TLC (Petroleum ether:Ethyl acetate=3/1) showed starting material was completely consumed. The mixture was filtered and the filter cake was dried over in vacuo. 2-[(6-bromo-3-ethoxycarbonyl-4-quinolyl)amino]benzoic acid (220 mg, 529.82 μmol, 83.33% yield) was obtained as yellow solid. $^1$H NMR (400 MHz,DMSO-d6) δ=11.56 (brs, 1H), 9.07 (s, 1H), 8.27 (s, 1H), 8.13-8.10 (m, 2H), 8.06 (d, J=7.6 Hz, 1H), 7.56 (t, J=7.2 Hz, 1H), 7.41 (t, J=7.6 Hz, 1H), 7.25 (d, J=8.0 Hz, 1H), 4.20 (brs, 2H), 1.20 (d, J=7.2 Hz, 3H).

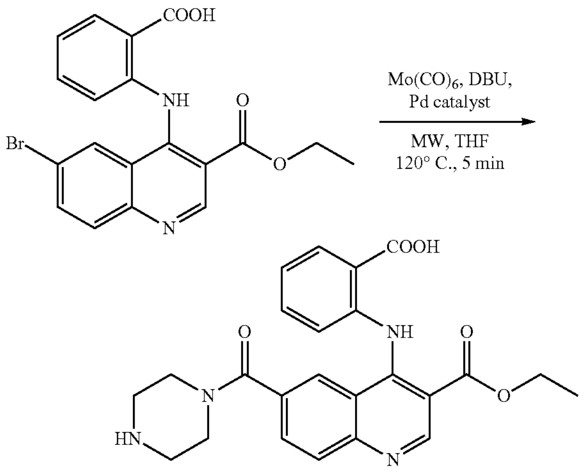

Step 3—Synthesis of 2-[[3-ethoxycarbonyl-6-(piperazine-1-carbonyl)-4-quinolyl]amino]benzoic acid: To a sealed tube was added: 2-[(6-bromo-3-ethoxycarbonyl-4-quinolyl)amino]benzoic acid (100 mg, 240.83 μmol, 1 eq), piperazine (31.12 mg, 361.24 μmol, 1.5 eq), carbon monoxide;molybdenum (127.16 mg, 481.65 μmol, 64.88 μL, 2.0 eq), DBU (109.99 mg, 722.48 μmol, 108.90 μL, 3.0 eq), tritert-butylphosphonium;tetrafluoroborate (13.97 mg, 48.17 μmol, 0.2 eq), acetoxy-[[2-(bis-o-tolylphosphanyl)phenyl] methyl]palladium (11.29 mg, 12.04 μmol, 0.05 eq) and THF (4 mL). Then the sealed tube was bubble with nitrogen for 30 sec and heated to 120° C. Then the mixture was stirred at 120° C. for 5 min. LCMS showed starting material was completely consumed and desired product was formed. The mixture was concentrated to afford the crude product. The crude product was purified by prep-HPLC: column: Phenomenex Luna C18 100×30 m×5 μm; mobile phase: [water (0.04% HCl)-ACN]; B %: 10%-40%, 10 min. 2-[[3-ethoxy carbonyl-6-(piperazine-1-carbonyl)-4-quinolyl]amino]benzoic acid (19.93 mg, 43.92 μmol, 18.24% yield, 98.84% purity) was obtained as yellow solid. $^1$H NMR (400 MHz, MeOD-$d_4$) δ=9.26 (s, 1H), 8.22 (d, J=6.4 Hz, 1H), 8.07 (s, 2H), 7.27 (s, 1H), 7.59 (t, J=3.6 Hz, 1H), 7.57 (d, J=7.6 Hz, 1H), 7.40 (d, J=8.0 Hz, 2H), 4.48-4.43 (m, 2H), 3.90-3.48 (m, 4H), 3.30-3.10 (m, 4H), 1.39 (t, J=7.2 Hz, 3H). MS $(M+H)^+$=449.2.

Example 13

Preparation of Compound 19A

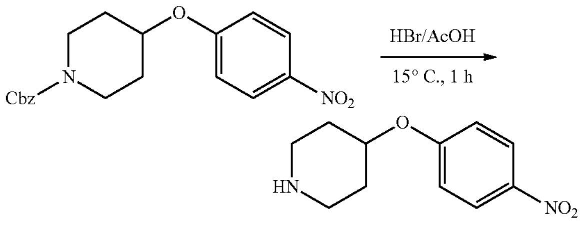

Step 1—Synthesis of 4-(4-nitrophenoxy)piperidine: A solution of benzyl 4-(4-nitrophenoxy)piperidine-1-carboxylate (1.8 g, 5.05 mmol, 1 eq) in HBr (30% AcOH solution) (5 mL) was stirred for 1 h at 15° C. LCMS showed the desired ms was formed. MTBE (20 mL) was added into the mixture, stirred for 5 mins, filtered to give 4-(4-nitrophenoxy)piperidine (1.3 g, 4.29 mmol, 84.90% yield, HBr) as pink solid. $^1$H NMR (400 MHz, CHLOROFORM-d) δ=8.55 (br s, 2H), 8.26-8.11 (m, 2H), 7.29-7.08 (m, 2H), 4.87 (tt, J=3.6, 7.6 Hz, 1H), 3.51 (br s, 1H), 3.26 (br s, 2H), 3.15-3.00 (m, 2H), 2.14 (ddd, J=3.4, 7.0, 10.3 Hz, 2H), 1.93-1.74 (m, 2H). MS $(M+H)^+$=223.1.

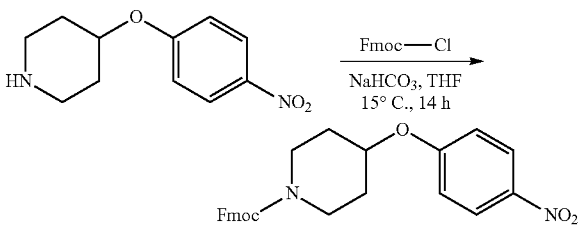

Step 2—Synthesis of 9H-fluoren-9-ylmethyl 4-(4-nitrophenoxy)piperidine-1-carboxylate: To a solution of 4-(4-nitrophenoxy)piperidine (1.3 g, 4.29 mmol, 1 eq, HBr) and $NaHCO_3$ (1.44 g, 17.15 mmol, 667.15 μL, 4 eq) in a mixture solution of THF (12 mL) and $H_2O$ (3 mL) was added dropwise Fmoc-Cl (1.66 g, 6.43 mmol, 1.5 eq) at 0° C., then stirred 3 h at 15° C. TLC (Petroleum ether:Ethyl acetate=3:1, $R_f$=0.69) showed the reaction was complete. The mixture was separated. The aqueous layer was extracted with ethyl acetate (20 mL). The combined organic phase was dried with anhydrous $Na_2SO_4$, concentrated in vacuum to dryness. The crude product was purified by flash column (ISCO 20 g silica, 0-8% ethyl acetate in petroleum ether, gradient over 30 min) to give 9H-fluoren-9-ylmethyl 4-(4-nitrophenoxy) piperidine-1-carboxylate (1.8 g, 4.05 mmol, 94.44% yield) as yellow solid. $^1$H NMR (400 MHz, DMSO-d6) δ=7.40-7.34 (m, 2H), 7.07 (d, J=7.5 Hz, 2H), 6.81 (d, J=7.3 Hz, 2H), 6.62-6.56 (m, 2H), 6.54-6.49 (m, 2H), 6.39-6.34 (m, 2H), 3.97-3.90 (m, 1H), 3.59 (br s, 2H), 3.48-3.43 (m, 1H), 2.43-2.33 (m, 2H), 1.68 (td, J=1.7, 3.6 Hz, 2H), 1.05 (br s, 2H), 0.65 (br s, 2H).

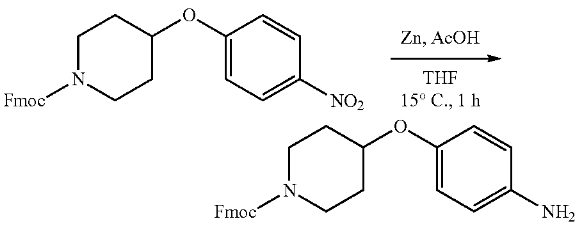

Step 3—Synthesis of 9H-fluoren-9-ylmethyl 4-(4-aminophenoxy)piperidine-1-carboxylate: 9H-fluoren-9-ylmethyl 4-(4-nitrophenoxy)piperidine-1-carboxylate (1.6 g, 3.60 mmol, 1 eq) was dissolved in THF (20 mL) and acetic acid (2.16 g, 36.00 mmol, 2.06 mL, 10 eq) was added. The mixture was cooled to 0° C., followed by Zn (4.71 g, 71.99 mmol, 20 eq) in portions. The reaction was allowed to 15° C. and held for 1 h. TLC (Petroleum ether:Ethyl acetate=3:1, $R_f$=0.10) showed the reaction was complete. The mixture was filtered over celite to give filtrate. The filtrate was washed with 10% $NaHCO_3$ solution (20 mL) and brine (20 mL), dried over $Na_2SO_4$, concentrated in vacuo to give 9H-fluoren-9-ylmethyl 4-(4-aminophenoxy)piperidine-1-carboxylate (1.7 g, crude) as yellow gum. $^1$H NMR (400 MHz, DMSO-$d_6$) δ=7.89 (d, J=7.5 Hz, 2H), 7.63 (d, J=7.3 Hz, 2H), 7.47-7.38 (m, 2H), 7.37-7.28 (m, 2H), 6.72-6.62 (m, 2H), 6.53-6.46 (m, 2H), 4.64 (br s, 2H), 4.39 (br d, J=5.9 Hz, 2H), 4.30-4.25 (m, 1H), 4.21 (tt, J=3.6, 7.7 Hz, 1H), 3.57 (br s, 2H), 3.22-3.08 (m, 2H), 1.83-1.65 (m, 2H), 1.38 (br d, J=15.8 Hz, 2H).

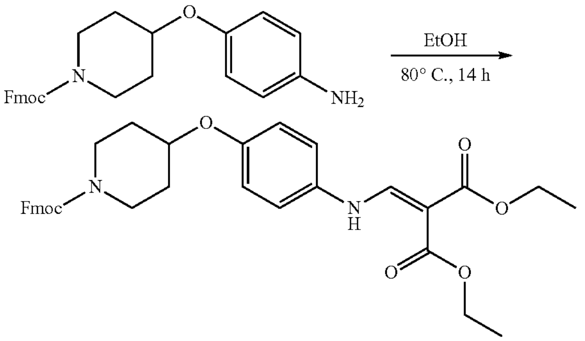

Step 4—Synthesis of diethyl 2-[[4-[[1-(9H-fluoren-9-ylmethoxycarbonyl)-4-piperidyl]oxy]anilino]methylene]propanedioate: A solution of diethyl 2-(ethoxymethylene)propanedioate (1.57 g, 7.24 mmol, 1.46 mL, 2 eq) and 9H-fluoren-9-ylmethyl 4-(4-aminophenoxy)piperidine-1-carboxylate (1.5 g, 3.62 mmol, 1 eq) in EtOH (20 mL) was stirred for 14 h at 80° C. TLC (Petroleum ether:Ethyl acetate=2:1, $R_f$=0.43) showed the reaction was complete. The mixture was concentrated in vacuo to give Diethyl 2-[[4-[[1-(9H-fluoren-9-ylmethoxycarbonyl)-4-piperidyl] oxy]anilino]methylene]propanedioate (3.4 g, crude) as yellow gum.

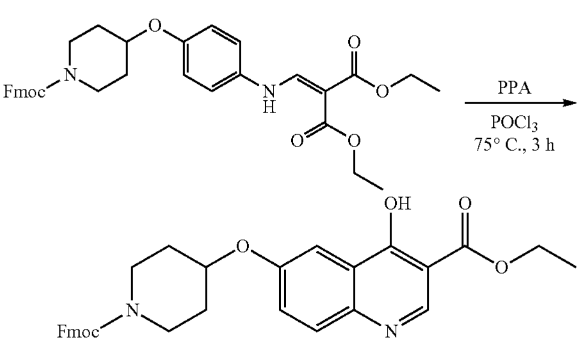

Step 5Synthesis of ethyl 6-[[1-(9H-fluoren-9-ylmethoxycarbonyl)-4-piperidyl]oxy]-4-hydroxy-quinoline-3-carboxylate: Diethyl2-[[4-[[1-(9H-fluoren-9-ylmethoxycarbonyl)-4-piperidyl]oxy]anilino]methylene]propanedioate (300 mg, 513.12 μmol, 1 eq) in $POCl_3$ (3 mL) and PPA (150 mg) was stirred for 2 h at 75° C. LCMS showed the reaction was complete. The mixture was concentrated in vacuo, dissolved in ethyl acetate (2 mL). The solution was added dropwise into ice-water (5 mL) and stirred for 5 mins, separated. The aqueous was extracted with ethyl acetate (5 mL×2). Combined organic phases were dried over $Na_2SO_4$, concentrated in vacuo. The crude product was purified by flash column (ISCO 10 g silica, 0~100% ethyl acetate in petroleum ether, gradient over 30 min) to give ethyl 6-[[1-(9H-fluoren-9-ylmethoxycarbonyl)-4-piperidyl]oxy]-4-hydroxy-quinoline-3-carboxylate (170 mg, 315.64 μmol, 61.51% yield) as yellow gum. MS $(M+H)^+$=539.2

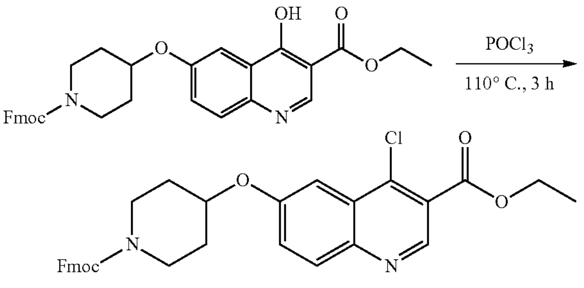

Step 6—Synthesis of ethyl 4-chloro-6-[[1-(9H-fluoren-9-ylmethoxycarbonyl)-4-piperidyl]oxy]quinoline-3-carboxylate: Synthesis of 2-[[3-ethoxycarbonyl-6-[[1-(9H-fluoren-9-ylmethoxy carbonyl)-4-piperidyl]oxy]-4-quinolyl]amino] benzoic acid: Ethyl6-[[1-(9H-fluoren-9-ylmethoxy carbonyl)-4-piperidyl]oxy]-4-hydroxy-quinoline-3-carboxylate (170 mg, 315.64 μmol, 1 eq) in $POCl_3$ (2 mL) was stirred for 3 h at 110° C. LCMS showed the desired ms was detected. The mixture was concentrated in vacuo, dissolved in ethyl acetate (3 mL). The solution was added dropwise ice-water (4 mL), separated, extracted with ethyl acetate (5 mL×2). The combined organic layers were washed with 10% $NaHCO_3$ (3 mL), dried over $Na_2SO_4$, concentrated in vacuo. The crude product was purified by flash column (ISCO 10 g silica, 0~30% ethyl acetate in petroleum ether, gradient over 30 min) to give ethyl 4-chloro-6-[[1-(9H-fluoren-9-ylmethoxycarbonyl)-4-piperidyl]oxy]quinoline-3-carboxylate (70 mg, 125.67 μmol, 39.81% yield) as yellow solid. MS $(M+H)^+$=557.1

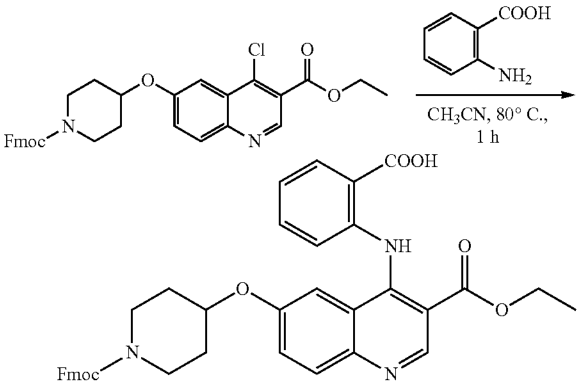

Step 7—Synthesis of 2-[[3-ethoxycarbonyl-6-[[1-(9H-fluoren-9-ylmethoxycarbonyl)-4-piperidyl]oxy]-4-quinolyl]amino]benzoic acid: A solution of ethyl 4-chloro-6-[[1-(9H-fluoren-9-ylmethoxycarbonyl)-4-piperidyl]oxy]quinoline-3-carboxylate (58 mg, 104.12 μmol, 1 eq) and 2-aminobenzoic acid (14.56 mg, 106.21 μmol, 1.02 eq) in ACN (1 mL) was stirred for 2 h at 90° C. LCMS showed the desired ms was found. The mixture was filtered to give 2-[[3-ethoxycarbonyl-6-[[1-(9H-fluoren-9-ylmethoxycarbonyl)-4-piperidyl]oxy]-4-quinolyl]amino]benzoic acid (50 mg, 76.02 μmol, 73.01% yield) as yellow solid. $^1H$ NMR (400 MHz, DMSO-$d_6$) δ=11.55 (br s, 1H), 9.07 (s, 1H), 8.11 (d, J=9.3 Hz, 1H), 8.05 (br d, J=7.5 Hz, 1H), 7.90 (d, J=7.7 Hz, 2H), 7.67-7.60 (m, 3H), 7.56-7.50 (m, 1H), 7.46-7.39 (m, 2H), 7.35 (br t, J=7.4 Hz, 3H), 7.19-7.12 (m, 2H), 4.43 (br s, 2H), 4.28 (br t, J=6.0 Hz, 1H), 4.20 (br s, 3H), 3.72-3.50 (m, 2H), 3.04-2.84 (m, 2H), 1.59 (br s, 2H), 1.29 (t, J=7.1 Hz, 5H). MS $(M+H)^+$=658.2.

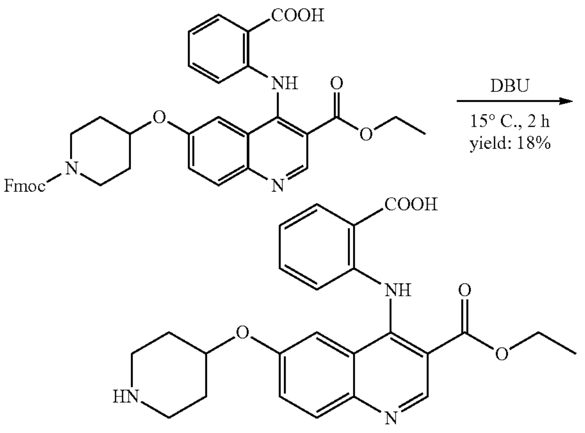

Step 8—Synthesis of 2-[[3-ethoxycarbonyl-6-(4-piperidyloxy)-4-quinolyl]amino]benzoic acid: 2-[[3-ethoxycarbonyl-6-[[1-(9H-fluoren-9-ylmethoxycarbonyl)-4-piperidyl]oxy]-4-quinolyl]amino]benzoic acid (45 mg, 68.42 μmol, 1 eq) and DBU (11.46 mg, 75.26 μmol, 11.34 μL, 1.1 eq) in DCM (1 mL) was stirred for 4 h at 15° C. LCMS showed the reaction was complete. The mixture was concentrated in vacuo, dissolved in DMF (3 mL). The crude product was purified by prep-HPLC (Waters Xbridge BEH C18 100×25 mm×5 μm column; 15%-45% acetonitrile in a 10 mM $NH_4HCO_3$ in water, 8 min gradient) to give 2-[[3-ethoxycarbonyl-6-(4-piperidyloxy)-4-quinolyl]amino]benzoic acid (5.45 mg, 12.17 μmol, 17.78% yield, 97.22% purity) as pale yellow solid. $^1H$ NMR (400 MHz, DMSO-$d_6$) δ=11.71 (s, 1H), 9.22 (br s, 2H), 8.99 (s, 1H), 8.19 (d, J=9.0 Hz, 1H), 8.05 (d, J=7.9 Hz, 1H), 7.75 (dd, J=2.3, 9.2 Hz, 1H), 7.61-7.55 (m, 1H), 7.49 (br s, 1H), 7.45-7.39 (m, 1H), 7.29 (d, J=7.7 Hz, 1H), 5.75 (s, 1H), 4.53 (br s, 1H), 3.92 (br s, 2H), 3.14 (br s, 2H), 2.94 (br s, 2H), 1.98 (br s, 2H), 1.78 (br s, 2H), 1.22 (t, J=7.1 Hz, 3H). MS $(M/2+H)^+$=218.7

Example 14

Preparation of Compound 23A

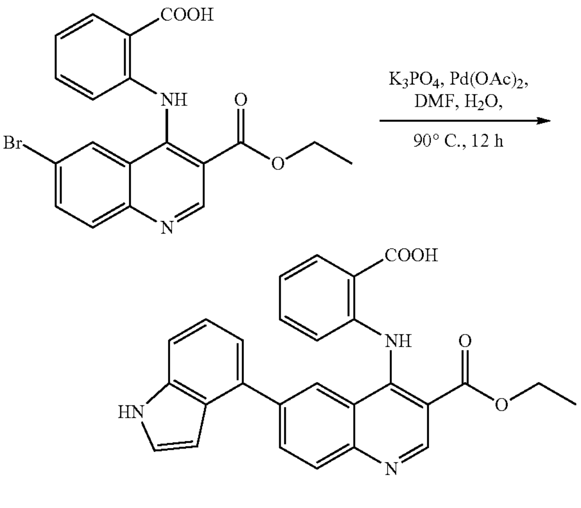

To a solution of 2-[(6-bromo-3-ethoxycarbonyl-4-quinolyl)amino]benzoic acid (100 mg, 240.83 μmol, 1 eq), $Pd(OAc)_2$ (5.41 mg, 24.08 μmol, 0.1 eq), $PPh_3$ (12.63 mg, 48.17 μmol, 0.2 eq) and $K_3PO_4$ (204.48 mg, 963.31 μmol, 4 eq) in DMF (1 mL) and $H_2O$ (0.1 mL) was added 1H-indol-4-ylboronic acid (77.53 mg, 481.65 μmol, 2 eq). The mixture was degassed and purged with Na for 5 times, then stirred for 14 h at 80° C. under $N_2$. LCMS showed the reaction was complete. The mixture was filtered to obtain filtrate. The crude product was purified by prep-HPLC (Phenomenex Luna C18 150×30 mm×5 μm column; 20%-50% acetonitrile in a 0.04% HCl solution in water, 10 min gradient) to give 2-[[3-ethoxycarbonyl-6-(1H-indol-4-yl)-4-quinolyl]amino]benzoic acid (63.1 mg, 134.83 μmol, 55.99% yield, 96.47% purity) as yellow solid. $^1H$ NMR (400 MHz, DMSO-$d_6$) δ=11.69 (br s, 1H), 11.40 (br s, 1H), 9.17 (s, 1H), 8.37-8.30 (m, 1H), 8.29-8.24 (m, 1H), 8.18 (s, 1H), 8.05 (d, J=7.7 Hz, 1H), 7.65-7.57 (m, 1H), 7.49-7.36 (m, 3H), 7.33 (br d, J=7.9 Hz, 1H), 7.13 (t, J=7.7 Hz, 1H), 6.86 (d, J=7.2 Hz, 1H), 6.28 (br s, 1H), 4.19 (br s, 2H), 1.28 (t, J=7.1 Hz, 3H). MS $(M+H)^+$=452.0.

Example 15

Preparation of Compound 25A

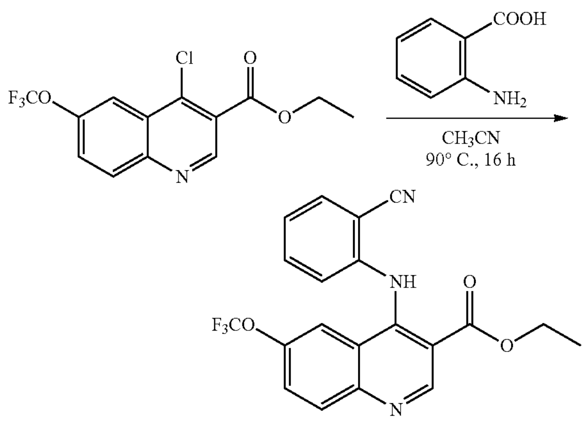

Synthesis of ethyl 4-(2-cyanoanilino)-6-(trifluoromethoxy)quinoline-3-carboxylate: Ethyl 4-chloro-6-(trifluoromethoxy)quinoline-3-carboxylate (50 mg, 156.41 μmol, 1 eq) and 2-aminobenzonitrile (20.33 mg, 172.06 μmol, 1.1 eq) were added into ACN (2 mL), then stirred for 12 h at 90° C. LCMS showed the reaction was complete. The mixture was filtered to give filter cake. The crude product was purified by prep-HPLC (Waters Xbridge Prep OBD C18 150×40 mm×10 μm column; 25%-55% acetonitrile in a 0.04% ammonia solution and 10 mM $NH_4HCO_3$ in water, 10 min gradient) to give ethyl 4-(2-cyanoanilino)-6-(trifluoromethoxy)quinoline-3-carboxylate (17.5 mg, 43.39 μmol, 27.74% yield, 99.5% purity) as off-white solid. $^1H$ NMR (400 MHz, DMSO-$d_6$) δ=9.88 (br s, 1H), 8.98 (br s, 1H), 8.13 (br s, 2H), 7.82 (br s, 2H), 7.54 (br s, 1H), 7.34-6.99 (m, 2H), 3.98 (br s, 2H), 1.14 (br s, 3H). MS $(M+H)^+$=402.0.

Example 16

Preparation of Compound 26A

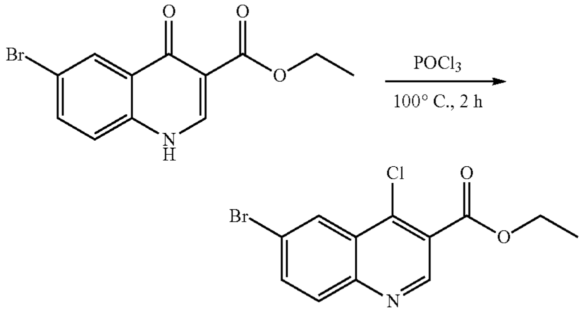

Step 1—Synthesis of ethyl 6-bromo-4-chloro-quinoline-3-carboxylate: Ethyl 6-bromo-4-oxo-1H-quinoline-3-carboxylate (1.5 g, 5.07 mmol, 1.0 eq) was added into $POCl_3$ (15 mL) at 0° C., then stirred for 3 h at 110° C. LCMS showed ~2% starting material was remained. The mixture was cooled to room temperature, concentrated in vacuo to remove excess solvents. The residual was added dropwise into a mixture of ice-water (10 mL) and ethyl acetate (10 mL), separated, extracted with ethyl acetate (10 mL×2). The combined organic layers were washed with 10% $NaHCO_3$, concentrated in vacuo. to give ethyl 6-bromo-4-chloroquinoline-3-carboxylate (1.41 g, 4.48 mmol, 88.49% yield) as off-white solid. $^1H$ NMR (400 MHz, CHLOROFORM-d) δ=9.20 (s, 1H), 8.56 (d, J=2.0 Hz, 1H), 8.03 (d, J=8.8 Hz, 1H), 7.91 (dd, J=2.1, 8.9 Hz, 1H), 4.51 (q, J=7.1 Hz, 2H), 1.47 (t, J=7.1 Hz, 3H). MS $(M+H)^+$=315.9.

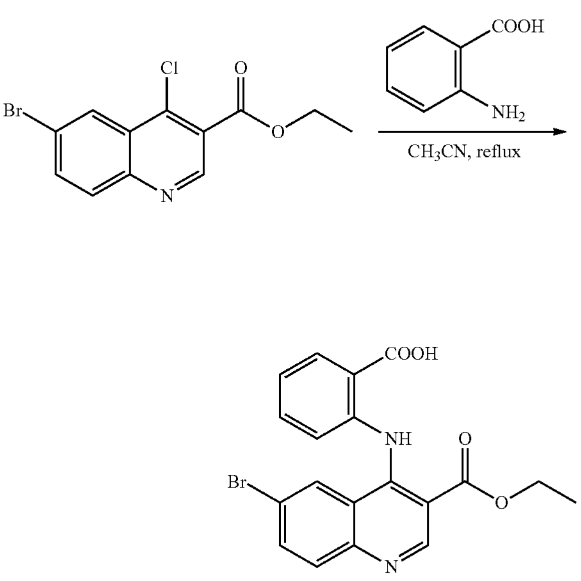

Step 2—Synthesis of 2-[(6-bromo-3-ethoxycarbonyl-4-quinolyl)amino]benzoic acid: 2-aminobenzoic acid (191.82 mg, 1.40 mmol, 1.1 eq) and ethyl 6-bromo-4-chloro-quinoline-3-carboxylate (400 mg, 1.27 mmol, 1 eq) were added into ACN (2 mL), then stirred for 12 h at 90° C. LCMS showed the reaction was complete. The mixture was filtered to give crude product (503.5 mg). 50 mg crude product was purified by prep-HPLC (Phenomenex Luna C18 150×30 mm×5 μm column; 15%-50% acetonitrile in a 0.04% HCl solution in water, 10 min gradient) to give 2-[(6-bromo-3-ethoxycarbonyl-4-quinolyl)amino]benzoic acid (39.14 mg) as yellow solid. $^1H$ NMR (400 MHz, DMSO-$d_6$) δ=11.57 (br s, 1H), 9.05 (s, 1H), 8.26 (s, 1H), 8.17-8.11 (m, 2H), 8.09-8.03 (m, 1H), 7.59-7.51 (m, 1H), 7.39 (t, J=7.5 Hz, 1H), 7.24 (d, J=8.1 Hz, 1H), 4.04 (br s, 2H), 1.20 (t, J=7.1 Hz, 3H). MS $(M+H)^+$=415.0.

Example 17

Preparation of Compound 27A

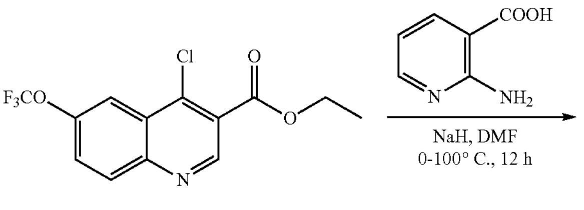

-continued

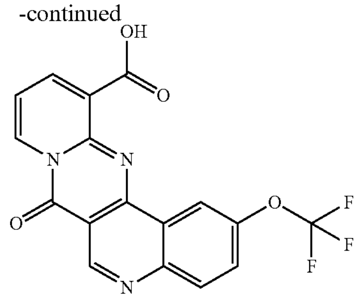

Synthesis of 14-oxo-7-(trifluoromethoxy)-17,18,19-triazatetracyclooctadeca-(4),1(8),2(7),3(9),5(10),6(17),11,13(18)-octaene-8-carboxylic acid: To a stirred solution of 2-aminopyridine-3-carboxylic acid (64.81 mg, 469.24 µmol, 3 eq) in DMF (2 mL) was added NaH (50.05 mg, 1.25 mmol, 60% purity, 8.0 eq) at 0° C. After the suspension was stirred at 0° C. for 20 min, ethyl 4-chloro-6-(trifluoromethoxy)quinoline-3-carboxylate (50 mg, 156.41 µmol, 1 eq) dissolved in DMF (0.5 mL) was added in dropwise. Then the mixture was heated to 100° C. and stirred at 100° C. for 12 h. LCMS showed starting material was completely consumed and desired product was formed. The crude product was purified by prep-HPLC: column: Phenomenex Luna C18 100x30 mmx5 µtm; mobile phase: [water(0.04% HCl)-ACN]; B %: 10%-40%, 10 min. 14-oxo-7-(trifluoromethoxy)-17,18,19-triazatetracyclooctadeca-(4),1(8),2(7),3(9),5(10),6(17),11,13(18)-octaene-8-carboxylic acid (2.75 mg, 6.60 µmol, 4.22% yield, 98.82% purity, HCl) was obtained as yellow solid. $^1$H NMR (400 MHz, CDCl3) δ=9.59 (s, 1H), 9.27 (d, J=5.6 Hz, 1H), 8.65 (d, J=5.6 Hz, 1H), 8.49 (s, 1H), 8.31 (d, J=9.2 Hz, 1H), 8.03 (dd, J=2.4, 9.2 Hz, 1H), 7.53 (s, J=7.2 Hz, 1H), 7.17 (t, J=10.8 Hz, 1H). MS (M−H)$^+$=376.1.

Example 18

Preparation of Compound 28A

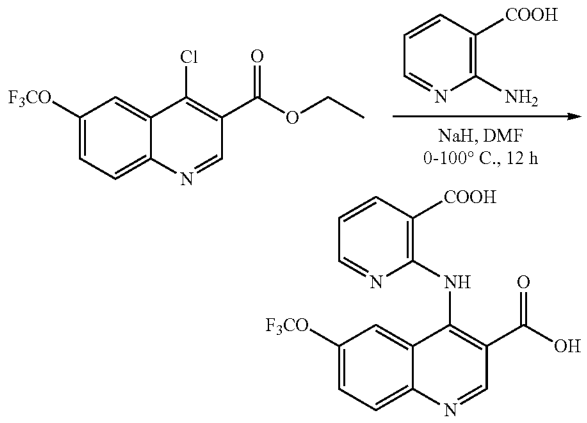

Synthesis of 4-[(3-carboxy-2-pyridyl)amino]-6-(trifluoromethoxy)quinoline-3-carboxylic acid: To a stirred solution of 2-aminopyridine-3-carboxylic acid (129.63 mg, 938.49 µmol, 3 eq) in DMF (4 mL) was added NaH (100.10 mg, 2.50 mmol, 60% purity, 8.0 eq) at 0° C. After the suspension was stirred at 0° C. for 20 min, ethyl 4-chloro-6-(trifluoromethoxy)quinoline-3-carboxylate (100 mg, 312.83 µmol, 1 eq) dissolved in DMF (0.5 mL) was added in dropwise. Then the mixture was heated to 100° C. and stirred at 100° C. for 12 h. LCMS showed starting material was completely consumed and desired product was formed. The mixture was quenched with sat.$NH_4Cl$ (8 mL), adjusted to pH-7 by adding 12N HCl, then concentrated to remove solvent. The crude product was purified by prep-HPLC: column: Waters Xbridge BEH C18 100x25 mmx5 µm; mobile phase: [water(10 mM $NH_4HCO_3$)-ACN]; B %: 5%-35%, 8 min. 4-[(3-carboxy-2-pyridyl)amino]-6-(trifluoromethoxy)quinoline-3-carboxylic acid (6.72 mg, 14.20 µmol, 4.54% yield, 83.11% purity) was obtained as yellow solid. $^1$H NMR (400 MHz, CDCl3) δ=9.12 (s, 1H), 8.25 (d, J=6.0 Hz, 1H), 8.12 (d, J=12.0 Hz, 1H), 8.05 (d, J=2.8 Hz, 1H), 7.78-7.60 (m, 2H), 7.19 (brs, 2H), 6.95-6.92 (m, 1H). MS (M−H)$^+$=391.9.

Example 19

Preparation of Compound 29A

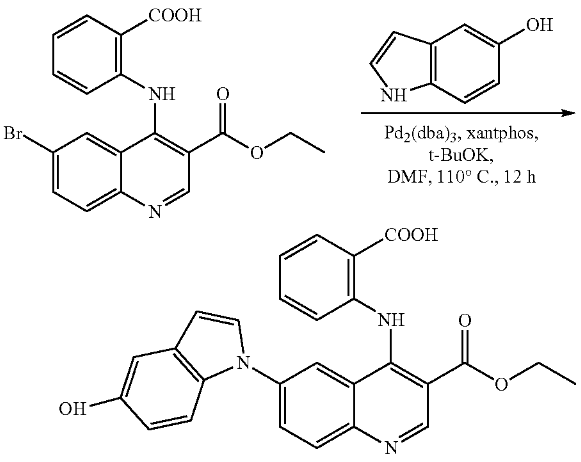

Synthesis of 2-[[3-ethoxycarbonyl-6-(5-hydroxyindol-1-yl)-4-quinolyl]amino]benzoic acid: A solution of 2-[(6-bromo-3-ethoxycarbonyl-4-quinolyl)amino]benzoic acid (100 mg, 240.83 µmol, 1 eq), $Pd_2(dba)_3$ (29.99 mg, 32.75 µmol, 0.136 eq), t-BuOK (81.07 mg, 722.48 µmol, 3 eq) and Xantphos (29.96 mg, 51.78 µmol, 0.215 eq) in DMF (1 mL) was added 1H-indol-5-ol (48.10 mg, 361.24 µmol, 1.5 eq), degassed and purged with $N_2$ for 3 times, then stirred for 110° C. for 14 h under $N_2$. LCMS showed the reaction was complete. The mixture was filtered to give filtrate. The crude product was purified by prep-HPLC Welch Xtimate C18 150x25 mmx5 µm column; 5%-35% acetonitrile in an a 0.05% HCl solution in water, min gradient) to give 2-[[3-ethoxycarbonyl-6-(5-hydroxyindol-1-yl)-4-quinolyl]amino]benzoic acid (6.11 mg, 13.00 µmol, 5.40% yield, 99.49% purity) as yellow solid. $^1$H NMR (400 MHz, DMSO-$d_6$) δ=13.76 (br s, 1H), 8.92 (s, 1H), 8.18-8.07 (m, 2H), 8.02-7.98 (m, 1H), 7.93 (d, J=7.5 Hz, 1H), 7.56 (d, J=3.2 Hz, 1H), 7.29-7.14 (m, 3H), 6.97-6.86 (m, 2H), 6.75 (d, J=8.1 Hz, 1H), 6.63 (dd, J=1.9, 8.9 Hz, 1H), 6.54 (d, J=3.2 Hz, 1H), 3.99 (q, J=6.9 Hz, 2H), 1.04 (t, J=7.1 Hz, 3H). MS (M−H)$^+$=466.0.

Example 20

Preparation of Compound 30A

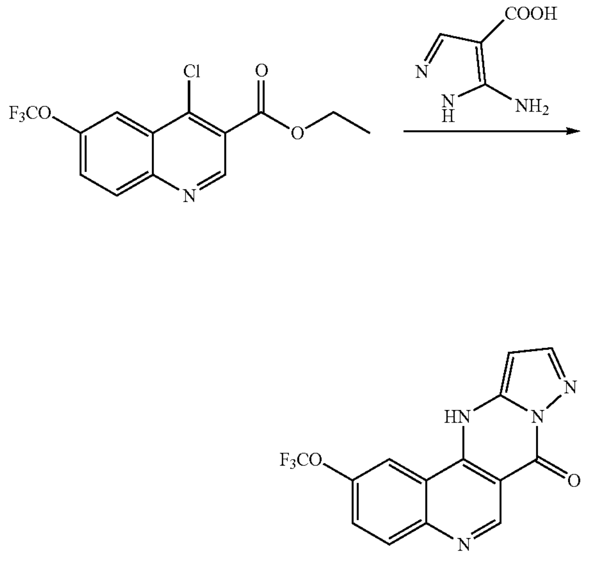

Synthesis of 6-(trifluoromethoxy)-14,15,16,17-tetrazatetracycloheptadeca-(6),1(7),2(8),3(15),4(9),5(16),10-heptaen-12-one: A solution of ethyl 4-chloro-6-(trifluoromethoxy)quinoline-3-carboxylate (100 mg, 312.83 μmol, 1 eq) and 5-amino-1Hpyrazole-4-carboxylic acid (119.28 mg, 938.49 μmol, 3 eq) in DMF (1 mL) was stirred for 14 h at 110° C. LCMS showed the reaction was complete, desired product was detected. The mixture was filtered to give filtrate. The crude product was purified by prep-HPLC (Waters Xbridge BEH C18 100×25 mm×5 μm column; 20%-50% acetonitrile in 10 mM $NH_4HCO_3$ in water, 8 min gradient) to give (trifluoromethoxy)-14,15,16,17-tetrazatetracycloheptadeca-(6),1 (7),2(8),3(15),4(9),5 (16),10-heptaen-12-one (6.80 mg, 21.00 μmol, 6.71% yield, 98.89% purity) as yellow solid. $^1H$ NMR (400 MHz, DMSO-d6) δ=13.95-13.35 (m, 1H), 9.31 (s, 1H), 8.56 (br s, 1H), 8.08 (d, J=1.8 Hz, 1H), 8.05 (br d, J=9.0 Hz, 1H), 7.94-7.79 (m, 1H), 6.48 (d, J=1.8 Hz, 1H). MS $(M+H)^+$=321.0.

Example 21

Preparation of Compound 31A

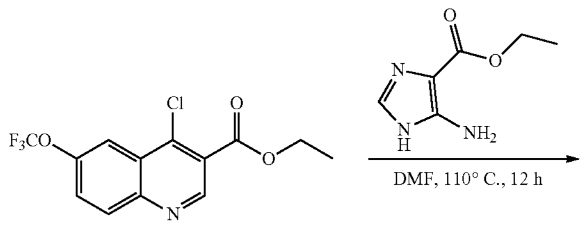

-continued

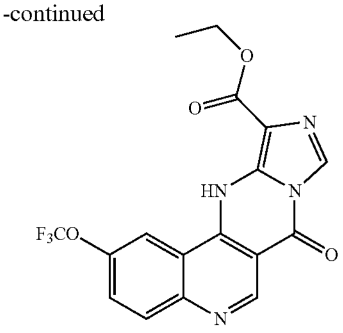

Synthesis of ethyl 14-oxo-7-(trifluoromethoxy)-17,18,19,20-tetrazatetracycloheptadeca-1(7),2(8),3(9),4(18),5(19),10,12-heptaene-12-carboxylate: A solution of ethyl 4-chloro-6-(trifluoromethoxy)quinoline-3-carboxylate (100 mg, 312.83 μmol, 1 eq) and ethyl 5-amino-1H-imidazole-4-carboxylate (145.61 mg, 938.49 μmol, 3 eq) in DMF (1 mL) was stirred for 14 h at 110° C. LCMS showed the reaction was complete. The mixture was filtered to give filtrate. The crude product was purified by prep-HPLC (Waters Xbridge BEH C18 100×25 mm×5 μm column; 25%-45% acetonitrile in a 10 mM $NH_4HCO_3$ in water, 8 min gradient) to give ethyl 14-oxo-7-(trifluoromethoxy)-17,18,19,20-tetrazatetracycloheptadeca-1(7),2(8),3(9),4(18),5(19),10,12-heptaene-12-carboxylate (1.56 mg, 3.78 μmol, 1.21% yield, 95.02% purity). $^1H$ NMR (400 MHz, DMSO-$d_6$) δ=9.54 (s, 1H), 9.05 (s, 1H), 8.81-8.74 (m, 1H), 8.40 (d, J=9.2 Hz, 1H), 8.08 (br d, J=8.9 Hz, 1H), 4.35 (q, J=7.1 Hz, 2H), 1.33 (t, J=7.0 Hz, 3H). MS $(M+H)^+$=393.1.

Example 22

Preparation of Compound 32A

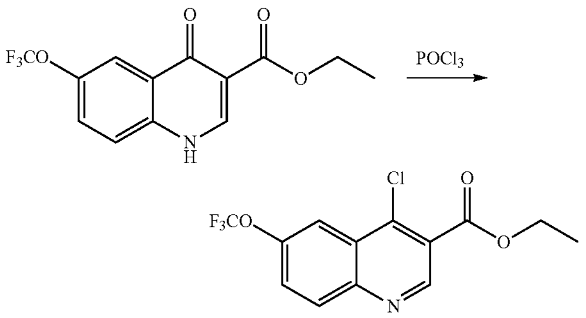

Step 1—Synthesis of ethyl 4-chloro-6-(trifluoromethoxy)quinoline-3-carboxylate: Ethyl 4-hydroxy-6-(trifluoromethoxy)quinoline-3-carboxylate (3.00 g, 9.96 mmol, 1 eq) was added into $POCl_3$ (20 mL) at 0° C., then stirred for 2 h at 110° C. LCMS showed starting material was consumed completely, the reaction was complete. The mixture was cooled to room temperature, concentrated in vacuo to remove excess solvents. The residual was added dropwise a mixture of ice-water (10 mL) and ethyl acetate (20 ml), separated and extracted with ethyl acetate (20 ml×2). The combined organic layers were washed with 10% $NaHCO_3$, dried over anhydrous sodium sulfate, concentrated in vacuo. The crude product was purified by flash column (ISCO 20 g silica, 0~6% ethyl acetate in petroleum ether, gradient over 30 min) to give ethyl 4-chloro-6-(trifluoromethoxy)quinoline-3-carboxylate (2.6 g, 8.13 mmol, 81.67% yield, –purity) as white solid. MS $(M+H)^+$=320.0.

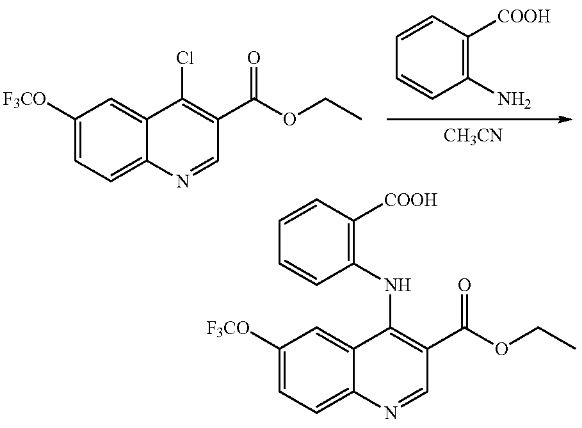

Step 2—Synthesis of 2-[[3-ethoxycarbonyl-6-(trifluoromethoxy)-4-quinolyl]amino]benzoic acid: 2-aminobenzoic acid (707.85 mg, 5.16 mmol, 1.1 eq) and ethyl 4-chloro-6-(trifluoromethoxy)quinoline-3-carboxylate (1.5 g, 4.69 mmol, 1 eq) were added into ACN (15 mL), then stirred for 14 h at 90° C. LCMS showed the reaction was complete. The mixture was filtered to give filter cake. The crude product was purified by re-crystallization from methanol(5 mL) at 65° C., cooled to room temperature and stirred for 0.5 h and filtered to give 2-[[3-ethoxycarbonyl-6-(trifluoromethoxy)-4-quinolyl]amino]benzoic acid (1610.97 mg, 3.83 mmol, 81.78% yield, 98.63% purity) as yellow solid. $^1$H NMR (400 MHz, DMSO-$d_6$) δ=11.84 (br s, 1H), 9.09 (s, 1H), 8.41 (d, J=9.3 Hz, 1H), 8.15-7.99 (m, 2H), 7.89 (s, 1H), 7.59-7.51 (m, 1H), 7.47-7.40 (m, 1H), 7.33 (d, J=7.9 Hz, 1H), 4.13 (br s, 2H), 1.25 (t, J=7.2 Hz, 3H). MS $(M+H)^+$=421.0.

Example 23

Preparation of Compound 33A

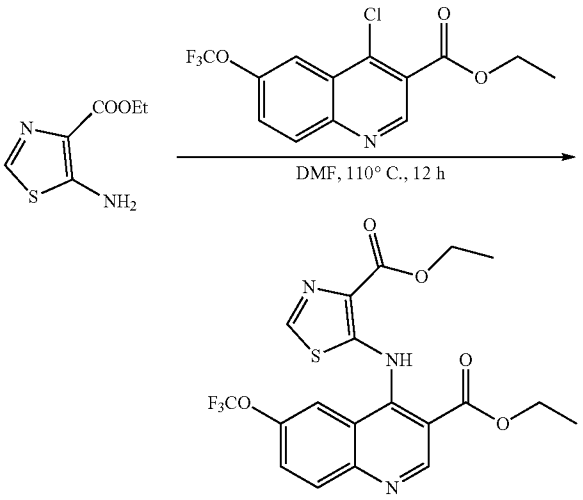

Synthesis of ethyl 5-[[3-ethoxycarbonyl-6-(trifluoromethoxy)-4-quinolyl]amino]thiazole-4-carboxylate: A solution of ethyl 4-chloro-6-(trifluoromethoxy)quinoline-3-carboxylate (100 mg, 312.83 μmol, 1 eq) and ethyl 5-aminothiazole-4-carboxylate (161.61 mg, 938.49 μmol, 3.0 eq) in DMF (4 mL) were stirred at 110° C. for 12 h. LCMS showed starting material was completely consumed and desired product was formed. The mixture was purified by prep-HPLC: column: Waters Xbridge BEH C18 100×25 mm×5 μm; mobile phase: [water(10 mM $NH_4HCO_3$)-ACN]; B %: 35%-65%, 8 min ethyl 5-[[3-ethoxycarbonyl-6-(trifluoromethoxy)-4-quinolyl]amino]thiazole-4-carboxylate (5.51 mg, 12.08 μmol, 2.75% yield, 99.86% purity) was obtained as pale yellow solid. $^1$H NMR (400 MHz, CHLOROFORM-d) δ=9.38 (s, 1H), 8.19 (d, J=9.2 Hz, 1H), 8.09 (s, 1H), 7.77 (s, 1H), 7.67 (d, J=9.2 Hz, 1H), 4.59-4.49 (m, 4H), 1.52-1.34 (m, 6H). MS $(M+H)^+$=456.1.

Example 24

Preparation of Compound 34A

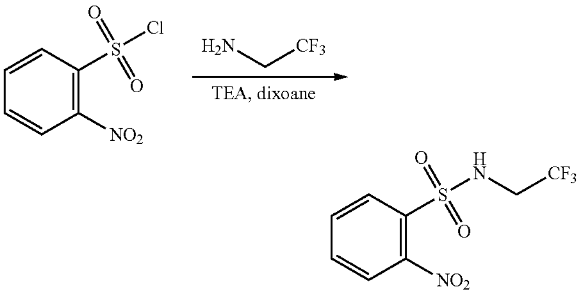

Step 1—Synthesis of 2-nitro-N-(2,2,2-trifluoroethyl)benzenesulfonamide: To a solution of 2-nitrobenzenesulfonyl chloride (1 g, 4.51 mmol, 1 eq) in dioxane (10 mL) was added 2,2,2-trifluoroethanamine (491.66 mg, 4.96 mmol, 390.21 μL, 1.1 eq) and TEA (502.26 mg, 4.96 mmol, 690.86 μL, 1.1 eq) at 0° C., then stirred for 14 h at 15° C. TLC (Petroleum ether:Ethyl acetate=5:1, Rf=0.28) showed the reaction was complete, no starting material was remained. The mixture was poured into ice-water (5 mL) and stirred for 5 mins. Ethyl acetate (10 mL) was added into the above solution, separated, extracted with ethyl acetate (5 mL×2). The combined organic layers were dried over anhydrous $Na_2SO_4$, filtered, concentrated in vacuo to give 2-nitro-N-(2,2,2-trifluoroethyl)benzenesulfonamide (1 g, crude) as pale yellow solid. $^1$H NMR (400 MHz, DMSO-$d_6$) δ=9.16 (t, J=6.5 Hz, 1H), 8.07-8.03 (m, 1H), 8.03-7.98 (m, 1H), 7.91-7.86 (m, 2H), 3.96-3.80 (m, 2H).

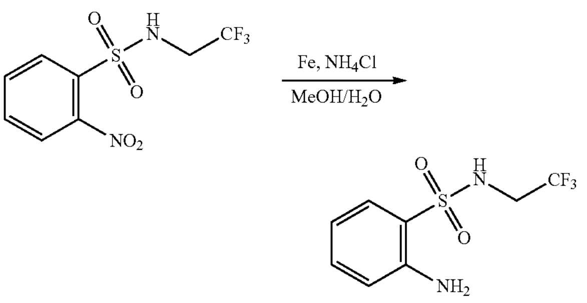

Step 2—Synthesis of 2-amino-N-(2,2,2-trifluoroethyl) benzenesulfonamide: A solution of 2-nitro-N-(2,2,2-trifluoroethyl)benzenesulfonamide (500 mg, 1.76 mmol, 1 eq), Fe (491.23 mg, 8.80 mmol, 5 eq) and $NH_4Cl$ (282.31 mg, 5.28 mmol, 3 eq) in a mixture of METHANOL (4 mL) and $H_2O$ (2 mL) was stirred for 14 h at 80° C. LCMS showed the desired ms was found. The mixture was filtered to give filtrate, concentrated in vacuo to give 2-amino-N-(2,2,2-trifluoroethyl)benzenesulfonamide (350.2 mg, 1.38 mmol, 78.30% yield) as pale yellow solid. $^1H$ NMR (400 MHz, DMSO-d6) δ=8.48 (br t, J=6.5 Hz, 1H), 7.51 (dd, J=1.0, 8.0 Hz, 1H), 7.33-7.20 (m, 1H), 6.86-6.80 (m, 1H), 6.62 (t, J=7.4 Hz, 1H), 5.97-5.89 (m, 2H), 3.75-3.52 (m, 2H).

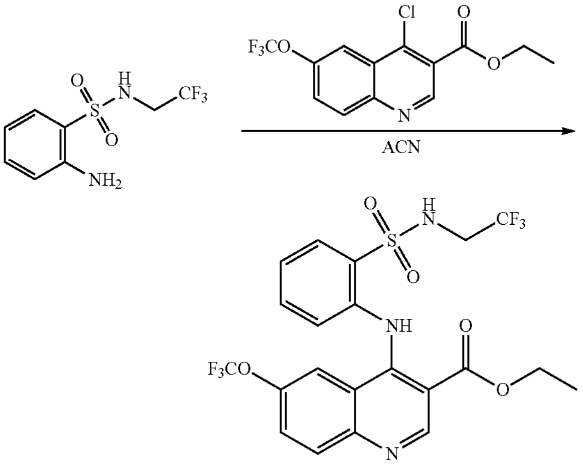

Step 3—Synthesis of ethyl 4-[2-(2,2,2-trifluoroethylsulfamoyl)anilino]-6-(trifluoromethoxy)quinoline-3-carboxylate: A solution of 2-amino-N-(2,2,2-trifluoroethyl)benzenesulfonamide (209.96 mg, 825.87 μmol, 1.1 eq) and ethyl 4-chloro-6-(trifluoromethoxy)quinoline-3-carboxylate (240 mg, 750.79 μmol, 1 eq) in ACN (2 mL) was stirred for 4 h at 90° C. LCMS showed the desired ms was detected. The mixture was concentrated in vacuo to remove solvent. The crude product was purified by prep-HPLC (Waters Xbridge Prep OBD C18 150×40 mm×10 μm column; 15%-45% acetonitrile in a 0.04% ammonia solution and 10 mM $NH_4HCO_3$ in water, 10 min gradient) to give ethyl 4-[2-(2,2,2-trifluoroethylsulfamoyl)anilino]-6-(trifluoromethoxy)quinoline-3-carboxylate (78.65 mg, 139.11 μmol, 18.53% yield, 95.06% purity) as off-white solid. 1H NMR (400 MHz, DMSO-d6) δ=10.30 (br s, 1H), 9.26 (br s, 1H), 9.12 (br s, 1H), 8.13 (br d, J=9.3 Hz, 1H), 7.91 (d, J=6.8 Hz, 1H), 7.79-7.72 (m, 1H), 7.47-7.35 (m, 1H), 7.31-7.22 (m, 2H), 6.83 (d, J=7.9 Hz, 1H), 4.40 (br d, J=6.6 Hz, 2H), 3.93-3.79 (m, 2H), 1.37 (t, J=7.1 Hz, 3H). MS $(M+H)^+$=538.1.

Example 25

Preparation of Compound 51A

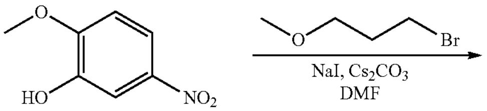

-continued

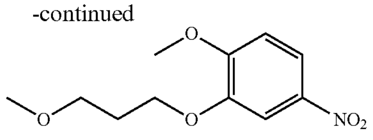

Step 1—Synthesis of 1-methoxy-2-(3-methoxypropoxy)-4-nitro-benzene: To a solution of 2-methoxy-5-nitro-phenol (25 g, 147.81 mmol, 1 eq), NaI (33.23 g, 221.72 mmol, 1.5 eq) and $Cs_2CO_3$ (96.32 g, 295.62 mmol, 2 eq) in DMF (250 mL) was added dropwise 1-bromo-3-methoxy-propane (22.62 g, 147.81 mmol, 1 eq), stirred for 2 h at 100° C. TLC (Petroleum ether:Ethyl acetate=3:1, Rf=0.43) showed the reaction was complete. The suspension was filtered to give filtrate. The filtrate was dissolved in ethyl acetate (100 mL) and water (30 mL), separated, extracted with ethyl acetate (50×2 mL). The combined organic layers were washed with water (20 mL×3), dried over $Na_2SO_4$, filtered, concentrated in vacuo to give 1-methoxy-2-(3-methoxypropoxy)-4-nitro-benzene (20.4 g, 84.56 mmol, 57.21% yield, –purity) as pale yellow solid. $^1H$ NMR (400 MHz, DMSO-$d_6$) δ=7.89 (dd, J=2.7, 8.9 Hz, 1H), 7.71 (d, J=2.7 Hz, 1H), 7.16 (d, J=8.9 Hz, 1H), 4.11 (t, J=6.4 Hz, 2H), 3.90 (s, 3H), 3.47 (t, J=6.3 Hz, 2H), 3.28-3.23 (m, 3H), 1.97 (quin, J=6.4 Hz, 2H).

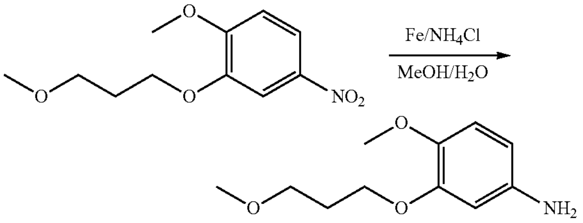

Step 2—Synthesis of 4-methoxy-3-(3-methoxypropoxy)aniline: A solution of 1-methoxy-2-(3-methoxypropoxy)-4-nitro-benzene (20.4 g, 84.56 mmol, 1 eq), Fe (40.14 g, 718.79 mmol, 8.5 eq) and $NH_4Cl$ (40.71 g, 761.07 mmol, 9 eq) in a mixture of Methanol (160 mL) and $H_2O$ (80 mL) was stirred for 4 h at 80° C. TLC (Petroleum ether:Ethyl acetate=3:1, Rf=0.24) showed the starting material was consumed completely. The mixture was filtered to give filtrate, concentrated in vacuo. The residual was dissolved in ethyl acetate (100 mL), separated, extracted with ethyl acetate (100 ml×3). The combined organic layers were dried over $Na_2SO_4$, concentrated in vacuo to give 4-methoxy-3-(3-methoxypropoxy)aniline (19 g, crude) was obtained as a brown oil.

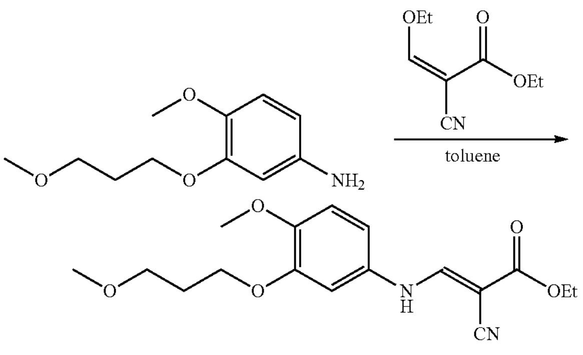

Step 3—Synthesis of ethyl (E)-2-cyano-3-[4-methoxy-3-(3-methoxypropoxy)anilino]prop-2-enoate: A solution of 4-methoxy-3-(3-methoxypropoxy)aniline (19 g, 89.94 mmol, 1 eq) and ethyl (E)-2-cyano-3-ethoxy-prop-2-enoate (15.22 g, 89.94 mmol, 1 eq) in toluene (200 mL) was stirred for 14 h at 110° C. TLC (Petroleum ether:Ethyl acetate=3:1, Rf=0.43) showed the reactant was consumed completely. The mixture was concentrated in vacuo to give ethyl (E)-2-cyano-3-[4-methoxy-3-(3-methoxypropoxy)anilino]prop-2-enoate (29.3 g, crude) was obtained as a yellow solid. $^1$H NMR (400 MHz, DMSO-$d_6$) δ=10.74-10.57 (m, 1H), 8.51-8.40 (m, 0.5H), 8.25 (br s, 0.5H), 7.21 (d, J=1.8 Hz, 0.5H), 7.07 (d, J=1.5 Hz, 0.5H), 6.96-6.83 (m, 2H), 4.30-4.10 (m, 2H), 4.06-3.95 (m, 2H), 3.74 (s, 3H), 3.47 (t, J=6.1 Hz, 2H), 3.25 (s, 3H), 2.02-1.91 (m, 2H), 1.32-1.21 (m, 1H), 1.25 (td, J=7.0, 11.8 Hz, 2H).

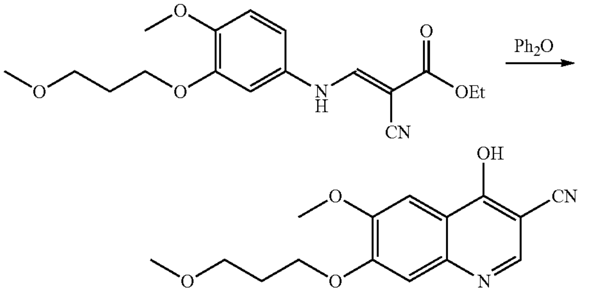

Step 4—Synthesis of 4-hydroxy-6-methoxy-7-(3-methoxypropoxy)quinoline-3-carbonitrile: A solution of ethyl (E)-2-cyano-3-[4-methoxy-3-(3-methoxypropoxy)anilino]prop-2-enoate (400 mg, 1.20 mmol, 1 eq) in $Ph_2O$ (10 mL) was stirred for 5 h at 270° C. TLC (Petroleum ether: Ethyl acetate=2:1, Rf=0.00) showed the new spot was found. The mixture was cooled to room temperature, followed by Petroleum ether (10 mL), filtered to give filter cake, dried in vacuo to give 4-hydroxy-6-methoxy-7-(3-methoxy propoxy)quinoline-3-carbonitrile (100 mg, 346.86 μmol, 28.99% yield) as pale solid. $^1$H NMR (400 MHz, DMSO-$d_6$) δ=12.51 (br s, 1H), 8.59 (s, 1H), 7.44 (s, 1H), 7.13-7.01 (m, 1H), 4.11 (t, J=6.4 Hz, 2H), 3.86 (s, 3H), 3.49 (t, J=6.2 Hz, 2H), 3.33 (s, 5H), 3.25 (s, 3H), 2.08-1.97 (m, 2H). MS $(M+H)^+$=289.1.

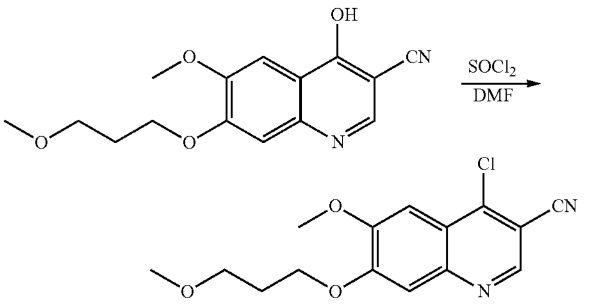

Step 5—Synthesis of 4-chloro-6-methoxy-7-(3-methoxypropoxy)quinoline-3-carbonitrile: To a solution of 4-hydroxy-6-methoxy-7-(3-methoxypropoxy)quinoline-3-carbonitrile (80 mg, 277.49 μmol, 1 eq) in $SOCl_2$ (1 mL) was added DMF (2.03 mg, 27.75 μmol, 2.14 μL, 0.1 eq), then stirred for 14 h at 25° C. LCMS showed no reactant was detected and desired ms was detected. The mixture was concentrated in vacuo to give 4-chloro-6-methoxy-7-(3-methoxypropoxy)quinoline-3-carbonitrile (90 mg, crude) was obtained as a brown gum. MS $(M+H)^+$=307.1.

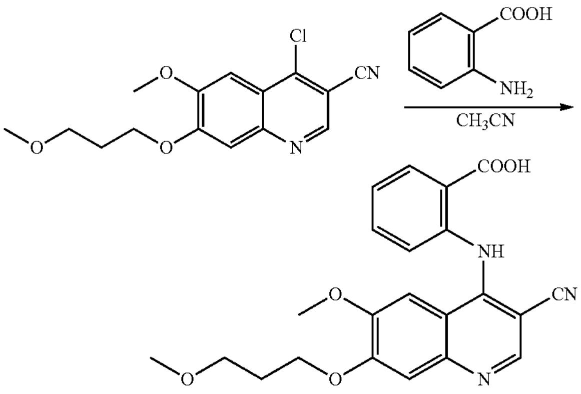

Step 6—Synthesis of 2-[[3-cyano-6-methoxy-7-(3-methoxypropoxy)-4-quinolyl]amino]benzoic acid: A solution of 4-chloro-6-methoxy-7-(3-methoxypropoxy)quinoline-3-carbonitrile (80 mg, 260.80 μmol, 1 eq) and 2-aminobenzoic acid (35.77 mg, 260.80 μmol, 1 eq) in ACN (1 mL) was stirred for 3 h at 90° C. LCMS showed ~70% desired product was detected. The suspension was concentrated in vacuo. The crude product was purified by prep-HPLC (Kromasil 150×25 mm×10 μm column; 35%-55% acetonitrile in an a 0.04% ammonia solution and 10 mM $NH_4HCO_3$ in water, 10 min gradient) to give 2-[[3-cyano-6-methoxy-7-(3-methoxypropoxy)-4-quinolyl]amino]benzoic acid (20.23 mg, 49.65 μmol, 19.04% yield, 100% purity) as pale yellow solid. $^1$H NMR (400 MHz, DMSO-$d_6$) δ=10.36 (br s, 1H), 8.60 (s, 1H), 7.97 (d, J=7.7 Hz, 1H), 7.54-7.46 (m, 2H), 7.39 (s, 1H), 7.17 (t, J=7.5 Hz, 1H), 7.11 (d, J=8.2 Hz, 1H), 4.23 (t, J=6.3 Hz, 2H), 3.85 (s, 3H), 3.51 (t, J=6.2 Hz, 2H), 3.27 (s, 3H), 2.04 (quin, J=6.2 Hz, 2H). MS $(M+H)^+$=408.2.

Example 26

Preparation of Compound 53A

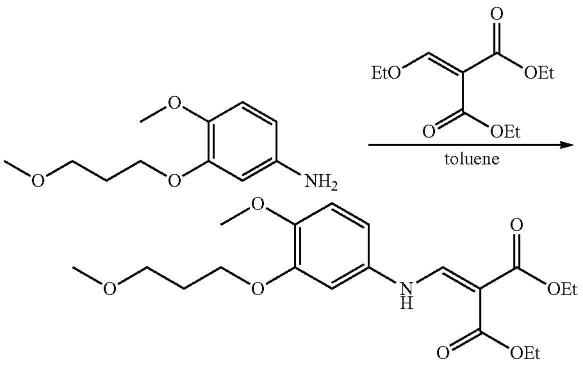

Step 1—Synthesis of diethyl 2-[[4-methoxy-3-(3-methoxypropoxy)anilino]methylene]propanedioate: A solution of 4-methoxy-3-(3-methoxypropoxy)aniline (3 g, 14.20 mmol, 1 eq) and diethyl 2-(ethoxymethylene)propanedioate (3.07 g, 14.20 mmol, 2.87 mL, 1 eq) in toluene (30 mL) was stirred for 14 h at 110° C. TLC (Petroleum ether:Ethyl acetate=3:1, $R_f$=0.43) showed the reactant was consumed completely. The mixture was concentrated in vacuo to give diethyl 2-[[4-methoxy-3-(3-methoxypropoxy)anilino]methylene]propanedioate (5.8 g, crude) as yellow solid.

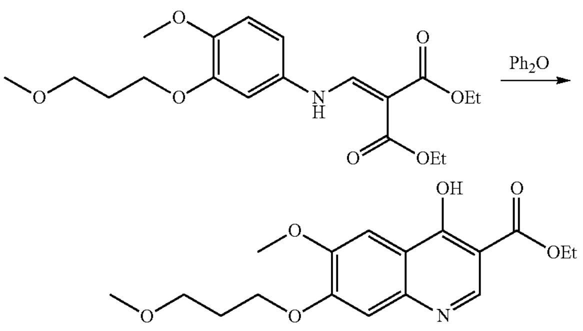

Step 2—Synthesis of ethyl 4-hydroxy-6-methoxy-7-(3-methoxypropoxy)quinoline-3-carboxylate: A solution of diethyl 2-[[4-methoxy-3-(3-methoxypropoxy)anilino]methylene]propanedioate (5.3 g, 13.90 mmol, 1 eq) in $Ph_2O$ (100 mL) was stirred for 1 h at 260° C. TLC (Petroleum ether: Ethyl acetate=2:1, $R_f$=0.00) showed the reaction was complete. The mixture was cooled to room temperature, followed by Petroleum ether (100 mL), stirred for 10 mins, filtered to give ethyl 4-hydroxy-6-methoxy-7-(3-methoxypropoxy)quinoline-3-carboxylate (2.88 g, 8.59 mmol, 61.80% yield) as brown solid. MS $(M+H)^+$=336.1

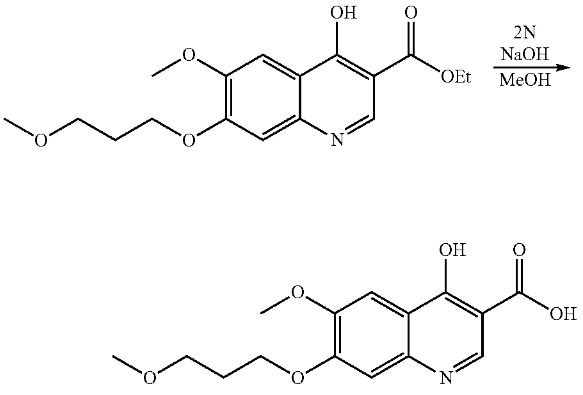

Step 3—Synthesis of 4-hydroxy-6-methoxy-7-(3-methoxypropoxy)quinoline-3-carboxylic acid: A solution of ethyl 4-hydroxy-6-methoxy-7-(3-methoxypropoxy)quinoline-3-carboxylate (2.8 g, 8.35 mmol, 1 eq) in MeOH (30 mL) was added NaOH (2 M, 41.75 mL, 10 eq), then stirred for 14 h at 60° C. LCMS showed no reactant was remained, desired ms was found. The mixture was concentrated in vacuo, dissolved in ethyl acetate (30 mL), separated to give aqueous layer. The layer was acidified to pH=5 by 1N HCl solution, filtered to give 4-hydroxy-6-methoxy-7-(3-methoxypropoxy)quinoline-3-carboxylic acid (2.2 g, 7.16 mmol, 85.74% yield) as pale solid. $^1$H NMR (400 MHz, DMSO-$d_6$) δ=15.86 (br s, 1H), 8.73 (s, 1H), 7.54 (s, 1H), 7.24 (s, 1H), 4.15 (br t, J=6.2 Hz, 2H), 3.90 (s, 3H), 3.50 (br t, J=6.1 Hz, 2H), 3.26 (s, 3H), 2.10-2.00 (m, 2H).

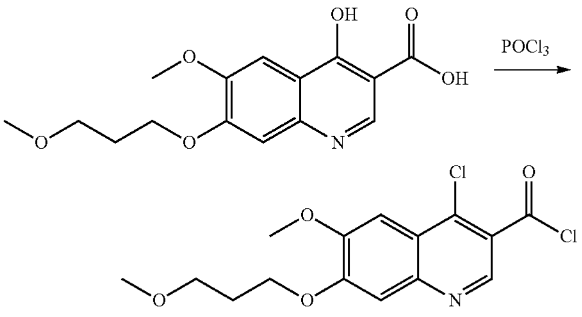

Step 4—Synthesis of 4-chloro-6-methoxy-7-(3-methoxypropoxy)quinoline-3-carbonyl chloride: A solution of 4-hydroxy-6-methoxy-7-(3-methoxypropoxy)quinoline-3-carboxylic acid (500 mg, 1.63 mmol, 1 eq) in $POCl_3$ (5 mL) was stirred for 1 h at 100° C. LCMS (a sample was quench with 1 mL ice-MeOH) showed the reaction was complete. The mixture was concentrated in vacuo to give 4-chloro-6-methoxy-7-(3-methoxypropoxy)quinoline-3-carbonyl chloride (580 mg, crude) as brown oil.

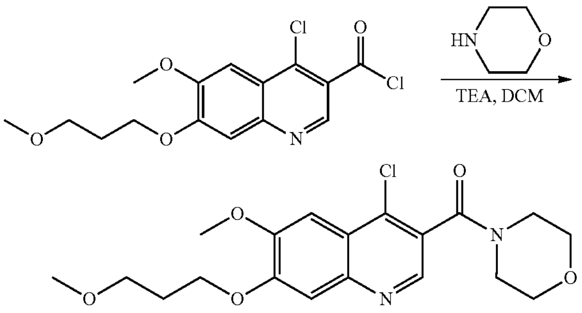

Step 5—Synthesis of 4-chloro-6-methoxy-7-(3-methoxypropoxy)quinoline-3-carbonyl chloride: To a solution of 4-chloro-6-methoxy-7-(3-methoxypropoxy)quinoline-3-carbonyl chloride (560 mg, 1.63 mmol, 1 eq) in DCM (6 mL) was added TEA (658.55 mg, 6.51 mmol, 905.84 μL, 4 eq) and morpholine (141.75 mg, 1.63 mmol, 143.18 μL, 1 eq) at 0° C., then stirred for 14 h at 25° C. LCMS showed the reactant was consumed, desired ms was detected. The mixture was dissolved in water (5 mL), separated, extracted with ethyl acetate (5 mL×3). The combined organic layers were dried over $Na_2SO_4$, filtered, concentrated in vacuo. The crude product was purified by flash column (ISCO 20 g silica, 0~100% ethyl acetate in petroleum ether, gradient over 30 min) to give [4-chloro-6-methoxy-7-(3-methoxypropoxy)-3-quinolyl]-morpholino-methanone (310 mg, 785.11 μmol, 48.25% yield) as white solid. MS $(M+H)^+$=395.1.

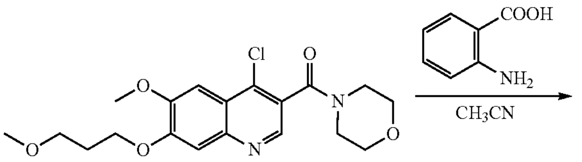

-continued

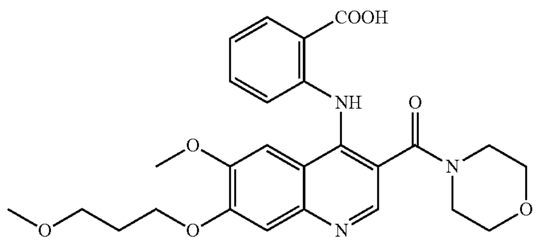

Step 6—Synthesis of [4-chloro-6-methoxy-7-(3-methoxypropoxy)-3-quinolyl]-morpholino-methanone: A solution of [4-chloro-6-methoxy-7-(3-methoxypropoxy)-3-quinolyl]-morpholino-methanone (150 mg, 379.89 μmol, 1 eq) and 2-aminobenzoic acid (62.52 mg, 455.87 μmol, 1.2 eq) in ACN (2 mL) was stirred for 14 h at 90° C. LCMS showed ~50% desired product and ~20% reactant were detected. The mixture was concentrated in vacuo. The crude product was purified by prep-HPLC (Waters Xbridge BEH C18 100×25 mm×5 μm column; 15%-45% acetonitrile in a solution 10 mM $NH_4HCO_3$ in water, 8 min gradient) to give 2-[[6-methoxy-7-(3-methoxypropoxy)-3-(morpholine-4-carbonyl)-4-quinolyl]amino]benzoic acid (91.92 mg, 185.50 μmol, 48.83% yield, 100% purity) as yellow solid. $^1H$ NMR (400 MHz, DMSO-$d_6$, T=273+80K) δ=8.50 (s, 1H), 7.99-7.93 (m, 1H), 7.40 (s, 1H), 7.27 (s, 1H), 7.24-7.17 (m, 1H), 6.82 (t, J=7.5 Hz, 1H), 6.60 (d, J=8.2 Hz, 1H), 4.24 (t, J=6.4 Hz, 2H), 3.76 (s, 3H), 3.54 (t, J=6.3 Hz, 2H), 3.37 (br d, J=4.5 Hz, 4H), 3.29 (s, 3H), 3.27 (br d, J=8.2 Hz, 4H), 2.06 (quin, J=6.4 Hz, 2H). MS $(M+H)^+$=496.3.

Example 27

Preparation of Compound 54A

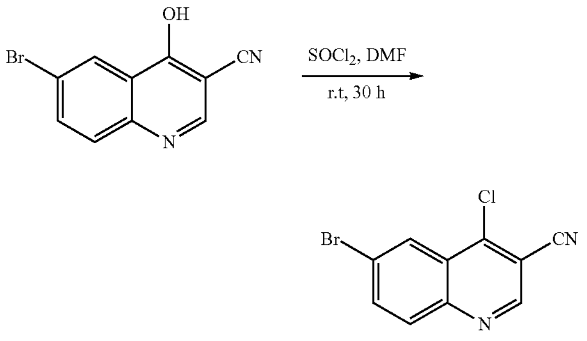

Step 1—Synthesis of 6-bromo-4-chloro-quinoline-3-carbonitrile: To a suspension of 6-bromo-4-hydroxy-quinoline-3-carbonitrile (0.23 g, 923.46 μmol, 1 eq) in $SOCl_2$ (4.92 g, 41.35 mmol, 3 mL, 44.78 eq) was added DMF (6.75 mg, 92.35 μmol, 7.11 μL, 0.1 eq) at 0° C., then the mixture solution was stirred at 25° C. for 24 h. TLC (Petroleum ether:Ethyl acetate=0:1) showed the reactant was consumed, and one new spot was formed. The mixture was concentrated, dissolved in toluene (5 mL×2) and concentrated in vacuo to obtain 6-bromo-4-chloro-quinoline-3-carbonitrile (0.25 g, crude) as light yellow solid.

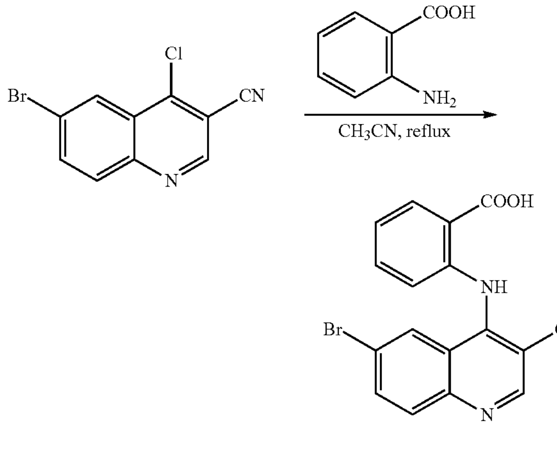

Step 2—Synthesis of 2-[(6-bromo-3-cyano-4-quinolyl)amino]benzoic acid: A suspension of 6-bromo-4-chloro-quinoline-3-carbonitrile (0.15 g, 560.73 μmol, 1 eq) and 2-aminobenzoic acid (92.28 mg, 672.87 μmol, 1.2 eq) in ACN (7 mL) were stirred at 90° C. for 12 h. TLC (Petroleum ether:Ethyl acetate=0:1) showed the reactant was consumed, and one new spot was formed. The mixture was concentrated in vacuo to obtain 2-[(6-bromo-3-cyano-4-quinolyl)amino]benzoic acid (0.2 g, crude) light yellow solid. Note: Another 0.1 g desired product was obtained using the same synthesis method.

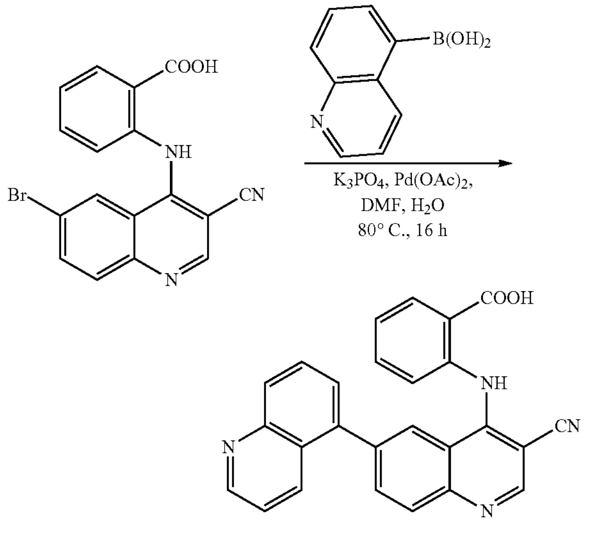

Step 3—Synthesis of 2-[[3-cyano-6-(5-quinolyl)-4-quinolyl]amino]benzoic acid: To a solution of 2-[(6-bromo-3-cyano-4-quinolyl)amino]benzoic acid (220 mg, 597.53 μmol, 1 eq), $Pd(OAc)_2$ (13.42 mg, 59.75 μmol, 0.1 eq), PPh3 (31.35 mg, 119.51 μmol, 0.2 eq) and $K_3PO_4$ (507.35 mg, 2.39 mmol, 4 eq) in DMF (4 mL) and $H_2O$ (1 mL) was added 5-quinolylboronic acid (206.72 mg, 1.20 mmol, 2 eq). The mixture reaction was degassed and purged with $N_2$ for 5 times, then stirred for 14h at 80° C. under $N_2$. LCMS showed the reactant was consumed and desired MS was detected. The mixture was filtered to obtain filtrate. The crude product was purified by prep-HPLC (Waters Xbridge BEH C18 100×25 mm×5 μm column; 15%-45% acetonitrile in a solution 10 mM $NH_4HCO_3$ in water, 8 min gradient) to give 2-[[3-cyano-6-(5-quinolyl)-4-quinolyl]amino]benzoic acid (136.08 mg, 320.24 μmol, 53.59% yield, 98.00% purity) as yellow solid. $^1$H NMR (400 MHz, DMSO-d6) δ=10.96-10.41 (m, 1H), 9.02 (d, J=2.9 Hz, 1H), 8.76 (s, 1H), 8.58 (s, 1H), 8.28 (d, J=8.4 Hz, 1H), 8.17 (dd, J=5.3, 8.4 Hz, 2H), 8.05 (br d, J=8.6 Hz, 1H), 8.00-7.90 (m, 2H), 7.74 (d, J=7.1 Hz, 1H), 7.66-7.57 (m, 2H), 7.41 (d, J=7.9 Hz, 1H), 7.34 (t, J=7.5 Hz, 1H). MS $(M+H)^+$=417.2.

Example 28

Preparation of Compound 55A

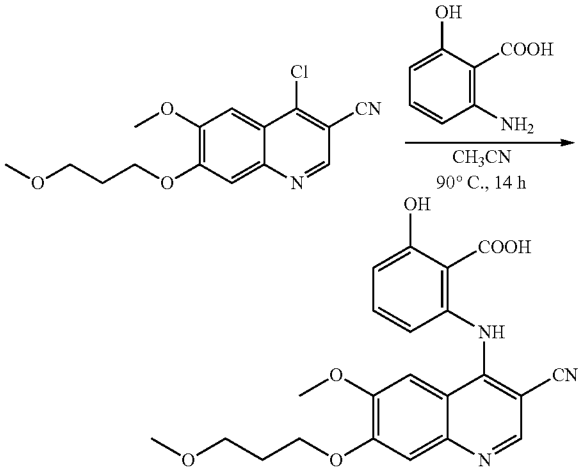

Synthesis of 2-[[3-cyano-6-methoxy-7-(3-methoxy propoxy)-4-quinolyl]amino]-6-hydroxy-benzoic acid: A solution of 4-chloro-6-methoxy-7-(3-methoxypropoxy)quinoline-3-carbonitrile (150 mg, 489.01 μmol, 1 eq) and 2-amino-6-hydroxy-benzoic acid (89.86 mg, 586.81 μmol, 1.2 eq) in ACN (0.5 mL) was stirred for 14 h at 90° C. LCMS showed the reaction was complete. The mixture was concentrated in vacuo. The crude product was purified by prep-HPLC (Waters Xbridge Prep OBD C18 150×40 mm×10 μm column; 10%-40% acetonitrile in an 10 mM $NH_4HCO_3$ in water, 8 min gradient) to give 2-[[3-cyano-6-methoxy-7-(3-methoxypropoxy)-4-quinolyl]amino]-6-hydroxy-benzoic acid (13.96 mg, 32.43 μmol, 6.63% yield, 98.35% purity) as yellow solid. 1H NMR (400 MHz, DMSO-d6) δ=8.67 (s, 1H), 7.54 (s, 1H), 7.35 (s, 1H), 7.17 (t, J=8.0 Hz, 1H), 6.52 (dd, J=2.5, 8.0 Hz, 2H), 4.21 (br t, J=6.3 Hz, 2H), 3.87 (s, 3H), 3.48-3.45 (m, 2H), 3.26 (s, 3H), 2.10-1.98 (m, 2H). MS $(M+H)^+$=424.0.

Example 29

Preparation of Compound 56A

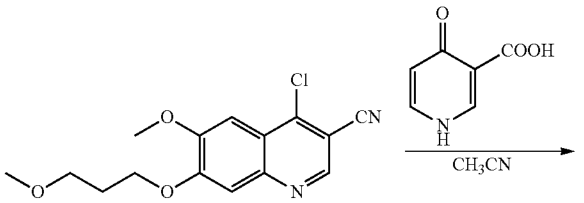

-continued

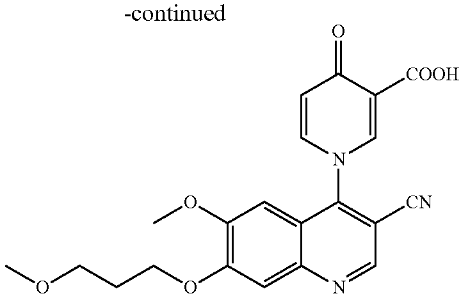

Synthesis of 1-[3-cyano-6-methoxy-7-(3-methoxypropoxy)-4-quinolyl]-4-oxo-pyridine-3-carboxylic acid: A solution of 4-chloro-6-methoxy-7-(3-methoxypropoxy)quinoline-3-carbonitrile (150 mg, 489.01 μmol, 1 eq) and 4-oxo-1H-pyridine-3-carboxylic acid (95.24 mg, 684.61 μmol, 1.4 eq) in ACN (2 mL) was stirred for 14 h at 90° C. LCMS showed the reaction was complete. The mixture was concentrated in vacuo. The crude product was purified by prep-HPLC (Waters Xbridge BEH C18 100×25 mm×5 μm column; 5%-35% acetonitrile in a solution 10 mM $NH_4HCO_3$ in water, 8 min gradient) to give 1-[3-cyano-6-methoxy-7-(3-methoxypropoxy)-4-quinolyl]-4-oxo-pyridine-3-carboxylic acid (14.55 mg, 35.54 μmol, 7.27% yield, 100% purity) as pale yellow solid. $^1$H NMR (400 MHz, DMSO-$d_6$) δ=9.19 (s, 1H), 9.07 (d, J=2.2 Hz, 1H), 8.42 (dd, J=2.3, 7.6 Hz, 1H), 7.66 (s, 1H), 7.03 (d, J=7.5 Hz, 1H), 6.93 (s, 1H), 4.32 (t, J=6.4 Hz, 2H), 3.87 (s, 3H), 3.50 (t, J=6.2 Hz, 2H), 3.26 (s, 3H), 2.06 (quin, J=6.3 Hz, 2H). MS $(M+H)^+$=410.2.

Example 30

Preparation of Compound 57A

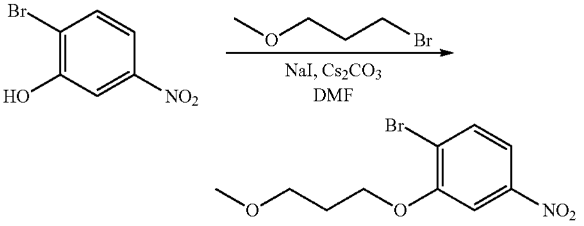

Step 1—Synthesis of 1-bromo-2-(3-methoxypropoxy)-4-nitro-benzene: A solution of 2-bromo-5-nitro-phenol (5 g, 22.94 mmol, 1 eq), 1-bromo-3-methoxy-propane (3.51 g, 22.94 mmol, 1 eq), NaI (5.16 g, 34.40 mmol, 1.5 eq) and $Cs_2CO_3$ (14.95 g, 45.87 mmol, 2 eq) in DMF (10 mL) was stirred for 2 h at 100° C. TLC (Petroleum ether:Ethyl acetate=3:1, $R_f$=0.43) showed the reaction was complete. The suspension was filtered to give filtrate. The filtrate was dissolved in ethyl acetate (20 mL) and water (30 mL), separated, extracted with ethyl acetate (10 mL). The combined organic layers were washed with water (5 mL×3), dried over $Na_2SO_4$, filtered, concentrated to give 1-bromo-2-(3-methoxypropoxy)-4-nitro-benzene (6.3 g, 21.72 mmol, 94.68% yield) as yellow solid. $^1$H NMR (400 MHz, DMSO-d6) δ=7.88 (dd, J=1.5, 8.6 Hz, 1H), 7.81 (s, 1H), 7.77-7.72 (m, 1H), 4.25 (t, J=6.2 Hz, 2H), 3.51 (t, J=6.3 Hz, 2H), 3.28-3.24 (m, 3H), 2.01 (quin, J=6.0 Hz, 2H).

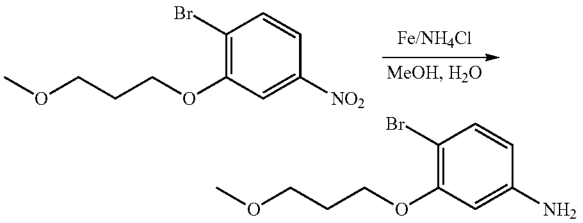

Step 2—Synthesis of 4-bromo-3-(3-methoxypropoxy) aniline: A solution of 1-bromo-2-(3-methoxypropoxy)-4-nitro-benzene (5.3 g, 18.27 mmol, 1 eq), Fe (8.67 g, 155.29 mmol, 8.5 eq) and $NH_4Cl$ (8.80 g, 164.42 mmol, 9 eq) in a mixture of Methanol (40 mL) and $H_2O$ (20 mL) was stirred for 4 h at 80° C. TLC (Petroleum ether:Ethyl acetate=3:1, Rf=0.24) showed the reaction was complete. The mixture was filtered to give filtrate, concentrated in vacuo. The residual was dissolved in ethyl acetate (20 mL) and water (10 mL), separated, extracted with ethyl acetate (20 mL×2). The combined organic layers were dried over $Na_2SO_4$, concentrated in vacuo to give 4-bromo-3-(3-methoxypropoxy)aniline (4.0 g, 15.38 mmol, 84.17% yield) as pale yellow oil. $^1H$ NMR (400 MHz, DMSO-d6) δ=7.10 (d, J=8.4 Hz, 1H), 6.31 (d, J=2.3 Hz, 1H), 6.10 (dd, J=2.4, 8.5 Hz, 1H), 5.25 (br s, 2H), 3.96 (t, J=6.3 Hz, 2H), 3.50 (t, J=6.3 Hz, 2H), 3.25 (s, 3H), 1.94 (quin, J=6.3 Hz, 2H).

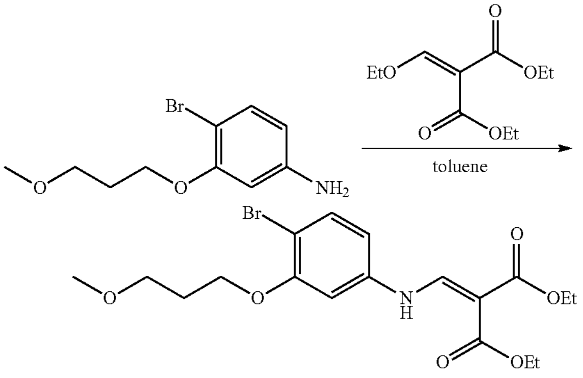

Step 3—Synthesis of diethyl 2-[[4-bromo-3-(3-methoxypropoxy)anilino]methylene]propanedioate: A solution of 4-bromo-3-(3-methoxypropoxy)aniline (4.0 g, 15.38 mmol, 1 eq) and diethyl 2-(ethoxymethylene)propanedioate (3.32 g, 15.38 mmol, 3.11 mL, 1 eq) in toluene (40 mL) was stirred for 4 h at 110° C. LCMS showed the reaction was complete. The reaction mixture was concentrated in vacuo to give diethyl 2-[[4-bromo-3-(3-methoxypropoxy)anilino]methylene]propanedioate (6.8 g, crude) as brown gum. $^1H$ NMR (400 MHz, DMSO-$d_6$) δ=10.63 (br d, J=13.9 Hz, 1H), 8.36 (d, J=13.7 Hz, 1H), 7.51 (d, J=8.6 Hz, 1H), 7.21 (d, J=1.8 Hz, 1H), 6.89 (dd, J=1.9, 8.5 Hz, 1H), 4.19 (q, J=7.1 Hz, 2H), 4.14-4.04 (m, 4H), 3.49 (t, J=6.2 Hz, 2H), 3.24 (s, 3H), 1.96 (quin, J=6.2 Hz, 2H), 1.23 (q, J=7.7 Hz, 6H).

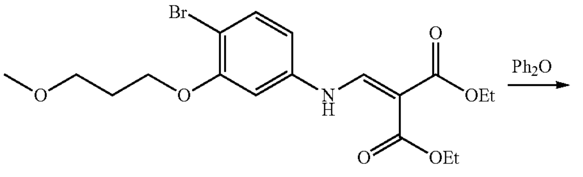

-continued

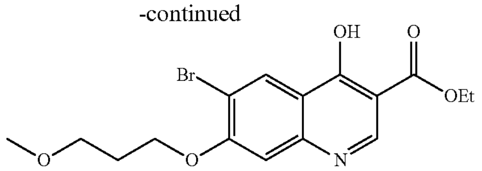

Step 4—Synthesis of ethyl 6-bromo-4-hydroxy-7-(3-methoxypropoxy)quinoline-3-carboxylate: A solution of diethyl 2-[[4-bromo-3-(3-methoxypropoxy)anilino]methylene]propanedioate (2 g, 4.65 mmol, 1 eq) in $Ph_2O$ (20 mL) was stirred for 0.5 h at 260° C. LCMS (added into petroleum ether, the solid was dissolved MeOH) showed the desired ms was detected. The mixture was cooled into room temperature, followed addition by petroleum ether (20 mL), filtered to give ethyl 6-bromo-4-hydroxy-7-(3-methoxypropoxy) quinoline-3-carboxylate (1.2 g, crude) was obtained as a pale solid. MS $(M+H)^+$=384.0.

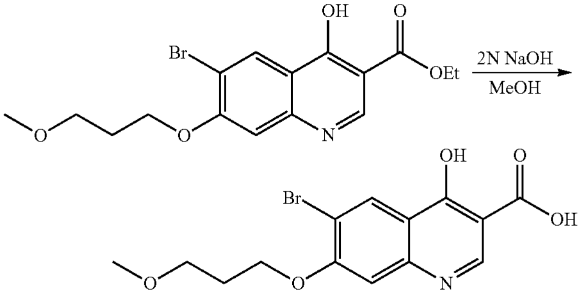

Step 5—Synthesis of 6-bromo-4-hydroxy-7-(3-methoxypropoxy)quinoline-3-carboxylic acid: To a solution of ethyl 6-bromo-4-hydroxy-7-(3-methoxypropoxy)quinoline-3-carboxylate (800 mg, 2.08 mmol, 1 eq) in MeOH (10 mL) was added NaOH (2 M, 10.41 mL, 10 eq), stirred for 14 h at 50° C. LCMS showed the reaction was complete. The mixture was concentrated in vacuo, acidified to PH=4 with 1N HCl solution, filtered to give 6-bromo-4-hydroxy-7-(3-methoxypropoxy)quinoline-3-carboxylic acid (760 mg, crude) as pale solid. $^1H$ NMR (400 MHz, DMSO-$d_6$) δ=13.82 (br s, 1H), 8.75 (br d, J=4.2 Hz, 1H), 8.33-8.24 (m, 1H), 7.42-7.35 (m, 1H), 4.20 (t, J=6.2 Hz, 2H), 3.54 (t, J=6.2 Hz, 2H), 3.26 (s, 3H), 2.06 (quin, J=6.2 Hz, 2H). MS $(M+H)^+$=356.0

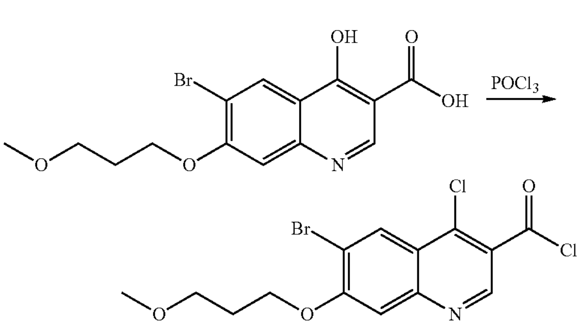

Step 6—Synthesis of 6-bromo-4-chloro-7-(3-methoxypropoxy)quinoline-3-carbonyl chloride: A solution of 6-bromo-4-hydroxy-7-(3-methoxypropoxy)quinoline-3-carboxylic acid (400 mg, 1.12 mmol, 1 eq) in $POCl_3$ (4 mL) was stirred for 1 h at 100° C. LCMS (a sample was quench with 1 mL ice-EtOH) showed the reaction was complete. The mixture was concentrated in vacuo to give 6-bromo-4-chloro-7-(3-methoxypropoxy)quinoline-3-carbonyl chloride (520 mg, crude) as brown oil.

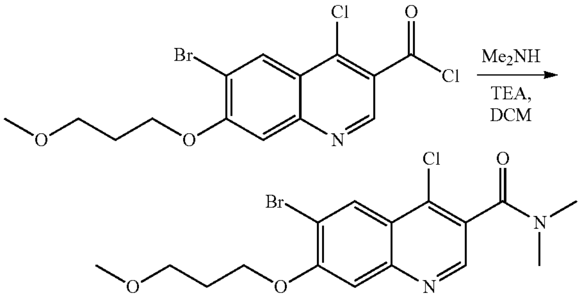

Step 7—Synthesis of 6-bromo-4-chloro-7-(3-methoxypropoxy)-N,N-dimethyl-quinoline-3-carboxamide: To a solution of 6-bromo-4-chloro-7-(3-methoxypropoxy)quinoline-3-carbonyl chloride (440 mg, 1.12 mmol, 1 eq) in DCM (5 mL) was added TEA (339.82 mg, 3.36 mmol, 467.43 μL, 3 eq) and N-methylmethanamine (82.15 mg, 1.01 mmol, 92.31 μL, 0.9 eq, HCl) at 0° C., then stirred for 14 h at 25° C. LCMS showed the reaction was complete. Water (5 mL) was added into, separated, extracted DCM (5 mL×3). The combined organic layers were dried over $Na_2SO_4$, concentrated in vacuo to give 6-bromo-4-chloro-7-(3-methoxypropoxy)-N,N-dimethyl-quinoline-3-carboxamide (490 mg, crude) as a yellow gum. MS $(M+H)^+$=401.0

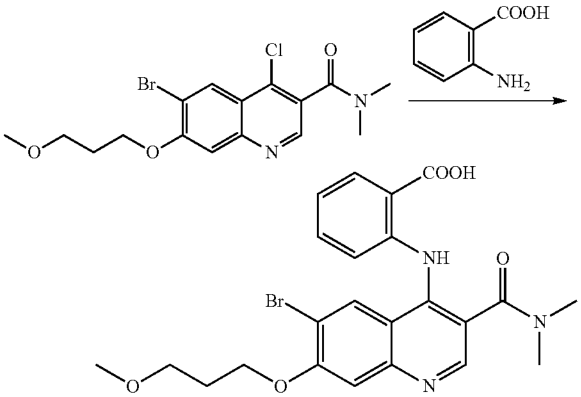

Step 8—Synthesis of 2-[[6-bromo-3-(dimethylcarbamoyl)-7-(3-methoxypropoxy)-4-quinolyl]amino]benzoic acid: A solution of 6-bromo-4-chloro-7-(3-methoxypropoxy)-N,N-dimethyl-quinoline-3-carboxamide (160 mg, 398.33 μmol, 1 eq) and 2-aminobenzoic acid (65.55 mg, 477.99 μmol, 1.2 eq) in ACN (2 mL) was stirred for 14 h at 90° C. LCMS showed the rection was complete. The mixture was concentrated in vacuo. The crude product was purified by prep-HPLC (Waters Xbridge BEH C18 100×25 mm×5 μm column; 25%-55% acetonitrile in an 10 mM $NH_4HCO_3$ in water, 8 min gradient) to give 2-[[6-bromo-3-(dimethylcarbamoyl)-7-(3-methoxypropoxy)-4-quinolyl]amino]benzoic acid (33.45 mg, 65.15 μmol, 16.36% yield, 97.85% purity) as yellow solid. $^1$H NMR (400 MHz, DMSO-$d_6$) δ=11.78 (br d, J=6.1 Hz, 1H), 8.59 (s, 1H), 8.27 (s, 1H), 7.92 (dd, J=1.3, 7.8 Hz, 1H), 7.50 (s, 1H), 7.29-7.19 (m, 2H), 6.88 (t, J=7.5 Hz, 1H), 6.69 (d, J=8.1 Hz, 1H), 4.29 (t, J=6.2 Hz, 2H), 3.57 (t, J=6.2 Hz, 2H), 3.28 (s, 3H), 2.71 (s, 3H), 2.54 (s, 3H), 2.07 (quin, J=6.2 Hz, 2H). MS $(M+H)^+$=502.0.

Example 31

Preparation of Compound 58A

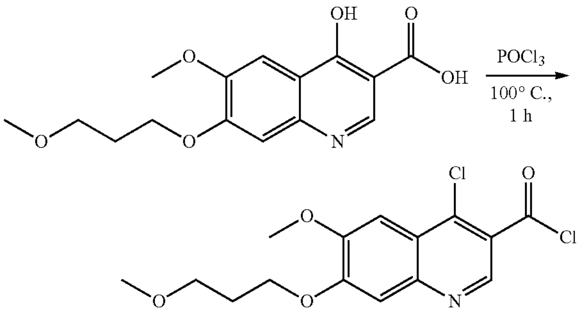

Step 1—Synthesis of 4-chloro-6-methoxy-7-(3-methoxypropoxy)quinoline-3-carbonyl chloride: A solution of 4-hydroxy-6-methoxy-7-(3-methoxypropoxy)quinoline-3-carboxylic acid (900 mg, 2.93 mmol, 1 eq) in $POCl_3$ (8 mL) was stirred for 1 h at 100° C. LCMS (a sample was quench with 1 mL ice-MeOH) showed the reaction was complete. The mixture was concentrated in vacuo to give 4-chloro-6-methoxy-7-(3-methoxypropoxy)quinoline-3-carbonyl chloride (1 g, crude) as a brown oil.

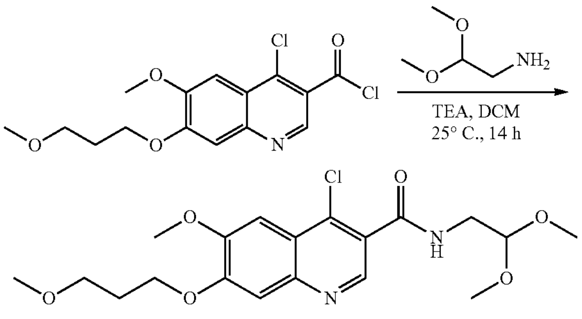

Step 2—Synthesis of 4-chloro-N-(2,2-dimethoxyethyl)-6-methoxy-7-(3-methoxypropoxy)quinoline-3-carboxamide: To a solution of 4-chloro-6-methoxy-7-(3-methoxypropoxy)quinoline-3-carbonyl chloride (1 g, 2.91 mmol, 1 eq) in DCM (10 mL) was added TEA (1.18 g, 11.62 mmol, 1.62 mL, 4 eq) and 2,2-dimethoxyethanamine (305.46 mg, 2.91 mmol, 316.54 μL, 1 eq) at 0° C., then stirred for 14 h at 25° C. LCMS showed the reaction was complete. The mixture was dissolved in water (10 mL), separated, extracted with DCM (20 mL×2). The combined organic layers were dried over $Na_2SO_4$, concentrated in vacuum. The crude product was purified by flash column (ISCO 20 g silica, 0~100% ethyl acetate in petroleum ether, gradient over 30 min) to give 4-chloro-N-(2,2-dimethoxyethyl)-6-methoxy-7-(3-methoxypropoxy)quinoline-3-carboxamide (500 mg, 1.21 mmol, 41.68% yield) as white solid.

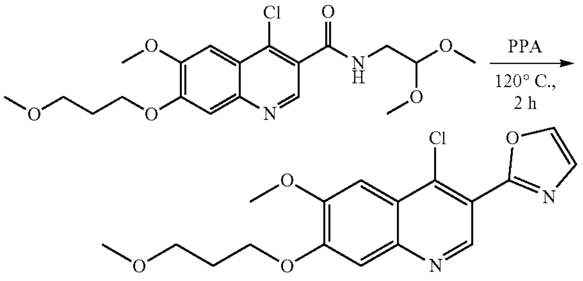

Step 3—Synthesis of 2-[4-chloro-6-methoxy-7-(3-methoxypropoxy)-3-quinolyl]Oxazole: A solution of 4-chloro-N-(2,2-dimethoxyethyl)-6-methoxy-7-(3-methoxypropoxy)quinoline-3-carboxamide (105 mg, 254.32 μmol, 1 eq) in PPA (2 g) was stirred for 4 h at 90° C. LCMS showed the reaction was complete. 2 batches reaction mixture was combined, followed addition into ice-water (10 mL), dissolved in ethyl acetate (20 mL), separated, extracted with ethyl acetate (20 mL×3). The combined organic layers were dried over $Na_2SO_4$ and concentrated in vacuum. The crude product was purified by flash column (ISCO 10 g silica, 0~30% ethyl acetate in petroleum ether, gradient over 30 min) to give 2-[4-chloro-6-methoxy-7-(3-methoxypropoxy)-3-quinolyl]oxazole (36 mg, 103.22 μmol, 20.29% yield) as pale yellow solid. MS $(M+H)^+$=349.2

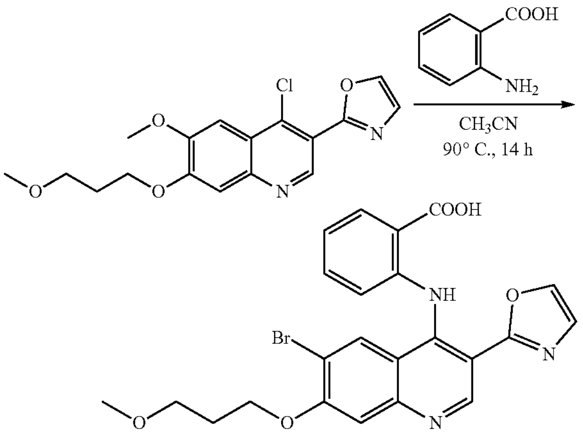

Step 4—Synthesis of 2-[[6-methoxy-7-(3-methoxypropoxy)-3-oxazol-2-yl-4-quinolyl]amino]benzoic acid: A solution of 2-[4-chloro-6-methoxy-7-(3-methoxypropoxy)-3-quinolyl]oxazole (20 mg, 57.34 μmol, 1 eq), 2-aminobenzoic acid (19.97 mg, 145.65 μmol, 2.54 eq) and HCl (12 M, 23.89 μL, 5.0 eq) in ACN (0.6 mL) was stirred for 14 h at 90° C. LCMS showed the reaction was complete. The mixture was concentrated in vacuum. The crude product was purified by prep-HPLC (Waters Xbridge BEH C18 100×30 mm×10 μm column; 5%-25% acetonitrile in an 10 mM $NH_4HCO_3$ in water, 10 min gradient) to give 2-[[6-methoxy-7-(3-methoxypropoxy)-3-oxazol-2-yl-4-quinolyl]amino] benzoic acid (12.64 mg, 27.76 μmol, 48.41% yield, 98.71% purity) as yellow solid. $^1H$ NMR (400 MHz, DMSO-$d_6$) δ=11.40 (br s, 1H), 9.10 (s, 1H), 8.19 (s, 1H), 7.95 (dd, J=1.5, 7.9 Hz, 1H), 7.45-7.37 (m, 2H), 7.26-7.15 (m, 1H), 6.97 (s, 1H), 6.89 (t, J=7.6 Hz, 1H), 6.43 (d, J=7.9 Hz, 1H), 4.21 (t, J=6.4 Hz, 2H), 3.53-3.49 (m, 5H), 3.27 (s, 3H), 2.04 (quin, J=6.3 Hz, 2H).

Example 32

Preparation of Compound 61A

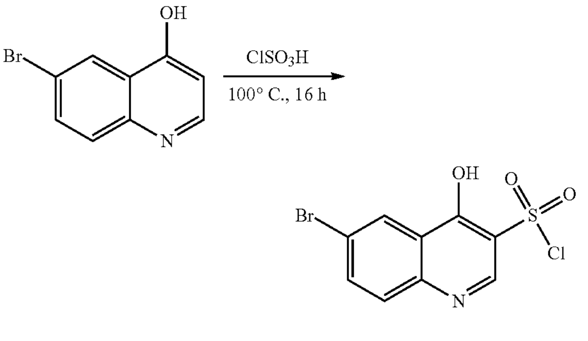

Step 1—Synthesis of 6-bromo-4-hydroxy-quinoline-3-sulfonyl chloride: A solution of 6-bromoquinolin-4-ol (1 g, 4.46 mmol, 1 eq) in sulfurchloridic acid (13 mL) was stirred for 10 h at 100° C. under $N_2$. LCMS showed no reactant 1 was remained. The mixture was added into ice-water (10 mL), filtered to give filter cake, dried in vacuum to give 6-bromo-4-hydroxy-quinoline-3-sulfonyl chloride (1.7 g, crude) as off-white solid. $^1H$ NMR (400 MHz, DMSO-d6) δ=8.83 (s, 1H), 8.36 (d, J=2.2 Hz, 1H), 8.01 (dd, J=2.2, 8.8 Hz, 1H), 7.85 (d, J=9.0 Hz, 1H).

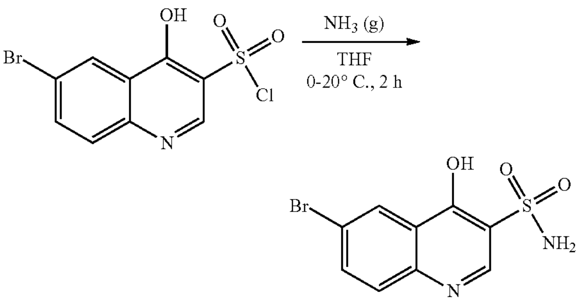

Step 2—Synthesis of 6-bromo-4-hydroxy-quinoline-3-sulfonamide: To a stirred solution of THF (4 mL) was bubbled with $NH_3$ to pH~14 at 0° C., then 6-bromo-4-hydroxy-quinoline-3-sulfonyl chloride (1.0 g, 3.10 mmol, 1 eq) was added at 0° C. Then the mixture was stirred at 25° C. for 2 hr. LCMS showed the reaction was complete. The mixture was concentrated in vacuum, triturated with MTBE (5 ml) at room temperature, filtered to give filter cake, dried in vacuum to give 6-bromo-4-hydroxy-quinoline-3-sulfonamide (1 g, crude) as pale solid. $^1H$ NMR (400 MHz, DMSO-$d_6$) δ=8.52 (s, 1H), 8.26 (d, J=2.2 Hz, 1H), 7.92 (dd, J=2.2, 8.8 Hz, 1H), 7.72 (d, J=8.8 Hz, 1H), 6.86 (br s, 2H).

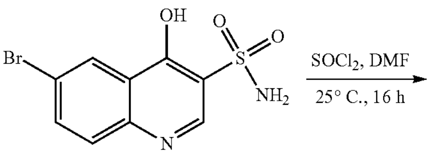

-continued

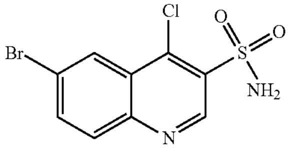

Step 3—Synthesis of 6-bromo-4-chloro-quinoline-3-sulfonamide: A solution of 6-bromo-4-hydroxy-quinoline-3-sulfonamide (200 mg, 659.78 μmol, 1 eq) and DMF (4.82 mg, 65.98 μmol, 5.08 μL, 0.1 eq) in $SOCl_2$ (3 mL) was stirred for 14 h at 25° C. LCMS showed no reactant 1 was remained. The mixture was concentrated in vacuum to give 6-bromo-4-chloro-quinoline-3-sulfonamide (190 mg, crude) as off-white solid.

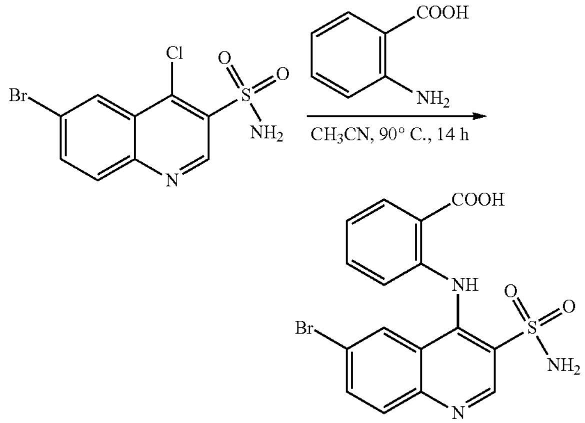

Step 4—Synthesis of 2-[(6-bromo-3-sulfamoyl-4-quinolyl)amino]benzoic acid: A solution of 6-bromo-4-chloro-quinoline-3-sulfonamide (150 mg, 466.45 μmol, 1 eq), HCl (236.21 mg, 2.33 mmol, 231.58 μL, 36% purity, 5 eq) and 2-aminobenzoic acid (70.36 mg, 513.09 μmol, 1.1 eq) in ACN (1 mL) was stirred for 14 h at 90° C. LCMS showed the desired MS was detected. The reaction solution was concentrated in vacuum. The crude product was purified by prep-HPLC (Waters Xbridge BEH C18 100×25 mm×5 μm column; 15%-35% acetonitrile in an 10 mM $NH_4HCO_3$ in water, 8 min gradient) to give 2-[(6-bromo-3-sulfamoyl-4-quinolyl)amino]benzoic acid (16.76 mg, 37.74 μmol, 8.09% yield, 95.09% purity) as yellow solid. $^1H$ NMR (400 MHz, DMSO-$d_6$) δ=11.28 (br s, 1H), 9.15 (s, 1H), 8.01-7.94 (m, 2H), 7.93-7.89 (m, 1H), 7.79 (d, J=2.0 Hz, 1H), 7.23-7.16 (m, 1H), 6.95 (t, J=7.5 Hz, 1H), 6.43 (d, J=8.2 Hz, 1H). MS $(M-H)^-$=419.9.

Example 33

Preparation of Compound 63A

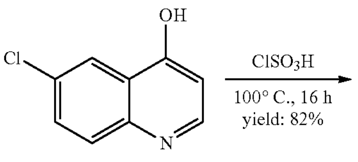

-continued

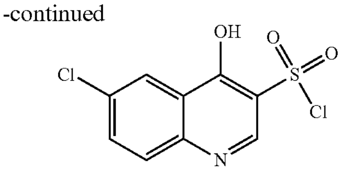

Step 1—Synthesis of 6-chloro-4-hydroxy-quinoline-3-sulfonyl chloride: A solution of 6-chloroquinolin-4-ol (1.5 g, 8.35 mmol, 1 eq) in chlorosulfonic acid (15 mL) was stirred for 14 h at 100° C. LCMS showed the reaction was complete. The mixture was added dropwise ice-water (50 mL) at 0~5° C., filtered to give filter cake and dried in vacuum to give 6-chloro-4-hydroxy-quinoline-3-sulfonyl chloride (1.9 g, 6.83 mmol, 81.80% yield) as off-white solid. $^1H$ NMR (400 MHz, DMSO-$d_6$) δ=8.90 (s, 1H), 8.23 (d, J=2.2 Hz, 1H), 8.00-7.97 (m, 1H), 7.95-7.91 (m, 1H).

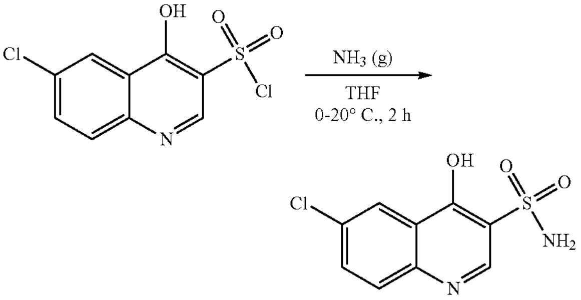

Step 2—Synthesis of 6-chloro-4-hydroxy-quinoline-3-sulfonamide: $NH_3$ (36.74 mg, 2.16 mmol, 1 eq) was bubbled into THF (10 mL) until pH=14 at 0° C., followed by 6-chloro-4-hydroxyquinoline-3-sulfonyl chloride (600 mg, 2.16 mmol, 1 eq). The mixture was stirred for 2 h at 25° C. LCMS showed the reactant was consumed, new main peak was detected. The mixture was concentrated in vacuum, triturated with MTBE (5 mL) and filtered to give 6-chloro-4-hydroxy-quinoline-3-sulfonamide (600 mg, crude) as off-white solid. $^1H$ NMR (400 MHz, DMSO-$d_6$) δ=8.52 (s, 1H), 8.11 (s, 1H), 7.84-7.76 (m, 2H), 6.84 (br s, 2H).

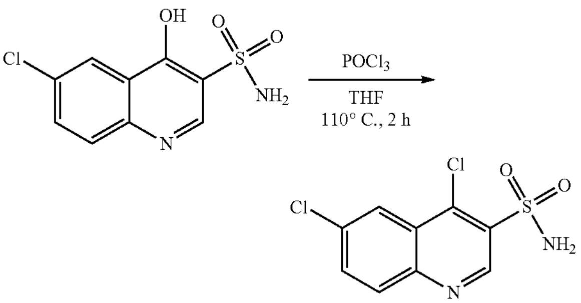

Step 3—Synthesis of 4,6-dichloroquinoline-3-sulfonamide: A solution of 6-chloro-4-hydroxy-quinoline-3-sulfonamide (50 mg, 193.29 μmol, 1 eq) in $POCl_3$ (2 mL) was stirred for 2 h at 110° C. LCMS showed the reaction was complete. The mixture was concentrated in vacuum to give 4,6-dichloroquinoline-3-sulfonamide (52 mg, crude) as yellow gum.

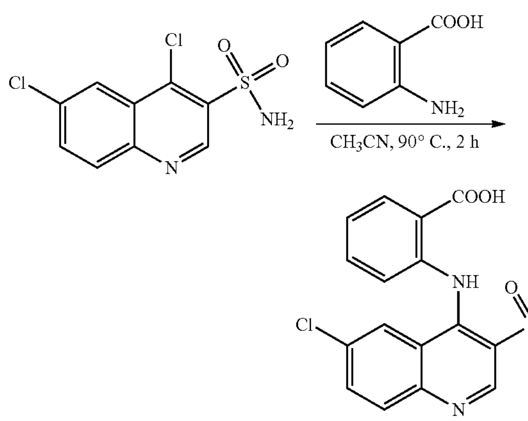

Step 4—Synthesis of 2-[(6-chloro-3-sulfamoyl-4-quinolyl)amino]benzoic acid: To a stirred solution of 4,6-dichloroquinoline-3-sulfonamide (50 mg, 180.42 μmol, 1 eq) in $CH_3CN$ (2 mL) was added 2-aminobenzoic acid (24.74 mg, 180.42 μmol, 1 eq). Then the mixture was stirred at 90° C. for 2hr. LCMS showed the reaction was complete. The mixture was concentrated in vacuo. The crude residue was purified by prep-HPLC (Nano-micro Kromasil C18 80×25 mm μm column; 22-42% acetonitrile in a 0.04% HCl acid solution in water, 7 min gradient) to give 2-[(6-chloro-3-sulfamoyl-4-quinolyl)amino]benzoic acid (17.70 mg, 46.49 μmol, 25.77% yield, 99.24% purity) as yellow solid. $^1H$ NMR (400 MHz, DMSO-$d_6$) δ=10.39 (br s, 1H), 9.18 (s, 1H), 8.14 (d, J=8.8 Hz, 1H), 8.07-7.98 (m, 3H), 7.91 (dd, J=2.2, 9.0 Hz, 1H), 7.51 (d, J=2.2 Hz, 1H), 7.41-7.33 (m, 1H), 7.17 (t, J=7.5 Hz, 1H), 6.71 (br d, J=7.9 Hz, 1H). MS $(M+H)^+$=377.9.

Example 34

Preparation of Compound 64A

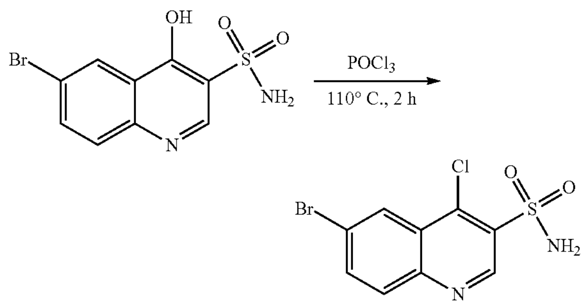

Step 1—Synthesis of 6-bromo-4-chloro-quinoline-3-sulfonamide: A suspension of 6-bromo-4-hydroxy-quinoline-3-sulfonamide (300 mg, 989.67 μmol, 1 eq) in $POCl_3$ (1 mL) was stirred at 110° C. for 2 h. LCMS showed starting material was completely consumed and desired product was formed. The mixture was concentrated in vacuo, the residue azeotroped with toluene (3 mL×2) to give 6-bromo-4-chloro-quinoline-3-sulfonamide (300 mg, crude) was obtained as yellow gum.

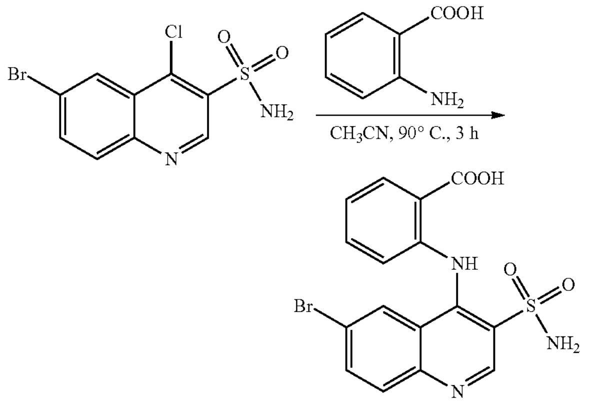

Step 2—Synthesis of 2-[(6-bromo-3-sulfamoyl-4-quinolyl)amino]benzoic acid: To a stirred solution of 6-bromo-4-chloro-quinoline-3-sulfonamide (300 mg, 932.90 μmol, 1 eq) in $CH_3CN$ (8 mL) was added 2-aminobenzoic acid (127.93 mg, 932.90 μmol, 1 eq). Then the mixture was stirred at 90° C. for 3 h. LCMS showed starting material was completely consumed and desired product was formed. The mixture was concentrated in vacuo. The crude product was purified by prep-HPLC: column: Nano-micro Kromasil C18 80×25 mm μm; mobile phase: [water(0.04% HCl)-ACN]; B %: 15%-45%, 7 min to give 2-[(6-bromo-3-sulfamoyl-4-quinolyl)amino]benzoic acid (170 mg, 402.60 μmol, 43.16% yield) as yellow solid. MS $(M+H)^+$=422.0.

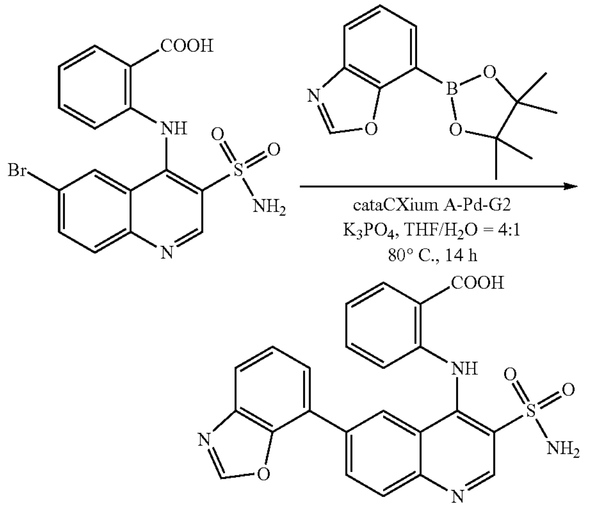

Step 3—Synthesis of 2-[[6-(1,3-benzoxazol-7-yl)-3-sulfamoyl-4-quinolyl]amino]benzoic acid: To a solution of 2-[(6-bromo-3-sulfamoyl-4-quinolyl)amino]benzoic acid (80 mg, 189.46 μmol, 1 eq), $K_3PO_4$ (0.4 M, 947.30 μL, 2 eq), [2-(2-aminophenyl)phenyl]-chloro-palladium; bis(1-adamantyl)-butyl-phosphane (12.67 mg, 18.95 μmol, 0.1 eq) in THF (2 mL) and $H_2O$ (0.5 mL) was added 7-(4,4,5,5-tetramethyl-1,3,2-dioxaborolan-2-yl)-1,3-benzoxazole (55.72 mg, 227.35 μmol, 1.2 eq). The mixture further was degassed and purged with $N_2$ for 5 times, then stirred for 14 h at 80° C. under $N_2$. LCMS showed the reaction was complete. The mixture was concentrated in vacuo. The crude product was purified by prep-HPLC (Waters Xbridge Prep OBD C18 150×40 mm×10 μm column; 15%-45% acetonitrile in a solution of 10 mM NH4HCO3 in water, 8 min gradient) to give 2-[[6-(1,3-benzoxazol-7-yl)-3-sulfamoyl-4-quinolyl]amino]benzoic acid (24.45 mg, 52.50 μmol, 27.71% yield, 98.88% purity) as yellow solid. $^1$H NMR (400 MHz, DMSO-d6+D2O) δ=9.13 (s, 1H), 8.55 (s, 1H), 8.31 (qd, J=2.2, 4.6 Hz, 2H), 8.19-8.16 (m, 1H), 7.97 (dd, J=1.6, 7.8 Hz, 1H), 7.77 (dd, J=1.0, 7.7 Hz, 1H), 7.53-7.47 (m, 1H), 7.45-7.40 (m, 1H), 7.18-7.11 (m, 1H), 7.00-6.91 (m, 1H), 6.56 (d, J=7.7 Hz, 1H). $^1$H NMR (400 MHz, DMSO-d6) δ=9.15 (s, 1H), 8.58 (s, 1H), 8.34-8.27 (m, 2H), 8.18 (d, J=9.3 Hz, 1H), 7.98 (dd, J=1.5, 7.7 Hz, 1H), 7.78 (dd, J=1.1, 7.7 Hz, 1H), 7.51-7.40 (m, 3H), 7.20-7.11 (m, 1H), 6.94 (t, J=7.5 Hz, 1H), 6.56 (d, J=7.7 Hz, 1H). MS $(M+H)^+$=461.1.

Example 35

Preparation of Compound 70A

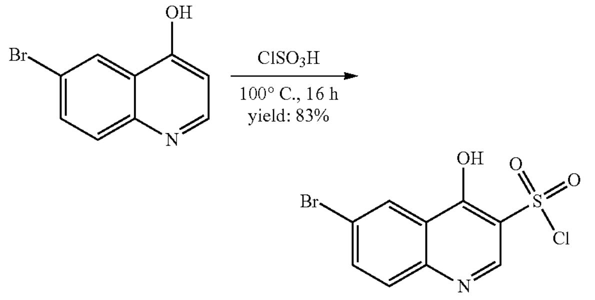

Step 1—Synthesis of 6-bromo-4-hydroxy-quinoline-3-sulfonyl chloride: A solution of 6-bromoquinolin-4-ol (3.5 g, 15.62 mmol, 1 eq) in Chlorosulfonic acid (30 mL) was stirred for 14 h at 100° C. LCMS showed no reactant was remained, two new spots were formed. The mixture was added into ice-water (100 mL) and filtered to 6-bromo-4-hydroxy-quinoline-3-sulfonyl chloride (4.2 g, 13.02 mmol, 83.35% yield) as off-white solid. $^1$H NMR (400 MHz, DMSO-d6) δ=8.89 (s, 1H), 8.38 (d, J=2.0 Hz, 1H), 8.04 (dd, J=2.2, 8.8 Hz, 1H), 7.90 (d, J=8.8 Hz, 1H).

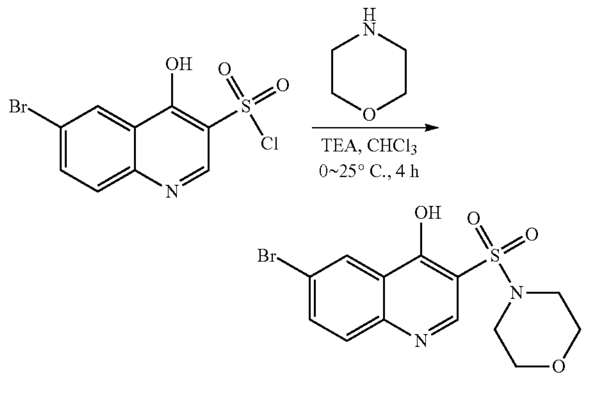

Step 2—Synthesis of 6-bromo-3-morpholinosulfonyl-quinolin-4-ol: To a solution of 6-bromo-4-hydroxy-quinoline-3-sulfonyl chloride (700 mg, 2.17 mmol, 1 eq) in chloroform (0.5 mL) and TEA (658.78 mg, 6.51 mmol, 906.17 μL, 3 eq) was added morpholine (378.12 mg, 4.34 mmol, 381.94 μL, 2 eq) at 0° C. The resulting solution was stirred for 1 h at 0° C. and 3 h at 25° C. LCMS showed the reaction was complete. The suspension was filtered to give filter cake, dried in vacuo to afford 6-bromo-3-morpholino-sulfonyl-quinolin-4-ol (460 mg, 1.23 mmol, 56.79% yield) as off-white solid. $^1$H NMR (400 MHz, DMSO-d6) δ=8.54 (s, 1H), 8.24 (d, J=2.2 Hz, 1H), 7.93 (dd, J=2.4, 8.8 Hz, 1H), 7.68 (d, J=8.8 Hz, 1H), 3.81-3.75 (m, 2H), 3.62-3.56 (m, 2H), 3.20-3.16 (m, 2H), 3.14-3.10 (m, 2H). MS $(M+H)^+$=372.9.

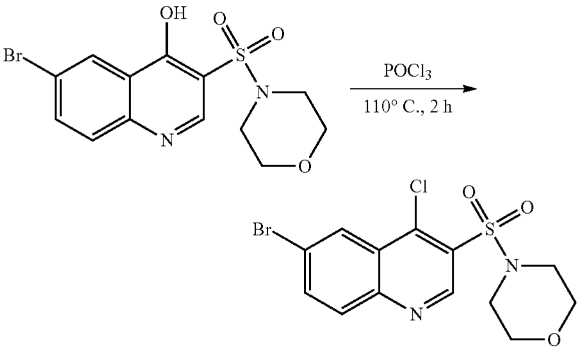

Step 3—Synthesis of 4-[(6-bromo-4-chloro-3-quinolyl)sulfonyl]morpholine: A solution of 6-bromo-3-morpholino-sulfonyl-quinolin-4-ol (330 mg, 884.19 μmol, 1 eq) in $POCl_3$ (15 mL) was stirred for 6 h at 110° C. LCMS showed ~30% reactant was remained. The mixture was stirred for another 4 h at 110° C. LCMS showed the reaction was complete. The solution was concentrated in vacuo, diluted with toluene (2 mL), concentrated in vacuo and dissolved in ethyl acetate (5 mL). The solution was added dropwise into ice-water (5 mL), separated and extracted with ethyl acetate (5 mL×2). Combined organic layers were washed with brine (2 mL), dried over $Na_2SO_4$, filtered and concentrated in vacuo. The crude product was purified by flash column (ISCO 10 g silica, 0~30% ethyl acetate in petroleum ether, gradient over 30 min) to give 4-[(6-bromo-4-chloro-3-quinolyl)sulfonyl]morpholine (190 mg, 485.11 μmol, 54.86% yield) as off-white solid. $^1$H NMR (400 MHz, DMSO-d6) δ=9.24 (s, 1H), 8.60 (d, J=1.8 Hz, 1H), 8.22-8.17 (m, 1H), 8.16-8.12 (m, 1H), 3.67-3.57 (m, 4H), 3.31-3.25 (m, 4H). MS $(M+H)^+$=390.9.

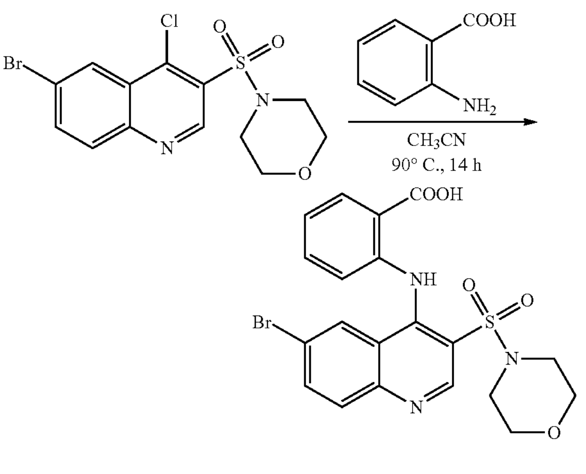

Step 4—Synthesis of 2-[(6-bromo-3-morpholinosulfonyl-4-quinolyl)amino]benzoic acid: A solution of 4-[(6-bromo- 4-chloro-3-quinolyl)sulfonyl]morpholine (180 mg, 459.57 µmol, 1 eq) and 2-aminobenzoic acid (75.63 mg, 551.49 µmol, 1.2 eq) in ACN (5 mL) was stirred for 14 h at 90° C. LCMS showed the reaction was complete. The mixture was concentrated in vacuo. The crude product was purified by prep-HPLC (Nano-micro Kromasil C18 80×25 mm µm column; 35%-60% acetonitrile in an 0.04% HCl solution in water, 7 min gradient) to give 2-[(6-bromo-3-morpholino-sulfonyl-4-quinolyl)amino]benzoic acid (114.5 mg, 232.56 µmol, 50.60% yield, 100% purity) as yellow solid. $^1$H NMR (400 MHz, DMSO-$d_6$) δ=10.45 (br s, 1H), 9.10 (s, 1H), 8.12-7.97 (m, 3H), 7.74 (d, J=2.0 Hz, 1H), 7.42-7.31 (m, 1H), 7.10 (t, J=7.5 Hz, 1H), 6.73 (d, J=8.2 Hz, 1H), 3.54-3.31 (m, 4H), 3.14-2.97 (m, 4H). MS $(M+H)^+$=491.9.

Example 36

Preparation of Compound 78A

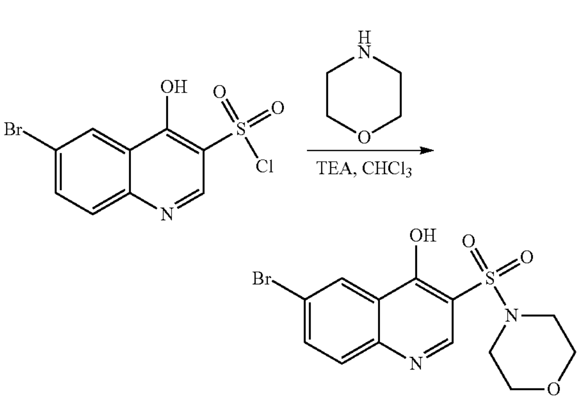

Step 1—Synthesis of 6-bromo-3-morpholinosulfonyl-quinolin-4-ol: A solution of 6-bromo-4-hydroxy-quinoline-3-sulfonyl chloride (2 g, 6.20 mmol, 1 eq) in CHC13 (20 mL) was added morpholine (1.08 g, 12.40 mmol, 1.09 mL, 2 eq) at 0° C., TEA (1.88 g, 18.60 mmol, 2.59 mL, 3 eq) was added dropwise. The mixture was stirred for 1 h at 20° C. LCMS showed the reaction was complete. The suspension was filtered to give filter cake and dried in vacuo. 6-bromo-3-morpholinosulfonyl-quinolin-4-ol (2.7 g, crude) was obtained as off-white solid. MS $(M+H)^+$=372.9.

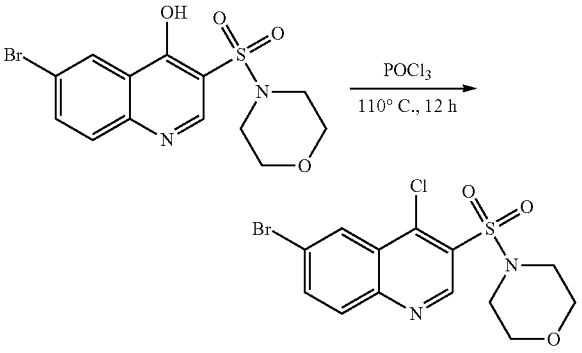

Step 2—Synthesis of 4-[(6-bromo-4-chloro-3-quinolyl) sulfonyl]morpholine: A solution of 6-bromo-3-morpholino-sulfonyl-quinolin-4-ol (2.5 g, 6.70 mmol, 1 eq) in $POCl_3$ (25 mL) was stirred for 12 h at 110° C. LCMS showed desired ms was detected. The reaction mixture was concentrated in vacuo to remove $POCl_3$. Ethyl acetate (20 mL) was added dropwise into the residue. The solution was added dropwise into above solution, separated and extracted with ethyl acetate (20 mL×2). Combined organic layers were dried over $Na_2SO_4$ and concentrated in vacuo. The crude product was purified by flash column (ISCO 20 g silica, 0~20% ethyl acetate in petroleum ether, gradient over 30 min) to give 4-[(6-bromo-4-chloro-3-quinolyl)sulfonyl]morpholine (1.2 g, 3.06 mmol, 45.74% yield) as yellow solid. $^1$H NMR (400 MHz, DMSO-d6) δ 9.20 (s, 1H), 8.57 (s, 1H), 8.25-8.09 (m, 2H), 3.59 (br s, 4H), 3.25 (br s, 4H).

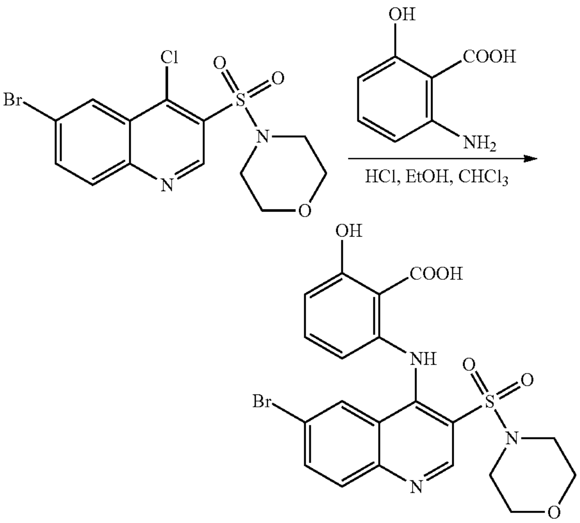

Step 3—Synthesis of 2-[(6-bromo-3-morpholinosulfonyl-4-quinolyl)amino]-6-hydroxy-benzoic acid: A solution of 4-[(6-bromo-4-chloro-3-quinolyl)sulfonyl]morpholine (100 mg, 255.32 µmol, 1 eq) and 2-amino-6-hydroxybenzoic acid (46.92 mg, 306.38 µmol, 1.2 eq) in EtOH (5 mL) and $CHCl_3$ (1 mL) was stirred for 0.5 h at 70° C. LCMS showed the reaction was complete. The mixture was concentrated in vacuo. The crude product was purified by prep-HPLC (Phenomenex luna C18 80×40 mm×3 µm column; 27%-55% acetonitrile in a 0.04% HCl in water, 7 min gradient) to give 2-[(6-bromo-3-morpholinosulfonyl-4-quinolyl)amino]-6-hydroxy-benzoic acid (9.4 mg, 17.38 µmol, 6.81% yield, 94.00% purity) as pale yellow solid. $^1$H NMR (400 MHz, DMSO-d6) δ 10.48-10.05 (m, 1H), 9.04 (s, 1H), 8.03 (s, 2H), 7.70 (s, 1H), 7.21 (t, J=8.1 Hz, 1H), 6.74 (d, J=8.0 Hz, 1H), 6.38 (d, J=8.0 Hz, 1H), 3.60-3.46 (m, 4H), 3.19-3.07 (m, 4H). MS $(M+H)^+$=508.0.

Example 37

Preparation of Compounds 78A-INT and 78A-BR

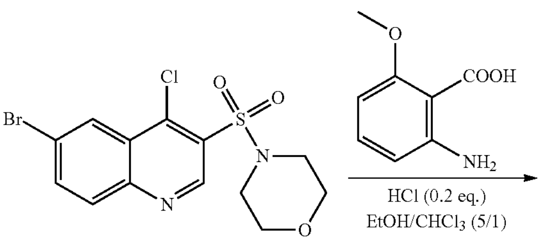

-continued

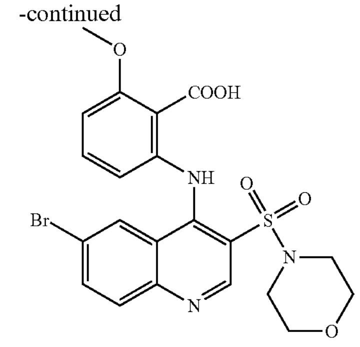

Step 1—Synthesis of 2-[(6-bromo-3-morpholinosulfonyl-4-quinolyl)amino]-6-methoxy-benzoic acid: A solution of 4-[(6-bromo-4-chloro-3-quinolyl)sulfonyl]morpholine (100 mg, 255.32 μmol, 1 eq), HCl (5.17 mg, 51.06 μmol, 5.07 μL, 36% purity, 0.2 eq) and 2-amino-6-methoxy-benzoic acid (51.22 mg, 306.38 μmol, 1.2 eq) in EtOH (5 mL) and $CHCl_3$ (1 mL) was stirred for 0.5 h at 70° C. LCMS showed the reaction was complete. The mixture was concentrated in vacuo and dissolved in DMSO (1 mL). The crude product was purified by prep-HPLC (Phenomenex luna C18 80×40 mm×3 μm column; 28%-55% acetonitrile in an 0.04% HCl in water, 7 min gradient) to give 2-[(6-bromo-3-morpholinosulfonyl-4-quinolyl)amino]-6-methoxy-benzoic acid (60 mg, 114.86 μmol, 44.99% yield, 100% purity) as yellow solid. $^1$H NMR (400 MHz, DMSO-$d_6$) δ 8.98 (s, 1H), 8.02-7.98 (m, 1H), 7.96-7.91 (m, 1H), 7.73 (s, 1H), 7.27 (t, J=8.3 Hz, 1H), 6.94 (d, J=8.2 Hz, 1H), 6.43 (d, J=8.2 Hz, 1H), 3.89 (s, 3H), 3.54 (br s, 4H), 3.14 (br s, 4H). MS $(M+H)^+$=522.0.

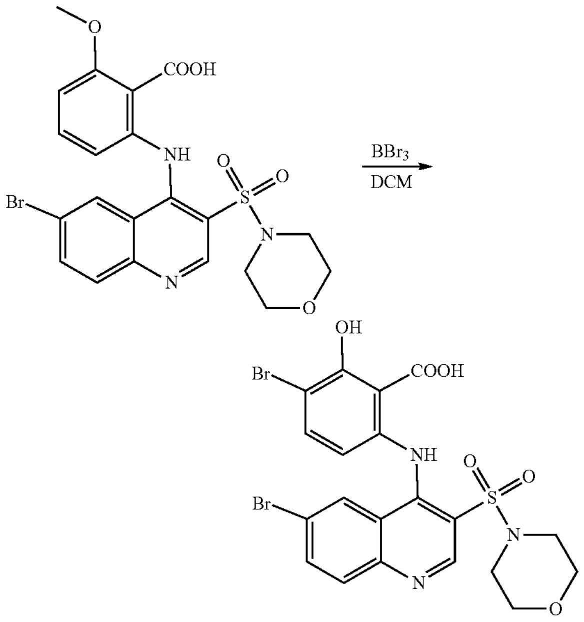

Step 2—Synthesis of 3-bromo-6-[(6-bromo-3-morpholinosulfonyl-4-quinolyl)amino]-2-hydroxy-benzoic acid: To a solution of 2-[(6-bromo-3-morpholinosulfonyl-4-quinolyl)amino]-6-methoxy-benzoic acid (60 mg, 114.86 μmol, 1 eq) in DCM (0.5 mL) at −78° C., $BBr_3$ (86.33 mg, 344.58 μmol, 33.20 μL, 3 eq) was added dropwise. The reaction mixture was stirred for 3 h at 20° C. under $N_2$. LCMS showed the desired ms was detected. The mixture was concentrated in vacuo. The crude product was purified by prep-HPLC (Waters Xbridge Prep OBD C18 150×40 mm×10 μm column; 15%-45% acetonitrile in an 10 mM $NH_4HCO_3$ in water, 8 min gradient) to give 3-bromo-6-[(6-bromo-3-morpholinosulfonyl-4-quinolyl)amino]-2-hydroxy-benzoic acid (5.7 mg, 9.59 μmol, 8.35% yield, 98.76% purity) as reddish brown solid. $^1$H NMR (400 MHz, DMSO-$d_6$) δ 11.37 (br s, 1H), 9.12 (s, 1H), 8.06 (d, J=0.9 Hz, 2H), 7.89 (s, 1H), 7.42 (d, J=8.9 Hz, 1H), 6.09 (d, J=8.8 Hz, 1H), 3.62-3.54 (m, 2H), 3.53-3.46 (m, 2H), 3.22-3.08 (m, 4H). MS $(M+H)^+$=585.9.

Example 38

Preparation of Compound 79A-INT and 79A

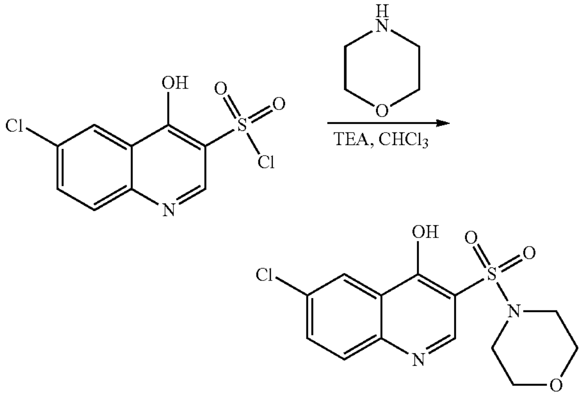

Step 1—Synthesis of 6-chloro-3-morpholinosulfonyl-quinolin-4-ol: To a solution of 6-chloro-4-hydroxy-quinoline-3-sulfonyl chloride (650 mg, 2.34 mmol, 1 eq) in $CHCl_3$ (7 mL) was added morpholine (407.23 mg, 4.67 mmol, 411.35 μL, 2 eq) and TEA (709.50 mg, 7.01 mmol, 975.93 μL, 3 eq) at 0° C. . The mixture was stirred for 1 h at 20° C. LCMS showed the reaction was complete. The suspension was filtered to give filter cake, dried in vacuo to give 6-chloro-3-morpholinosulfonyl-quinolin-4-ol (930 mg, crude) as off-white solid, which was used in next step directly. $^1$H NMR (400 MHz, DMSO-$d_6$) δ 8.52 (s, 1H), 8.16-8.05 (m, 1H), 7.86-7.76 (m, 2H), 3.19 (br s, 4H), 3.11-3.02 (m, 4H).

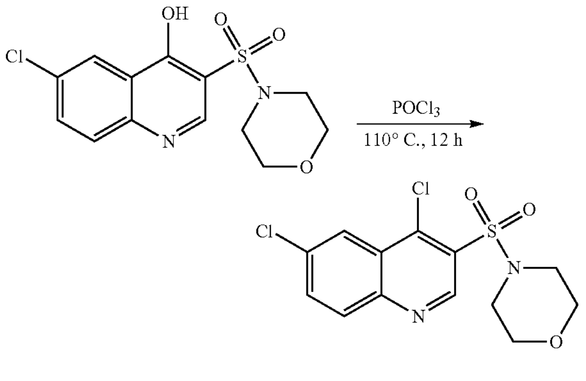

Step 2—Synthesis of 4-[(4,6-dichloro-3-quinolyl)sulfonyl]morpholine: A solution of 6-chloro-3-morpholinosulfonyl-quinolin-4-ol (800 mg, 2.43 mmol, 1 eq) in $POCl_3$ (8 mL) was stirred for 14 h at 110° C. LCMS showed desired ms was detected. The reaction mixture was concentrated in vacuo to remove excess $POCl_3$. Ethyl acetate (10 mL) was added dropwise into the residue. The solution was added into ice-water (10 mL), separated and extracted with ethyl acetate (10 mL×2). Combined organic layers were dried over $Na_2SO_4$ and concentrated in vacuo. The crude product was purified by flash column (ISCO 10 g silica, 0~30% ethyl acetate in petroleum ether, gradient over 30 min) to give 4-[(4,6-dichloro-3-quinolyl)sulfonyl]morpholine (380 mg, 1.09 mmol, 44.98% yield) as off-white solid. MS $(M+H)^+$=347.0.

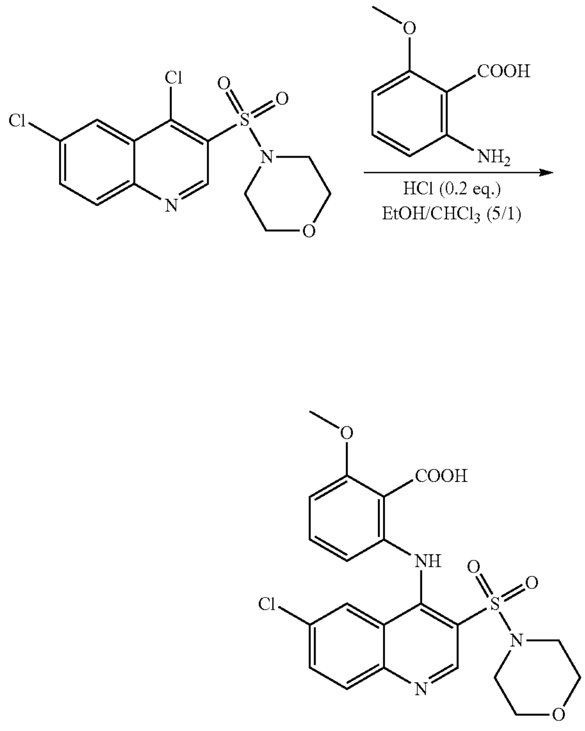

Step 3—Synthesis of 2-[(6-chloro-3-morpholinosulfonyl-4-quinolyl)amino]-6-methoxy-benzoic acid: A solution of 4-[(4,6-dichloro-3-quinolyl)sulfonyl]morpholine (120 mg, 345.61 μmol, 1 eq), HCl (7.00 mg, 69.12 μmol, 6.86 μL, 36% purity, 0.2 eq) and 2-amino-6-methoxy-benzoic acid (69.33 mg, 414.73 μmol, 1.2 eq) in EtOH (7.5 mL) and $CHCl_3$ (1.5 mL) was stirred for 0.5 h at 70° C. LCMS showed the reaction was complete. The mixture was concentrated in vacuo. The crude product was purified by prep-HPLC (Phenomenex luna C18 80×40 mm×3 μm column; 30%-55% acetonitrile in an 0.04% HCl in water, 7 min gradient) to give 2-[(6-chloro-3-morpholinosulfonyl-4-quinolyl)amino]-6-methoxy-benzoic acid (50.6 mg, 98.11 μmol, 28.39% yield, 99.73% purity, HCl) as yellow solid. 5.6 mg desired product was shipped out. $^1H$ NMR (400 MHz, DMSO-$d_6$) δ 9.16-8.89 (m, 2H), 8.14-8.01 (m, 1H), 7.85 (br d, J=8.6 Hz, 1H), 7.53 (s, 1H), 7.24 (t, J=8.2 Hz, 1H), 6.89 (br d, J=8.6 Hz, 1H), 6.39 (d, J=8.1 Hz, 1H), 3.86 (s, 3H), 3.59-3.42 (m, 4H), 3.20-2.95 (m, 4H). MS $(M+H)^+$=478.0.

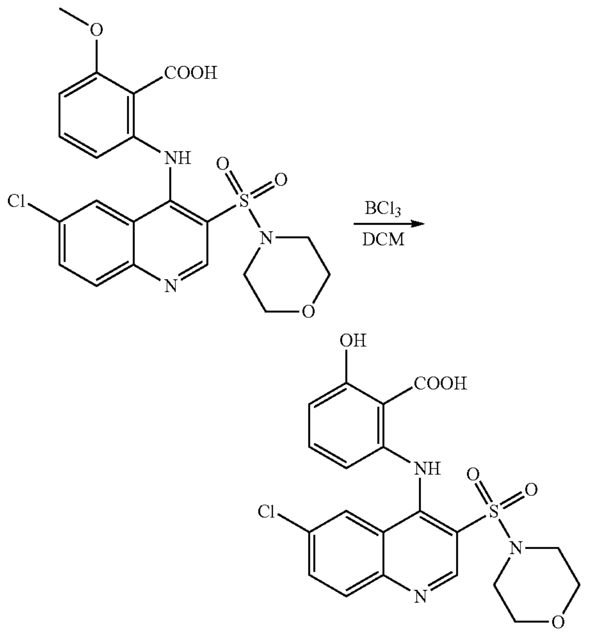

Step 4—Synthesis of 2-[(6-chloro-3-morpholinosulfonyl-4-quinolyl)amino]-6-hydroxy-benzoic acid: To a solution of 2-[(6-chloro-3-morpholinosulfonyl-4-quinolyl)amino]-6-methoxy-benzoic acid (50 mg, 104.62 μmol, 1 eq) in DCM (1 mL) at 0° C., $BCl_3$ (1 M, 418.48 μL, 4 eq) was added dropwise. The reaction mixture was stirred for 2 h at 25° C. under $N_2$. LCMS showed the reaction was complete. The mixture was concentrated in vacuo. The crude product was purified by prep-HPLC (Waters Xbridge BEH C18 100×25 mm×5 μm column; 20%-44% acetonitrile in an 10 mM $NH_4HCO_3$ in water, 10 min gradient). Twice purification: The crude product was purified by prep-HPLC (Phenomenex luna C18 80×40 mm×4tm column; 10%-70% acetonitrile in an a 0.04% HCl in water, 7 min gradient) to give 2-[(6-chloro-3-morpholinosulfonyl-4-quinolyl)amino]-6-hydroxy-benzoic acid (12.9 mg, 27.45 μmol, 26.24% yield, 98.71% purity) as brown solid. $^1H$ NMR (400 MHz, DMSO-$d_6$) δ 10.23-10.07 (m, 1H), 9.03 (s, 1H), 8.08 (d, J=9.0 Hz, 1H), 7.89 (dd, J=2.2, 9.0 Hz, 1H), 7.58 (d, J=2.2 Hz, 1H), 7.17 (t, J=8.2 Hz, 1H), 6.64 (d, J=8.6 Hz, 1H), 6.22 (d, J=7.9 Hz, 1H), 3.62-3.50 (m, 2H), 3.48-3.38 (m, 2H), 3.18-2.99 (m, 4H). MS $(M+H)^+$=464.1.

Example 39

Preparation of Compound 80A

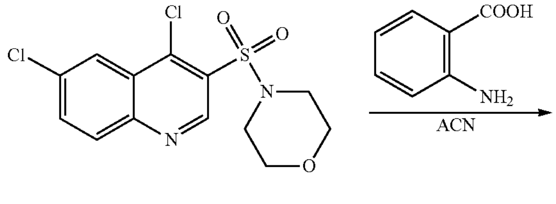

-continued

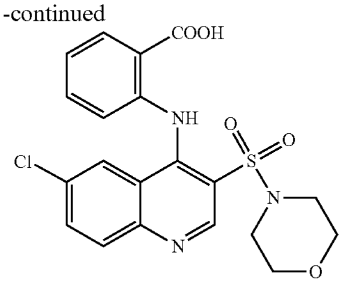

Synthesis of 2-[6-chloro-3-morpholinosulfonyl-4-quinolyl)amino]benzoic acid: A solution of 4-[(4,6-dichloro-3-quinolyl)sulfonyl]morpholine (100 mg, 288.00 μmol, 1 eq) and 2-aminobenzoic acid (47.39 mg, 345.61 μmol, 1.2 eq) in ACN (1 mL) was stirred for 4 h at 90° C. LCMS showed the reaction was complete. TEA (0.1 mL) was added into the above mixture and filtered to give filtrate. The crude product was purified by prep-HPLC (Phenomenex Gemini-NX C18 75×30 mm×μm column; 10%-40% acetonitrile in a 10 mM $NH_4HCO_3$ in water, 8 min gradient) to give 2-[(6-chloro-3-morpholinosulfonyl-4-quinolyl)amino]benzoic acid (38.3 mg, 84.67 μmol, 29.40% yield, 99.01% purity) as pale yellow solid. $^1H$ NMR (400 MHz, DMSO-d6) δ 10.55 (br s, 1H), 9.11 (s, 1H), 8.17 (d, J=9.0 Hz, 1H), 8.02 (dd, J=1.4, 7.9 Hz, 1H), 7.94 (dd, J=2.3, 9.1 Hz, 1H), 7.57 (d, J=2.3 Hz, 1H), 7.45-7.31 (m, 1H), 7.14 (t, J=7.4 Hz, 1H), 6.81 (d, J=8.3 Hz, 1H), 3.54-3.47 (m, 2H), 3.44-3.34 (m, 2H), 3.15-3.01 (m, 4H). MS $(M+H)^+$=448.1.

Example 40

Preparation of Compound 81A-INT and 81A

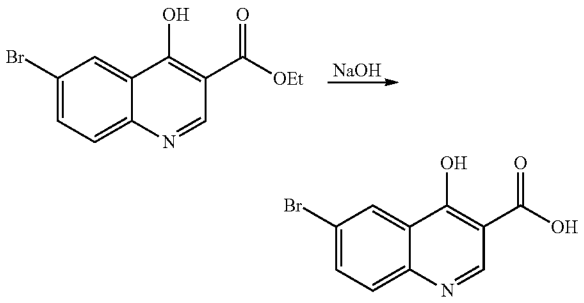

Step 1—Synthesis of 6-bromo-4-hydroxy-quinoline-3-carboxylic acid: A solution of ethyl 6-bromo-4-hydroxy-quinoline-3-carboxylate (3 g, 10.13 mmol, 1 eq) in 2N NaOH (30 mL) was stirred at 100° C. for 3 h. LCMS showed the starting material was consumed completely and desired MS was detected. The mixture was acidified with 1M HCl to pH=3, filtered and to give 6-bromo-4-hydroxy-quinoline-3-carboxylic acid (2.7 g, 10.07 mmol, 99.42% yield) was obtained as white solid. MS $(M+H)^+$=269.9.

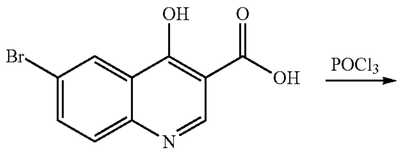

-continued

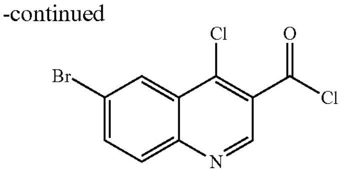

Step 2—Synthesis of 6-bromo-4-chloro-quinoline-3-carbonyl chloride: A solution of 6-bromo-4-hydroxy-quinoline-3-carboxylic acid (2.7 g, 10.07 mmol, 1 eq) in $POCl_3$ (30 mL) was stirred at 100° C. for 1 h. LCMS showed the reaction was complete. LCMS showed the starting material was consumed completely and desired MS was detected. The mixture was cooled to room temperature and concentrated in vacuo. The residual was dissolved in toluene (10 mL), concentrated in vacuo to give 6-bromo-4-chloro-quinoline-3-carbonyl chloride (3 g, crude) as brown gum.

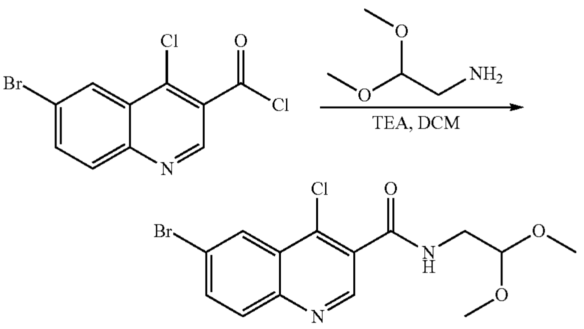

Step 3—Synthesis of 6-bromo-4-chloro-N-(2,2-dimethoxyethyl)quinoline-3-carboxamide: A solution of 6-bromo-4-chloro-quinoline-3-carbonyl chloride (3 g, 9.84 mmol, 1 eq) in DCM (25 mL) was added 2,2-dimethoxyethanamine (1.03 g, 9.84 mmol, 1.07 mL, 1 eq) and TEA (2.99 g, 29.51 mmol, 4.11 mL, 3 eq) at 0° C., the mixture was stirred at 15° C. for 10 h. LCMS showed the starting material was consumed completely and desired MS was detected. Water (6 mL) was added into the above solution, separated, extracted with DCM (10 mL×2). The combined organic layers were dried over sodium sulfate, concentrated in vacuo to get crude product. The crude product was purified by flash column (ISCO 40 g silica, 0~70% ethyl acetate in petroleum ether, gradient over 30 min) to give 6-bromo-4-chloro-N-(2,2-dimethoxyethyl)quinoline-3-carboxamide (2.6 g, 6.96 mmol, 70.74% yield) as white solid. MS $(M+H)^+$=373.1.

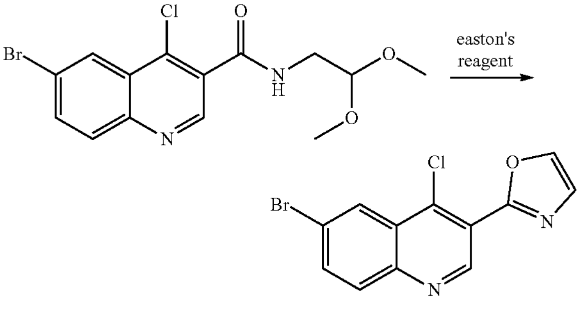

Step 4—Synthesis of 2-(6-bromo-4-chloro-3-quinolyl) Oxazole: A solution of 6-bromo-4-chloro-N-(2,2-dimethoxy ethyl)quinoline-3-carboxamide (100 mg, 267.65 μml, 1 eq) in eaton's reagent (267.65 μmol, 1 mL) was stirred at 80° C. for 3 h. LCMS showed the reaction was complete. The mixture was added dropwise into cold water (5 mL) filtered to give filtrate. The filtrate was extracted with EtOAc (10 mL×3), dried over $Na_2SO_4$ and concentrated in vacuum to get crude product. The residue was purified by flash column (ISCO 25 g silica, 0-30% Ethyl acetate in Petroleum ether, gradient over 30 min) to give 2-(6-bromo-4-chloro-3-quinolyl)oxazole (56 mg, 32.31 μmol, 12.07% yield) as white solid. $^1H$ NMR (400 MHz, chloroform-d) δ 9.48 (s, 1H), 8.61 (d, J=2.0 Hz, 1H), 8.04 (d, J=9.0 Hz, 1H), 7.94-7.88 (m, 2H), 7.45 (d, J=0.7 Hz, 1H). MS $(M+H)^+$=309.2.

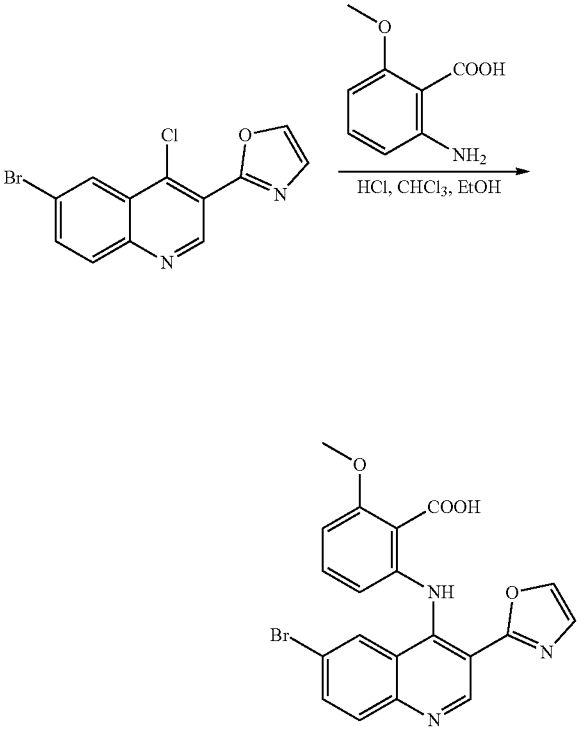

Step 5—Synthesis of 2-[(6-bromo-3-oxazol-2-yl-4-quinolyl)amino]-6-methoxy-benzoic acid: A solution of 2-amino-6-methoxy-benzoic acid (32.40 mg, 193.83 μmol, 1.2 eq), HCl (3.27 mg, 32.31 μmol, 3.21 μL, 36% purity, 0.2 eq) and 2-(6-bromo-4-chloro-3-quinolyl)oxazole (50 mg, 161.53 μmol, 1 eq) in a mixture of $CHCl_3$ (0.3 mL) and EtOH (1.5 mL) was stirred for 0.5 h at 70° C. LCMS showed desired ms was detected. The mixture was concentrated in vacuo. The crude product was purified by prep-HPLC (Phenomenex luna C18 80×40 mm×3 μm column; 22%-48% acetonitrile in an 0.04% HCl in water, 7 min gradient) to give 2-[(6-bromo-3-oxazol-2-yl-4-quinolyl)amino]-6-methoxy-benzoic acid (24 mg, 50.22 μmol, 31.09% yield, 99.76% purity, HCl) as pale yellow solid. 3.0 mg desired product was shipped out. $^1H$ NMR (400 MHz, DMSO-$d_6$) δ 11.92-11.74 (m, 1H), 9.42 (s, 1H), 8.47 (s, 1H), 8.19-7.99 (m, 2H), 7.71 (d, J=1.8 Hz, 1H), 7.63 (s, 1H), 7.49-7.36 (m, 1H), 7.17 (d, J=8.3 Hz, 1H), 6.80 (d, J=7.9 Hz, 1H), 3.90 (s, 3H). MS $(M+H)^+$=440.0.

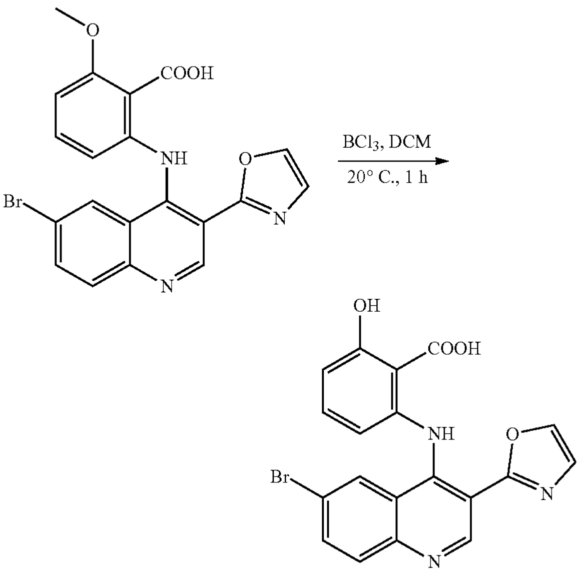

Step 6—Synthesis of 2-[(6-bromo-3-oxazol-2-yl-4-quinolyl)amino]-6-hydroxy-benzoic acid: To a solution of 2-[(6-bromo-3-oxazol-2-yl-4-quinolyl)amino]-6-methoxy-benzoic acid (14 mg, 31.80 μmol, 1 eq) in DCM (0.5 mL) at 0° C., $BCl_3$ (1 M, 127.20 μL, 4 eq) was added dropwise. The reaction mixture was stirred for 2 h at 25° C. under $N_2$. LCMS showed the reaction was complete. The mixture was concentrated in vacuo. The crude product was purified by prep-HPLC (Phenomenex luna C18 80×40 mm×3 μm column; 15%-55% acetonitrile in an 0.04% HCl in water, 7 min gradient) to give 2-[(6-bromo-3-oxazol-2-yl-4-quinolyl) amino]-6-hydroxy-benzoic acid (6.8 mg, 15.45 μmol, 48.58% yield, 96.83% purity) as brown solid. $^1H$ NMR (400 MHz, DMSO-$d_6$) δ 12.11 (br s, 1H), 9.34 (s, 1H), 8.39 (s, 1H), 8.19-7.99 (m, 2H), 7.84 (d, J=1.5 Hz, 1H), 7.57 (s, 1H), 7.28 (t, J=8.1 Hz, 1H), 6.95 (d, J=8.4 Hz, 1H), 6.64 (d, J=7.9 Hz, 1H). MS $(M+H)^+$=425.9.

Example 41

Preparation of Compound 82A

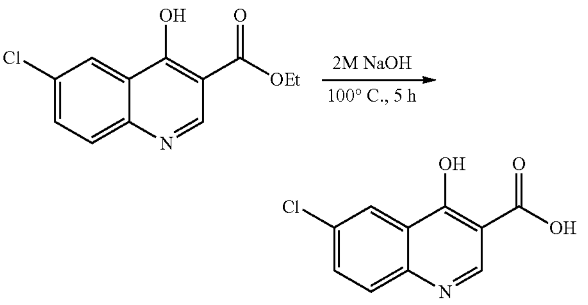

Step 1—Synthesis of 6-chloro-4-hydroxy-quinoline-3-carboxylic acid: A suspension of ethyl 6-chloro-4-hydroxy-quinoline-3-carboxylate (950 mg, 3.77 mmol, 1 eq) in NaOH (3 mL) was stirred for 5 h at 100° C. LCMS showed the reaction was complete. The mixture was acidified with 1 N HCl to pH=3. The resulting precipitate was collected by filtration. 6-chloro-4-hydroxy-quinoline-3-carboxylic acid (890 mg, crude) was obtained as off-white solid. MS $(M+H)^+=224.0$. $^1H$ NMR (400 MHz, DMSO-$d_6$) δ 8.85 (s, 1H), 8.18 (s, 1H), 7.91 (s, 2H).

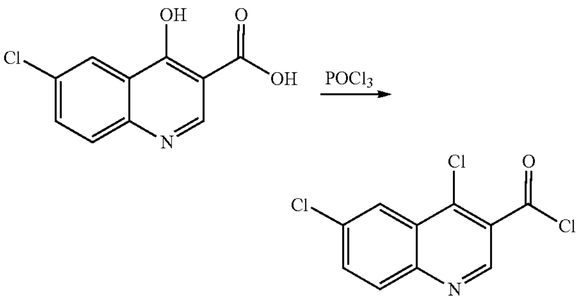

Step 2—Synthesis of 4,6-dichloroquinoline-3-carbonyl chloride: A solution of 6-chloro-4-hydroxy-quinoline-3-carboxylic acid (890 mg, 3.98 mmol, 1 eq) in $POCl_3$ (10 mL) was stirred for 2 h at 100° C. LCMS showed the reaction was complete. The reaction mixture was concentrated to give 4,6-dichloroquinoline-3-carbonyl chloride (1.2 g, crude) as brown gum.

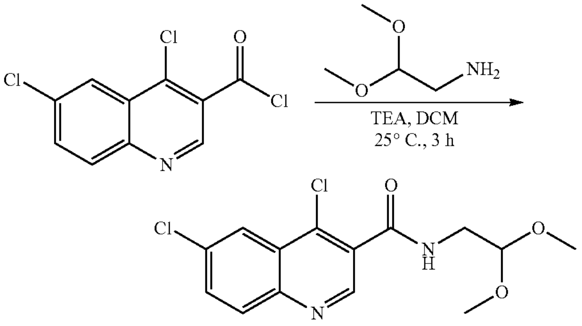

Step 3—Synthesis of 4,6-dichloro-N-(2,2-dimethoxyethyl)quinoline-3-carboxamide: To a solution of 4,6-dichloroquinoline-3-carbonyl chloride (1 g, 3.84 mmol, 1 eq) and TEA (1.17 g, 11.52 mmol, 1.60 mL, 3eq) in DCM (12 mL) was added dropwise 2,2-dimethoxyethanamine (403.58 mg, 3.84 mmol, 418.22 μL, 1 eq), then stirred for 3 h at 25° C. LCMS showed the reaction was complete. Water (20 ml) was added dropwise into the resulting mixture, separated, extracted with DCM (10 mL×2). The combined organic phase was washed with water (5 mL), dried with anhydrous $Na_2SO_4$, concentrated in vacuum to dryness. The crude product was purified by flash column (ISCO 20 g silica, 0~100% ethyl acetate in petroleum ether, gradient over 30 min) to give 4,6-dichloro-N-(2,2-dimethoxyethyl)quinoline-3-carboxamide (780 mg, 2.37 mmol, 61.73% yield) as off-white solid. MS $(M+H)^+=329.0$.

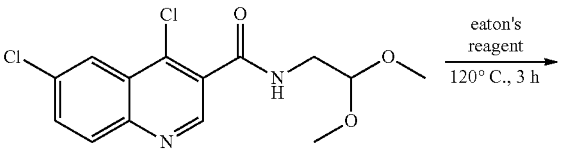

-continued

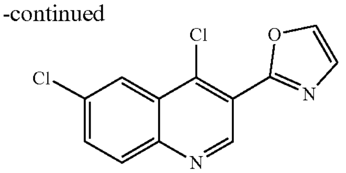

Step 4—Synthesis of 2-(4,6-dichloro-3-quinolyl)Oxazole: A solution of 4,6-dichloro-N-(2,2-dimethoxyethyl)quinoline-3-carboxamide (780 mg, 2.37 mmol, 1 eq) and EATON'S REAGENT (15.23 g, 63.98 mmol, 10.02 mL, 27 eq) was stirred for 3 h at 120° C. TLC (Petroleum ether: Ethyl acetate=3:1, $R_f$=0.69) showed the reaction was complete. The reaction mixture was added dropwise into ice-water (10 mL), followed acetate (20 mL) and separated. The aqueous layer was extracted with acetate (20 mL×2). Combined organic layers were washed with water (5 ml), dried over $Na_2SO_4$ and concentrated in vacuo. The crude product was purified by flash column (ISCO 20 g silica, 0~20% ethyl acetate in petroleum ether, gradient over 30 min) to give 2-(4,6-dichloro-3-quinolyl)oxazole (80 mg, 301.78 μmol, 12.74% yield) as pale solid. $^1H$ NMR (400 MHz, DMSO-$d_6$) δ 9.42 (s, 1H), 8.50 (s, 1H), 8.40 (d, J=2.1 Hz, 1H), 8.19 (d, J=8.9 Hz, 1H), 7.99 (dd, J=2.2, 8.9 Hz, 1H), 7.63 (s, 1H).

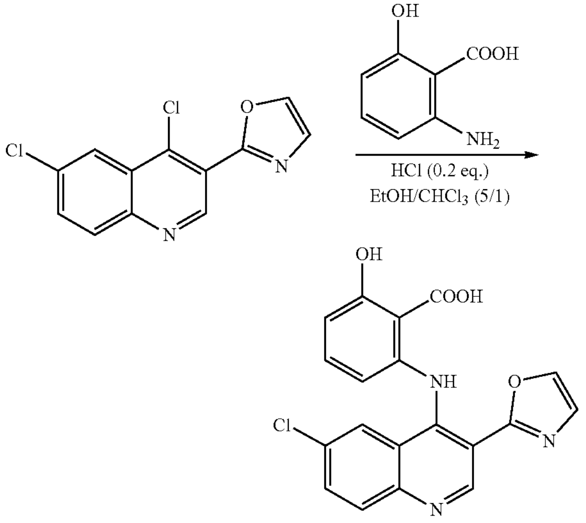

Step 5—Synthesis of 2-[(6-chloro-3-oxazol-2-yl-4-quinolyl)amino]-6-hydroxy-benzoic acid: A solution of 2-amino-6-hydroxy-benzoic acid (20.80 mg, 135.80 μmol, 1.2 eq), HCl (2.29 mg, 22.63 μmol, 2.25 μL, 36% purity, 0.2 eq) and 2-(4,6-dichloro-3-quinolyl)oxazole (30 mg, 113.17 μmol, 1 eq) in a mixture of $CHCl_3$ (0.3 mL) and EtOH (1.5 mL) was stirred for 0.5 h at 70° C. LCMS showed desired ms was detected. The mixture was concentrated in vacuo. The crude product was purified by prep-HPLC (Phenomenex luna C18 80×40 mm×3 μm column; 22%-48% acetonitrile in an a 0.04% HCl solution in water, 7 min gradient) to give 2-[(6-chloro-3-oxazol-2-yl-4-quinolyl)amino]-6-hydroxy-benzoic acid (6.4 mg, 16.07 μmol, 14.20% yield, 95.83% purity) as reddish brown solid. $^1H$ NMR (400 MHz, DMSO-$d_6$) δ 12.17-11.91 (m, 1H), 9.35 (s, 1H), 8.39 (s, 1H), 8.16 (d, J=9.0 Hz, 1H), 7.96 (dd, J=1.8, 8.9 Hz, 1H), 7.69 (d, J=1.8 Hz, 1H), 7.57 (s, 1H), 7.25 (t, J=8.1 Hz, 1H), 6.90 (d, J=8.3 Hz, 1H), 6.58 (d, J=7.9 Hz, 1H). MS $(M+H)^+=382.0$.

Example 42

Preparation of Compound 83A-OMe

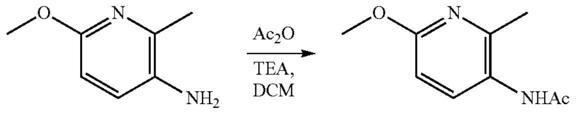

Step 1—Synthesis of N-(6-methoxy-2-methyl-3-pyridyl) acetamide: To a solution of 6-methoxy-2-methyl-pyridin-3-amine (900 mg, 6.51 mmol, 900.00 μL, 1 eq) and TEA (1.98 g, 19.54 mmol, 2.72 mL, 3 eq) in DCM (10 mL) was added acetyl acetate (997.49 mg, 9.77 mmol, 915.12 μL, 1.5 eq) at 0° C., then stirred for 1 h at 20° C. TLC (Petroleum ether:Ethyl acetate=1:1, $R_f$=0.17) showed the reaction was complete. The mixture was concentrated in vacuo. The crude product was purified by flash column (ISCO 20 g silica, 0~60% ethyl acetate in petroleum ether, gradient over 30 min) to give N-(6-methoxy-2-methyl-3-pyridyl)acetamide (1 g, 5.55 mmol, 85.19% yield) as off-white solid.

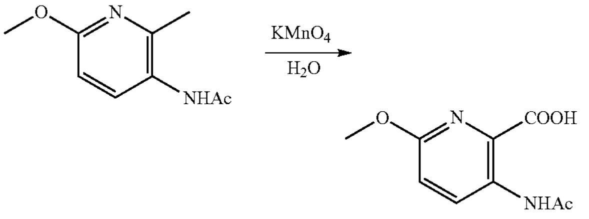

Step 2—Synthesis of 3-acetamido-6-methoxy-pyridine-2-carboxylic acid: To a suspension of N-(6-methoxy-2-methyl-3-pyridyl)acetamide (1 g, 5.55 mmol, 1 eq) in $H_2O$ (10 mL) was added $KMnO_4$ (3.51 g, 22.20 mmol, 4 eq) at 100° C., then stirred for 12 h at 100° C. LCMS showed the reaction was complete. The suspension was filtered to give filtrate, then acidified with 1M HCl to PH=3 and filtered to give 3-acetamido-6-methoxy-pyridine-2-carboxylic acid (290 mg, 1.38 mmol, 24.86% yield) as white solid. MS $(M+H)^+$=211.1

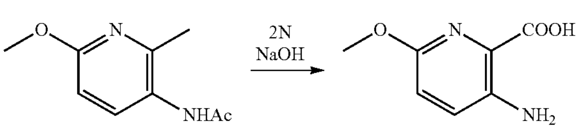

Step 3—Synthesis of 3-amino-6-methoxy-pyridine-2-carboxylic acid: A solution of 3-acetamido-6-methoxy-pyridine-2-carboxylic acid (270 mg, 1.28 mmol, 1 eq) in NaOH (2M, 2 mL) was stirred for 1 h at 100° C. LCMS showed the reaction was complete. The mixture was concentrated in vacuo. The crude product was purified by prep-HPLC (Kromasil C18 250×50 mm×10 μm column; 1%-20% acetonitrile in an 10 Mm $NH_4HCO_3$ in water, 10 min gradient) to give 3-amino-6-methoxy-pyridine-2-carboxylic acid (120 mg, 713.65 μmol, 55.56% yield) as pink solid. MS $(M+H)^+$=169.1.

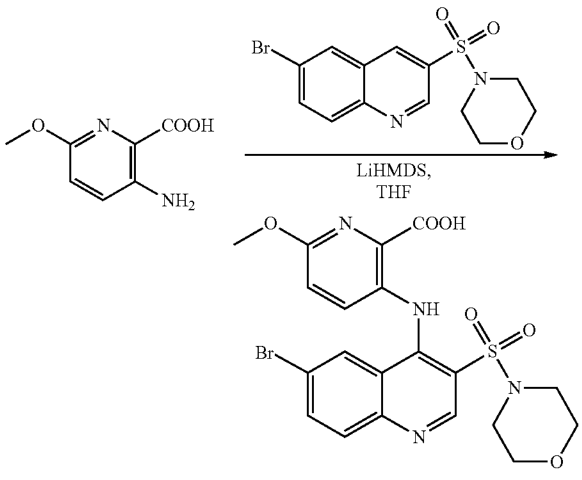

Step 4—Synthesis of 2 3-[(6-bromo-3-morpholinosulfonyl-4-quinolyl)amino]-6-methoxy-pyridine-2-carboxylic acid: A solution of 3-amino-6-methoxy-pyridine-2-carboxylic acid (20 mg, 118.94 μmol, 1 eq) and LiHMDS (1 M, 237.88 μL, 2 eq) in THF (1 mL) was stirred for 0.5 h at −60° C. under $N_2$, followed addition 4-[(6-bromo-4-chloro-3-quinolyl)sulfonyl]morpholine (46.59 mg, 118.94 μmol, 1 eq), then stirred for another 5 h at 20° C. LCMS showed desired ms was detected, the reaction was complete. The mixture was added into ice-water (5 mL) and concentrated in vacuo. The crude product was purified by prep-HPLC (Phenomenex luna C18 80×40 mm×3 μm column; 35%-51% acetonitrile in a 0.04% HCl in water, 7 min gradient) to give 3-[(6-bromo-3-morpholinosulfonyl-4-quinolyl)amino]-6-methoxy-pyridine-2-carboxylic acid (2.6 mg, 4.62 μmol, 3.89% yield, 99.52% purity, HCl) as yellow solid. $^1H$ NMR (400 MHz, DMSO-d6) δ 10.48-10.05 (m, 1H), 9.04 (s, 1H), 8.03 (s, 2H), 7.70 (s, 1H), 7.21 (t, J=8.1 Hz, 1H), 6.74 (d, J=8.0 Hz, 1H), 3.35 (s, 3H), 3.60-3.46 (m, 4H), 3.19-3.07 (m, 4H). MS $(M+H)^+$=523.0.

Example 43

Preparation of Compounds 85A and 85A-BP

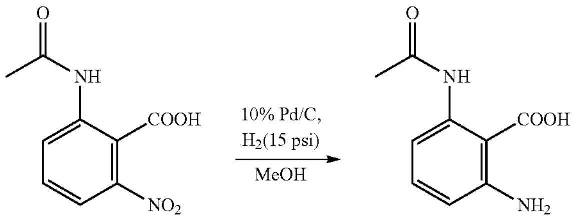 [SMILES: "MeOH" ; CC(=O)Nc1cccc([N+](=O)[O-])c1C(=O)O ; CC(=O)Nc1cccc(N)c1C(=O)O]

Step 1—Synthesis of 2-acetamido-6-amino-benzoic acid: A suspension of 2-acetamido-6-nitro-benzoic acid (320 mg, 1.43 mmol, 1 eq) and 10% Pd/C (30 mg) in MeOH (5 mL) was stirred for 12 h at 20° C. under 15 psi $H_2$. LCMS showed desired ms was detected and no reactant 1 was remained. The suspension was filtered to give filtrate, concentrated in vacuo to give 2-acetamido-6-amino-benzoic acid (260 mg, crude) as pale brown solid. MS $(M+H)^+$=195.1.

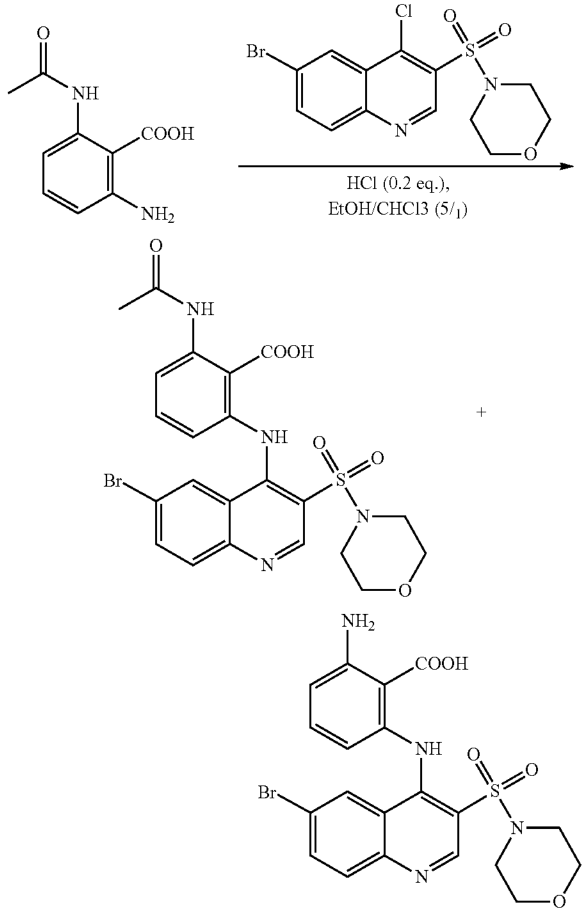

Step 2—Synthesis of 2-acetamido-6-[(6-bromo-3-morpholinosulfonyl-4-quinolyl)amino]benzoic acid (85A) and 2-amino-6-[(6-bromo-3-morpholinosulfonyl-4-quinolyl) amino]benzoic acid (85A-BP): A solution of 4-[(6-bromo-4-chloro-3-quinolyl)sulfonyl]morpholine (100 mg, 255.32 μmol, 1 eq), HCl (5.17 mg, 51.06 μmol, 5.07 μL, 36% purity, 0.2 eq) and 2-acetamido-6-amino-benzoic acid (49.58 mg, 255.32 μmol, 1 eq) in EtOH (10 mL) and $CHCl_3$ (2 mL) was stirred for 0.5 h at 70° C. LCMS showed the reaction was complete. The mixture was concentrated in vacuo. The crude product was purified by prep-HPLC (Welch Xtimate C18 150×25 mm×5 μm column; 30%-45% acetonitrile in an 0.04% HCl solution and MeOH in water, 8 min gradient) to give 2-acetamido-6-[(6-bromo-3-morpholinosulfonyl-4-quinolyl)amino]benzoic acid (18.9 mg, 31.24 μmol, 12.23% yield, 96.83% purity, HCl) as brown solid. And 2-amino-6-[(6-bromo-3-morpholinosulfonyl-4-quinolyl)amino]benzoic acid (7.3 mg, 13.31 μmol, 5.21% yield, 99.15% purity, HCl) as brown solid. 85A: $^1H$ NMR (400 MHz, DMSO-$d_6$) δ 10.26 (br s, 1H), 9.00 (s, 1H), 8.11-8.03 (m, 1H), 8.03-7.97 (m, 1H), 7.60 (br d, J=8.1 Hz, 1H), 7.51 (d, J=1.8 Hz, 1H), 7.31 (br t, J=8.1 Hz, 1H), 6.84-6.75 (m, 1H), 3.65-3.44 (m, 4H), 3.22-3.03 (m, 4H), 2.05 (s, 3H). MS $(M+H)^+$=549.0. 85A-BP: $^1H$ NMR (400 MHz, DMSO-$d_6$) δ 10.69-10.13 (m, 1H), 9.02 (s, 1H), 8.18-7.90 (m, 3H), 7.66 (d, J=1.8 Hz, 1H), 7.06 (t, J=8.1 Hz, 1H), 6.69 (d, J=8.3 Hz, 1H), 6.18 (br d, J=7.7 Hz, 2H), 3.67-3.49 (m, 4H), 3.25-3.03 (m, 4H). MS $(M+H)^+$=507.0.

Example 44

Preparation of compound 86A

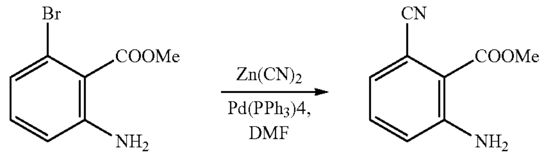

Step 1—Synthesis of methyl 2-amino-6-cyano-benzoate: To a solution of methyl 2-amino-6-bromo-benzoate (300 mg, 1.30 mmol, 1 eq) in DMF (3 mL) was added $Zn(CN)_2$ (107.19 mg, 912.81 μmol, 57.94 μL, 0.7 eq) and $Pd(PPh_3)_4$ (301.37 mg, 260.80 μmol, 0.2 eq). Then the mixture was stirred at 100° C. for 10 h. LCMS showed the starting material was consumed completely, and desired MS was detected. The mixture was filtered to give filtrate. The filtrate was dissolved in ethyl acetate (10 mL) and water (10 mL), separated, extracted with ethyl acetate (10 mL×2). The combined organic layer was washed with water (3 mL×2), dried over $Na_2SO_4$ and concentrated in vacuo. The residue was purified by flash column (ISCO 20 g silica, 0-30% Ethyl acetate in Petroleum ether, gradient over 30 min) to give methyl 2-amino-6-cyano-benzoate (200 mg, 1.14 mmol, 87.06% yield) was obtained as yellow solid. $^1H$ NMR (400 MHz, CHLOROFORM-d) δ 7.27-7.16 (m, 1H), 7.01 (d, J=7.3 Hz, 1H), 6.81 (d, J=8.4 Hz, 1H), 5.85 (br s, 2H), 3.91 (s, 3H). MS $(M+H)^+$=177.1.

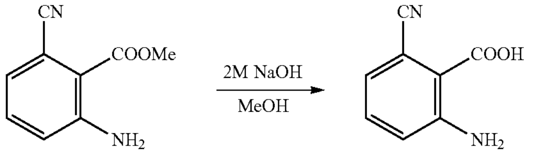 [SMILES: "MeOH" ; COC(=O)c1c(N)cccc1C#N ; "2M NaOH" ; N#Cc1cccc(N)c1C(=O)O]

Step 2—Synthesis of 2-amino-6-cyano-benzoic acid: To a solution of methyl 2-amino-6-cyano-benzoate (200 mg, 1.14 mmol, 1 eq) in MeOH (2 mL) was added NaOH (2 M, 1.70 mL, 3 eq),the mixture was stirred at 15° C. for 10 h. LCMS showed the starting material was consumed completely, and desired MS was detected. The mixture was acidified with 1M HCl to pH=4-5. The mixture was filtered to give 2-amino-6-cyano-benzoic acid (100 mg, 616.73 μmol, 54.33% yield) as yellow solid. $^1H$ NMR (400 MHz, DMSO-$d_6$) δ 0.11 (br s, 2H), 7.34 (t, J=7.9 Hz, 1H), 7.07 (d, J=8.5 Hz, 1H), 7.00 (d, J=7.1 Hz, 1H). MS $(M+H)^+$=163.1.

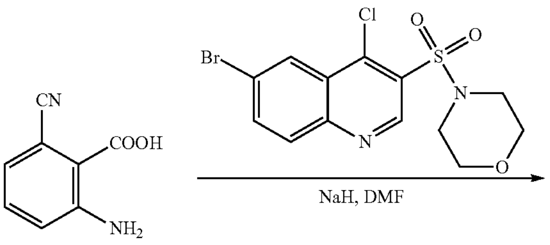

-continued

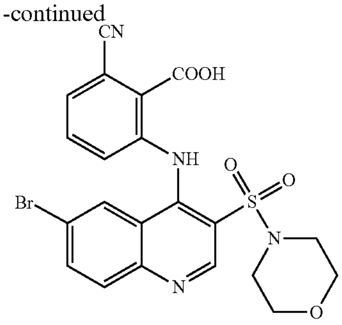

Step 3—Synthesis of 2-[(6-bromo-3-morpholinosulfonyl-4-quinolyl)amino]-6-cyano-benzoic acid: A solution of 2-amino-6-cyano-benzoic acid (28.98 mg, 178.72 μmol, 1 eq) and NaH (28.59 mg, 714.89 μmol, 60% purity, 4 eq) in DMF (1 mL) was stirred for 0.5 h at 20° C., followed addition 4-[(6-bromo-4-chloro-3-quinolyl)sulfonyl]morpholine (70 mg, 178.72 μmol, 1 eq), stirred for another 12 h at 20° C. LCMS showed the reaction was complete. The mixture was added into methanol (1 mL) and concentrated in vacuo. The crude product was purified by prep-HPLC (Phenomenex Gemini-NX C18 75×30 mm×μm column; 5%-25% acetonitrile in a 10 mM $NH_4HCO_3$ in water, 8 min gradient) to give 2-[(6-bromo-3-morpholinosulfonyl-4-quinolyl)amino]-6-cyano-benzoic acid (33.6 mg, 61.80 μmol, 34.58% yield, 98.47% purity, $NH_4$) as light yellow solid. $^1H$ NMR (400 MHz, DMSO-$d_6$) δ 12.14 (br s, 1H), 9.05 (s, 1H), 8.08-7.87 (m, 2H), 7.72 (d, J=1.6 Hz, 1H), 7.28 (br d, J=7.4 Hz, 5H), 7.20-7.06 (m, 1H), 6.73 (br d, J=8.1 Hz, 1H), 3.48-3.34 (m, 4H), 3.17-2.97 (m, 4H). $^1H$ NMR (400 MHz, DMSO-$d_6$+1 drop $D_2O$) δ 9.03 (s, 1H), 8.03-7.92 (m, 2H), 7.70 (d, J=2.0 Hz, 1H), 7.29 (d, J=7.4 Hz, 1H), 7.16 (t, J=7.9 Hz, 1H), 6.73 (d, J=8.1 Hz, 1H), 3.42 (br d, J=2.9 Hz, 2H), 3.37-3.25 (m, 2H), 3.19-3.07 (m, 2H), 3.07-2.98 (m, 2H). $^1H$ NMR (400 MHz, DMSO-d6 T=273+80K) δ 9.05 (s, 1H), 8.03-7.96 (m, 1H), 7.94-7.90 (m, 1H), 7.76 (s, 1H), 7.25 (d, J=7.5 Hz, 1H), 7.13 (t, J=7.8 Hz, 1H), 6.66 (d, J=8.2 Hz, 1H), 3.52-3.34 (m, 4H), 3.12 (br d, J=12.1 Hz, 4H). MS $(M+H)^+$=517.0.

Example 45

Preparation of Compound 93A and 93A-INT

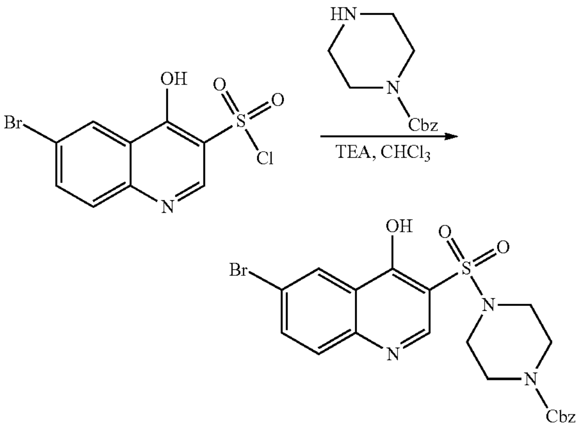

Step 1—Synthesis of benzyl 4-[(6-bromo-4-hydroxy-3-quinolyl)sulfonyl]piperazine-1-carboxylate: A solution of 6-bromo-4-hydroxy-quinoline-3-sulfonyl chloride (570 mg, 1.77 mmol, 1 eq), benzyl piperazine-1-carboxylate 778.47 mg, 3.53 mmol, 682.87 μL, 2 eq) and TEA (536.43 mg, 5.30 mmol, 737.87 μL, 3 eq) in $CHCl_3$ (5 mL) was stirred for h at 20° C. LCMS showed the reaction was complete. The suspension was filtered to give benzyl 4-[(6-bromo-4-hydroxy-3-quinolyl)sulfonyl]piperazine-1-carboxylate (440 mg, 868.93 μmol, 49.17% yield) as off-white solid. MS $(M+H)^+$=506.1.

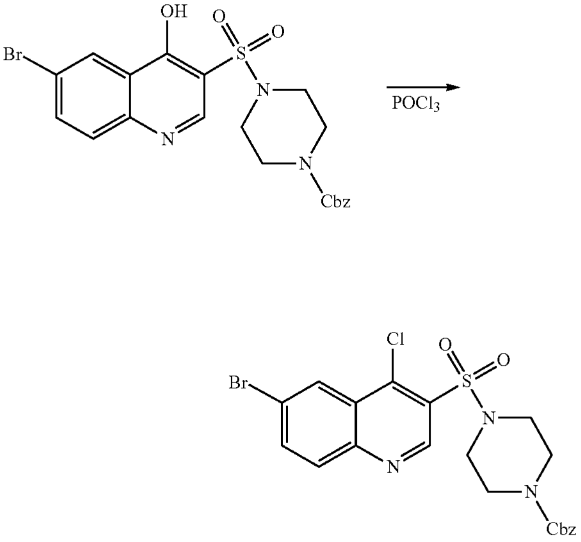

Step 2—Synthesis of benzyl 4-[(6-bromo-4-chloro-3-quinolyl)sulfonyl]piperazine-1-carboxylate: A solution of benzyl 4-[(6-bromo-4-hydroxy-3-quinolyl)sulfonyl]piperazine-1-carboxylate (440 mg, 868.93 μmol, 1 eq) in $POCl_3$ (5 mL) was stirred for 4 h at 110° C. LCMS showed desired ms was detected. The mixture was concentrated in vacuo to remove excess solvents. The residual was dissolved in ethyl acetate (2 mL), added dropwisely into ice-water (1 mL). The biphasic mixture was separated, extracted with ethyl acetate (2 mL) and dried over $Na_2SO_4$. Combined organic layer was concentrated in vacuo. The crude product was purified by flash column (ISCO 10 g silica, 0-20% ethyl acetate in petroleum ether, gradient over 10 min) to give benzyl 4-[(6-bromo-4-chloro-3-quinolyl)sulfonyl]piperazine-1-carboxylate (140 mg, 266.76 μmol, 30.70% yield) as white solid. MS $(M+H)^+$=524.0.

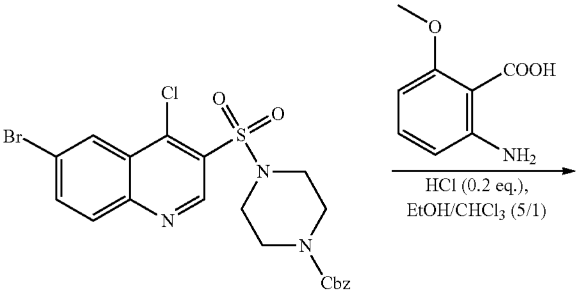

-continued

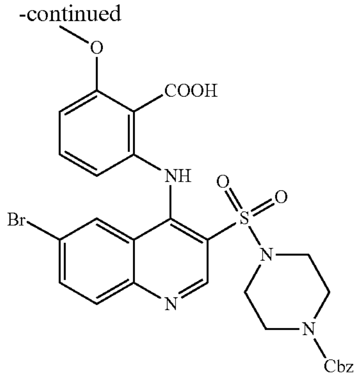

Step 3—Synthesis of 2-[[3-(4-benzyloxycarbonylpiperazin-1-yl)sulfonyl-6-bromo-4-quinolyl]amino]-6-methoxy-benzoic acid: A solution of 2-amino-6-methoxy-benzoic acid (45.87 mg, 274.38 μmol, 1.2 eq), HCl (4.63 mg, 45.73 μmol, 4.54 μL, 36% purity, 0.2 eq) and benzyl 4-[(6-bromo-4-chloro-3-quinolyl)sulfonyl]piperazine-1-carboxylate (120 mg, 228.65 μmol, 1 eq) in EtOH (0.2 mL) and $CHCl_3$ (0.05 mL) was stirred for 0.5 h at 70° C. LCMS showed the reaction was complete. The mixture was concentrated in vacuo. The crude product was purified by prep-HPLC (Phenomenex luna C18 80×40 mm×3 μm column; 38%-65% acetonitrile in an 0.04% HCl in water, 7 min gradient) to give 2-[[3-(4-benzyloxycarbonylpiperazin-1-yl)sulfonyl-6-bromo-4-quinolyl]amino]-6-methoxy-benzoic acid (60.3 mg, 83.46 μmol, 36.50% yield, 95.77% purity, HCl) as pale yellow solid. 4.5 mg of desired product was shipped out and the rest was used for next step. $^1H$ NMR (400 MHz, DMSO-$d_6$) δ 9.30-9.06 (m, 1H), 9.03-8.90 (m, 1H), 7.96 (s, 2H), 7.65 (s, 1H), 7.40-7.15 (m, 6H), 6.91 (d, J=8.6 Hz, 1H), 6.44 (d, J=8.1 Hz, 1H), 5.01 (d, J=1.3 Hz, 2H), 3.86 (s, 3H), 3.51-3.26 (m, 4H), 3.20-3.02 (m, 4H). MS $(M+H)^+$=655.0.

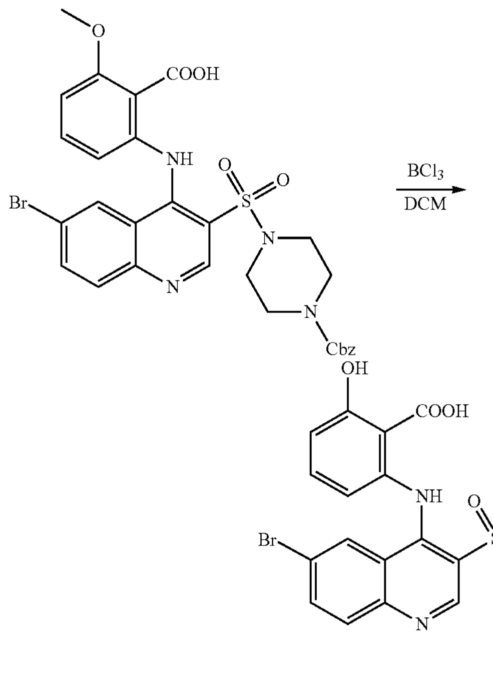

Step 4—Synthesis of 2-[(6-bromo-3-piperazin-1-ylsulfonyl-4-quinolyl)amino]-6-hydroxy-benzoic acid: To a solution of 2-[[3-(4-benzyloxycarbonylpiperazin-1-yl)sulfonyl-6-bromo-4-quinolyl]amino]-6-methoxy-benzoic acid (45 mg, 68.65 μmol, 1 eq) in DCM (1 mL) at 0° C., $BCl_3$ (1 M, 274.59 μL, 4 eq) was added dropwise. The reaction mixture was stirred for 3 h at 25° C. under $N_2$. The mixture was added dropwise to 0.5 mL 10% $NaHCO_3$ and concentrated in vacuo. The crude product was purified by prep-HPLC Waters Xbridge BEH C18 100×25 mm×5 μm column; 20%-44% acetonitrile in an 0.04% ammonia solution and 10 mM $NH_4HCO_3$ in water, 10 min gradient) to give 2-[(6-bromo-3-piperazin-1-ylsulfonyl-4-quinolyl)amino]-6-hydroxy-benzoic acid (14.4 mg, 28.10 μmol, 40.94% yield, 99.02% purity) as pale yellow solid. $^1H$ NMR (400 MHz, DMSO-d6) δ 12.34 (s, 1H), 9.04 (s, 1H), 8.01-7.89 (m, 2H), 7.86 (d, J=1.5 Hz, 1H), 6.85 (t, J=8.1 Hz, 1H), 6.27 (d, J=8.1 Hz, 1H), 5.74 (d, J=8.0 Hz, 1H), 3.31-3.26 (m, 4H), 3.19-3.05 (m, 2H), 3.02-2.92 (m, 2H). $^1H$ NMR (400 MHz, DMSO-$d_6$ 273+80K) δ 12.50-12.20 (m, 1H), 9.06 (s, 1H), 7.99-7.81 (m, 3H), 6.83 (t, J=8.2 Hz, 1H), 6.28 (d, J=8.2 Hz, 1H), 5.72 (d, J=8.2 Hz, 1H), 3.38 (t, J=5.1 Hz, 4H), 3.01 (br s, 4H). MS $(M+H)^+$=507.0.

Numbered Paragraphs

Some embodiments of the present disclosure is described in a form of the following numbered paragraphs:

Paragraph 1. A compound of Formula (I):

(I)

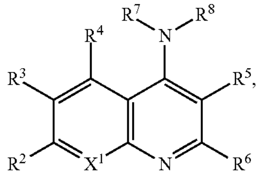

or a pharmaceutically acceptable salt thereof, wherein:

$X^1$ is selected from N and $CR^1$;

$R^1$, $R^2$, $R^3$, $R^4$, $R^5$, and $R^6$ are each independently selected from H, $C_{1-6}$ alkyl, $C_{2-6}$ alkenyl, $C_{2-6}$ alkynyl, $C_{1-4}$ haloalkyl, $Cy^1$, halo, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2R^{b1}$, $S(O)R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, 3, 4, or 5 substituents independently selected from $Cy^1$, halo, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2R^{b1}$, $S(O)_2R^{b1}$, and $S(O)_2NR^{c1}R^{d1}$;

each $Cy^1$ is independently selected from $C_{6-10}$ aryl, 5-10 membered heteroaryl, and 4-7 membered heterocycloalkyl, each of which is optionally substituted with 1, 2, or 3 substituents independently selected from $R^{Cy}$;

$R^7$ is selected from H, $C_{1-3}$ alkyl, $C(O)C_{1-6}$ alkyl, $C(O)OR^{a1}$, $S(O)_2NR^{c1}R^{d1}$, and phenyl, wherein said phenyl is optionally substituted with $R^{Cy}$, halo, CN, $OR^{a1}$, $SR^{a1}$, or $NR^{c1}R^{d1}$;

$R^8$ is selected from a 4-7 membered heterocycloalkyl, $C_{3-10}$ cycloalkyl, and a 5-10 membered heteroaryl, which is substituted with W, and is optionally substituted with 1, 2, or 3 substituents independently selected from $R^{Cy}$;

W is selected from $C(O)OR^{a2}$ and a carboxylic acid bioisostere;

$R^{Cy}$ is selected from halo, CN, $NO_2$, $C_{1-6}$ alkyl, $C_{1-6}$ haloalkyl, $C_{2-6}$ alkenyl, $C_{2-6}$ alkynyl, $OR^{a2}$, $C(O)R^{b2}$, $C(O)NR^{c2}R^{d2}$, $NR^{c2}R^{d2}$, $NR^{c2}C(O)R^{b2}$, $NR^{c2}C(O)OR^{a2}$, $NR^{c2}S(O)_2R^{b2}$, $S(O)_2R^{b2}$, and $S(O)_2NR^{c2}R^{d2}$; wherein said $C_{1-6}$ alkyl, $C_{2-6}$ alkenyl, and $C_{2-6}$ alkynyl are each optionally substituted with 1, 2, or 3 substituents independently selected from halo, CN, $NO_2$, $OR^{a2}$, $C(OR^{b2}$, $C(O)NR^{c2}R^{d2}$, $C(O)OR^{a2}$, $NR^{c2}R^{d2}$, $NR^{c2}C(O)R^{b2}$, $NR^{c2}C(O)OR^{a2}$, $NR^{c2}S(O)_2R^{b2}$, $S(O)_2R^{b2}$, and $S(O)_2NR^{c2}R^{d2}$;

or $R^5$ and $R^8$, together with the atoms to which they are attached, form a 5-10 membered heteroaryl ring or a 4-7 membered heterocycloalkyl ring, each of which is optionally substituted with 1, 2, 3, 4, or 5 substituents independently selected from $R^{Cy1}$;

or $R^4$ and $R^8$, together with the atoms to which they are attached, form a 5-10 membered heteroaryl ring or a 4-10 membered heterocycloalkyl ring, each of which is optionally substituted with 1, 2, 3, 4, or 5 substituents independently selected from $R^{Cy1}$;

$R^{Cy1}$ is selected from halo, CN, $NO_2$, $C_{1-6}$ alkyl, $C_{1-6}$ haloalkyl, $C_{2-6}$ alkenyl, $C_{2-6}$ alkynyl, $OR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}C(O)OR^{a3}$, $NR^{c3}S(O)_2R^{b3}$, $S(O)_2R^{b3}$, and $S(O)_2NR^{c3}R^{d3}$; wherein said $C_{1-6}$ alkyl, $C_{2-6}$ alkenyl, and $C_{2-6}$ alkynyl are each optionally substituted with 1, 2, or 3 substituents independently selected from halo, CN, $NO_2$, $OR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}C(O)OR^{a3}$, $NR^{c3}S(O)_2R^{b3}$, $S(O)_2R^{b3}$, and $S(O)_2NR^{c3}R^{d3}$;

or any two $R^{Cy1}$ together with the atoms to which they are attached, form a 5-10 membered heteroaryl ring or a 4-7 membered heterocycloalkyl ring, each of which is optionally substituted with 1, 2, 3, 4, or 5 substituents independently selected from $R^{Cy2}$;

or $R^7$ and $R^{Cy1}$, together with the atoms to which they are attached, form a 5-10 membered heteroaryl ring or a 4-7 membered heterocycloalkyl ring, each of which is optionally substituted with 1, 2, 3, 4, or 5 substituents independently selected from $R^{Cy2}$;

$R^{Cy2}$ is selected from halo, CN, $NO_2$, $C_{1-6}$ alkyl, $C_{1-6}$ haloalkyl, $C_{2-6}$ alkenyl, $C_{2-6}$ alkynyl, $OR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}S(O)_2R^{b4}$, $S(O)_2R^{b4}$, and $S(O)_2NR^{c4}R^{d4}$; wherein said $C_{1-6}$ alkyl, $C_{2-6}$ alkenyl, and $C_{2-6}$ alkynyl are each optionally substituted with 1, 2, or 3 substituents independently selected from halo, CN, $NO_2$, $OR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}S(O)_2R^{b4}$, $S(O)_2R^{b4}$, and $S(O)_2NR^{c4}R^{d4}$;

each $R^{a1}$, $R^{b1}$, $R^{c1}$, $R^{d1}$, $R^{a2}$, $R^{b2}$, $R^{d2}$, $R^{a3}$, $R^{b3}$, $R^{c3}$, $R^{d3}$, $R^{a4}$, $R^{b4}$, $R^{c4}$, and $R^{d4}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally to substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$;

or any $R^{c2}$ and $R^{d2}$ together with the N atom to which they are attached form a 4-7 membered heterocycloalkyl, which is optionally substituted with 1, 2, or 3 substituents independently selected from $R^g$;

or any $R^{c3}$ and $R^{d3}$ together with the N atom to which they are attached form a 4-7 membered heterocycloalkyl, which is optionally substituted with 1, 2, or 3 substituents independently selected from $R^g$; and or any $R^{c4}$ and $R^{d4}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

Paragraph 2. The compound of paragraph 1, wherein:

$X^1$ is selected from N and $CR^1$;

$R^1$, $R^2$, $R^3$, $R^4$, $R^5$, and $R^6$ are each independently selected from H, $C_{1-6}$ alkyl, $C_{2-6}$ alkenyl, $C_{2-6}$ alkynyl, $C_{1-4}$ haloalkyl, $Cy^1$, halo, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1l}$, $NR^{c1}S(O)_2R^{b1}$, $S(O)R^{b1}$, $S(O)_2R_{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, 3, 4, or 5 substituents independently selected from $Cy^1$, halo, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2R^{b1}$, $S(O)_2R^{b1}$, and $S(O)_2NR^{c1}R^{d1}$;

each $Cy^1$ is independently selected from $C_{6-10}$ aryl, 5-10 membered heteroaryl, and 4-7 membered heterocycloalkyl, each of which is optionally substituted with 1, 2, or 3 substituents independently selected from $R^{Cy}$;

$R^7$ is selected from H, $C_{1-3}$ alkyl, $C(O)C_{1-6}$ alkyl, $C(O)OR^{a1}$, $S(O)_2NR^{c1}R^{d1}$, and phenyl, wherein said phenyl is optionally substituted with halo, CN, $OR^{a1}$, $SR^{a1}$, or $NR^{c1}R^{d1}$.

$R^8$ is selected from a 4-7 membered heterocycloalkyl and a 5-10 membered heteroaryl, which is substituted with W, and is optionally substituted with 1, 2, or 3 substituents independently selected from $R^{Cy}$;

W is selected from $C(O)OR^{a2}$ and a carboxylic acid bioisostere;

$R^{Cy}$ is selected from halo, CN, $NO_2$, $C_{1-6}$ alkyl, $C_{1-6}$ haloalkyl, $C_{2-6}$ alkenyl, $C_{2-6}$ alkynyl, $OR^{a2}$, $C(O)R^{b2}$, $C(O)NR^{c2}R^{d2}$, $NR^{c2}R^{d2}$, $NR^{c2}C(O)R^{b2}$, $NR^{c2}C(O)OR^{a2}$, $NR^{c2}S(O)_2R^{b2}$, $S(O)_2R^{b2}$, and $S(O)_2NR^{c2}R^{d2}$; wherein said $C_{1-6}$ alkyl, $C_{2-6}$ alkenyl, and $C_{2-6}$ alkynyl are each optionally substituted with 1, 2, or 3 substituents independently selected from halo, CN, $NO_2$, $OR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$, $NR^{c2}C(O)OR^{a2}$, $NR^{c2}S(O)_2R^{b2}$, $S(O)_2R^{b2}$, and $S(O)_2NR^{c2}R^{d2}$;

or $R^5$ and $R^8$, together with the atoms to which they are attached, form a 5-10 membered heteroaryl ring or a 4-7 membered heterocycloalkyl ring, each of which is optionally substituted with 1, 2, 3, 4, or 5 substituents independently selected from $R^{Cy1}$;

$R^{Cy1}$ is selected from halo, CN, $NO_2$, $C_{1-6}$ alkyl, $C_{1-6}$ haloalkyl, $C_{2-6}$ alkenyl, $C_{2-6}$ alkynyl, $OR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}C(O)OR^{a3}$, $NR^{c3}S(O)_2R^{b3}$, $S(O)_2R^{b3}$, and $S(O)_2NR^{c3}R^{d3}$; wherein said $C_{1-6}$ alkyl, $C_{2-6}$ alkenyl, and $C_{2-6}$ alkynyl are each optionally substituted with 1, 2, or 3 substituents independently selected from halo, CN, $NO_2$, $OR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}C(O)OR^{a3}$, $NR^{c3}S(O)_2R^{b3}$, $S(O)_2R^{b3}$, and $S(O)_2NR^{c3}R^{d3}$;

or any two $R^{Cy1}$ together with the atoms to which they are attached, form a 5-10 membered heteroaryl ring or a 4-7 membered heterocycloalkyl ring, each of which is optionally substituted with 1, 2, 3, 4, or 5 substituents independently selected from $R^{Cy2}$;

or $R^7$ and $R^{Cy1}$, together with the atoms to which they are attached, form a 5-10 membered heteroaryl ring or a 4-7 membered heterocycloalkyl ring, each of which is optionally substituted with 1, 2, 3, 4, or 5 substituents independently selected from $R^{Cy2}$, $R^{Cy2}$ is selected from halo, CN, $NO_2$, $C_{1-6}$ alkyl, $C_{1-6}$ haloalkyl, $C_{2-6}$ alkenyl, $C_{2-6}$ alkynyl, $OR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}S(O)_2R^{b4}$, $S(O)_2R^{b4}$, and $S(O)_2NR^{c4}R^{d4}$; wherein said $C_{1-6}$ alkyl, $C_{2-6}$ alkenyl, and $C_{2-6}$ alkynyl are each optionally substituted with 1, 2, or 3 substituents independently selected from halo, CN, $NO_2$, $OR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}S(O)_2R^{b4}$, $S(O)_2R^{b4}$, and $S(O)_2NR^{c4}R^{d4}$;

each $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, $R^{d3}$, $R^{a4}$, $R^{b4}$, $R^{c4}$, and $R^{d4}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$;

or any $R^{c2}$ and $R^{c2}$ together with the N atom to which they are attached form a 4-7 membered heterocycloalkyl, which is optionally substituted with 1, 2, or 3 substituents independently selected from $R^g$;

or any $R^{c3}$ and $R^{d3}$ together with the N atom to which they are attached form a 4-7 membered heterocycloalkyl, which is optionally substituted with 1, 2, or 3 substituents independently selected from $R^g$; and or any $R^{c4}$ and $R^{d4}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

Paragraph 3. The compound of paragraph 1 or 2, wherein:

$R^1$, $R^2$, $R^3$, $R^4$, $R^5$, and $R^6$ are each independently selected from H, $C_{1-6}$ alkyl, $C_{2-6}$ alkenyl, $C_{2-6}$ alkynyl, $C_{1-4}$ haloalkyl, $Cy^1$, halo, CN, $NO_2$, $OR^{a1}$, $SR^{a1}$, $C(O)R^{b1}$, $C(O)NR^{c1}R^{d1}$, $C(O)OR^{a1}$, $NR^{c1}R^{di}$, $NR^{c1}C(O)R^{b1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, 3, 4, or 5 substituents independently selected from $Cy^1$, halo, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2R^{b1}$, $S(O)_2R^{b1}$, and $S(O)_2NR^{c1}R^{d1}$; and $R^7$ is selected from H and $C_{1-3}$ alkyl.

Paragraph 4. The compound of any one of paragraphs 1-3, wherein $R^1$, $R^2$, $R^3$, $R^4$, $R^5$, and $R^6$ are each independently selected from H, $Cy^1$, halo, CN, $OR^{a1}$, $C(O)NR^{c1}R^{d1}$, $C(O)OR^{a1}$, and $S(O)_2NR^{c1}R^{d1}$.

Paragraph 5. The compound of paragraph 4, wherein:

$R^1$, $R^2$, $R^4$, and $R^6$ are each H, and $R^3$ and $R^5$ are each independently selected from $Cy^1$, halo, CN, $OR^{a1}$, $C(O)NR^{c1}R^{d1}$, $C(O)OR^{a1}$, and $S(O)_2NR^{c1}R^{d1}$.

Paragraph 6. The compound of paragraph 4, wherein:

$R^1$, $R^2$, $R^4$, and $R^6$ are each H, $R^3$ is selected from $Cy^1$, $OR^{a1}$, $C(O)NR^{c1}R^{d1}$, and halo, and $R^5$ is selected from $Cy^1$, $C(O)OR^{a1}$, $C(O)NR^{c1}R^{d1}$, $S(O)_2NR^{c1}R^{d1}$, and CN.

Paragraph 7. The compound of paragraph 4, wherein:

$R^1$, $R^4$, and $R^6$ are each H, $R^2$ is selected from H, $Cy^1$, $OR^{a1}$, $C(O)NR^{c1}R^{d1}$, and halo, $R^3$ is selected from $Cy^1$, $OR^{a1}$, $C(O)NR^{c1}R^{d1}$, and halo, and $R^5$ is selected from $Cy^1$, $C(O)OR^{a1}$, $C(O)NR^{c1}R^{d1}$, $S(O)_2NR^{c1}R^{d1}$, and CN.

Paragraph 8. The compound of paragraph 7, wherein:

$R^2$ is selected from H and $OR^{a1}$;

$R^3$ is selected from $C_{1-6}$ alkoxy and $C_{1-6}$ haloalkoxy; and $R^5$ is $C(O)OR^{a1}$.

Paragraph 9. The compound of any one of paragraphs 6-8, wherein:

$R^3$ is $C_{1-6}$haloalkoxy, and $R^5$ is $C(O)OR^{a1}$.

Paragraph 10. The compound of any one of paragraphs 1-9, wherein $Cy^1$ is selected from $C_{6-10}$ aryl and 5-10 membered heteroaryl, each of which is optionally substituted with 1 or 2 substituents independently selected from $R^{Cy}$.

Paragraph 11. The compound of any one of paragraphs 1-9, wherein $Cy^1$ is 5-10 membered heteroaryl, optionally substituted with $R^{Cy}$.

Paragraph 12. The compound of paragraph 11, wherein $Cy^1$ is selected from indolyl and isoxazolyl, each of which is optionally substituted with $R^{Cy}$.

Paragraph 13. The compound of any one of paragraphs 1-12, wherein $R^{a1}$ is selected from H, $C_{1-6}$ alkyl, $C_{1-4}$haloalkyl, 5-10 membered heteroaryl, and 4-10 membered heterocycloalkyl.

Paragraph 14. The compound of any one of paragraphs 1-13, wherein $R^{c1}$ and $R^{d1}$ are each independently selected from H and $C_{1-6}$ alkyl.

Paragraph 15. The compound of any one of paragraphs 1-14, wherein $R^{c1}$ and $R^{d1}$ together with the N atom to which they are attached form a 4-7 membered heterocycloalkyl, which is optionally substituted with $R^g$.

Paragraph 16. The compound of any one of paragraphs 1-15, wherein $R^7$ is H.

Paragraph 17. The compound of any one of paragraphs 1-16, wherein $R^8$ is a 4-7 membered heterocycloalkyl, optionally substituted with $R^{Cy}$.

Paragraph 18. The compound of any one of paragraphs 1-17, wherein $R^8$ is a 5-10 membered heteroaryl, optionally substituted with $R^{Cy}$.

Paragraph 19. The compound of paragraph 18, wherein $R^8$ is selected from pyridinyl, imidazolyl, thiazolyl, pyrazinyl, pyrimidinyl, oxazolyl, isoxazolyl, isothiazolyl, and pyrazolyl, each of which is optionally substituted with $R^{Cy}$.

Paragraph 20. The compound of paragraph 1, wherein:

- $R^1$, $R^2$, $R^3$, $R^4$, $R^5$, and $R^6$ are each independently selected from H, $Cy^1$, halo, CN, $OR^{a1}$, $C(O)NR^{c1}R^{d1}$, $C(O)OR^{a1}$, and $S(O)_2NR^{c1}R^{d1}$;
- $Cy^1$ is selected from $C_{6-10}$ aryl and 5-10 membered heteroaryl, each of which is optionally substituted with 1 or 2 substituents independently selected from $R^{Cy}$;
- $R^{a1}$ is selected from H, $C_{1-6}$ alkyl, $C_{1-4}$ haloalkyl, 5-10 membered heteroaryl, and 4-10 membered heterocycloalkyl;
- $R^{c1}$ and $R^{d1}$ are each independently selected from H and $C_{1-6}$ alkyl; or
- $R^{c1}$ and $R^{d1}$ together with the N atom to which they are attached form a 4-7 membered heterocycloalkyl, which is optionally substituted with $R^g$;
- $R^7$ is H; and
- $R^8$ is a 4-7 membered heterocycloalkyl or 5-10 membered heteroaryl, each of which is optionally substituted with $R^{Cy}$.

Paragraph 21. The compound of paragraph 1, wherein:

- $R^1$, $R^2$, $R^4$, and $R^6$ are each H;
- $R^3$ and $R^5$ are each independently selected from $Cy^1$, halo, CN, $OR^{a1}$, $C(O)NR^{c1}R^1$, $C(O)OR^{a1}$, and $S(O)_2NR^{c1}R^{d1}$;
- $Cy^1$ is 5-10 membered heteroaryl, optionally substituted with $R^{Cy}$;
- $R^{a1}$ is selected from H, $C_{1-6}$ alkyl, $C_{1-4}$ haloalkyl, 5-10 membered heteroaryl, and 4-10 membered heterocycloalkyl;
- $R^{c1}$ and $R^{d1}$ are each independently selected from H and $C_{1-6}$ alkyl; or
- $R^{c1}$ and $R^{d1}$ together with the N atom to which they are attached form a 4-7 membered heterocycloalkyl, which is optionally substituted with $R^g$;

- $R^7$ is H; and
- $R^8$ is a 5-10 membered heteroaryl, optionally substituted with $R^{Cy}$.

Paragraph 22. The compound of paragraph 1, wherein:

- $R^1$, $R^2$, $R^4$, and $R^6$ are each H,
- $R^3$ is $C_{1-6}$ haloalkoxy,
- $R^5$ is $C(O)OR^{a1}$,
- $R^{a1}$ is selected from H and $C_{1-6}$ alkyl;
- $R^7$ is H; and
- $R^8$ is selected from pyridinyl, imidazolyl, thiazolyl, pyrazinyl, pyrimidinyl, oxazolyl, isoxazolyl, isothiazolyl, and pyrazolyl, each of which is optionally substituted with $R^{Cy}$.

Paragraph 23. The compound of any one of paragraphs 5-15, wherein the compound of Formula (I) is selected from any one of the following formulae:

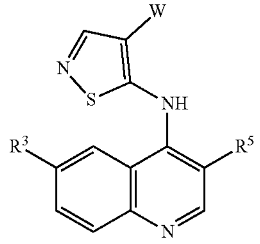
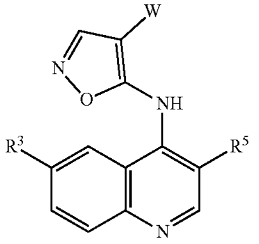
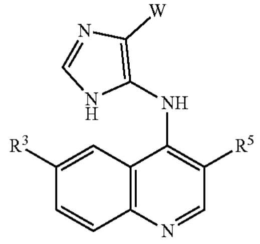
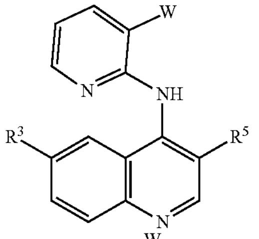
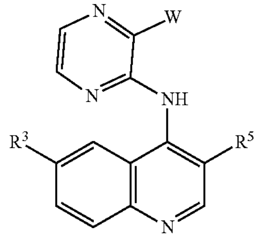
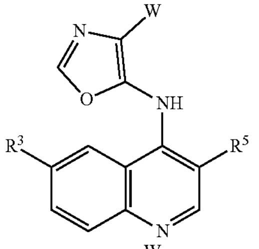
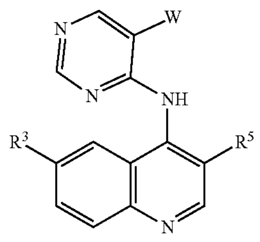
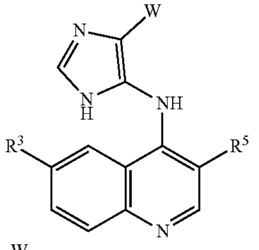
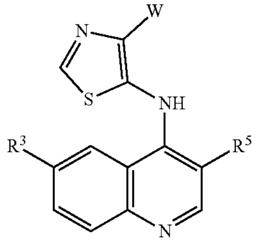

or a pharmaceutically acceptable salt thereof.

Paragraph 24. The compound of paragraph 23, wherein:

$R^3$ and $R^5$ are each independently selected from $Cy^1$, halo, CN, $OR^{a1}$, $C(O)NR^{c1}R^{d1}$, $C(O)OR^{a1}$, and $S(O)_2NR^{c1}R^{d1}$;

$Cy^1$ is 5-10 membered heteroaryl, optionally substituted with $R^{Cy}$;

$R^{a1}$ is selected from H, $C_{1-6}$ alkyl, $C_{1-4}$ haloalkyl, 5-10 membered heteroaryl, and 4-10 membered heterocycloalkyl; and $R^{c1}$ and $R^{d1}$ are each independently selected from H and $C_{1-6}$ alkyl; or $R^{c1}$ and $R^{d1}$ together with the N atom to which they are attached form a 4-7 membered heterocycloalkyl, which is optionally substituted with $R^g$.

Paragraph 25. The compound of paragraph 23, wherein:

$R^3$ is $C_{1-6}$ haloalkoxy, $R^5$ is $C(O)OR^{a1}$, and $R^{a1}$ is selected from H and $C_{1-6}$ alkyl.

Paragraph 26. The compound of any one of paragraphs 1-25, wherein W is C(O)OH.

Paragraph 27. The compound of any one of paragraphs 1-25, wherein:

W is $C(O)OR^{a1}$, and $R^{a1}$ is $C_{1-6}$ alkyl.

Paragraph 28. The compound of any one of paragraphs 1-25, wherein W is a carboxylic acid bioisostere.

Paragraph 29. The compound of paragraph 28, wherein the carboxylic acid bioisostere is selected from a moiety of any one of the following formulae:

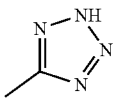
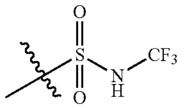
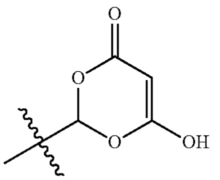
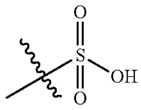
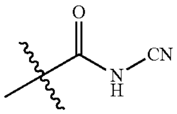
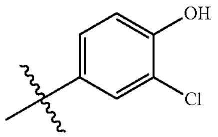
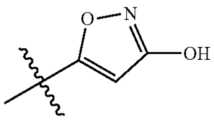
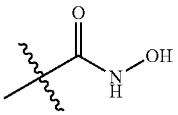
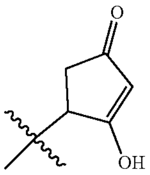

Paragraph 30. The compound of paragraph 1, wherein the compound of Formula (I) is selected from any one of the following compounds:

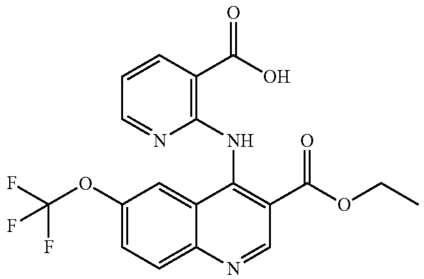

-continued

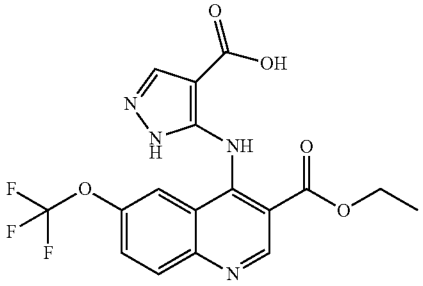
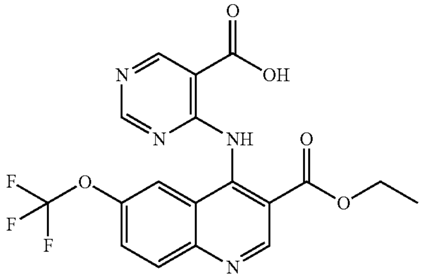
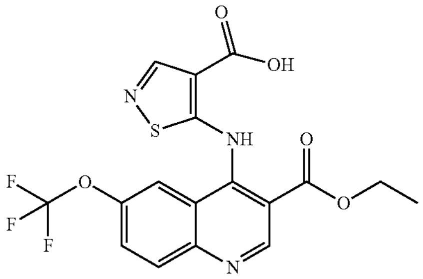
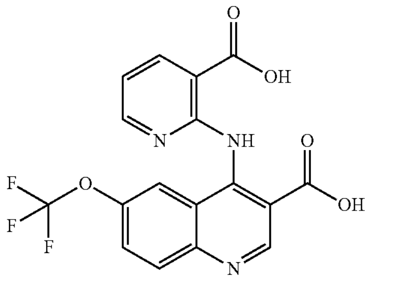
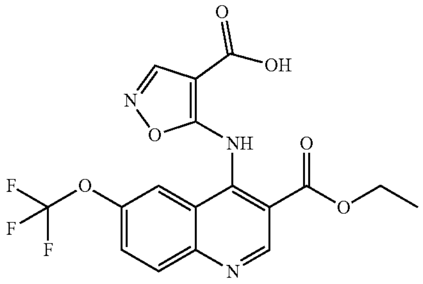
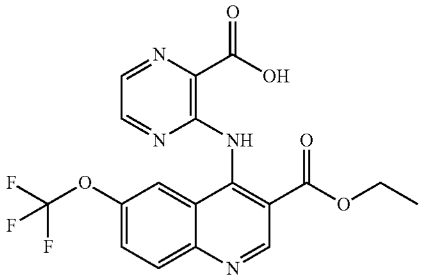

-continued
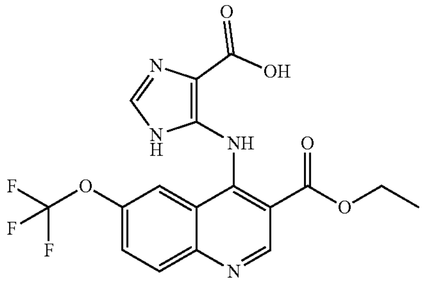
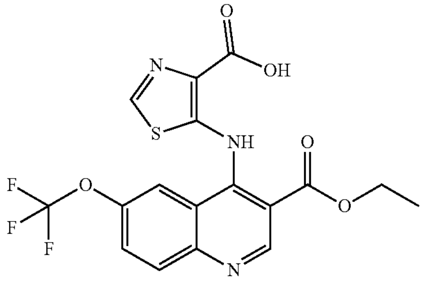
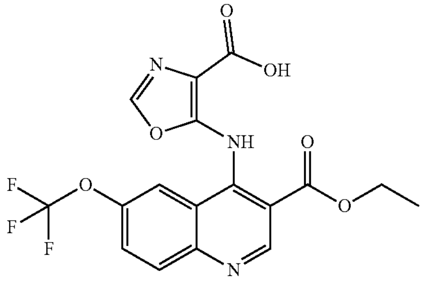
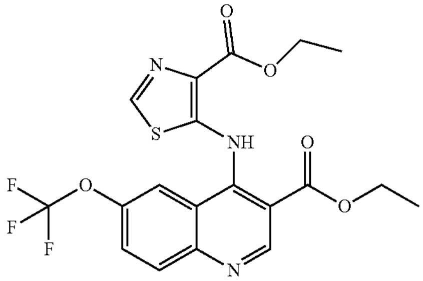
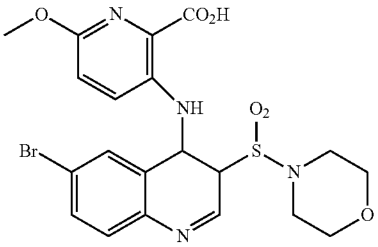
or a pharmaceutically acceptable salt thereof.
Paragraph 31. The compound of paragraph 1, wherein the compound of Formula (I) is selected from any one of the following compounds:
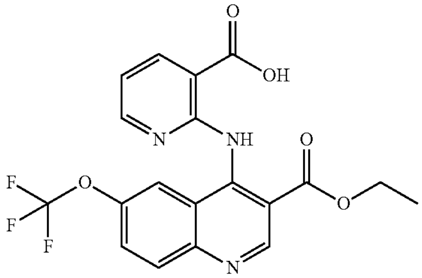
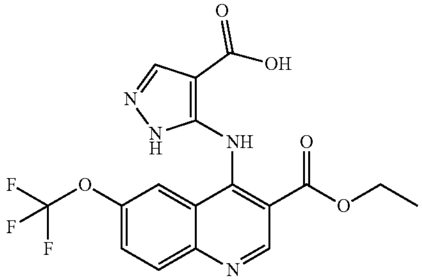
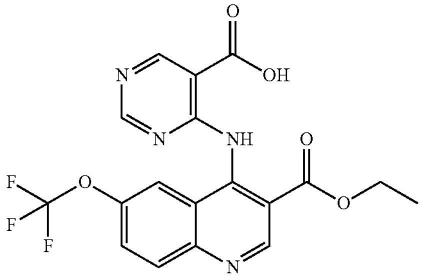
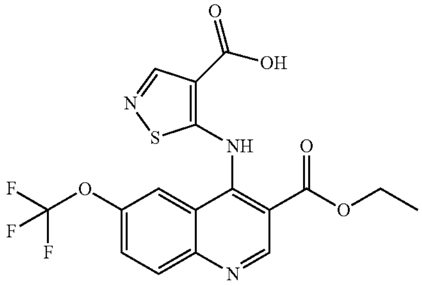
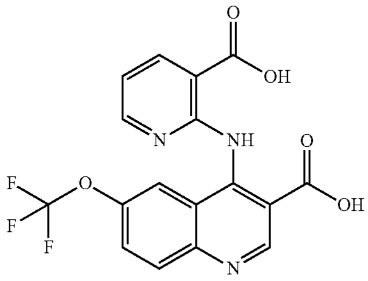

-continued

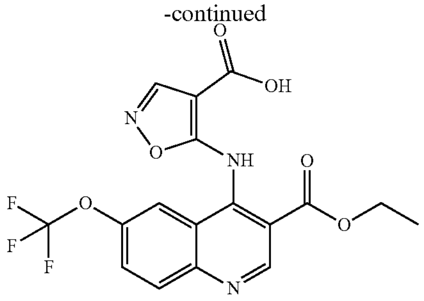

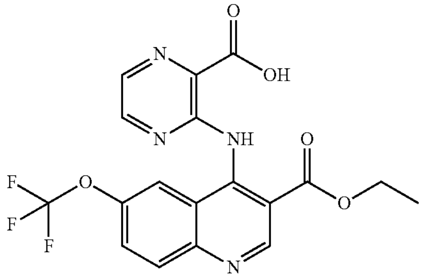

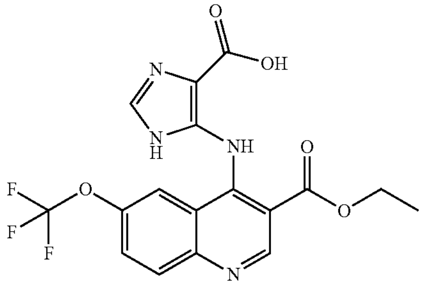

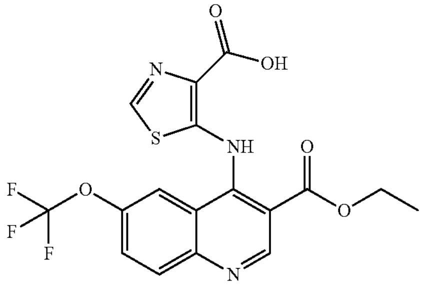

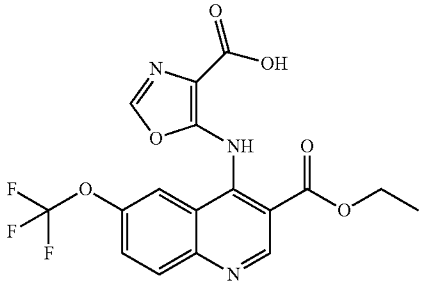

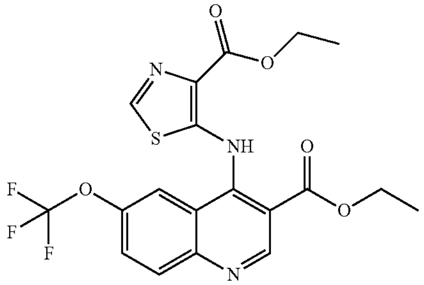

or a pharmaceutically acceptable salt thereof.

Paragraph 32. The compound of paragraph 1, wherein the compound of Formula (I) is selected from any one of the following compounds:

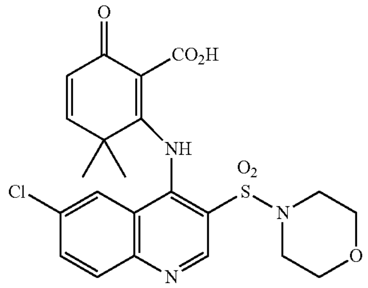

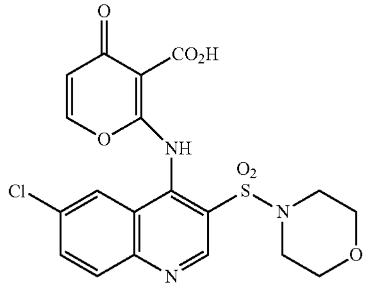

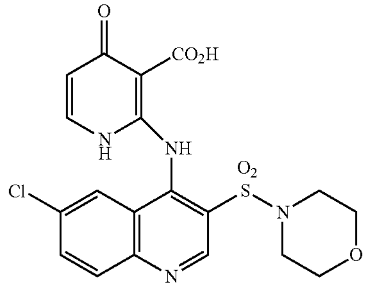

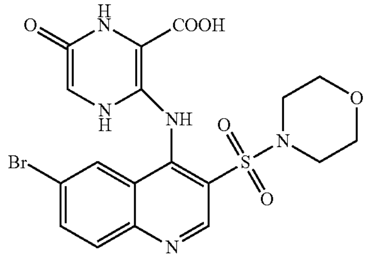

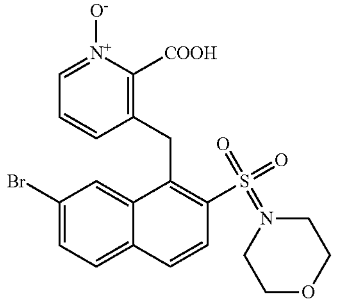

or a pharmaceutically acceptable salt thereof.

Paragraph 33. The compound of paragraph 1, wherein $R^5$ and $R^8$, together with the atoms to which they are attached, form a 5-10 membered heteroaryl ring, which is substituted with 1, 2, or 3 substituents independently selected from $R^{Cy1}$.

Paragraph 34. The compound of paragraph 1, wherein $R^5$ and $R^8$, together with the atoms to which they are attached, form a 4-7 membered heterocycloalkyl ring, which is substituted with 1, 2, or 3 substituents independently selected from $R^{Cy1}$.

Paragraph 35. The compound of paragraph 33 or 34, wherein any two $R^{Cy1}$ together with the atoms to which they are attached, form a 5-10 membered heteroaryl ring, which is substituted with 1, 2, or 3 substituents independently selected from $R^{Cy2}$.

Paragraph 36. The compound of paragraph 33 or 34, wherein any two $R^{Cy1}$ together with the atoms to which they are attached, form a 4-7 membered heterocycloalkyl ring, which is optionally substituted with 1, 2, or 3 substituents independently selected from $R^{Cy2}$.

Paragraph 37. The compound of paragraph 33 or 34, wherein $R^7$ and $R^{Cy1}$, together with the atoms to which they are attached, form a 5-10 membered heteroaryl ring, which is optionally substituted with 1, 2, or 3 substituents independently selected from $R^{Cy2}$.

Paragraph 38. The compound of paragraph 33 or 34, wherein $R^7$ and $R^{Cy1}$, together with the atoms to which they are attached, form a 4-7 membered heterocycloalkyl ring, which is optionally substituted with 1, 2, or 3 substituents independently selected from $R^{Cy2}$.

Paragraph 39. The compound of any one of paragraphs 35-38, wherein $R^{Cy2}$ is selected from halo, CN, $NO_2$, $C_{1-6}$ alkyl, $C_{1-6}$ haloalkyl, $OR^{a4}$, $C(O)NR^{c4}R^{d4}$, $C(O)OR^{a4}$, and $NR^{c4}R^{d4}$, wherein said $C_{1-6}$ alkyl is optionally substituted with 1, 2, or 3 substituents independently selected from halo, CN, $NO_2$, $OR^{a4}$, $C(O)NR^{c4}R^{d4}$, $C(O)OR^{a4}$, and $NR^{c4}R^{d4}$.

Paragraph 40. The compound of paragraph 39, wherein $R^{Cy2}$ is $C(O)OR^{a4}$.

Paragraph 41. The compound of any one of paragraphs 33-40, wherein $R^{a4}$ is selected from H, $C_{1-6}$ alkyl, and $C_{1-4}$ haloalkyl.

Paragraph 42. The compound of any one of paragraphs 33-41, wherein $R^1$, $R^2$, $R^3$, $R^4$, and $R^6$ are each independently selected from H, $Cy^1$, halo, CN, $OR^{a1}$, $C(O)NR^{c1}R^{d1}$, $C(O)OR^{a1}$, and $S(O)_2NR^{c1}R^{d10}$.

Paragraph 43. The compound of any one of paragraphs 33-41, wherein:

$R^1$, $R^2$, $R^4$, and $R^6$ are each H;

$R^3$ is selected from $Cy^1$, halo, CN, $OR^{a1}$, $C(O)NR^{c1}R^{d1}$, $C(O)OR^{a1}$, and $S(O)_2NR^{c1}R^{d1}$.

Paragraph 44. The compound of paragraph 43, wherein $R^3$ is selected from $Cy^1$, $OR^{a1}$, $C(O)NR^{c1}R^{d1}$, and halo.

Paragraph 45. The compound of paragraph 43, wherein $R^3$ is $C_{1-6}$ haloalkoxy.

Paragraph 46. The compound of any one of paragraphs 33-45, wherein the compound of Formula (I) is selected from any one of the following formulae:

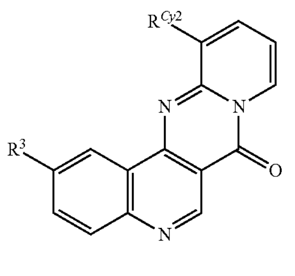

-continued

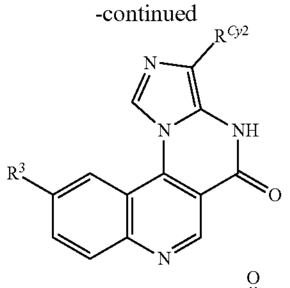

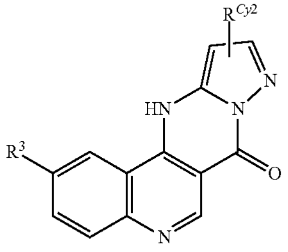

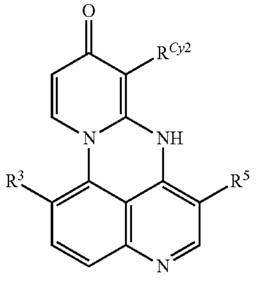

or a pharmaceutically acceptable salt thereof.

Paragraph 47. The compound of any one of paragraphs 33-45, wherein the compound of Formula (I) is selected from any one of the following compounds:

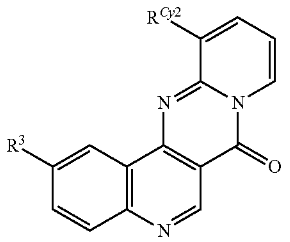

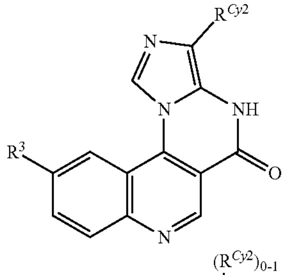

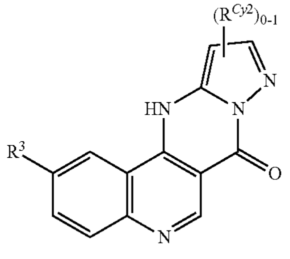

or a pharmaceutically acceptable salt thereof.

Paragraph 48. The compound of paragraph 46 or 47, wherein:

$R^3$ is selected from $Cy^1$, halo, CN, $OR^{a1}$, $C(O)NR^{c1}R^{d1}$, $C(O)OR^{a1}$, and $S(O)_2NR^{c1}R^{d1}$;

$R^{Cy2}$ is selected from halo, CN, $NO_2$, $C_{1-6}$ alkyl, $C_{1-6}$ haloalkyl, $OR^{a4}$, $C(O)NR^{c4}R^{d4}$, $C(O)OR^{a4}$, and $NR^{c4}R^{d4}$, wherein said $C_{1-6}$ alkyl is optionally substituted with 1, 2, or 3 substituents independently selected from halo, CN, $NO_2$, $OR^{a4}$, $C(O)NR^{c4}R^{d4}$, $C(O)OR^{a4}$, and $NR^{c4}R^{d4}$; and $R^{a4}$ is selected from H and $C_{1-6}$ alkyl.

Paragraph 49. The compound of paragraph 48, wherein:

$R^3$ is selected from $Cy^1$, $OR^{a1}$, $C(O)NR^{c1}R^{d1}$, and halo;

$R^{Cy2}$ is $C(O)OR^{a4}$; and $R^{a4}$ is selected from H and $C_{1-6}$ alkyl.

Paragraph 50. The compound of paragraph 48, wherein:

$R^3$ is $C_{1-6}$ haloalkoxy;

$R^{Cy2}$ is $C(O)OR^{a4}$; and $R^{a4}$ is selected from H and $C_{1-6}$ alkyl.

Paragraph 51. The compound of paragraph 1, wherein the compound is selected from any one of the following compounds:

31A

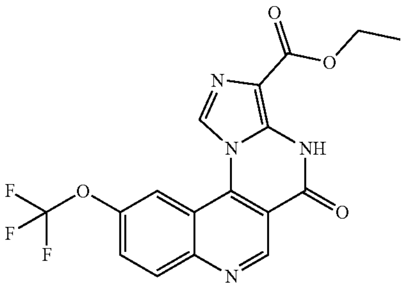

30A

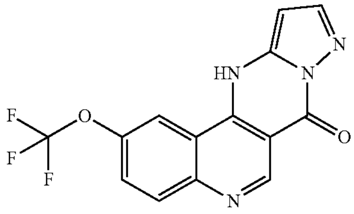

27A

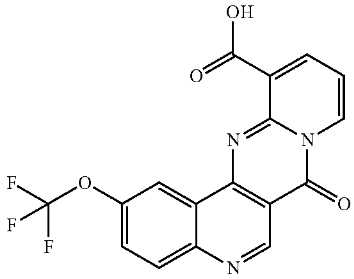

113A

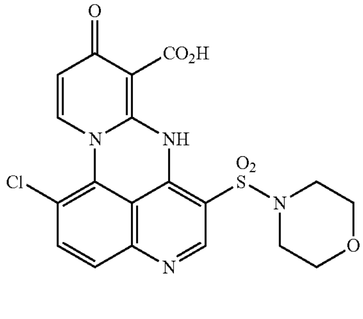

or a pharmaceutically acceptable salt thereof.

Paragraph 52. The compound of paragraph 1, wherein the compound is selected from any one of the following compounds:

31A

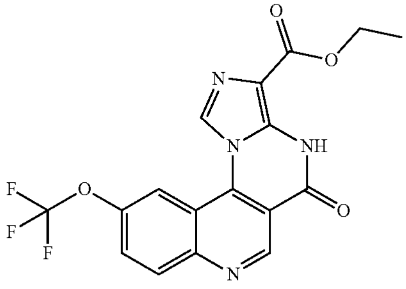

30A

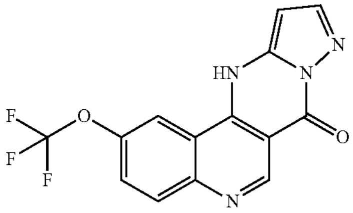

27A

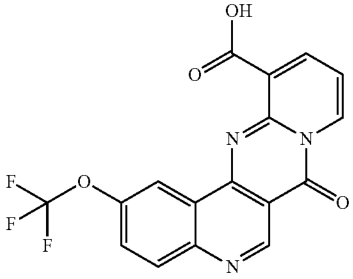

or a pharmaceutically acceptable salt thereof.

Paragraph 53. A compound of Formula (II):

(II)

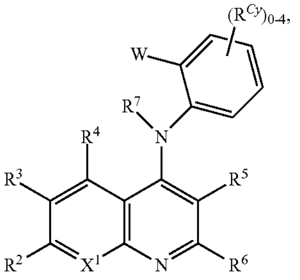

or a pharmaceutically acceptable salt thereof, wherein:

$X^1$ is selected from N and $CR^1$;

$R^1$, $R^2$, $R^3$, $R^4$, $R^5$, and $R^6$ are each independently selected from H, $C_{1-6}$ alkyl, $C_{2-6}$ alkenyl, $C_{2-6}$ alkynyl, $C_{1-4}$ haloalkyl, $Cy^1$, halo, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2R^{b1}$, $S(O)R^{b1}S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, 3, 4, or 5 substituents independently selected from $Cy^1$, halo, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2R^{b1}$, $S(O)_2R^{b1}$, and $S(O)_2NR^{c1}R^{d1}$;

each $Cy^1$ is independently selected from $C_{6-10}$ aryl, 5-10 membered heteroaryl, and 4-7 membered heterocycloalkyl, each of which is optionally substituted with 1, 2, or 3 substituents independently selected from $R^{Cy}$;

$R^7$ is selected from H, $C_{1-3}$ alkyl, $C(O)C_{1-6}$ alkyl, $C(O)OR^{a1}$, $S(O)_2NR^{c1}R^{d1}$, and phenyl, wherein said phenyl is optionally substituted with halo, CN, $OR^{a1}$, $SR^{a1}$, or $NR^{c1}R^{d1}$;

W is a carboxylic acid bioisostere;

$R^{Cy}$ is selected from halo, CN, $NO_2$, $C_{1-6}$ alkyl, $C_{1-6}$ haloalkyl, $C_{2-6}$ alkenyl, $C_{2-6}$ alkynyl, $OR^{a2}$, $C(O)R^{b2}$, $C(OL)NR^{c2}R^{d2}$, $NR^{c2}R^{d2}$, $NR^{c2}C(O)R^{b2}$, $NR^{c2}C(O)OR^{a2}$, $NR^{c2}S(O)_2R^{b2}$, $S(O)_2R^{b2}$, and $S(O)_2NR^{c2}R^{d2}$; wherein said $C_{1-6}$ alkyl, $C_{2-6}$ alkenyl, and $C_{2-6}$ alkynyl are each optionally substituted with 1, 2, or 3 substituents independently selected from halo, CN, $NO_2$, $OR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$, $NR^{c2}C(O)OR^{a2}$, $NR^{c2}S(O)_2R^{b2}$, $S(O)_2R^{b2}$, and $S(O)_2NR^{c2}R^{d2}$;

each $R^{a1}$, $R^{b1}$, $R^{c1}$, $R^{d1}$, $R^{a2}$, $R^{b2}$, $R^{c2}$, and $R^{d2}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$;

or any $R^{c2}$ and $R^{d2}$ together with the N atom to which they are attached form a 4-7 membered heterocycloalkyl, which is optionally substituted with 1, 2, or 3 substituents independently selected from $R^g$;

each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

Paragraph 54. The compound of paragraph 53, wherein:

$R^1$, $R^2$, $R^3$, $R^4$, $R^5$, and $R^6$ are each independently selected from H, $C_{1-6}$ alkyl, $C_{2-6}$ alkenyl, $C_{2-6}$ alkynyl, $C_{1-4}$ haloalkyl, $Cy^1$, halo, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, 3, 4, or 5 substituents independently selected from $Cy^1$, halo, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2R^{b1}$, $S(O)_2R^{b1}$, and $S(O)_2NR^{c1}R^{d1}$; and $R^7$ is selected from H and $C_{1-3}$ alkyl.

Paragraph 55. The compound of paragraph 53 or 54, wherein $R^1$, $R^2$, $R^3$, $R^4$, $R^5$, and $R^6$ are each independently selected from H, $Cy^1$, halo, CN, $OR^{a1}$, $C(O)NR^{c1}R^{d1}$, $C(O)OR^{a1}$, and $S(O)_2NR^{c1}R^{d1}$.

Paragraph 56. The compound of paragraph 53, wherein:

$R^1$, $R^2$, $R^4$, and $R^6$ are each H, and $R^3$ and $R^5$ are each independently selected from $Cy^1$, halo, CN, $OR^{a1}$, $C(O)NR^{c1}R^{d1}$, $C(O)OR^{a1}$, and $S(O)_2NR^{c1}R^{d1}$.

Paragraph 57. The compound of paragraph 53, wherein:

$R^1$, $R^4$, and $R^6$ are each H, $R^2$ is selected from H, $Cy^1$, $OR^{a1}$, $C(O)NR^{c1}R^{d1}$, and halo, $R^3$ is selected from $Cy^1$, $OR^{a1}$, $C(O)NR^{c1}R^{d1}$, and halo, and $R^5$ is selected from $Cy^1$, $C(O)OR^{a1}$, $C(O)NR^{c1}R^{d1}$, $S(O)_2NR^{c1}R^{d1}$, and CN.

Paragraph 58. The compound of paragraph 53, wherein:

$R^1$, $R^2$, $R^4$, and $R^6$ are each H, $R^3$ is selected from $Cy^1$, $OR^{a1}$, $C(O)NR^{c1}R^{d1}$, and halo, and $R^5$ is selected from $Cy^1$, $C(O)OR^{a1}$, $C(O)NR^{c1}R^{d1}$, $S(O)_2NR^{c1}R^{d1}$, and CN.

Paragraph 59. The compound of paragraph 53, wherein:

$R^2$ is selected from H and $OR^{a1}$;

$R^3$ is selected from $C_{1-6}$ alkoxy and $C_{1-6}$ haloalkoxy; and $R^5$ is $C(O)OR^{a1}$.

Paragraph 60. The compound of paragraph 53, wherein:

$R^3$ is $C_{1-6}$haloalkoxy, and $R^5$ is $C(O)OR^{a1}$.

Paragraph 61. The compound of any one of paragraphs 53-58, wherein $Cy^1$ is 5-10 membered heteroaryl, optionally substituted with $R^{Cy}$.

Paragraph 62. The compound of any one of paragraphs 53-59, wherein $R^{a1}$ is selected from H, $C_{1-6}$ alkyl, $C_{1-4}$haloalkyl, 5-10 membered heteroaryl, and 4-10 membered heterocycloalkyl.

Paragraph 63. The compound of any one of paragraphs 53-62, wherein $R^{c1}$ and $R^{d1}$ are each independently selected from H and $C_{1-6}$ alkyl.

Paragraph 64. The compound of any one of paragraphs 53-62, wherein $R^{c1}$ and $R^{d1}$ together with the N atom to which they are attached form a 4-7 membered heterocycloalkyl, which is optionally substituted with $R^g$.

Paragraph 65. The compound of any one of paragraphs 53-64, wherein $R^7$ is H.

Paragraph 66. The compound of paragraph 53, wherein:

$R^1$, $R^2$, $R^3$, $R^4$, $R^5$, and $R^6$ are each independently selected from H, $Cy^1$, halo, CN, $OR^{a1}$, $C(O)NR^{c1}R^{d1}$, $C(O)OR^{a1}$, and $S(O)_2NR^{c1}R^{d1}$;

$Cy^1$ is selected from $C_{6-10}$ aryl and 5-10 membered heteroaryl, each of which is optionally substituted with 1 or 2 substituents independently selected from $R^{Cy}$;

$R^{a1}$ is selected from H, $C_{1-6}$ alkyl, $C_{1-4}$ haloalkyl, 5-10 membered heteroaryl, and 4-10 membered heterocycloalkyl;

$R^{c1}$ and $R^{d1}$ are each independently selected from H and $C_{1-6}$ alkyl; or $R^{c1}$ and $R^{d1}$ together with the N atom to which they are attached form a 4-7 membered heterocycloalkyl, which is optionally substituted with $R^g$; and $R^7$ is H.

Paragraph 67. The compound of paragraph 53, wherein:

$R^1$, $R^2$, $R^4$, and $R^6$ are each H;

$R^3$ and $R^5$ are each independently selected from $Cy^1$, halo, CN, $OR^{a1}$, $C(O)NR^{c1}R^{d1}$, $C(O)OR^{a1}$, and $S(O)_2NR^{c1}R^{d1}$;

$Cy^1$ is 5-10 membered heteroaryl, optionally substituted with $R^{Cy}$;

$R^{a1}$ is selected from H, $C_{1-6}$ alkyl, $C_{1-4}$ haloalkyl, 5-10 membered heteroaryl, and 4-10 membered heterocycloalkyl;

$R^{c1}$ and $R^{d1}$ are each independently selected from H and $C_{1-6}$ alkyl; or $R^{c1}$ and $R^{d1}$ together with the N atom to which they are attached form a 4-7 membered heterocycloalkyl, which is optionally substituted with $R^g$; and $R^7$ is H.

Paragraph 68. The compound of paragraph 53, wherein:

$R^1$, $R^2$, $R^4$, and $R^6$ are each H, $R^3$ is $C_{1-6}$ haloalkoxy, $R^5$ is $C(O)OR^{a1}$, $R^{a1}$ is selected from H and $C_{1-6}$ alkyl; and $R^7$ is H.

Paragraph 69. The compound of any one of paragraph 53-68, wherein W is selected from any one of the following moieties:

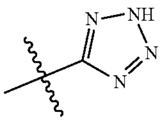
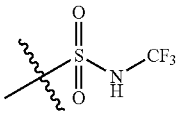
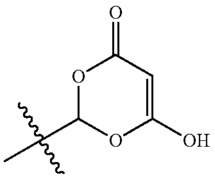
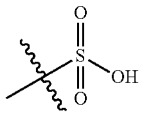
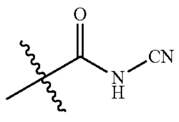
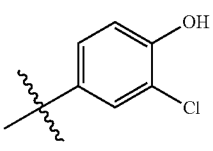
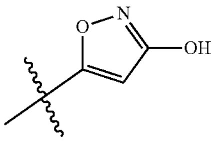
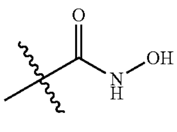
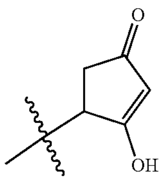

Paragraph 70. The compound of paragraph 53, wherein the compound of Formula (II) is selected from any one of the following compounds:

10A

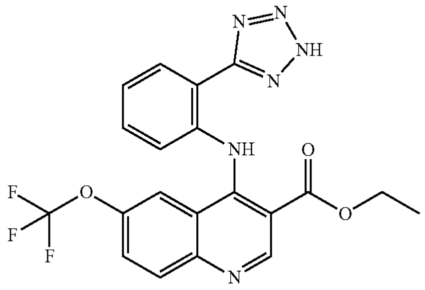

11

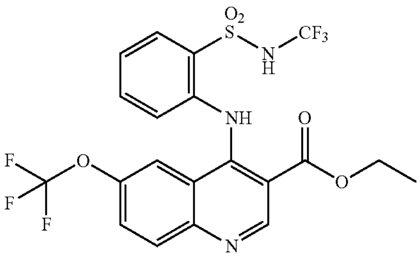

34A

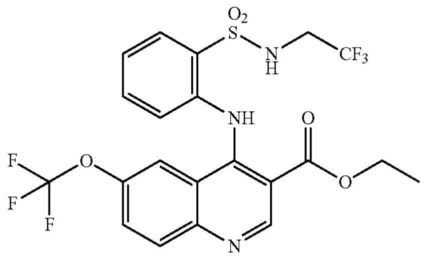

or a pharmaceutically acceptable salt thereof.

Paragraph 71. The compound of paragraph 53 wherein the compound of Formula (II) is selected from any one of the following compounds:

10A

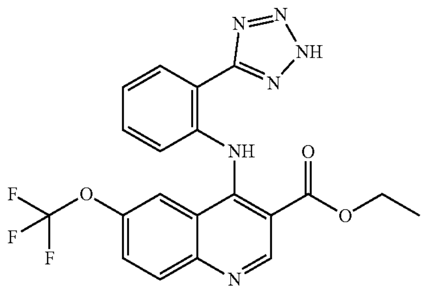

-continued

11

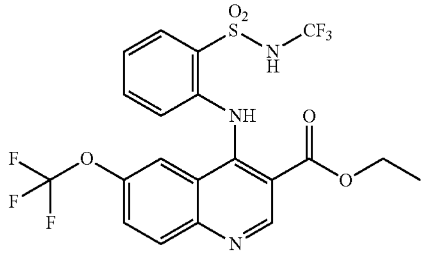

or a pharmaceutically acceptable salt thereof.

Paragraph 72. A compound of Formula (III):

(III)

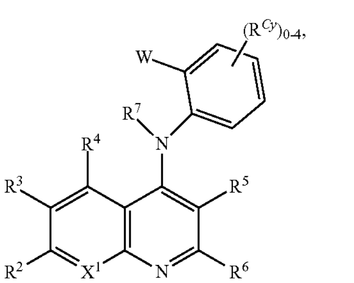

or a pharmaceutically acceptable salt thereof, wherein:

$X^1$ is selected from N and $CR^1$;

$R^1$, $R^2$, $R^3$, $R^4$, and $R^6$ are each independently selected from H, $C_{1-6}$ alkyl, $C_{2-6}$ alkenyl, $C_{2-6}$ alkynyl, $C_{1-4}$ haloalkyl, $Cy^1$, halo, CN, $NO_2$, $OR^{a1}$, $SR^{a1}$, $C(O)R^{b1}C(O)NR^{c1}R^{d1}$, $C(O)OR^{a1}$, $NR^{c1}R^{d1}$, $NR^{c1}C(O)R^{b1}$, $NR^{c1}S(O)_2R^{b1}$, $S(O)R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, 3, 4, or 5 substituents independently selected from $Cy^1$, halo, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2R^{b1}$, $S(O)_2R^{b1}$, and $S(O)_2NR^{c1}R^{d1}$;

$R^5$ is selected from $C(O)NR^{c1}R^{d1}$, $S(O)_2NR^{c1}R^{d1}$, and $Cy^1$;

each $Cy^1$ is independently selected from $C_{6-10}$ aryl, $C_{3-10}$cycloalkyl, 5-10 membered heteroaryl, and 4-7 membered heterocycloalkyl, each of which is optionally substituted with 1, 2, or 3 substituents independently selected from $R^{Cy}$;

$R^7$ is selected from H, $C_{1-3}$ alkyl, $C(O)C_{1-6}$ alkyl, $C(O)OR^{a1}$, $S(O)_2NR^{c1}R^{d1}$, and phenyl, wherein said phenyl is optionally substituted with halo, CN, OR, $SR^{a1}$, or $NR^{c1}R^{d1}$;

W is selected from $C(O)OR^{a2}$ and a carboxylic acid bioisostere;

$R^{Cy}$ is selected from halo, CN, $NO_2$, $C_{1-6}$ alkyl, $C_{1-6}$ haloalkyl, $C_{2-6}$ alkenyl, $C_{2-6}$ alkynyl, $C_{3-10}$ cycloalkyl, 5-10 membered heteroaryl, 4-6 membered heterocycloalkyl, $OR^{a2}$, $C(O)R^{b2}$, $C(O)OR^{a2}$, $C(O)NR^{c2}R^{d2}$, $C(O)NR^{c1}S(O)_2R^{b2}$, $NR^{c2}R^{d2}$, $NR^{c2}C(O)R^{b2}$, $NR^{c2}C(O)OR^{a2}$, $NR^{c2}S(O)_2R^{b2}$, $OC(O)R^{b1}$, $S(O)_2R^{b2}$, and $S(O)_2NR^{c2}R^{d2}$; wherein said $C_{1-6}$ alkyl, $C_{2-6}$ alkenyl, $C_{2-6}$ alkynyl, $C_{3-10}$ cycloalkyl, and 4-6 membered heterocycloalkyl are each optionally substituted with 1, 2, or 3 substituents independently selected from halo, CN, $NO_2$, $OR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$, $NR^{c2}C(O)OR^{a2}$, $NR^{c2}S(O)_2R^{b2}$, $S(O)_2R^{b2}$, and $S(O)_2NR^{c2}R^{d2}$;

each $R^{a1}$, $R^{b1}$, $R^{c1}$, $R^{d1}$, $R^{a2}$, $R^{b2}$, $R^{c2}$, and $R^{d2}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-10 membered heterocycloalkyl or 5-10 membered heteroaryl, each of which is optionally substituted with 1, 2, or 3 substituents independently selected from W;

or any $R^{c2}$ and $R^{d2}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{6-10}$ aryl-$C_{1-6}$ alkoxycarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

Paragraph 73. The compound of paragraph 72, wherein: each $Cy^1$ is independently selected from $C_{6-10}$ aryl, 5-10 membered heteroaryl, and 4-7 membered heterocycloalkyl, each of which is optionally substituted with 1, 2, or 3 substituents independently selected from $R^{Cy}$;

$R^{Cy}$ is selected from halo, CN, $NO_2$, $C_{1-6}$ alkyl, $C_{1-6}$ haloalkyl, $C_{2-6}$ alkenyl, $C_{2-6}$ alkynyl, $OR^{a2}$, $C(O)R^{b2}$, $C(O)OR^{a2}$, $C(O)NR^{c2}R^{d2}$, $NR^{c2}R^{d2}$, $NR^{c2}C(O)R^{b2}$, $NR^{c2}C(O)OR^{a2}$, $NR^{c2}S(O)_2R^{b2}$, $S(O)_2R^{b2}$, and $S(O)_2NR^{c2}R^{d2}$; wherein said $C_{1-6}$ alkyl, $C_{2-6}$ alkenyl, $C_{2-6}$ alkynyl, are each optionally substituted with 1, 2, or 3 substituents independently selected from halo, CN, $NO_2$, $OR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$, $NR^{c2}C(O)OR^{a2}$, $NR^{c2}S(O)_2R^{b2}$, $S(O)_2R^{b2}$, and $S(O)_2NR^{c2}R^{d2}$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl) aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

Paragraph 74. The compound of paragraph 72 or 73, wherein:

$R^1$, $R^2$, $R^3$, $R^4$, and $R^6$ are each independently selected from H, $C_{1-6}$ alkyl, $C_{2-6}$ alkenyl, $C_{2-6}$ alkynyl, $C_{1-4}$ haloalkyl, $Cy^1$, halo, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, 3, 4, or 5 substituents independently selected from $Cy^1$, halo, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2R^{b1}$, $S(O)_2R^{b1}$, and $S(O)_2NR^{c1}R^{d1}$; and $R^7$ is selected from H and $C_{1-3}$ alkyl.

Paragraph 75. The compound of paragraph 74, wherein $R^1$, $R^2$, $R^3$, $R^4$, and $R^6$ are each independently selected from H, $Cy^1$, halo, CN, $OR^{a1}$, $C(O)NR^{c1}R^{d1}$, $C(O)OR^{a1}$, and $S(O)_2NR^{c1}R^{d1}$.

Paragraph 76. The compound of paragraph 75, wherein:

$R^1$, $R^4$, and $R^6$ are each H, $R^2$ is selected from H, $Cy^1$, halo, CN, $OR^{a1}$, $C(O)NR^{c1}R^{d1}$, $C(O)OR^{a1}$, and $S(O)_2NR^{c1}R^{d1}$, and $R^3$ is selected from $Cy^1$, halo, CN, $OR^{a1}$, $C(O)NR^{c1}R^{d1}$, $C(O)OR^{a1}$, and $S(O)_2NR^{c1}R^{d1}$.

Paragraph 77. The compound of paragraph 76, wherein:

$R^1$, $R^4$, and $R^6$ are each H;

$R^2$ is selected from H and $OR^{a1}$; and $R^3$ is selected from $Cy^1$, $OR^{a1}$, and halo.

Paragraph 78. The compound of paragraph 76, wherein:

$R^1$, $R^2$, $R^4$, and $R^6$ are each H, and $R^3$ is selected from $Cy^1$, halo, CN, $OR^{a1}$, $C(O)NR^{c1}R^{d1}$, $C(O)OR^{a1}$, and $S(O)_2NR^{c1}R^{d1}$.

Paragraph 79. The compound of paragraph 78, wherein $R^3$ is selected from $Cy^1$, $OR^{a1}$, $C(O)NR^{c1}R^{d1}$, and halo.

Paragraph 80. The compound of paragraph 76, wherein:

$R^2$ is selected from H and $OR^{a1}$; and $R^3$ is selected from $C_{1-6}$ alkoxy and $C_{1-6}$ haloalkoxy.

Paragraph 81. The compound of paragraph 72, wherein $R^3$ is $C_{1-6}$ haloalkoxy.

Paragraph 82. The compound of any one of paragraphs 72-81, wherein $R^5$ is $C(O)NR^{c1}R^{d1}$.

Paragraph 83. The compound of any one of paragraphs 72-81, wherein $R^5$ is $S(O)_2NR^{c1}R^{d1}$.

Paragraph 84. The compound of any one of paragraphs 72-81, wherein $R^5$ is $Cy^1$.

Paragraph 85. The compound of any one of paragraphs 72-84, wherein $Cy^1$ is 5-10 membered heteroaryl, optionally substituted with $R^{Cy}$.

Paragraph 86. The compound of any one of paragraphs 72-85, wherein $R^{a1}$ is selected from H, $C_{1-6}$ alkyl, $C_{1-4}$haloalkyl, 5-10 membered heteroaryl, and 4-10 membered heterocycloalkyl.

Paragraph 87. The compound of any one of paragraphs 72-86, wherein $R^{c1}$ and $R^{d1}$ are each independently selected from H and $C_{1-6}$ alkyl.

Paragraph 88. The compound of paragraph 87, wherein $R^{c1}$ and $R^{d1}$ are both $C_{1-6}$ alkyl.

Paragraph 89. The compound of any one of paragraphs 72-88, wherein $R^{c1}$ and $R^{d1}$ together with the N atom to which they are attached form a 4-7 membered heterocycloalkyl, which is optionally substituted with $R^g$.

Paragraph 90. The compound of any one of paragraphs 72-89, wherein $R^7$ is H.

Paragraph 91. The compound of any one of paragraphs 72-90, wherein W is $C(O)OR^{a2}$.

Paragraph 92. The compound of paragraph 91, wherein Rae is selected from H and $C_{1-6}$ alkyl.

Paragraph 93. The compound of any one of paragraphs 72-90, wherein W is selected from any one of the following moieties:

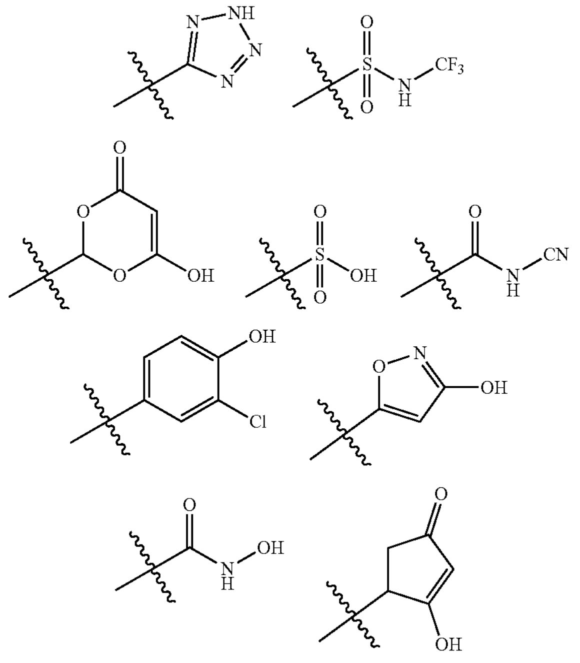

Paragraph 94. The compound of paragraph 72, wherein the compound of Formula (III) is selected from any one of the following compounds:

13A

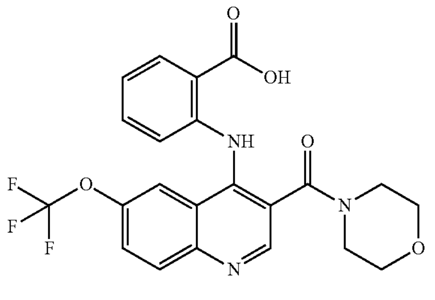

-continued
14A
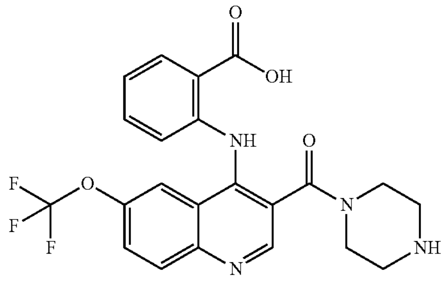
12A
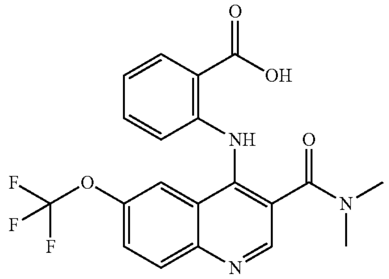
16A
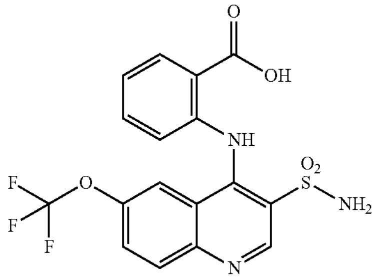
17A
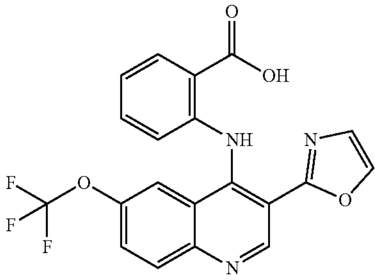
53A
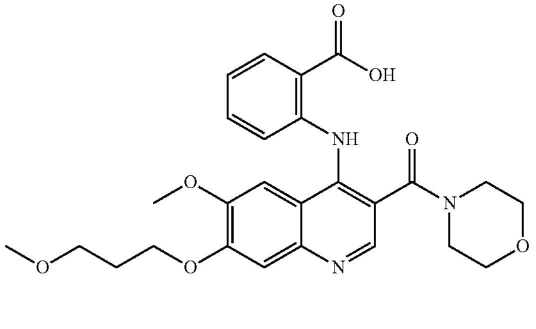
-continued
57A
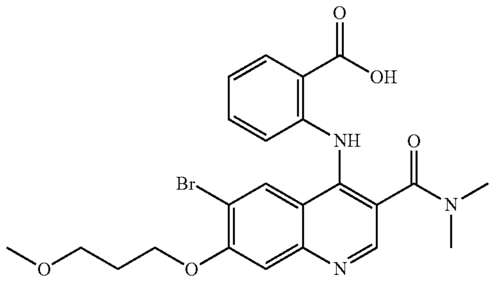
58A
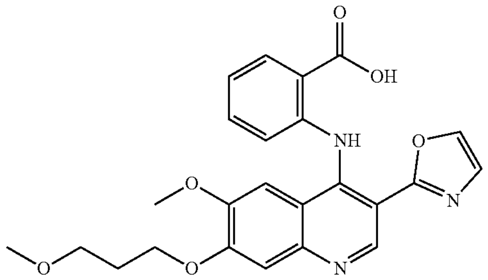
61A
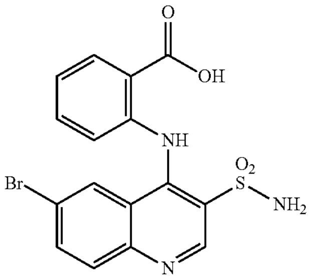
63A
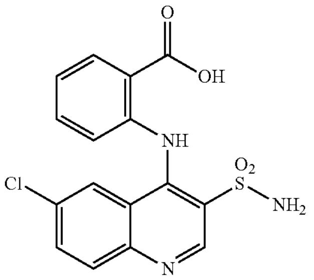
64A
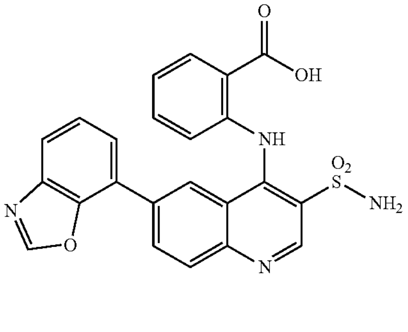

-continued
70A
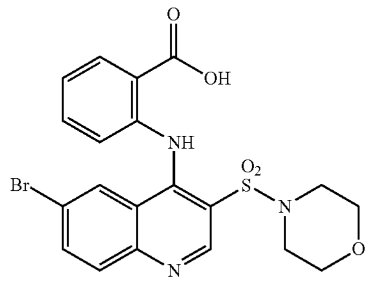
78A
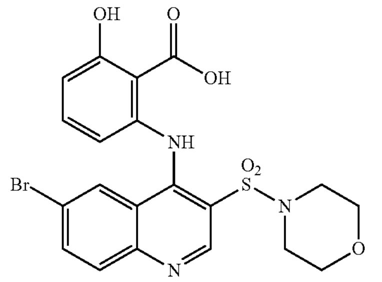
78A-BR
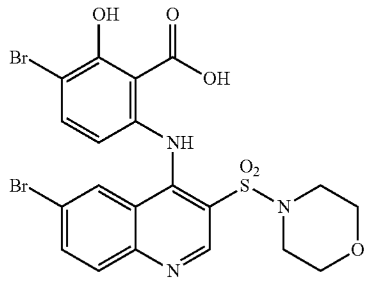
78A-INT
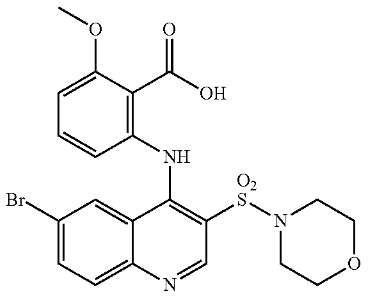
79A
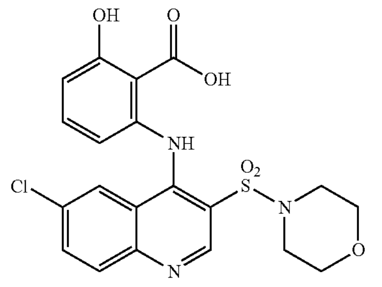
-continued
79A-INT
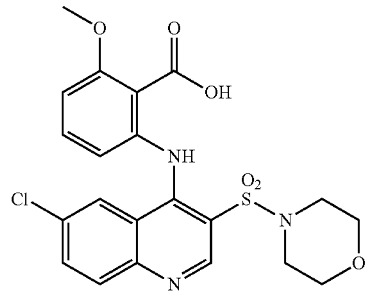
80A
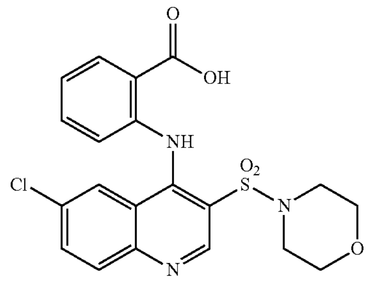
81A
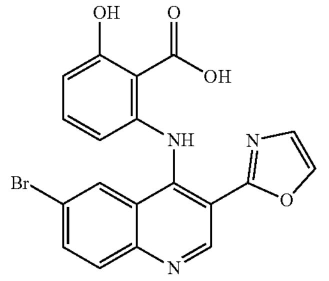
81A-INT
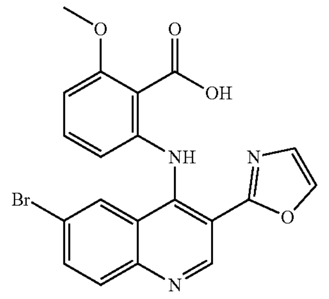
82A
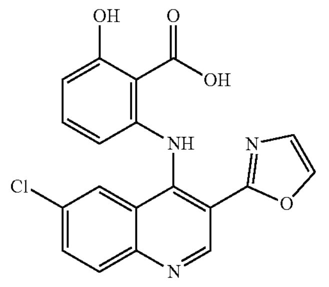

-continued
85A
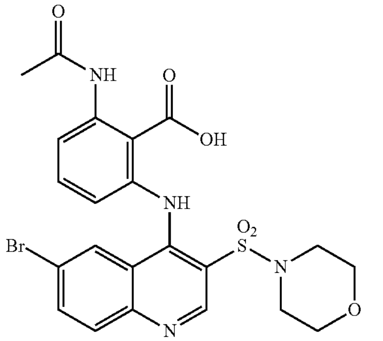
85A-BP
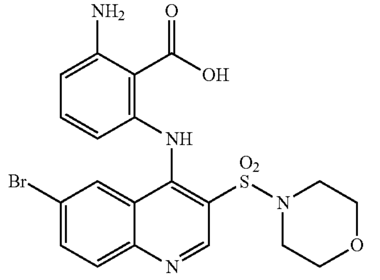
86A
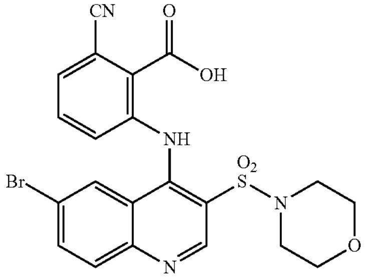
93A
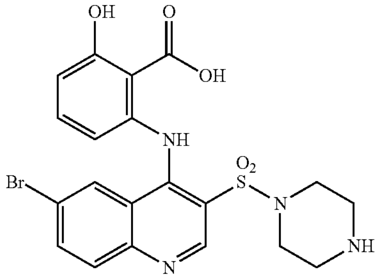
93A-INT
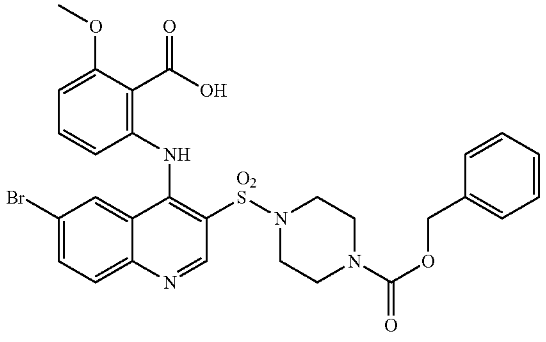
or a pharmaceutically acceptable salt thereof.
Paragraph 95. The compound of paragraph 72, wherein the compound of Formula (III) is selected from any one of the following compounds:
13A
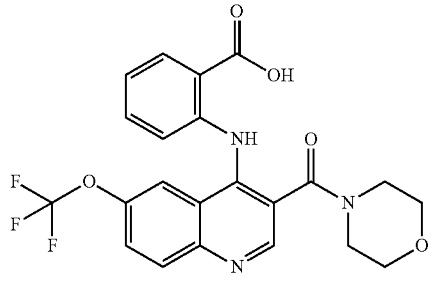
14A
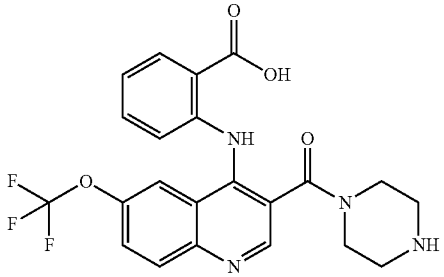
12A
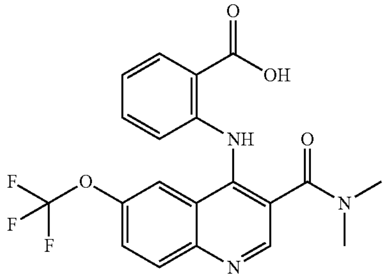
16A
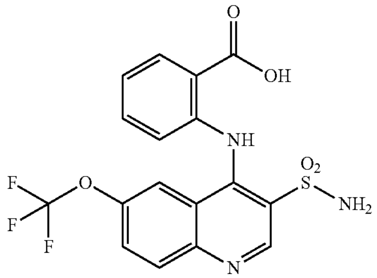
17A
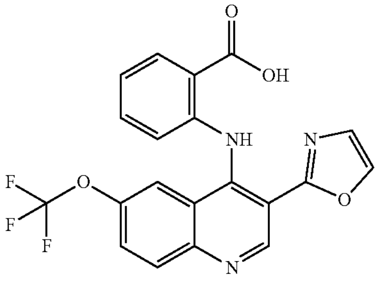
or a pharmaceutically acceptable salt thereof.

Paragraph 96. The compound of paragraph 72, wherein the compound of Formula (III) is selected from any one of the following compounds:
87A
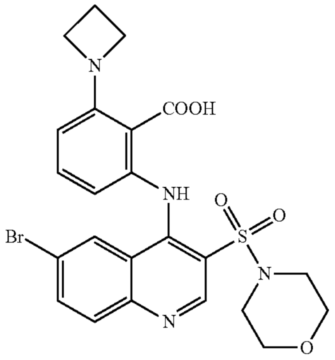
96A
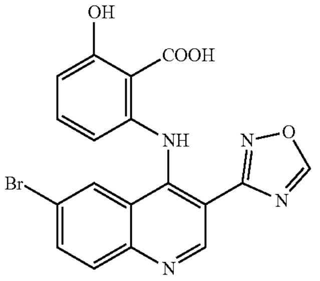
97A
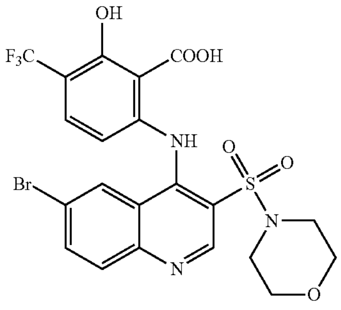
88A
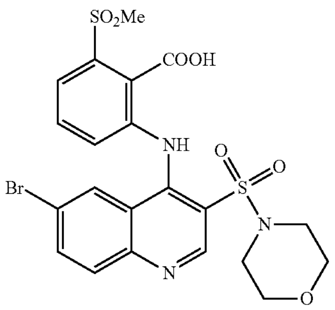
-continued
89A
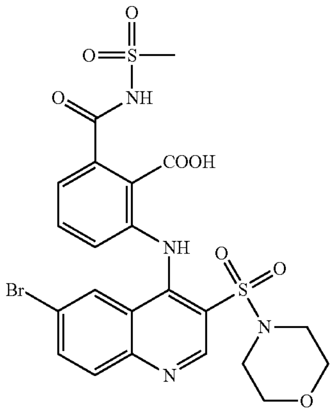
90A
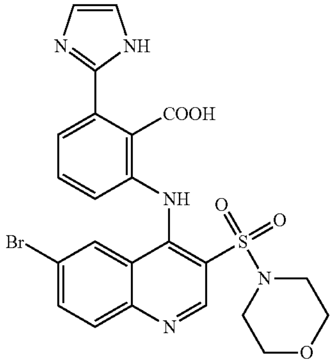
91A
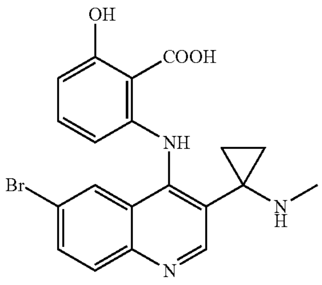
94A
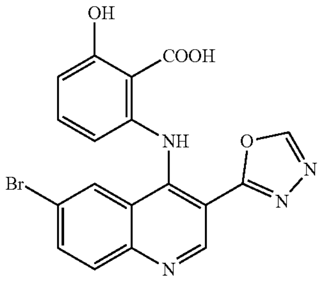
95A
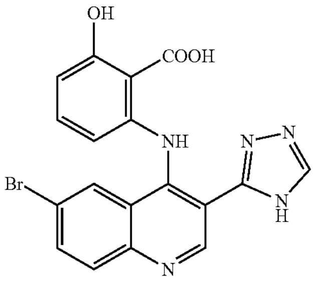

-continued
92A
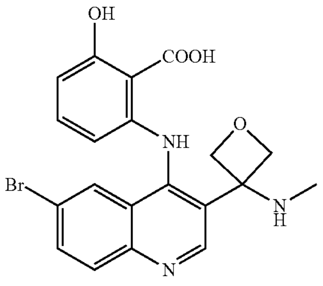
98A
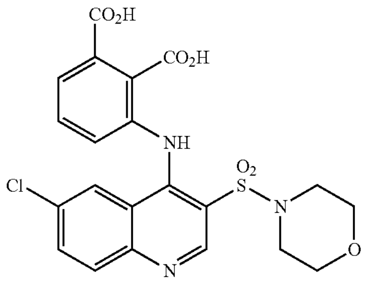
99A
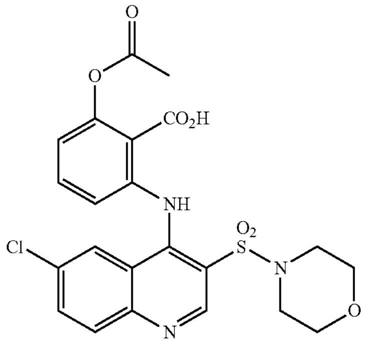
100A
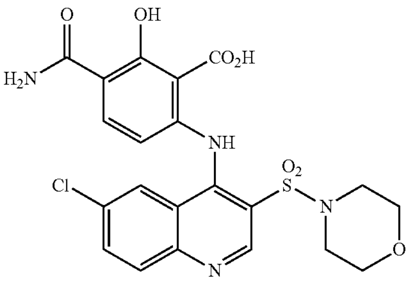
101A
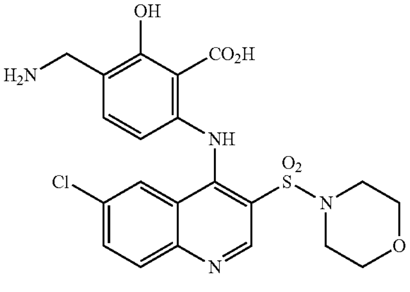
-continued
102A
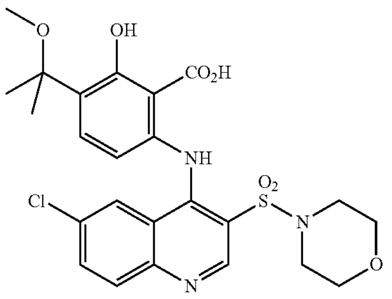
103A
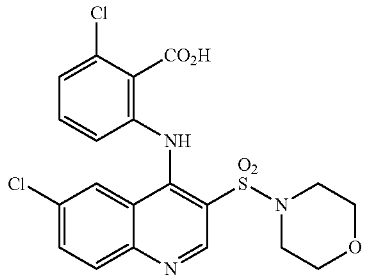
107A
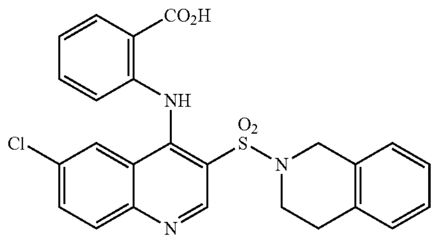
108A
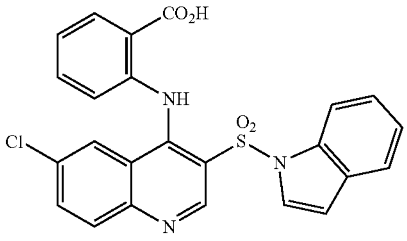
109A
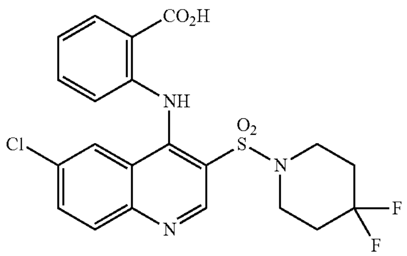
110A
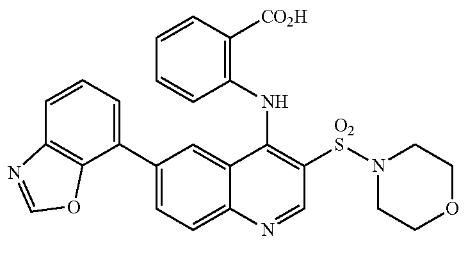

111A

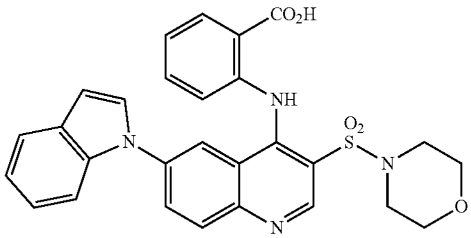

112A

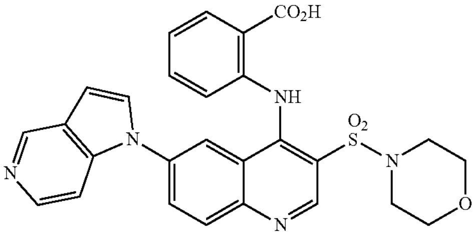

114A

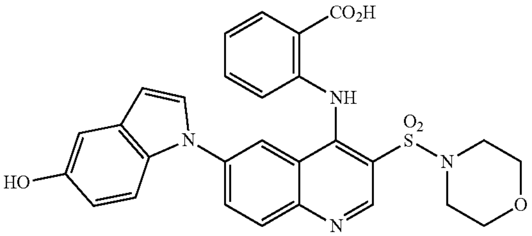

115A

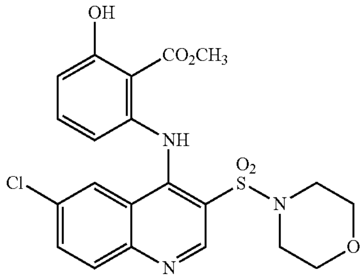

118A

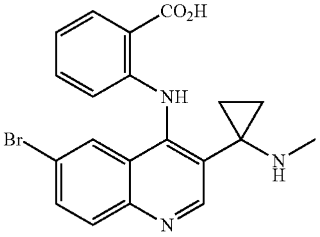

119A

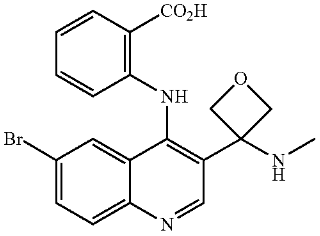

120A

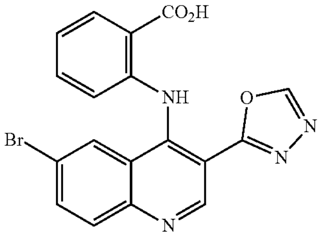

121A

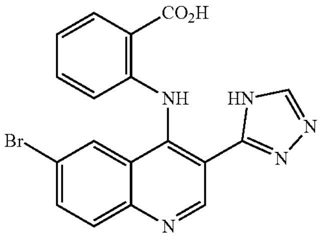

122A

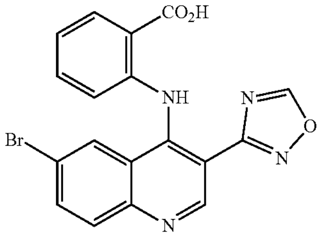

123A

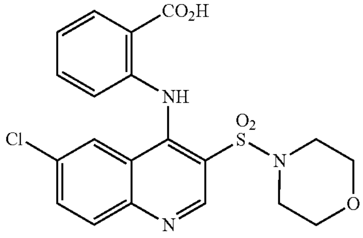

or a pharmaceutically acceptable salt thereof.

Paragraph 97. A compound of Formula (IV):

(IV)

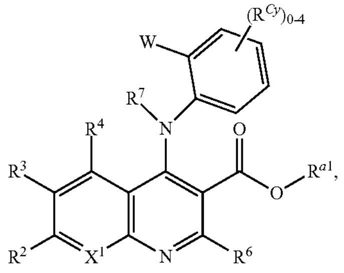

or a pharmaceutically acceptable salt thereof, wherein:

$X^1$ is selected from N and $CR^1$;

$R^1$, $R^2$, $R^4$, and $R^6$ are each independently selected from H, $C_{1-6}$ alkyl, $C_{2-6}$ alkenyl, $C_{2-6}$ alkynyl, $C_{1-4}$ haloalkyl, $Cy^1$, halo, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2R^{b1}$, $S(O)_2R^{b1}$, $S(O)_2NR^{c1}R^{d1}$; wherein said $C_{1-6}$ alkyl, $C_{2-6}$ alkenyl, and $C_{2-6}$ alkynyl are each optionally substituted with 1, 2, 3, 4, or 5 substituents independently selected from $Cy^1$, halo, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2R^{b1}$, $S(O)_2R^{b1}$, and $S(O)_2NR^{c1}R^{d1}$;

$R^3$ is selected from $C(O)Cy^1$, $OCy^1$, and $Cy^1$;

each $Cy^1$ is independently selected from 5-10 membered heteroaryl and 4-7 membered heterocycloalkyl, each of which is optionally substituted with 1, 2, or 3 substituents independently selected from $R^{Cy}$;

$R^7$ is selected from H and $C_{1-3}$ alkyl;

W is selected from $C(O)OR^{a2}$ and a carboxylic acid bioisostere;

$R^{Cy}$ is selected from halo, CN, $NO_2$, $C_{1-6}$ alkyl, $C_{1-6}$ haloalkyl, $C_{2-6}$ alkenyl, $C_{2-6}$ alkynyl, $OR^{a2}$, $C(O)R^{b2}$, $C(O)OR^{a2}$, $C(O)NR^{c2}R^{d2}$, $NR^{c2}R^{d2}$, $NR^{c2}C(O)R^{b}$, $NR^{c2}C(O)OR^{a2}$, $NR^{c2}S(O)_2R^{b2}$, $S(O)_2R^{b2}$, and $S(O)_2NR^{c2}R^{d2}$; wherein said $C_{1-6}$ alkyl, $C_{2-6}$ alkenyl, and $C_{2-6}$ alkynyl are each optionally substituted with 1, 2, or 3 substituents independently selected from halo, CN, $NO_2$, $OR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$, $NR^{c2}C(O)OR^{a2}$, $NR^{c2}S(O)_2R^{b2}$, $S(O)_2R^{b2}$, and $S(O)_2NR^{c2}R^{d2}$;

each $R^{a1}$, $R^{b1}$, $R^{c1}$, $R^{d1}$, $R^{a2}$, $R^{b2}$, $R^{c2}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$;

or any $R^{c2}$ and $R^{d2}$ together with the N atom to which they are attached form a 4-7 membered heterocycloalkyl, which is optionally substituted with 1, 2, or 3 substituents independently selected from $R^g$;

each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$alkyl)aminocarbonylamino.

Paragraph 98. The compound of paragraph 97, wherein $R^1$, $R^2$, $R^4$, and $R^6$ are each independently selected from H, $Cy^1$, halo, CN, $OR^{a1}$, $C(O)NR^{c1}R^{d1}$, $C(O)OR^{a1}$, and $S(O)_2NR^{c1}R^{d1}$.

Paragraph 99. The compound of paragraph 97, wherein $R^1$, $R^2$, $R^4$, and $R^6$ are each H.

Paragraph 100. The compound of any one of paragraphs 97-99, wherein $R^3$ is $C(O)Cy^1$.

Paragraph 101. The compound of any one of paragraphs 97-99, wherein $R^3$ is $OCy^1$.

Paragraph 102. The compound of any one of paragraphs 97-99, wherein $R^3$ is $Cy^1$.

Paragraph 103. The compound of any one of paragraphs 97-102, wherein $Cy^1$ is 5-10 membered heteroaryl, optionally substituted with $R^{Cy}$.

Paragraph 104. The compound of paragraph 103, wherein $Cy^1$ is indolyl, optionally substituted with $R^{Cy}$.

Paragraph 105. The compound of any one of paragraphs 97-102, wherein $Cy^1$ is 4-7 membered heterocycloalkyl, optionally substituted with $R^{Cy}$.

Paragraph 106. The compound of paragraph 105, wherein $Cy^1$ is selected from piperidine and piperazine, each of which is optionally substituted with $R^{Cy}$.

Paragraph 107. The compound of any one of paragraphs 97-106, wherein $R^{a1}$ is selected from H and $C_{1-6}$ alkyl.

Paragraph 108. The compound of any one of paragraphs 97-106, wherein $R^{c1}$ and $R^{d1}$ are each independently selected from H and $C_{1-6}$ alkyl.

Paragraph 109. The compound of any one of paragraphs 97-106, wherein $R^{c1}$ and $R^{d1}$ together with the N atom to which they are attached form a 4-7 membered heterocycloalkyl, which is optionally substituted with $R^g$.

Paragraph 110. The compound of any one of paragraphs 97-109, wherein $R^7$ is H.

Paragraph 111. The compound of any one of paragraphs 97-110, wherein W is $C(O)OR^{a2}$.

Paragraph 112. The compound of paragraph 111, wherein $R^{a2}$ is selected from H and $C_{1-6}$ alkyl.

Paragraph 113. The compound of any one of paragraphs 97-110, wherein W is selected from any one of the following moieties:

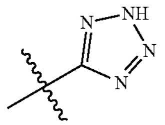

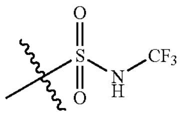

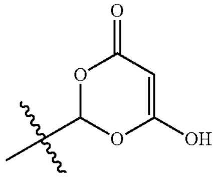

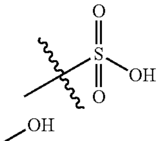

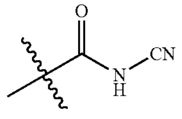

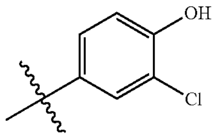

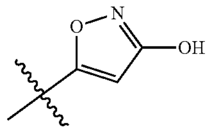

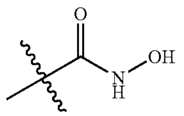

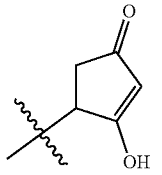

Paragraph 114. The compound of paragraph 97, wherein the compound is selected from any one of the following compounds:
23A
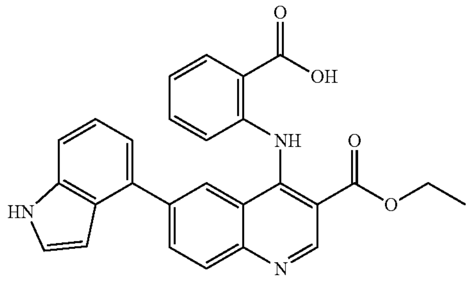
18A
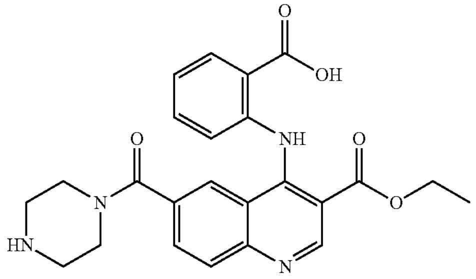
29A
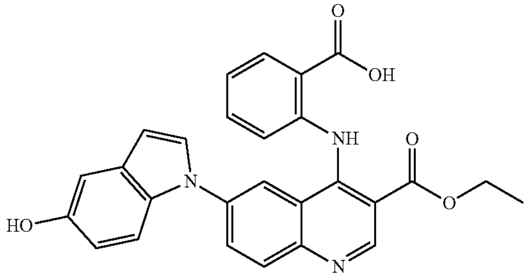
19A
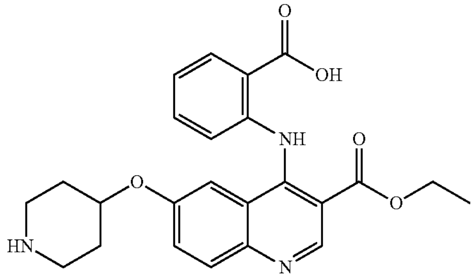
20
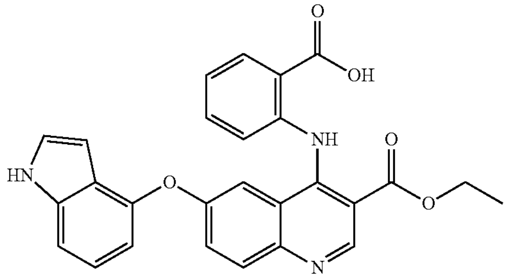
-continued
21
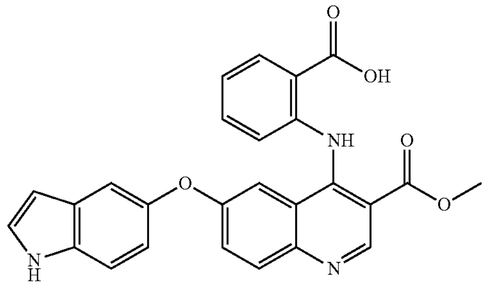
or a pharmaceutically acceptable salt thereof.
Paragraph 115. A compound selected from any one of the following compounds:
26A
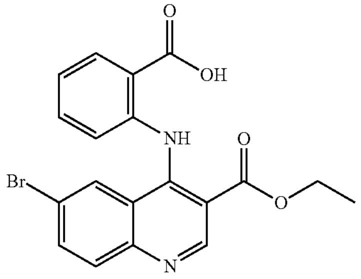
25A
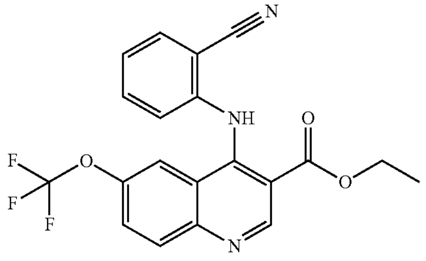
24
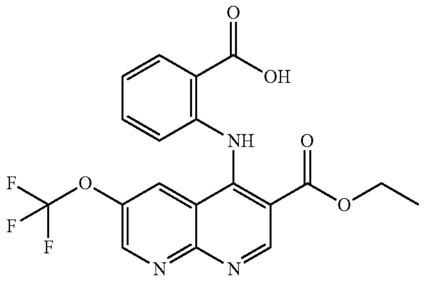
or a pharmaceutically acceptable salt thereof.

Paragraph 116. A compound of Formula (V):

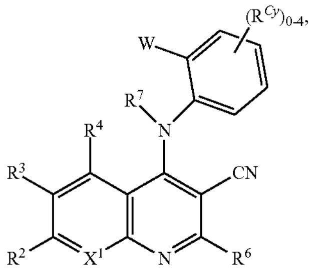

(V)

or a pharmaceutically acceptable salt thereof, wherein:

$X^1$ is selected from N and $CR^1$;

$R^1$, $R^2$, $R^3$, $R^4$, and $R^6$ are each independently selected from H, $C_{1-6}$ alkyl, $C_{2-6}$ alkenyl, $C_{2-6}$ alkynyl, $C_{1-4}$ haloalkyl, $C(O)Cy^1$, $OCy^1$, $Cy^1$, halo, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2R^{b1}$, $S(O)_2R^{b1}$, $S(O)_2NR^{c1}R^{d1}$; wherein said $C_{1-6}$ alkyl, $C_{2-6}$ alkenyl, and $C_{2-6}$ alkynyl are each optionally substituted with 1, 2, 3, 4, or 5 substituents independently selected from $Cy^1$, halo, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2R^{b1}$, $S(O)_2R^{b1}$, and $S(O)_2NR^{c1}R^{d1}$;

each $Cy^1$ is independently selected from 5-10 membered heteroaryl and 4-7 membered heterocycloalkyl, each of which is optionally substituted with 1, 2, or 3 substituents independently selected from $R^{Cy}$;

$R^7$ is selected from H and $C_{1-3}$ alkyl;

or $R^7$ and the phenyl group together with the N atom to which they are attached form a 5-10 membered heteroaryl ring or a 4-7 membered heterocycloalkyl ring, each of which is optionally substituted with 1, 2, or 3 substituents independently selected from W and $R^{Cy}$;

W is selected from $C(O)OR^{a2}$ and a carboxylic acid bioisostere;

RC' is selected from halo, CN, $NO_2$, $C_{1-6}$ alkyl, $C_{1-6}$ haloalkyl, $C_{2-6}$ alkenyl, $C_{2-6}$ alkynyl, $OR^{a2}$, $C(O)R^{b2}$, $C(O)OR^{a2}$, $C(O)NR^{c2}R^{d2}$, $NR^{c2}R^{d2}$, $NR^{c2}C(O)R^{b2}$, $NR^{c2}C(O)OR^{a2}$, $NR^{c2}S(O)_2R^{b2}$, $S(O)_2R^{b2}$, and $S(O)_2NR^{c2}R^{c2}$; wherein said $C_{1-6}$ alkyl, $C_{2-6}$ alkenyl, and $C_{2-6}$ alkynyl are each optionally substituted with 1, 2, or 3 substituents independently selected from halo, CN, $NO_2$, $OR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$, $NR^{c2}C(O)OR^{a2}$, $NR^{c2}S(O)_2R^{b2}$, $S(O)_2R^{b2}$, and $S(O)_2NR^{c2}R^{d2}$;

each $R^{a1}$, $R^{b1}$, $R^{c1}$, $R^{d1}$, $R^{a2}$, $R^{b2}$, $R^{c2}$, and $R^{d2}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$;

or any $R^{c2}$ and $R^{d2}$ together with the N atom to which they are attached form a 4-7 membered heterocycloalkyl, which is optionally substituted with 1, 2, or 3 substituents independently selected from $R^g$;

each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

Paragraph 117. The compound of paragraph 116, wherein $R^1$, $R^2$, $R^3$, $R^4$, and $R^6$ are each independently selected from H, $Cy^1$, halo, CN, $OR^{a1}$, $C(O)NR^{c1}R^{d1}$, $C(O)OR^{a1}$, and $S(O)_2NR^{c1}R^{d1}$.

Paragraph 118. The compound of paragraph 116, wherein:

$R^1$, $R^4$, and $R^6$ are each H;

$R^2$ is selected from H and $OR^{a1}$; and $R^3$ is selected from $Cy^1$ and $OR^{a1}$.

Paragraph 119. The compound of any one of paragraphs 116-118, wherein $R^{a1}$ is selected from $C_{1-6}$ alkyl and $C_{1-6}$ haloalkyl.

Paragraph 120. The compound of any one of paragraphs 116-119, wherein $R^7$ is H.

Paragraph 121. The compound of any one of paragraphs 116-120, wherein W is $C(O)OR^{a2}$.

Paragraph 122. The compound of paragraph 121, wherein $R^{a2}$ is selected from H and $C_{1-6}$ alkyl.

Paragraph 123. The compound of any one of paragraphs 116-122, wherein W is a carboxylic acid bioisostere selected from any one of the following moieties:

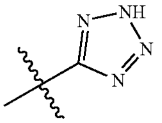
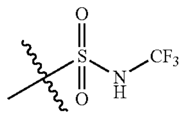
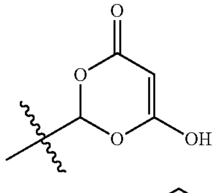
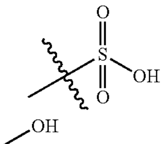
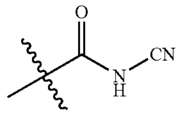
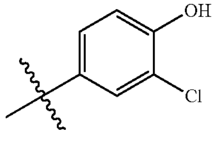
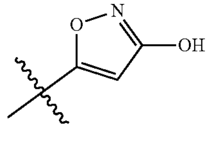

-continued

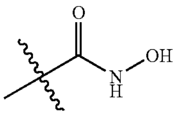

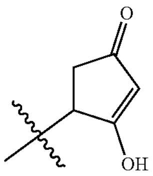

or a pharmaceutically acceptable salt thereof.

Paragraph 124. The compound of paragraph 116, wherein the compound of Formula (V) is selected from any one of the following compounds:

15A

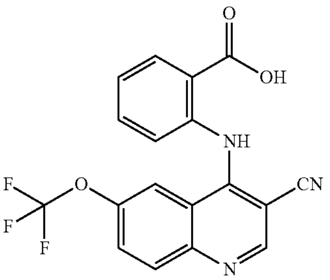

54A

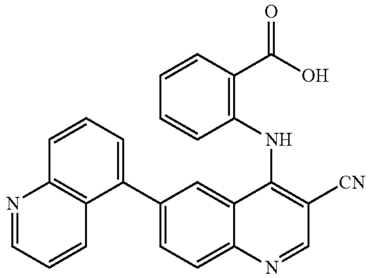

51A

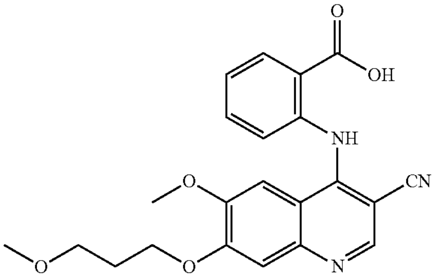

55A

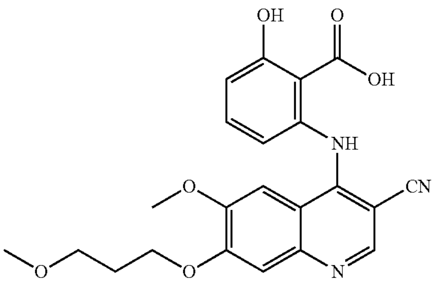

-continued

56A

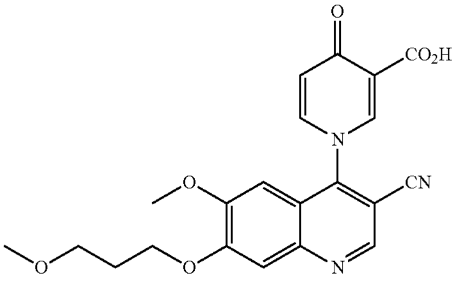

or a pharmaceutically acceptable salt thereof.

Paragraph 125. A pharmaceutical composition comprising a compound of any one of paragraphs 1-124, or a pharmaceutically acceptable salt thereof, and a pharmaceutically acceptable carrier.

Paragraph 126. A method of treating or preventing a disease or condition selected from: a disorder associated with telomere or telomerase dysfunction, a disorder associated with aging, a pre-leukemic or pre-cancerous condition, an HBV infection, a neurodevelopmental disorder, and an acquired or genetic disease or condition associated with alterations in RNA, the method comprising administering to a subject in need thereof a therapeutically effective amount of a compound of any one of paragraphs 1-124, or a pharmaceutically acceptable salt, or a pharmaceutical composition of paragraph 125.

Paragraph 127. The method of paragraph 126, wherein the disorder associated with telomere or telomerase dysfunction is dyskeratosis congenita, aplastic anemia, pulmonary fibrosis, myelodysplastic syndrome, idiopathic pulmonary fibrosis, hematological disorder, or hepatic fibrosis.

Paragraph 128. The method of paragraph 126, wherein the disorder associated with aging is macular degeneration, diabetes mellitus, osteoarthritis, rheumatoid arthritis, sarcopenia, cardiovascular disease, hypertension, atherosclerosis, coronary artery disease, ischemia/reperfusion injury, cancer, premature death, or age-related decline in cognitive function, cardiopulmonary function, muscle strength, vision, or hearing.

Paragraph 129. The method of paragraph 126, wherein the neurodevelopmental disorder is pontocerebellar hypoplasia.

Paragraph 130. A method of expanding a cell, the method comprising culturing the cell in the presence of an effective amount of a compound as recited in any one of paragraphs 1-124, or a pharmaceutically acceptable salt thereof.

Paragraph 131. The method of paragraph 130, wherein the cell is selected from the group consisting of: stem cell, pluripotent stem cell, hematopoietic stem cell, and embryonic stem cell.

Paragraph 132. The method of paragraph 131, wherein the cell is a pluripotent stem cell.

Paragraph 133. The method of paragraph 131, wherein the cell is a hematopoietic stem cell.

Paragraph 134. The method of paragraph 131, wherein the cell is an embryonic stem cell.

Paragraph 135. The method of any of paragraphs 131-135, wherein the cell is collected from a subject with a disease or condition selected from the group consisting of a disorder associated with telomere or telomerase dysfunction, a disorder associated with aging, a pre-leukemic or pre-cancerous condition, and a neurodevelopment disorder.

Paragraph 136. The method of any of paragraphs 131-135, further comprising culturing the cell with a feeder layer in a medium.

Paragraph 137. The method of any one of paragraphs 131-136, wherein the cell has at least one stem cell marker selected from the group consisting of FLK-1, AC133, CD34, c-kit, CXCR-4, Oct-4, Rex-1, CD9, CD13, CD29, CD34, CD44, CD166, CD90, CD105, SH-3, SH-4, TRA-1-60, TRA-1-81, SSEA-4, and Sox-2.

Paragraph 138. The method of paragraph 137, wherein the stem cell marker is CD34.

Paragraph 139. The method of paragraph 138, further comprising enriching stem cells by isolating CD34+ cells.

Paragraph 140. The method of paragraph 135, wherein the subject is a mammal.

Paragraph 141. The method of paragraph 140, wherein the subject is a human.

Paragraph 142. The method of any one of paragraphs 130-141, comprising culturing the cell in a medium selected from the group consisting of Iscove“s modified Dulbecco's Media (IMDM) medium, Dulbecco”s Modified Eagle Medium (DMEM), Roswell Park Memorial Institute (RPMI) medium, minimum essential medium alpha medium (α-MEM), Basal Media Eagle (BME) medium, Glasgow Minimum Essential Medium (GMEM), Modified Eagle Medium (MEM), Opti-MEM I Reduced Serum medium, neuroplasma medium, $CO_2$-Independent medium, and Leibovitz's L-15 medium.

Paragraph 143. The method of paragraph 130, wherein the cell is a Chimeric Antigen Receptor (CAR) T-Cell.

Paragraph 144. The method of paragraph 130, wherein the cell is a lymphocyte.

Paragraph 145. The method of paragraph 130, wherein the cell is a T cell, an engineered T cell, or a natural killer cell (NK).

REFERENCES

1. Neha Nagpal et al., Small-Molecule PAPD5 inhibitors restore telomerase activity in patient stem cells, *Cell Stem Cell,* 26 (2020), 1-14.
2. Wilson Chun Fok et al., Posttranslational modulation of TERC by PAPD5 inhibition rescues hematopoietic development in dyskeratosis congenita, *Blood,* 144, 12 (2019), 1308-1312.

OTHER EMBODIMENTS

It is to be understood that while the present application has been described in conjunction with the detailed description thereof, the foregoing description is intended to illustrate and not limit the scope of the present application, which is defined by the scope of the appended claims. Other aspects, advantages, and modifications are within the scope of the following claims.

---

What is claimed is:

1. A compound of Formula (III):

(III)

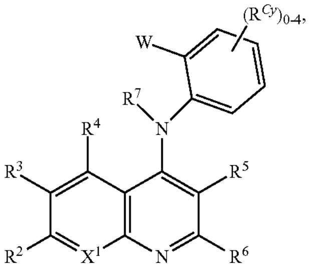

or a pharmaceutically acceptable salt thereof, wherein:

$X^1$ is $CR^1$;

$R^1$, $R^2$, $R^3$, $R^4$, and $R^6$ are each independently selected from H, $C_{1-6}$ alkyl, $C_{2-6}$ alkenyl, $C_{2-6}$ alkynyl, $C_{1-4}$ haloalkyl, $Cy^1$, halo, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2R^{b1}$, $S(O)R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, 3, 4, or 5 substituents independently selected from $Cy^1$, halo, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2R^{b1}$, $S(O)_2R^{b1}$, and $S(O)_2NR^{c1}R^{d1}$;

$R^5$ is selected from $C(O)NR^{c1}R^{d1}$, $S(O)_2NR^{c1}R^{d1}$, and $Cy^1$;

each $Cy^1$ is independently selected from $C_{6-10}$ aryl, $C_{3-10}$ cycloalkyl, 5-10 membered heteroaryl, and 4-7 membered heterocycloalkyl, each of which is optionally substituted with 1, 2, or 3 substituents independently selected from $R^{Cy}$;

$R^7$ is selected from H, $C_{1-3}$ alkyl, C(O) $C_{1-6}$ alkyl, $C(O)OR^{a1}$, $S(O)_2NR^{c1}R^{d1}$, and phenyl, wherein said phenyl is optionally substituted with halo, CN, $OR^{a1}$, $SR^{a1}$, or $NR^{c1}R^{d1}$;

W is selected from COOH and a moiety selected from any one of the following moieties:

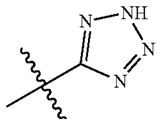

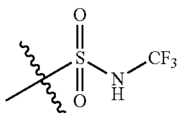

-continued

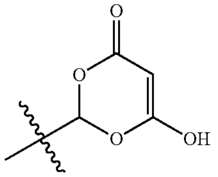
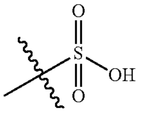
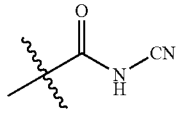
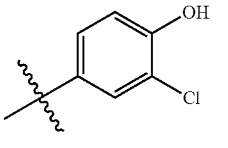
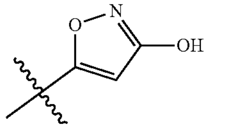
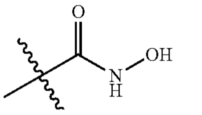
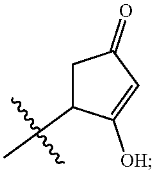
;

$R^{Cy}$ is selected from halo, CN, $NO_2$, $C_{1-6}$ alkyl, $C_{1-6}$ haloalkyl, $C_{2-6}$ alkenyl, $C_{2-6}$ alkynyl, $C_{3-10}$ cycloalkyl, 5-10 membered heteroaryl, 4-6 membered heterocycloalkyl, $OR^{a2}$, $C(O)R^{b2}$, $C(O)OR^{a2}$, $C(O)NR^{c2}R^{d2}$, $C(O)NR^{c1}S(O)_2R^{b2}$, $NR^{c2}R^{d2}$, $NR^{c2}C(O)R^{b2}$, $NR^{c2}C(O)OR^{a2}$, $NR^{c2}S(O)_2R^{b2}$, $OC(O)R^{b1}$, $S(O)_2R^{b2}$, and $S(O)_2NR^{c2}R^{d2}$; wherein said $C_{1-6}$ alkyl, $C_{2-6}$ alkenyl, $C_{2-6}$ alkynyl, $C_{3-10}$ cycloalkyl, and 4-6 membered heterocycloalkyl are each optionally substituted with 1, 2, or 3 substituents independently selected from halo, CN, $NO_2$, $OR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$, $NR^{c2}C(O)OR^{a2}$, $NR^{c2}S(O)_2R^{b2}$ $S(O)_2R^{b2}$, and $S(O)_2NR^{c2}R^{d2}$;

each $R^{a1}$, $R^{b1}$, $R^{c1}$, $R^{d1}$, $R^{a2}$, $R^{b2}$, $R^{c2}$, and $R^{d2}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-10 membered heterocycloalkyl or 5-10 membered heteroaryl, each of which is optionally substituted with 1, 2, or 3 substituents independently selected from $R^g$;

or any $R^{c2}$ and $R^{d2}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl) amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl) carbamyl, carboxy, $C_{1-6}$ alkylcarbonyl, $C_{6-10}$ aryl-$C_{1-6}$ alkoxycarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl) aminosulfonyl, aminosulfonylamino, $C_{1-6}$ alkylaminosulfonylamino, di($C_{1-6}$ alkyl) aminosulfonylamino, aminocarbonylamino, $C_{1-6}$ alkylaminocarbonylamino, and di($C_{1-6}$ alkyl)aminocarbonylamino.

2. The compound of claim 1, wherein:

each $Cy^1$ is independently selected from $C_{6-10}$ aryl, 5-10 membered heteroaryl, and 4-7 membered heterocycloalkyl, each of which is optionally substituted with 1, 2, or 3 substituents independently selected from $R^{Cy}$;

$R^{Cy}$ is selected from halo, CN, $NO_2$, $C_{1-6}$ alkyl, $C_{1-6}$ haloalkyl, $C_{2-6}$ alkenyl, $C_{2-6}$ alkynyl, $OR^{a2}$, $C(O)R^{b2}$, $C(O)OR^{a2}$, $C(O)NR^{c2}R^{d2}$, $NR^{c2}R^{d2}$, $NR^{c2}C(O)R^{b2}$, $NR^{c2}C(O)OR^{a2}$, $NR^{c2}S(O)_2R^{b2}$, $S(O)_2R^{b2}$, and $S(O)_2NR^{c2}R^{d2}$; wherein said $C_{1-6}$ alkyl, $C_{2-6}$ alkenyl, $C_{2-6}$ alkynyl, are each optionally substituted with 1, 2, or 3 substituents independently selected from halo, CN, $NO_2$, $OR^{a2}$, $C(O)R^{b2}$, $C(O)NR^{c2}R^{42}$, $C(O)OR^{a2}$, $NR^{c2}R^{d2}$, $NR^{c2}C(O)R^{b2}$, $NR^{c2}C(O)OR^{a2}$, $NR^{c2}S(O)_2R^{b2}$, $S(O)_2R^{b2}$, and $S(O)_2NR^{c2}R^{d2}$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl) amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl) carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl) aminosulfonyl, aminosulfonylamino, $C_{1-6}$ alkylaminosulfonylamino, di($C_{1-6}$ alkyl) aminosulfonylamino, aminocarbonylamino, $C_{1-6}$ alkylaminocarbonylamino, and di($C_{1-6}$ alkyl) aminocarbonylamino.

3. The compound of claim 1, wherein:

$R^1$, $R^2$, $R^3$, $R^4$, and $R^6$ are each independently selected from H, $C_{1-6}$ alkyl, $C_{2-6}$ alkenyl, $C_{2-6}$ alkynyl, $C_{1-4}$ haloalkyl, $Cy^1$, halo, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, 3, 4, or 5 substituents independently selected from $Cy^1$, halo, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2R^{b1}$, $S(O)_2R^{b1}$, and $S(O)_2NR^{c1}R^{d1}$; and $R^7$ is selected from H and $C_{1-3}$ alkyl.

4. The compound of claim 1, wherein $R^1$, $R^2$, $R^3$, $R^4$, and $R^6$ are each independently selected from H, $Cy^1$, halo, CN, $OR^{a1}$, $C(O)NR^{c1}R^{d1}$, $C(O)OR^{a1}$, and $S(O)_2NR^{c1}R^{d1}$.

5. The compound of claim 4, wherein:
$R^1$, $R^4$, and $R^6$ are each H,
$R^2$ is selected from H, $Cy^1$, halo, CN, $OR^{a1}$, $C(O)NR^{c1}R^{d1}$, $C(O)OR^{a1}$, and $S(O)_2NR^{c1}R^{d1}$, and
$R^3$ is selected from $Cy^1$, halo, CN, $OR^{a1}$, $C(O)NR^{c1}R^{d1}$, $C(O)OR^{a1}$, and $S(O)_2NR^{c1}R^{d1}$.

6. The compound of claim 5, wherein:
$R^1$, $R^4$, and $R^6$ are each H;
$R^2$ is selected from H and $OR^{a1}$; and
$R^3$ is selected from $Cy^1$, $OR^{a1}$, and halo.

7. The compound of claim 5, wherein:
$R^1$, $R^2$, $R^4$, and $R^6$ are each H, and
$R^3$ is selected from $Cy^1$, halo, CN, $OR^{a1}$, $C(O)NR^{c1}R^{d1}$, $C(O)OR^{a1}$, and $S(O)_2NR^{c1}R^{d1}$.

8. The compound of claim 7, wherein:
$R^3$ is selected from $Cy^1$, $OR^{a1}$, $C(O)NR^{c1}R^{d1}$, and halo.

9. The compound of claim 5, wherein:
$R^2$ is selected from H and $OR^{a1}$; and
$R^3$ is selected from $C_{1-6}$ alkoxy and $C_{1-6}$ haloalkoxy.

10. The compound of claim 1, wherein $R^5$ is selected from $C(O)NR^{c1}R^{d1}$, $S(O)_2NR^{c1}R^{d1}$, and $Cy^1$.

11. The compound of claim 10, wherein $Cy^1$ is selected from $C_{3-10}$ cycloalkyl, 5-10 membered heteroaryl, and 4-7 membered heterocycloalkyl, each of which is optionally substituted with $R^{Cy}$.

12. The compound of claim 10, wherein $R^{c1}$ and $R^{d1}$ are each independently selected from H and $C_{1-6}$ alkyl.

13. The compound of claim 10, wherein $R^{c1}$ and $R^{d1}$ together with the N atom to which they are attached form a 4-7 membered heterocycloalkyl, which is optionally substituted with $R^g$.

14. The compound of claim 1, wherein $R^7$ is selected from H and $C_{1-3}$ alkyl.

15. The compound of claim 1, wherein Roy is selected from halo, CN, $C_{1-6}$ alkyl, $C_{1-6}$ haloalkyl, 5-10 membered heteroaryl, 4-6 membered heterocycloalkyl, $OR^{a2}$, $C(O)OR^{a2}$, $C(O)NR^{c2}R^{d2}$, $C(O)NR^{c1}S(O)_2R^{b2}$, $NR^{c2}R^{d2}$, $NR^{c2}C(O)R^{b2}$, $OC(O)R^{b1}$, and $S(O)_2R^{b2}$; wherein said $C_{1-6}$ alkyl is optionally substituted with $OR^{a2}$ or $NR^{c2}R^{d2}$.

16. The compound of claim 1, wherein the compound of Formula (III) is selected from any one of the following compounds:

13A

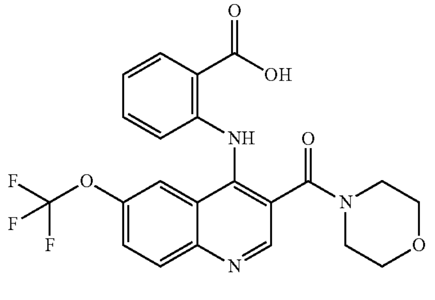

14A

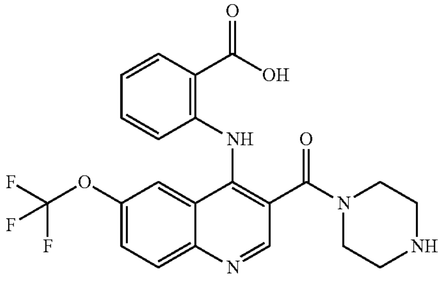

-continued

12A

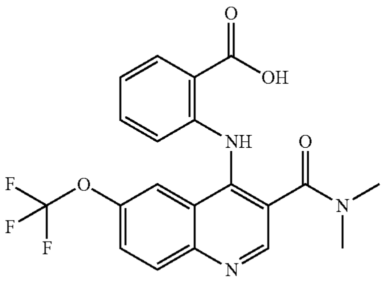

16A

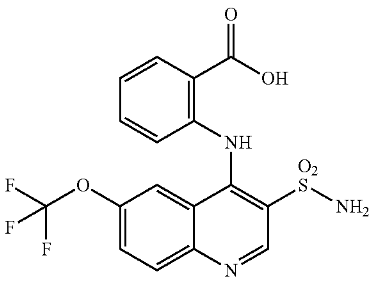

17A

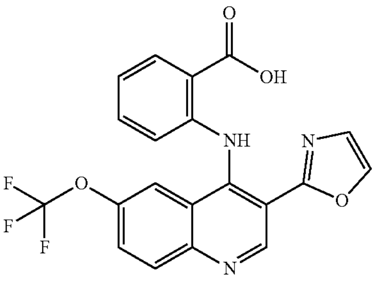

53A

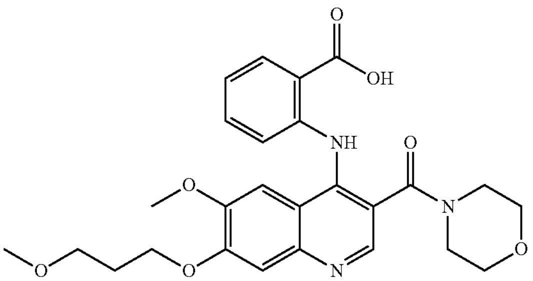

57A

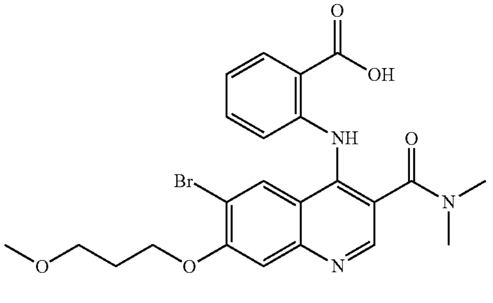

-continued
58A
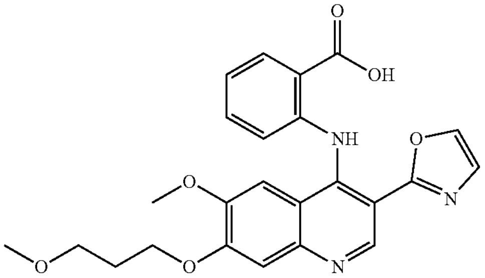
61A
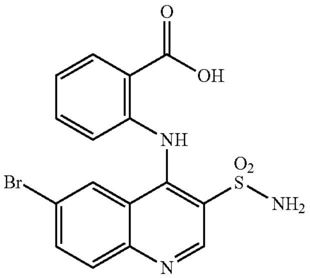
63A
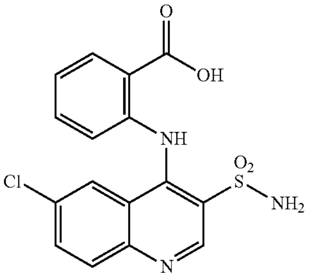
64A
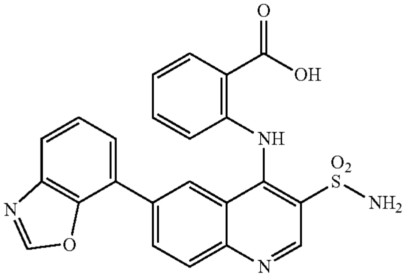
70A
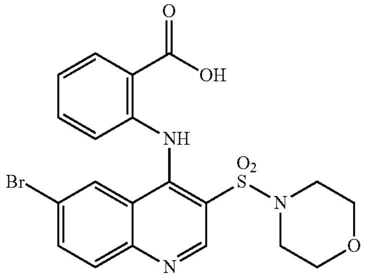
-continued
78A
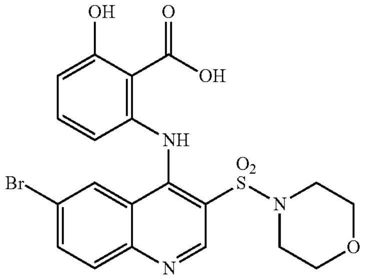
78A-BR
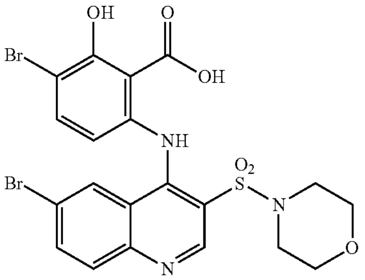
78A-INT
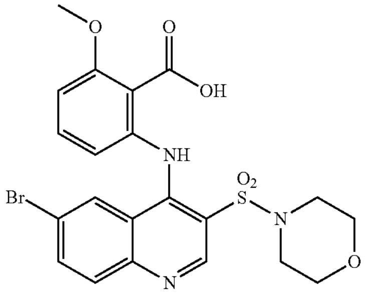
79A
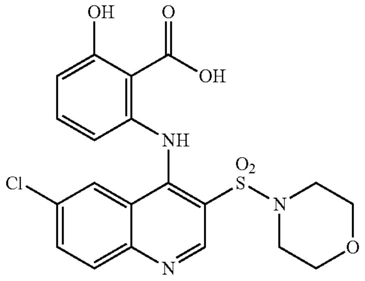
79A-INT
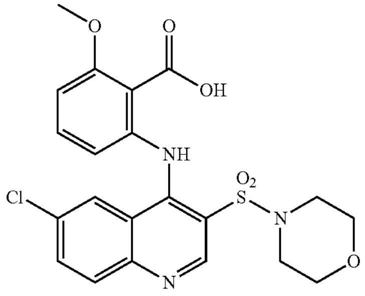

-continued
80A
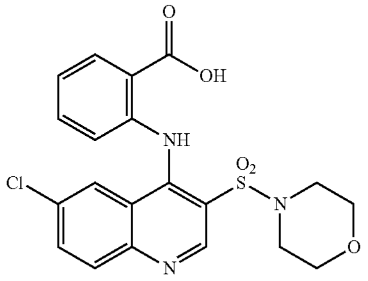
81A
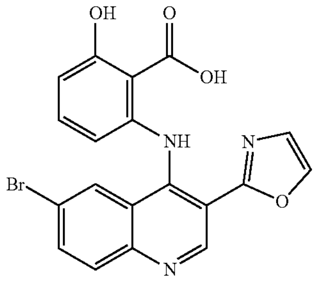
81A-INT
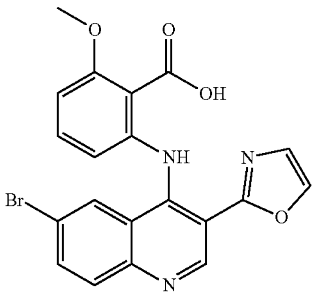
82A
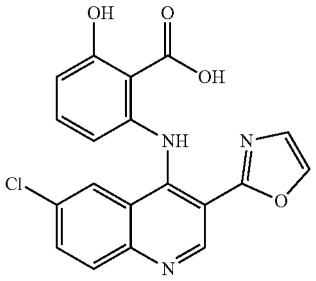
85A
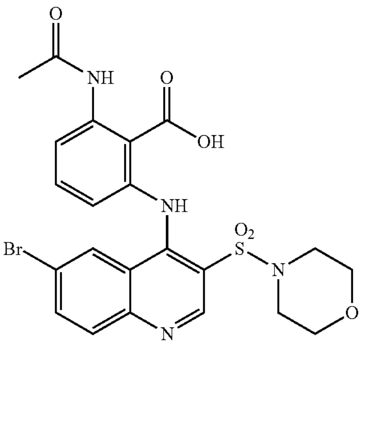
-continued
85A-BP
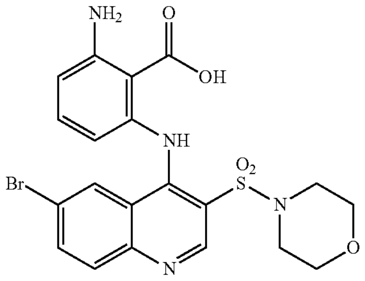
86A
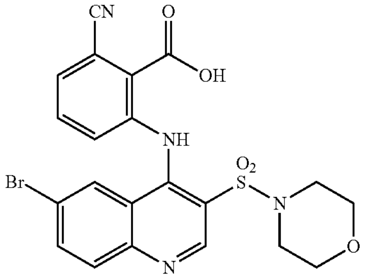
93A
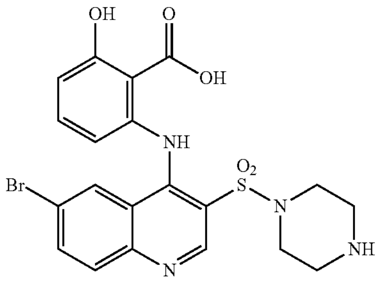
93A-INT
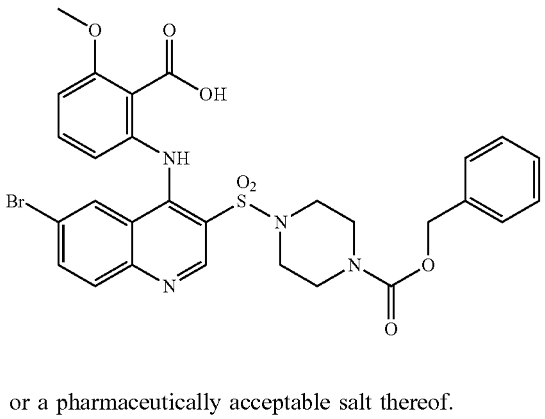
or a pharmaceutically acceptable salt thereof.

17. The compound of claim 1, wherein the compound of Formula (III) is selected from any one of the following compounds:
13A
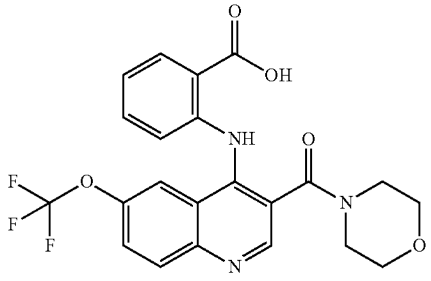
14A
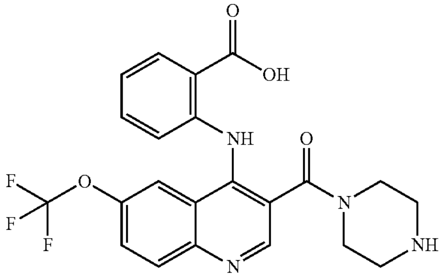
12A
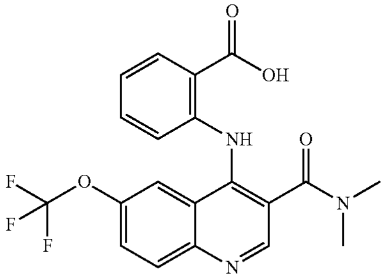
16A
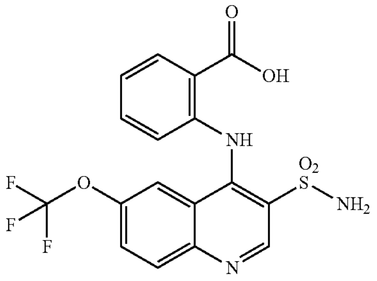
17A
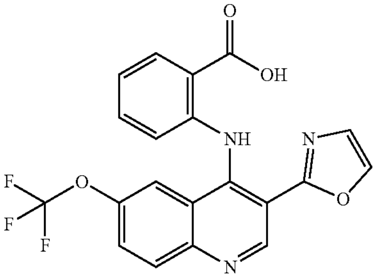
or a pharmaceutically acceptable salt thereof.
18. The compound of claim 1, wherein the compound of Formula (III) is selected from any one of the following compounds:
87A
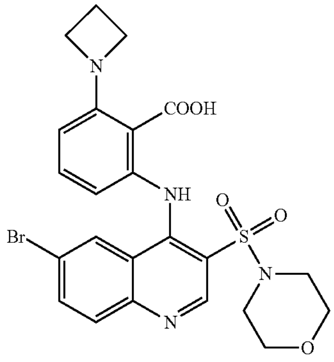
96A
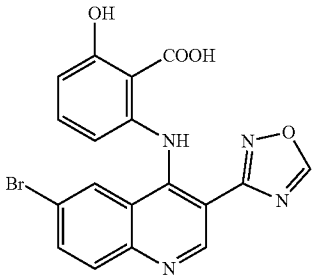
97A
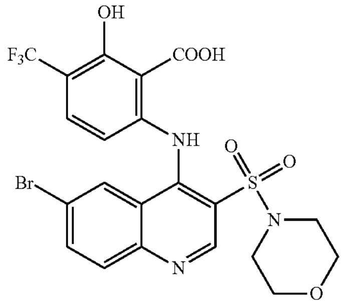
88A
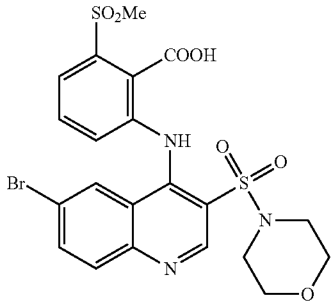

-continued
89A
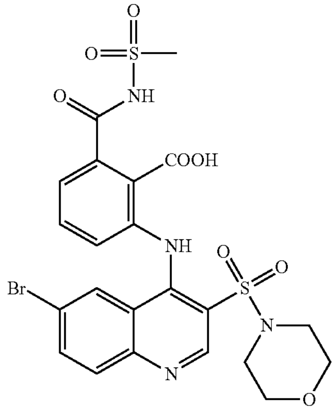
90A
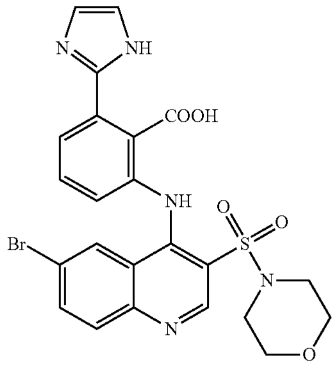
91A
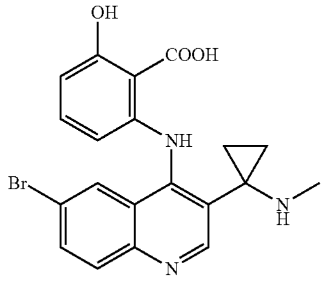
94A
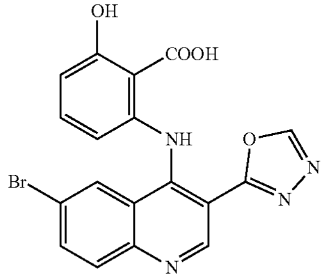
95A
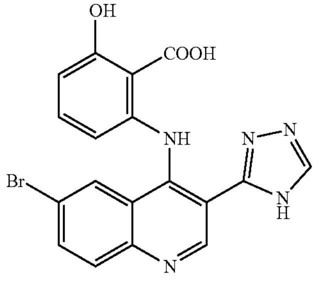
-continued
92A
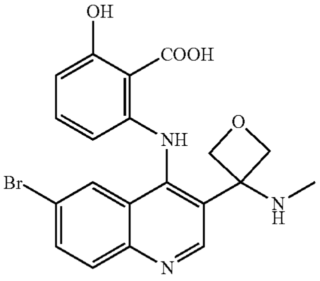
98A
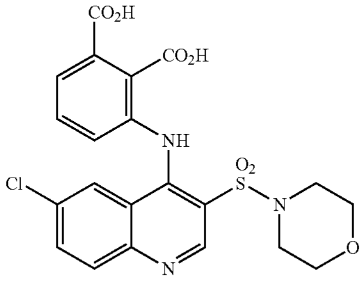
99A
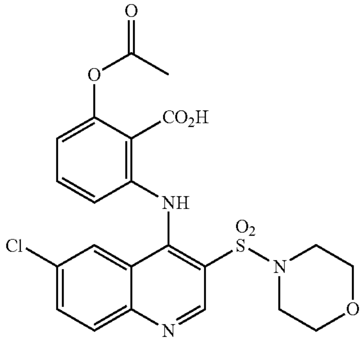
100A
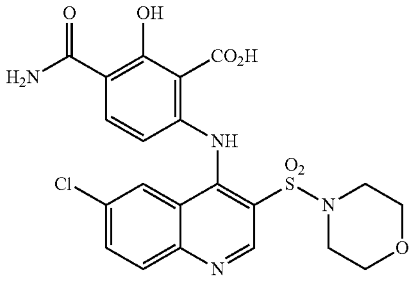
101A
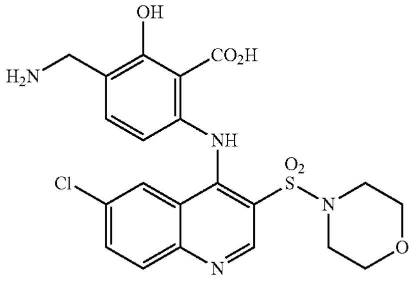

-continued
102A
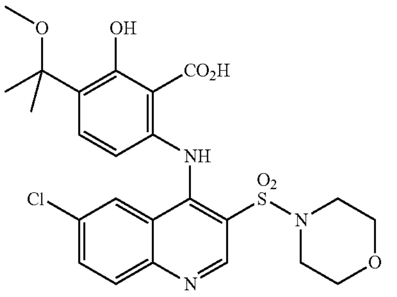
103A
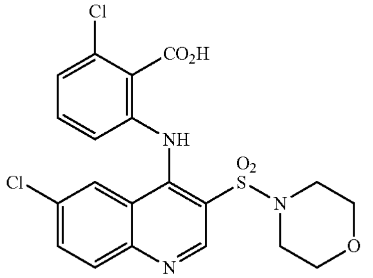
107A
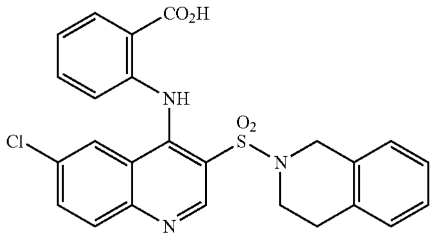
108A
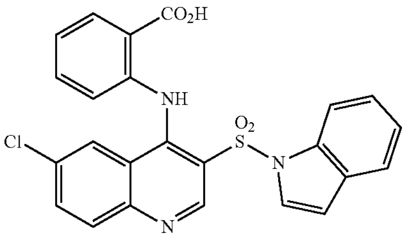
109A
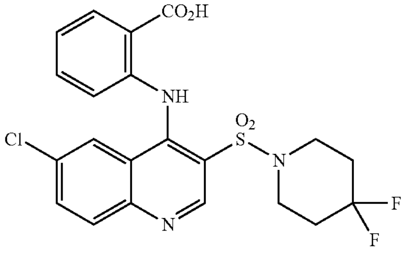
-continued
110A
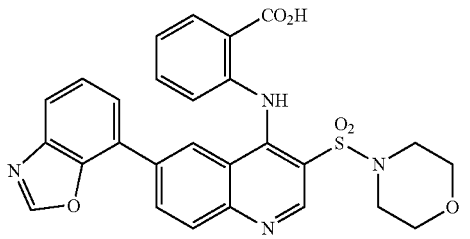
111A
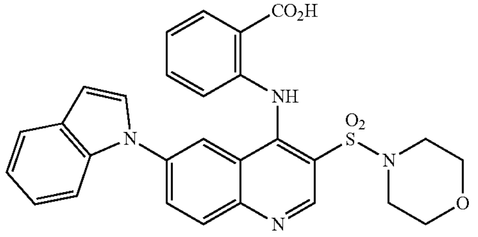
112A
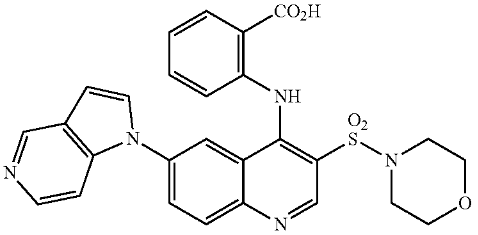
114A
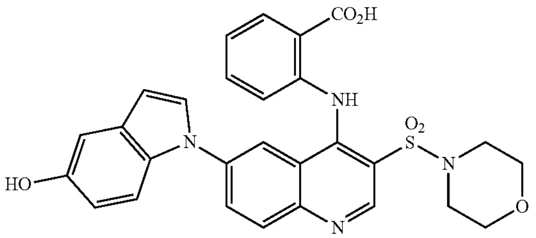
115A
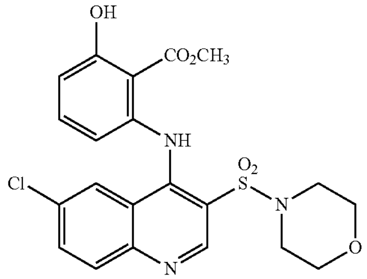
118A
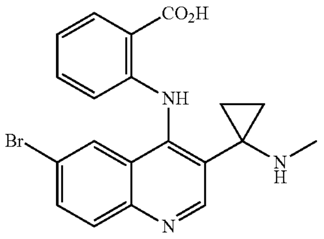

-continued

119A

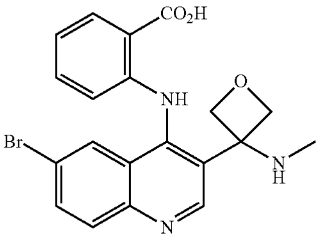

120A

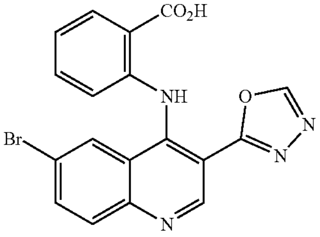

121A

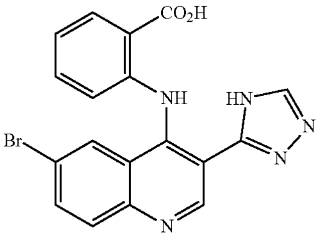

122A

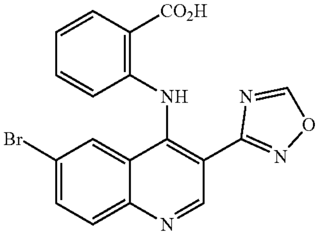

-continued

123A

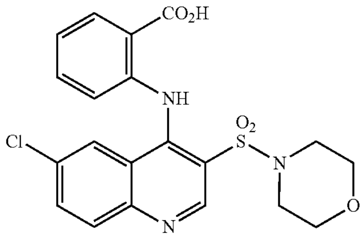

or a pharmaceutically acceptable salt thereof.

19. A pharmaceutical composition comprising a compound of claim 1, or a pharmaceutically acceptable salt thereof, and a pharmaceutically acceptable carrier.

20. A method of treating a disease or condition selected from dyskeratosis congenita, aplastic anemia, pulmonary fibrosis, myelodysplastic syndrome, idiopathic pulmonary fibrosis, hematological disorder, and hepatic fibrosis, the method comprising administering to a subject in need thereof a therapeutically effective amount of a compound of claim 1, or a pharmaceutically acceptable salt thereof.

21. A method of treating a disease or condition selected from macular degeneration, diabetes mellitus, osteoarthritis, rheumatoid arthritis, sarcopenia, cardiovascular disease, hypertension, atherosclerosis, coronary artery disease, ischemia/reperfusion injury, cancer, premature death, and age-related decline in cognitive function, cardiopulmonary function, muscle strength, vision, or hearing, the method comprising administering to a subject in need thereof a therapeutically effective amount of a compound of claim 1, or a pharmaceutically acceptable salt thereof.

22. A method of treating a disease or condition selected from hypoplasia, the method comprising administering to a subject in need thereof a therapeutically effective amount of a compound of claim 1, or a pharmaceutically acceptable salt thereof.

* * * * *

SEQUENCE LISTING

```
<160> NUMBER OF SEQ ID NOS: 4

<210> SEQ ID NO 1
<211> LENGTH: 631
<212> TYPE: PRT
<213> ORGANISM: Artificial
<220> FEATURE:
<223> OTHER INFORMATION: synthetic polypeptide

<400> SEQUENCE: 1

Met Tyr Arg Ser Gly Glu Arg Leu Leu Gly Ser His Ala Leu Pro Ala
1               5                   10                  15

Glu Gln Arg Asp Phe Leu Pro Leu Glu Thr Thr Asn Asn Asn Asn Asn
            20                  25                  30

His His Gln Pro Gly Ala Trp Ala Arg Arg Ala Gly Ser Ser Ala Ser
        35                  40                  45

Ser Pro Pro Ser Ala Ser Ser Ser Pro His Pro Ser Ala Ala Val Pro
    50                  55                  60

Ala Ala Asp Pro Ala Asp Ser Ala Ser Gly Ser Ser Asn Lys Arg Lys
65                  70                  75                  80

Arg Asp Asn Lys Ala Ser Thr Tyr Gly Leu Asn Tyr Ser Leu Leu Gln
                85                  90                  95

Pro Ser Gly Gly Arg Ala Ala Gly Gly Gly Arg Ala Asp Gly Gly Gly
            100                 105                 110

Val Val Tyr Ser Gly Thr Pro Trp Lys Arg Arg Asn Tyr Asn Gln Gly
        115                 120                 125

Val Val Gly Leu His Glu Glu Ile Ser Asp Phe Tyr Glu Tyr Met Ser
    130                 135                 140

Pro Arg Pro Glu Glu Glu Lys Met Arg Met Glu Val Val Asn Arg Ile
145                 150                 155                 160

Glu Ser Val Ile Lys Glu Leu Trp Pro Ser Ala Asp Val Gln Ile Phe
                165                 170                 175
```

-continued

```
Gly Ser Phe Lys Thr Gly Leu Tyr Leu Pro Thr Ser Asp Ile Asp Leu
            180                 185                 190

Val Val Phe Gly Lys Trp Glu Asn Leu Pro Leu Trp Thr Leu Glu Glu
        195                 200                 205

Ala Leu Arg Lys His Lys Val Ala Asp Glu Asp Ser Val Lys Val Leu
    210                 215                 220

Asp Lys Ala Thr Val Pro Ile Ile Lys Leu Thr Asp Ser Phe Thr Glu
225                 230                 235                 240

Val Lys Val Asp Ile Ser Phe Asn Val Gln Asn Gly Val Arg Ala Ala
                245                 250                 255

Asp Leu Ile Lys Asp Phe Thr Lys Lys Tyr Pro Val Leu Pro Tyr Leu
            260                 265                 270

Val Leu Val Leu Lys Gln Phe Leu Leu Gln Arg Asp Leu Asn Glu Val
        275                 280                 285

Phe Thr Gly Gly Ile Gly Ser Tyr Ser Leu Phe Leu Met Ala Val Ser
    290                 295                 300

Phe Leu Gln Leu His Pro Arg Glu Asp Ala Cys Ile Pro Asn Thr Asn
305                 310                 315                 320

Tyr Gly Val Leu Leu Ile Glu Phe Phe Glu Leu Tyr Gly Arg His Phe
                325                 330                 335

Asn Tyr Leu Lys Thr Gly Ile Arg Ile Lys Asp Gly Gly Ser Tyr Val
            340                 345                 350

Ala Lys Asp Glu Val Gln Lys Asn Met Leu Asp Gly Tyr Arg Pro Ser
        355                 360                 365

Met Leu Tyr Ile Glu Asp Pro Leu Gln Pro Gly Asn Asp Val Gly Arg
    370                 375                 380

Ser Ser Tyr Gly Ala Met Gln Val Lys Gln Ala Phe Asp Tyr Ala Tyr
385                 390                 395                 400

Val Val Leu Ser His Ala Val Ser Pro Ile Ala Lys Tyr Tyr Pro Asn
                405                 410                 415

Asn Glu Thr Glu Ser Ile Leu Gly Arg Ile Ile Arg Val Thr Asp Glu
            420                 425                 430

Val Ala Thr Tyr Arg Asp Trp Ile Ser Lys Gln Trp Gly Leu Lys Asn
        435                 440                 445

Arg Pro Glu Pro Ser Cys Asn Gly Asn Gly Val Thr Leu Ile Val Asp
    450                 455                 460

Thr Gln Gln Leu Asp Lys Cys Asn Asn Asn Leu Ser Glu Glu Asn Glu
465                 470                 475                 480

Ala Leu Gly Lys Cys Arg Ser Lys Thr Ser Glu Ser Leu Ser Lys His
                485                 490                 495

Ser Ser Asn Ser Ser Ser Gly Pro Val Ser Ser Ser Ser Ala Thr Gln
            500                 505                 510

Ser Ser Ser Ser Asp Val Asp Ser Asp Ala Thr Pro Cys Lys Thr Pro
        515                 520                 525

Lys Gln Leu Leu Cys Arg Pro Ser Thr Gly Asn Arg Val Gly Ser Gln
    530                 535                 540

Asp Val Ser Leu Glu Ser Ser Gln Ala Val Gly Lys Met Gln Ser Thr
545                 550                 555                 560

Gln Thr Thr Asn Thr Ser Asn Ser Thr Asn Lys Ser Gln His Gly Ser
                565                 570                 575

Ala Arg Leu Phe Arg Ser Ser Ser Lys Gly Phe Gln Gly Thr Thr Gln
            580                 585                 590
```

-continued

```
Thr Ser His Gly Ser Leu Met Thr Asn Lys Gln His Gln Gly Lys Ser
        595                 600                 605

Asn Asn Gln Tyr Tyr His Gly Lys Lys Arg Lys His Lys Arg Asp Ala
    610                 615                 620

Pro Leu Ser Asp Leu Cys Arg
625                 630


<210> SEQ ID NO 2
<211> LENGTH: 20
<212> TYPE: RNA
<213> ORGANISM: Artificial
<220> FEATURE:
<223> OTHER INFORMATION: synthetic oligonucleotide

<400> SEQUENCE: 2

ccucuuguug cugcugcccg                                                   20


<210> SEQ ID NO 3
<211> LENGTH: 20
<212> TYPE: RNA
<213> ORGANISM: Artificial
<220> FEATURE:
<223> OTHER INFORMATION: synthetic oligonucleotide

<400> SEQUENCE: 3

cggagcgaua caugccggcc                                                   20


<210> SEQ ID NO 4
<211> LENGTH: 20
<212> TYPE: RNA
<213> ORGANISM: Artificial
<220> FEATURE:
<223> OTHER INFORMATION: synthetic oligonucleotide

<400> SEQUENCE: 4

ccucuuguug cugcugcccg                                                   20
```